(12) United States Patent
Majtan et al.

(10) Patent No.: US 11,324,811 B2
(45) Date of Patent: May 10, 2022

(54) OPTIMIZATION OF ENZYME REPLACEMENT THERAPY FOR TREATMENT OF HOMOCYSTINURIA

(71) Applicants: THE REGENTS OF THE UNIVERSITY OF COLORADO, A BODY CORPORATE, Denver, CO (US); Travere Therapeutics Switzerland GmbH, Rapperswil-Jona (CH)

(72) Inventors: Tomas Majtan, Aurora, CO (US); Jan P. Kraus, Denver, CO (US); Erez M. Bublil, Ets Efraim (IL); Frank Glavin, Belmont, MA (US); Marcia Sellos-Moura, West Newbury, MA (US)

(73) Assignees: THE REGENTS OF THE UNIVERSITY OF COLORADO, A BODY CORPORATE, Denver, CO (US); TRAVERE THERAPEUTICS SWITZERLAND GMBH, Rapperswil-Jona (CH)

( * ) Notice: Subject to any disclaimer, the term of this patent is extended or adjusted under 35 U.S.C. 154(b) by 142 days.

(21) Appl. No.: 16/605,918

(22) PCT Filed: Apr. 17, 2018

(86) PCT No.: PCT/US2018/027854
§ 371 (c)(1),
(2) Date: Oct. 17, 2019

(87) PCT Pub. No.: WO2018/195006
PCT Pub. Date: Oct. 25, 2018

(65) Prior Publication Data
US 2020/0261555 A1 Aug. 20, 2020

Related U.S. Application Data

(60) Provisional application No. 62/486,246, filed on Apr. 17, 2017.

(51) Int. Cl.
*A61K 38/51* (2006.01)
*A61K 47/60* (2017.01)
*C12N 9/88* (2006.01)

(52) U.S. Cl.
CPC .............. *A61K 38/51* (2013.01); *A61K 47/60* (2017.08); *C12N 9/88* (2013.01); *C12Y 402/01022* (2013.01)

(58) Field of Classification Search
CPC .......... A61K 47/60; A61K 38/51; C12N 9/88; C12N 9/96; C12Y 402/01022
See application file for complete search history.

(56) References Cited

U.S. PATENT DOCUMENTS

| | | |
|---|---|---|
| 5,523,225 A | 6/1996 | Kraus |
| 5,635,375 A | 6/1997 | Kraus |
| 5,643,575 A | 7/1997 | Martinez |
| 5,656,425 A | 8/1997 | Kraus |
| 5,705,151 A | 1/1998 | Dow et al. |
| 5,730,990 A | 3/1998 | Greenwald |
| 5,902,588 A | 5/1999 | Greenwald |
| 5,919,455 A | 7/1999 | Greenwald |
| 6,113,906 A | 9/2000 | Greenwald |
| 6,153,655 A | 11/2000 | Martinez |
| 6,174,696 B1 | 1/2001 | Seman |
| 6,177,087 B1 | 1/2001 | Greenwald |
| 6,436,658 B1 | 8/2002 | Seman |
| 6,596,701 B1 | 7/2003 | Schwartz et al. |
| 7,485,307 B2 | 2/2009 | Kraus |
| 7,816,495 B2 | 10/2010 | Kingsland |
| 8,007,787 B2 | 8/2011 | Kraus |
| 8,398,989 B2 | 3/2013 | Kraus et al. |
| 9,011,844 B2 | 4/2015 | Kraus |
| 9,034,318 B2 | 5/2015 | Kraus |
| 9,243,239 B2 | 1/2016 | Carrillo et al. |
| 9,284,546 B2 | 3/2016 | Kraus |
| 9,447,406 B2 | 9/2016 | Kraus |
| 9,631,188 B2 | 4/2017 | Kraus |

(Continued)

FOREIGN PATENT DOCUMENTS

| | | |
|---|---|---|
| CN | 1552905 A | 12/2004 |
| CN | 101322840 A | 12/2008 |

(Continued)

OTHER PUBLICATIONS

Fee et al., PEG-proteins: Reaction engineering and separation issues. Chem. Eng. Sci., 2006, vol. 61: 924-939. (Year: 2006).*
Fekete et al., Theory and practice of size exclusion chromatography fro analysis of protein aggregates. J. Pharma. Bomed. Analysis., 2014, vol. 101: 161-173. (Year: 2014).*
Majtan et al., Engineering and Characterization of an Enzyme Replacement Therapy for Classical Homocystinuria. Biomacromol., 2017, vol. 18: 1747-1761. (Year: 2017).*
NOF Corporation, Activated PEGs; pp. 1-10, downloaded from https://www.dds-drug.com/dds-products/indexon Jun. 30, 2021 (Year: 2021).*
Pfister et al., Process for protein PEGylation. J. Control. Release., 2014, vol. 180: 134-149. (Year: 2014).*

(Continued)

*Primary Examiner* — Ganapathirama Raghu
(74) *Attorney, Agent, or Firm* — Seed Intellectual Property Group LLP

(57) ABSTRACT

The present invention provides a method of PEGylating a human truncated cystathionine β-synthase protein containing a mutation of a cysteine to a serine at amino acid position 15 (htCBS C15S). The htCBS C15S was PEGylated with one of 5 kDa, 10 kDa, or 20 kDa NHS ester PEG molecules. In-process monitoring of the PEGylation process was used in the method to reduce levels of unPEGylated htCBS C15S and htCBS C15S with insufficient PEGylation. Administration of the PEGylated htCBS C15S had efficacy throughout the course of treatment for homocystinuria.

12 Claims, 17 Drawing Sheets

Specification includes a Sequence Listing.

(56) References Cited

U.S. PATENT DOCUMENTS

| | | | |
|---|---|---|---|
| 9,675,678 | B2 | 6/2017 | Kraus |
| 10,046,036 | B2 | 8/2018 | Kraus et al. |
| 10,160,962 | B2 | 12/2018 | Carrillo et al. |
| 10,265,387 | B2 | 4/2019 | Kraus |
| 10,280,415 | B2 | 5/2019 | Kraus |
| 10,624,959 | B2 | 4/2020 | Kraus et al. |
| 10,653,755 | B2 * | 5/2020 | Kraus ............ C12N 9/88 |
| 10,729,753 | B2 * | 8/2020 | Kraus ............ A61K 45/06 |
| 10,941,392 | B2 | 3/2021 | Carrillo et al. |
| 11,077,175 | B2 | 8/2021 | Kraus et al. |
| 2003/0091543 | A1 | 5/2003 | Klein et al. |
| 2006/0251641 | A1 | 11/2006 | Keimel |
| 2007/0010492 | A1 | 1/2007 | Generale |
| 2010/0166725 | A1 | 7/2010 | Kraus |
| 2013/0251700 | A1 | 9/2013 | Carrillo et al. |
| 2016/0051648 | A1 | 2/2016 | Kraus et al. |
| 2017/0065687 | A1 | 3/2017 | Kraus |
| 2017/0224787 | A1 | 8/2017 | Kraus |
| 2018/0318404 | A1 | 11/2018 | Kraus |
| 2020/0316179 | A1 | 10/2020 | Kraus et al. |

FOREIGN PATENT DOCUMENTS

| | | |
|---|---|---|
| EP | 1396537 | 3/2004 |
| EP | 1396537 A1 | 3/2004 |
| EP | 1878739 | 1/2008 |
| EP | 1878739 A1 | 1/2008 |
| JP | 6146934 | 5/2017 |
| JP | 6146934 | 6/2017 |
| JP | 6453243 | 12/2018 |
| WO | 9507714 | 3/1995 |
| WO | 01/02600 A2 | 1/2001 |
| WO | 03/106971 A2 | 12/2003 |
| WO | 2003/106971 A2 | 12/2003 |
| WO | 2003106971 | 12/2003 |
| WO | 2011/097381 A1 | 8/2011 |
| WO | 2011097381 | 8/2011 |
| WO | 2012001336 | 1/2012 |
| WO | 2013148580 | 10/2013 |
| WO | 2014/120770 | 7/2014 |
| WO | 2014/120770 A1 | 8/2014 |
| WO | 2014120770 | 8/2014 |
| WO | 95/07714 | 3/2015 |
| WO | 2015033279 | 3/2015 |
| WO | 2015033279 A1 | 3/2015 |
| WO | 2017/018742 A1 | 2/2017 |
| WO | 2017/083327 A1 | 5/2017 |
| WO | 2018/195006 A1 | 10/2018 |
| WO | 2018195006 | 10/2018 |
| WO | 2018195006 A1 | 10/2018 |

OTHER PUBLICATIONS

Wu et al., Precise and combinatorial PEGylation genertaes a low-immunogenic and stable human growth hormone. J. Control. Release., 2017, vol. 249: 84-93. (Year: 2017).*

International Search Report and Written Opinion dated Jul. 10, 2018 in application No. PCT/US2018/027854, entitled: Optimization of Enzyme Replacement Therapy for Treatment of Homocystinuria.

Knudson, V. et al. "Evaluating Separations of PEGylated Proteins Using Gel Filtration Chromatography" Phenomenex TN-1048 Applications. 2008.

Koza, S. et al. "PEGylated Protein Analysis by Size-Exclusion and Reversed-Phase UPLC" Waters, Apr. 2014.

Bublil, E. M. et al. "Enzyme Replacement with PEGylated Cystathionine Beta-synthase Ameliorates Homocystinuria in Murine Model" The Journal of Clinical Investigation, 2016; 126(6):2372-2384.

Majtan, T. et al., "Pharmacokinetics and Pharmacodynamics of PEGylated Truncated Human Cystathionine Beta-synthase for Treatment of Homocystinuria" Life Sciences, 2018, vol. 200, p. 15-25.

Regnier et al, "Brain Phenotype of Transgenic Mice Overexpressing Cystathionine B-Synthase," (2012) PloS One, 7 (1): e29056, pp. 1-10.

Schiff et al. "Treatment of Inherited Homocystinurias," (2012) Neuropediatrics, vol. 43:295-304. entire document.

Yap, S. "Homocystinuria due to cystathionine beta-synthase difficiency," (2005) Orphanet Encyclopedia, pp. 1-13. Retrieved from the internet: <www.orpha.net/data/patho/GB/uk-CbS.pdf> on Dec. 21, 2016 (Dec. 21, 2016 entire document.

Harris & Chess, "Effect of PEGYLATION on Pharmaceuticals" Nature Reviews. Drug Discovery 2(3):214-21 (Mar. 2003).

Frank et al., "Solvent-accessible cysteines in human cystathionine beta-synthase: crucial role of cysteine 431 in S-adenosyl-L-methionine binding." Biochemistry 45(36):11021-29 (Sep. 2006).

Office Action dated Oct. 13, 2020 in corresponding Brazil application No. BR112018007768-2, entitled Compositions and Methods for Treatment of Homocystinuria.

Guanjun et al., "Effect of Hcy on lipid metabolism of liver in atherosclerotic mice" (2014) Chongqing Medical Science, vol. 43, No. 30, pp. 4030-4033. (Abstract Translated).

Office Action dated Oct. 12, 2020 in corresponding Chinese application No. 2016800762750, entitled Compositions and Methods for Treatment of Homocystinuria.

Aitken & Kirsch "Role of Active-Site Residues Thr81, Ser82, Thr85, Gln157, and Tyr158 in Yeast Cystathionine B-Synthase Catalysis and Reaction Specificity" Biochemistry 43:1963-71 (2004).

Bateman, 1997, "The structure of a domain common to archaebacteria and the homocystinuria disease protein." Trends Biochem. Sci. 22(1):12-13.

Belew et al., "Kinetic characterization of recombinant human cystathionine beta-synthase purified from E. coli," Protein Expression and Purification, 64(2):139-45 (2009).

Finkelstein & Martin, 1984, "Methionine metabolism in mammals. Distribution of homocysteine between competing pathways." J. Biol. Chem. 259:9508-13.

Finkelstein et al., 1975, "Activation of cystathionine synthase by adenosylmethionine and adenosylethionine." Biochem. Biophys. Res. Commun. 66:81-87.

Frank et al., "Purification and characterization of the wild type and truncated human cystathionine beta-synthase enzymes expressed in E. coli," Archives of Biochemistry and Biophysics, 470(1):64-72 (2007).

Jakubowski et al., 2008, "Mutations in cystathionine beta-synthase or methylenetetrahydrofolate reductase gene increase N-homocysteinylated protein levels in humans." FASEB J 22(12): 4071-6.

Janosik et al., 2001, "Regulation of human cystathionine beta-synthase by S-adenosyl-L-methionine: evidence for two catalytically active conformations involving an autoinhibitory domain in the C-terminal region." Biochemistry 40:10625-33.

Kery et al., 1998, "Trypsin cleavage of human cystathionine beta-synthase into an evolutionarily conserved active core: structural and functional consequences." Arch. Biochem. Biophys. 355:222-32.

Kozich & Kraus, 1992, "Screening for mutations by expressing patient cDNA segments in E. coli: homocystinuria due to cystathionine beta-synthase deficiency." Hum. Mutation 1:113-23.

Kraus, 1987, "Cystathionine beta-synthase (human)." Methods Enzymol. 143:388-94.

Lowry et al., 1951, "Protein measurement with the Folin phenol reagent." J. Biol. Chem. 193(1):265-75.

MacLean et al., 2002, "High homocysteine and thrombosis without connective tissue disorders are associated with a novel class of cystathionine beta-synthase (CBS) mutations." Hum. Mutat. 19(6):641-55.

Majtan & Kraus "Folding and activity of mutant cystathionine β-synthase depends on the position and nature of the purification tag: characterization of the R266K CBS mutant." Protein Expr Purif. 82(2):317-24 (2012).

Miles & Kraus, "Cystathionine beta-synthase: structure, function, regulation, and location of homocystinuriacausing mutations" J. Biol. Chem. 279(29):29871-74 (Jul. 2004).

Roper & Kraus, 1992, "Rat cystathionine beta-synthase: expression of four alternatively spliced isoforms in transfected cultured cells." Arch. Biochem. Biophys. 298(2):514-21.

Margas et al., 1993, "Detection of c-type cytochromes using enhanced chemiluminescence." Analytical Biochem. 209 (2):323-6.

(56) References Cited

OTHER PUBLICATIONS

Vozdek et al., "Novel structural arrangement of nematode cystathionine [beta]-synthases: characterization of Caenorhabditis elegans CBS-1," Biochemical Journal, 16(2):1066-547 (2012).
Wilcken et al., 1983, "Homocystinuria—the effects of betaine in the treatment of patients not responsive to pyridoxine." N. Engl. J. Med. 309(8):448-53.
International Search Report from International Application No. PCT/US2013/033716 dated Jun. 21, 2013, pp. 1-3.
International Preliminary Report on Patentability from International Application No. PCT/US2013/033716 dated Oct. 1, 2014, pp. 1-7.
Third Office Action (along with English translation) received in corresponding Chinese application No. 201380027463.0 dated May 3, 2017.
Jhee, K. et al. Domain Architecture of the Heme-Independent Yeast Cystathionine beta-synthase Provides Insights into Mechanisms of Catalysis and Regulation. 39:10548-10556 (Year: 2000).
Office Action received in corresponding Israel Application No. 234635, dated Aug. 21, 2017 along with its translation.
Examination Report received in corresponding Australian Application No. 2013240003, dated Oct. 5, 2017.
Extended European Search Report received in corresponding European Application No. 17165825.5, dated Dec. 4, 2017.
Wang, W. et al, "Expression, Purification and Characterization of Recombinant Human CBS in *Escherichia coli*" (Xiandai Shengwuyixue Jinzhan), 11(5) (2011), p. 830-833.
Kraus J. et al., "Purification and Properties of Cystathionine Beta-Synthasa from Human Liver" J. Biol. Chem., vol. 253, No. 18 (1978), p. 6523-6528.
Ono B. et al., "Purificaiton and Properties of *Saccharomyces cerevisiae* Cystathionine Beta-Synthase" YEAST, vol. 10(1994), p. 333-339.
Official Action dated Feb. 27, 2018 received in corresponding Japan Application No. 2017-78808.
Official Action dated May 21, 2018 received in corresponding Israel application No. 234635.
Office Action dated Oct. 25, 2018 in co-pending Japanese application No. 2017-078808, entitled "Purification of Cystathionine Beta-Synthase".
Canadian Office Action for corresponding Canadian Application No. 2867719 dated Jan. 9, 2019.
Indian Examination Report for corresponding Indian Application No. 7920/DELNP/2014 dated Jan. 29, 2019.
Israel Office Action for corresponding Israel Application No. 263162 dated Mar. 25, 2019.
Office Action dated Jun. 14, 2019 in co-pending Japanese application No. 2017-078808, entitled "Purification of Cystathionine Beta-Synthase".
Extended European Search Report for corresponding European Application No. 19179948.5 dated Oct. 7, 2019.
Regnier et al, "Brain Phenotype of Transgenic Mice Overexpressing Cystathionine B-Synthase," PloS One, Jan. 12, 2012 (Jan. 12, 2012), vol. 7, No. 1, e29056, pp. 1-10. entire.
Schiff et al. "Treatment of Inherited Homocystinurias," Neuropediatrics, Nov. 2, 2012, vol. 43, pp. 295-304. entire document.
Yap, S. "Homocystinuria due to cystathionine beta-synthase difficiency," Orphanet Encyclopedia, Feb. 1, 2005 (Feb. 1, 2005), pp. 1-13. Retrieved from the internet: <www.orpha.net/data/patho/GB/uk-CbS.pdf> on Dec. 21, 2016 (Dec. 21, 2016. entire document.
International Search Report & Written Opinion dated Jan. 23, 2017 in co-pending application No. PCT/US2016/061050, entitled Compositions and Methods for Treatment of Homocystinuria.
Office Action with English translation received for co-pending Japanese application No. 2015555429 dated Apr. 23, 2018.
Office Action with English translation received for co-pending Chinese application No. 201480006554.0 dated Apr. 26, 2018.
Taoka et al., "Assignment of enzymatic functions to specific regions of the PLP-dependent heme protein cystathionine beta-synthase." Biochemistry 38(40):13155-61 (Sep. 1999).
Levy, H.L., "Physician's Guide to the Homocystinurias" (2010) http://www.rarediseases.org/docs/Homocystinuria_11_29b.pdf.

Li jinping et al, "Research development on cystathionine beta-synthase enzyme" (2006) Medical Journal of West China 18(5):657-659.
Office Action received for co-pending Israel application No. 239783 dated Jun. 26, 2018.
Extended European Search Report dated Apr. 15, 2019 in Application No. 16864878.0, entitled: Compositions and Methods for Treatment of Homocystinuria.
Canadian Office Action for corresponding Canadian Application 2,898,772 entitled "Cystathionine Betasynthase Enzyme Fore Treatment of Homocystinuria" dated Oct. 18, 2019.
Japanese Office Action for corresponding Japanese Application 2018232350 entitled "Cystathionine Betasynthase Enzyme Fore Treatment of Homocystinuria" dated Nov. 8, 2019.
First Examination Report for corresponding India Application 6010/DELNP/2015 entitled "Cystathionine Betasynthase Enzyme Fore Treatment of Homocystinuria" dated Nov. 28, 2019.
Meier et al., "Structure of human cystathionine beta-synthase: a unique pyridoxal 5'-phosphate-dependent heme protein." EMBO 20(15):3910-16 (Aug. 2001).
Melenovska et al., "Chaperone therapy for homocystinuria: the rescue of CBS mutations by heme arginate." J. Inherit. Metab. Dis. 38(2); 284-297 (Mar. 2015).
Mudd et al., "Homocystinuria: An enzymatic defect." Science 143(3613):1443-45 (Mar. 1964).
Mudd et al., "The natural history of homocystinuria due to cystathionine beta-synthase deficiency." Am. J. Hum. Genet. 37(1):1-31 (Jan. 1985).
Mudd et al., "Homocysteine and its disulfide derivatives: A suggested consensus terminology." Arterioscler. Thromb. Vasc. Biol. 20:1704-1706 (Jul. 2000).
Mudd et al., "Disorders of Transsulfuration." In The Metabolic and molecular bases of inherited disease. C.R. Scriver, A.L. Beudet, W.S. Sly, V. D., C. B., K.K. W., and V. B., eds. (New York: McGraw-Hill), pp. 2007-2056 (2001).
Munke et al., "The gene for cystathionine beta-synthase (CBS) maps to the subtelomeric region on human chromosome 21q and to proximal mouse chromosome 17." Am. J. Hum. Genet. 42(4):550-59 (Apr. 1988).
Needleman & Wunsch, "A general method applicable to the search for similarities in the amino acid sequence of two proteins." J. Mol. Biol. 48(3):443-53 (Mar. 1970).
Pearson & Lipman, "Improved tools for biological sequence comparison" Proc. Nat'l. Acad. Sci. USA 85 (8):2444-2448 (Apr. 1988).
Picker & Levy, "Homocystinuria Caused by Cystathionine Beta-Synthase Deficiency." In GeneReviews. R.A. Pagon, M.P. Adam, T.D. Bird, C.R. Dolan, C.T. (Jan. 2004).
Refsum et al., "Facts and recommendations about total homocysteine determinations: an expert opinion." Clin. Them. 50:3-32 (Jan. 2004).
Seffernick et al., "Melamine Deaminase and Atrazine Chlorohydrolase: 98 Percent Identical but Functionally Different." J. Bacterial. 183(8):2405-10 (Apr. 2001).
Skovby et al., "Assignment of the genes for cystathionine beta-synthase to human chromosome 21 in somatic cell hybrids." Hum. Genet. 65(3):291-94 (Apr. 1984).
Mansoor et al., "Redox status and protein binding of plasma homocysteine and other aminothoils in patients with homocystinuria." Metabolism, 42(11):1481-85 (Nov. 1993).—Abstract submitted.
Pasut & Veronese, "State of the art in PEGylation: The great versatility achieved after forty years of research" Journal of Controlled Release, 161:461-72 (2012, Epub Nov. 7, 2011).
Pasut & Veronese, "PEGylation for improving the effectiveness of therapeutic biomolecules" Drugs of Today 45 (9): 687-95 (2009).
MacLean, Kenneth N. et al. "A novel transgenic mouse model of CBS-deficient homocystinuria does not incur hepatic steatosis or fibrosis and exhibits a hypercoagulative phenotype that is ameliorated by betaine treatment", Mol Genet Metab. Oct. 2010; 101(2-3): pp. 153-162.
English Translation of Office Action received in corresponding Japanese Application No. 2015-555429 dated Sep. 29, 2017.
Ohja S et al: "Effects of Heme Ligand Mutations Including A Pathogenic Variant, H65R, on the Properties of Human Cystathionine

(56) References Cited

OTHER PUBLICATIONS

Beta-Synthase", Biochemistry, Americal Chemical Society, US, vol. 41, No. 14, Apr. 9, 2002, pp. 4649-4654.
Extended European Search Report received in corresponding EP application No. 17172478.4 dated Dec. 11, 2017.
Smith & Waterman, "Comparison of biosequences" Adv. Appl. Math. 2(4):482-489 (Dec. 1981).
Sokolova et al., "Cystathionine beta-synthase deficiency in Central Europe: discrepancy between biochemical and molecular genetic screening for homocystinuric alleles." Hum Mutat.18(6):548-9 (Dec. 2001).
Stabler et al., "Elevated plasma total homocysteine in severe methionine adenosyltranferase I/III deficiency." Metabolism, 51(8):981-88 (Aug. 2002).
Tan et al., "Polyethylene Glycol Conjugation of Recombinant Methionase for Cancer Therapy," Protein Expression and Purification 12:45-52 (Feb. 1998).
Vargas et al., "Detection of c-type cytochromes using enhanced chemiluminescence." Anal. Biochem. 209(2):323-6 (Mar. 1993).
Volpe & Laster, "Transsulfuration in fetal and postnatal mammalian liver and brain. Cysthathionine synthase, its relation to hormonal influences and cystathionine.", Biol. Neonate 20(5):385-403 (1972).
Vugmeyster et al., "Pharmacokinetics and toxicology of therapeutic proteins: Advances and challenges." World Journal of Biological Chemistry 3(4):73-92 (Apr. 2012).
Walter, et al., "Strategies for the treatment of cystathionine beta-synthase deficiency: the experience of the Willink Biochemical Genetics Unit over the past 30 years." Eur J Pediatr 157(Suppl 2):S71-6 (Apr. 1998).
Watanabe et al., "Mice deficient in cysthathionine beta-synthase: animal models for mild and severe homocyst(e) inemia." Proc. Natl. Acad. Sci. U.S.A. 92(5):1585-89 (Feb. 1995).
Wilcken et al., "Homocystinuria—the effects of betaine in the treatment of patients not responsive to pyridoxine." N. Engl. J. Med. 309(8):448-53 (Aug. 1983).
Witkowski et al., "Conversion of a Beta-Ketoacyl Synthase to a Malonyl Decarboxylase by Replacement of the Active-Site Cysteine with Glutamine." Biochemistry 38:11643-50 (Aug. 1999).
Yap et al., "Vascular outcome in patients with homocystinuria due to cystathionine beta-synthase deficiency treated chronically: a Multicenter observational study." Arterioscler. Thromb. Vasc. Biol. 21(12):2080-85 (Dec. 2001).
International Search Report from International Application No. PCT/US2014/013602, dated Jun. 17, 2014, pp. 1-6.
Allen et al., "Serum betaine, N,N-dimethylglycine and N-methylglycine levels in patients with cobalamin and folate deficiency and related inborn errors of metabolism." Metabolism 42(11):1448-60. (Nov. 1993).
Altschul et al., "Gapped BLAST and PSI-BLAST: a new generation of protein database search programs." Nucleic Acids Res. 25(17)(17):3389-3402 (Sep. 1997).
Altschul et al., "Basic local alignment search tool." J. Mol. Biol. 215(3):403-10 (Oct. 1990).
Barber & Spaeth, "The successful treatment of homocystinuria with pyridoxine."J. Pediatr. 75(3):463-8 (Sep. 1969).
Carson & Neill, "Metabolic abnormalities detected in a survey of mentally backward individuals in Northern Ireland." Arch. Dis. Child 37(195):505-13 (Oct. 1962).
D'Souza et al., "Pharmaceutical amyloidosis associated with subcutaneous insulin and enfuvirtide administration." Amyloid 21(2):71-75 (Jun. 2014; epub Jan. 22, 2014).
El-Sayed et al., "PLP-dependent enzymes: a potent therapeutic approach to cancer and cardiovascular diseases," Targets in gene therapy, Prof. Yongping You (Ed.), 307-540-2, In Tech (Aug. 2011).
Finkelstein, "Methionine metabolism in mammals." J. Nutr. Biochem. 1(5):228-37 (May 1990).
Frank et al., "Purification and characterization of the wild type and truncated human cystathionine beta-synthase enzymes expressed in *E. coli*" Archives of Biochemistry and Biophysics, 470(1): 64-72 (Nov. 2007).

Gaustadnes et al., "Prevalence of congenital homocystinuria in Denmark." N Engl J Med. 340(19):1513 (May 1999).
Gupta et al., "Mouse models of cystathionine beta-synthase deficiency reveal significant threshold effects of hyperhomocysteinemia." FASEB J. 23(3):883-93 (Mar. 2009).
Gupta et al., "Cysthathionine beta-synthase-deficient mice thrive on a low-methionine diet." FASEB J. 28(2):781-90 (Feb. 2014).
Henikoff & Henikoff, "Amino acid substitution matrices from protein blocks." Proc. Natl. Acad. Sci. USA 89:10915-919 (Nov. 1992).
Jakubowski et al., "Mutations in cystathionine beta-synthase or methylenetetrahydrofolate reductase gene increase N-homocysteinylated protein levels in humans." FASEB J 22(12): 4071-6 (Aug. 2008).
Janosik et al., "Crystallization and preliminary X-ray diffraction analysis of the active core of human recombinant human cystathionine 13-synthase: an enzyme involved in vascular disease." Acta Cryst. D57:289-291 (Feb. 2001).
Kang et al., "Emerging PEGylated drugs." Expert opinion on emerging drugs 14:363-380 (Jun. 2009).
Kitano, "Biological robustness." Nature Reviews Genetics, 5(11):826-37 (Nov. 2004).
Komrower et al., "Dietary treatment of homocystinuria." Arch. Dis. Child 41(220):666-71(Dec. 1966).
Kozich & Kraus, "Screening for mutations by expressing patient cDNA segments in *E. coli*: homocystinuria due to cystathionine beta-synthase deficiency." Hum. Mutation 1:113-23 (Apr. 1992).
Kraus, "Cystathionine beta-synthase (human)." Methods Enzymol. 143:388-94 (1987).
Kraus & Rosenberg, "Cystathionine beta-synthase from human liver: improved purification scheme and additional characterization of the enzyme in crude and pure form." Arch. Biochem. Biophys. 222(1):44-52 (Apr. 1983).
Kraus & Kozich, "Cystathionine beta-synthase and its deficiency." In Homocysteine in health and disease. J.D. Carmel R, ed. (New York: Cambridge University Press), pp. 223-243 (2001).
Levy "Physician's Guide to The Homocystinurias" published by the National Organization for Rare Disorders, pp. 1-8 (2010).
Li & Stewart, "Homocystinuria and psychiatric disorder: a case report." Pathology 31(3):221-24 (Aug. 1999).
Linnebank et al., "High prevalence of the I278T mutation of the human cystathionine beta-synthase detected by a novel screening application." Thromb Haemost. 85(6):986-88 (Jun. 2001).
Linnebank et al., "Isolated thrombosis due to the cystathionine beta-synthase mutation c.833T>C (1278T)." J. Inherited Metabol. Dis. 26(5):509-11 (Jun. 2003).
Lowry et al., "Protein measurement with the Folin phenol reagent." J. Biol. Chem. 193(1):265-75 (May 1951).
MacLean et al., "High homocysteine and thrombosis without connective tissue disorders are associated with a novel class of cystathionine beta-synthase (CBS) mutations." Hum. Mutat. 19(6):641-55 (Jun. 2002).
MacLean et al., "Cystathionine beta-synthase null homocystinuric mice fail to exhibit altered hemostasis or lowering of plasma homocysteine in response to betaine treatment." Mol. Genet. Metab 101(2-3):163-71 (Oct.-Nov. 2010).
MacLean et al., "A novel trangenic mouse model of CBS-deficient homocystinuria does not incur hepatic steatosis or fibrosis and exhibits a hypercoagulative phenotype that is ameliorated by betaine treatment." Mol. Genet. Metab. 101(2-3):153-62 (Oct.-Nov. 2010).
MacLean et al., "Cystathionine protects against endoplasmic reticulum stress-induced lipid accumulation, tissue injury, and apoptotic cell death." J. Biol. Chem. 287(38):31994-32005 (Sep. 2012).
Majtan et al., "Rescue of cystathionine beta-synthase (CBS) mutants with chemical chaperones: purification and characterization of eight CBS mutant enzymes." J Biol Chem. 285(21):15866-73 (Mar. 2010).
Mansoor et al., "Redox status and protein binding of plasma homocysteine and other aminothiols in patients with early-onset peripheral vascular disease, homocysteine and peripheral vascular disease." Arterioscler Thromb Vasc Biol, 15(2):232-40 (Feb. 1995).
Mansoor et al., "Determination of the in vivo redox status of cysteine, cysteinylglycine, homocysteine, and gluthathione in human plasma." Anal. Biochem. 200(2):218-29 (Feb. 1992).

(56) References Cited

OTHER PUBLICATIONS

Australian Examination Report 1 received in corresponding Australian Application No. 2014212471 entitled "Cystathionine Beta-Synthase Enzyme for Treatment of Homocystinuria" dated Feb. 1, 2019.
Examination report No. 2 for standard patent application dated Jun. 14, 2019 in corresponding Australia application 2014212471, entitled Compositions and Methods for Treatment of Homocystinuria.
Ding et al., Bioconjugated PLGA-4-arm-PEG branched polymeric nanoparticles as novel tumor targeting carriers. Nanotechnology, 2011, 165101: 12 pages (2011).
Kim et al., Functional modeling of vitamin responsiveness in yeast: a common pyridoxine-responsive cystathionine beta-synthase mutation in homocystinuria. Human Mol. Genet., 1997, vol. 6(13); 2213-2221. (1997).
NOF America Corporation SUNBRIGHT MA series; 5 pages downloaded from https://nofamerica.com on Sep. 3, 2017.
Japanese Office Action received in corresponding Japanese Application No. 2015-555429 dated Sep. 22, 2017.
Gupta, S. et al., "Betaine supplementation is less effective than methionine restriction in correcting phenotypes of CBS deficient mice" (2016) J. Inherit Metab Dis 69:39-46.
Office Action dated Sep. 29, 2020 in corresponding Japanese application No. 2018-523444, titled Compositions and Methods for Treatment of Homocystinuria.
Japanese Office Action for corresponding Japanese Application 2018232350 entitled "Cystathionine Beta-Synthase Enzyme Fore Treatment of Homocystinuria" dated Jun. 8, 2020.
Belew M S et al, "Kinetic characterization of recombinant human cystathionine beta-synthase purified from *E. coli*", Protein Expression and Purification, (2009) vol. 64, No. 2, pp. 139-145.
Frank et al, "Purification and characterization of the wild type and truncated human cystathionine beta-synthase enzymes expressed in *E. coli*", Archives of Biochemistry and Biophysics, (2008) vol. 470, No. 1, pp. 64-72.
Kraus J. et al. "Purification and properties of cystathionine beta-synthase from human liver. Evidence for identical subunits". J. Biol. Chem., vol. 253, No. 18 (1978), pp. 6523-6528.
Ono B. et al. "Purification and properties of *Saccharomyces cerevisiae* cystathionine beta-synthase". Yeast, vol. 10 (1994), pp. 333-339.
Preliminary Office Action dated Jun. 10, 2020 in corresponding Brazil patent application No. BR112014023570-8, entitled Purification of Cystathionine Beta-Synthase.
Harris, J.M. & R.B. Chess, "Effect of Pegylation on Pharmaceuticals" (2003) Nature 2:214-221.
Pasut G. and F.M. Veronese, "Pegylation for Improving the Effectiveness of Therapeutic Biomolecules" (2009) 45(9):687-695.
Pasut G. and F.M. Veronese, "State of the are in PEGylation: The great versatility achieved after forty years of research" (2012) J. of Controlled Release 161:461-472.
Extended European Search Report dated Aug. 7, 2020 in corresponding European patent application 20168207.7, entitled Cystathionine Beta-Synthase Enzyme for Treatment of Homocystinuria.
"A novel protease for site-specific cleavage of GST fusion proteins," Science Tools from Pharmacia Biotech 2(1):18-19, 1997.
"Sequence alignment between SEQ ID No. 2 and AC P35520," Jun. 1, 1994, 2 pages.
Alexander et al., "Evolutionary relationships among pyridoxal-5'-phosphate-dependent enzymes. Regio-specific α, β and γ families," *Eur. J. Biochem.* 219: 953-960, 1994.
Aoki et al., "Angiogenesis induced by hepatocyte growth factor in non-infarcted myocardium and infarcted myocardium: up-regulation of essential transcription factor for antiogenesis, ets" *Gene Therapy* 7:417-427, 2000.
Banerjee et al., "Redox regulation and reaction mechanism of human cystathionine-β-synthase: a PLP-dependent hemesensor protein," *Archives of Biochemistry and Biophysics* 433:144-156, 2005.

Bennett et al., "Stable transgene expression in rod photoreceptors after recombinant adeno-associated virus-mediated gene transfer to monkey retina" *Proc. Natl. Acad. Sci. USA* 96:9920-9925, Aug. 1999.
Blaese et al., "T Lymphocyte-Directed Gene Therapy for ADA-SCID: Initial Trial Results After 4 Years," *Science* 270:475-480, Oct. 20, 1995.
Bordignon et al., "Gene Therapy in Peripheral Blood Lymphocytes and Bone Marrow for ADA-Immunodeficient Patients," *Science* 270(5235):470-475, Oct. 20, 1995 (7 pages).
Broun et al., "Catalytic Plasticity of Fatty Acid Modification Enzymes Underlying Chemical Diversity of Plant Lipids," *Science* 282:1315-1317, Nov. 13, 1998.
Bruno et al., "Functional Properties of the Active Core of Human Cystathione β-Synthase Crystals," *The Journal of Biological Chemistry* 276(1):16-19, Jan. 5, 2001.
Bukovska et al., "Expression of Human Cystathionine β-Synthase in *Escherichia coli*: Purification and Characterization," *Protein Expression and Purification* 5:442-448, Apr. 1, 1994.
Byrne et al., "DNA Sequences of the cysK regions of *Salmonella typhimurium* and *Escherichia coli* and Linkage of the cysK regions to ptsH." *Journal of Bacteriology* 170(7):3150-3157, Jul. 1988.
Carballal et al., "Dioxygen Reactivity and Heme Redox Potential of Truncated Human Cystathionine β-Synthase," *Biochemistry* 47(10): 3194-3201, Feb. 16, 2008.
Chassé et al., "Genomic Organization of the Human Cystathionine β-Synthase Gene: Evidence for Various cDNAs," *Biochemical and Biophysical Research Communications* 211(3):826-832, Jun. 26, 1995.
Chemey et al., "Ferrous Human Cystathionine β-Synthase Loses Activity during Enzyme Assay Due to a Ligand Switch Process," *Biochemistry* 46(45): 13199-13210, Oct. 23, 2007.
Devos et al., "Practical Limits of Function Prediction," *PROTEINS: Structure, Function, and Genetics* 41:98-107, Jun. 12, 2000.
Dong et al., "Secondary Structure of Recombinant Human Cystathionine β-Synthase in Aqueous Solution: Effect of Ligand Binding and Proteolytic Truncation," *Archives of Biochemistry and Biophysics* 344(1):125-132, Aug. 1, 1997.
Examination Report received in Australian Application No. 2013240003, dated Oct. 5, 2017, 3 pages.
Extended European Search Report for European Application No. 19179948.5 dated Oct. 7, 2019, 9 pages.
Extended European Search Report received in European Application No. 17165825.5, dated Dec. 4, 2017, 8 pages.
Finkelstein et al., "Inactivation of Betaine-Homocysteine Methyltransferase by Adenosylmethionine and Adenosylethionine," *Biochemical and Biophysical Research Communications* 118(1):14-19, Jan. 13, 1984.
First Examination Report for India Application 6010/DELNP/2015 entitled "Cystathionine Beta-Synthase Enzyme For Treatment of Homocystinuria," dated Nov. 28, 2019, 7 pages.
Gallagher et al., "Structure and control of pyridoxal phosphate dependent allosteric threonine deaminase," *Structure* 6(4):465-475, Apr. 15, 1998.
Green et al., "Molecular Cloning: A Laboratory Manual," Cold Spring Harbor Laboratory Press, Fourth Edition, vol. 1, 2012 (34 pages).
Guanjun et al., "Hcy promotes the formation of atherosclerotic and effect of liver lipid metabolism disorder in ApoE mice," *Chongqing Medical Science* 43(30):4030-4033, 2014 (English Abstract only).
Halperin et al., "The Influence of Environmental Enrichment, Cognitive Enhancement, and Physical Exercise on Brain Development: Can we Alter the Developmental Trajectory of ADHD?" *Neurosci Biohehav Rev.* 35(3):621-634. Jan. 2011 (NIH Public Access Author Manuscript, available in PMC Jan. 1, 2012)(31 pages).
Huang et al., "Liposomal gene delivery: A complex package," *Nature Biotechnology* 15:620-621, Jul. 1997.
International Search Report for International Application No. PCT/US2013/033716, dated Jun. 21, 2013, 5 pages.
International Search Report for International Application No. PCT/US2014/013602, dated Jun. 17, 2014, 6 pages.

(56) References Cited

OTHER PUBLICATIONS

Janošik et al., "Impaired Heme Binding and Aggregation of Mutant Cystathionine β-Synthase Subunits in Homocystinuria," *Am. J. Hum. Genet.* 68(6):1506-1513, May 15, 2001.
Japanese Office Action received in Japanese Application No. 2015-555429 dated Sep. 22, 2017, 19 pages (with English Translation).
Jhee et al., "Forum Review: The Role of Cystathionine β-Synthase in Homocysteine Metabolism," *Antioxid. Redox Signal.* 7(5-6):813-22, 2005.
Jhee et al., "Yeast Cystathionine β-Synthase Is a Pyridoxal Phosphate Enzyme but, Unlike the Human Enzyme, Is Not a Heme Protein." *The Journal of Biological Chemistry* 275(16):11541-11544, Apr. 21, 2000.
Jinping et al., "Advance in Cystathionine beta-Synthase Research," *Med. J. West China* 18(5):657-659, Sep. 2006 (7 pages) (with English Translation).
Kabil et al., "Deletion of the Regulatory Domain in the Pyridoxal Phosphate-dependent Heme Protein Cystathionine β-Synthase Alleviates the Defect Observed in a Catalytic Site Mutant," *The Journal of Biological Chemistry* 274(44):31256-31260, Oct. 29, 1999.
Kaneda et al., "Prevention of Restenosis by Gene Therapy," *Annals New York Academy of Science* pp. 299-310, 1997.
Kery et al., "Binding of Pyridoxal 5'-Phosphate to the Heme Protein Human Cystathionine β-Synthase," Biochemistry 38(9):2716-2724, Feb. 9, 1999.
Kery et al., "Transsulfuration Depends on Heme in Addition to Pyridoxal 5'-Phosphate. Cystathionine β-Synthase is a Heme Protein," *The Journal of Biological Chemistry* 269(41):25283-25288, Oct. 14, 1994.
Kery et al., "δ-Aminolevulinate Increases Heme Saturation and Yield of Human Cystathionine β-Synthase Expressed in *Escherichia coli,*" *Archives of Biochemistry and Biophysics* 316(1):24-29, Jan. 10, 1995.
Kluijtmans et al., "Defective Cystathionine β-Synthase Regulation by S-Adenosylmethionine in a Partially Pyridoxine Responsive Homocystinuria Patient," *J. Clin. Invest.* 98(2):285-289, Apr. 18, 1996.
Koeberl et al., "Persistent expression of human clotting factor IX from mouse liver after intravenous injection of adeno-associated virus vectors," *Proc. Natl. Acad. Sci. USA* 94:1426-1431, Feb. 1997.
Kraus et al., "Human cystathionine β-Synthase cDNA: sequence, alternative splicing and expression in cultured cells," *Human Molecular Genetics* 2(10):1633-1638, Jul. 22, 1993.
Kruger et al., "A yeast system for expression of human cystathionine β-synthase: Structural and functional conservation of the human and yeast genes," *Proc. Natl. Acad. Sci. USA* 91:6614-6618, Jul. 1994.
Kutzbach et al., "Feedback inhibition of methylene-tetrahydrofolate reductase in rat liver by S-adenosylmethionine," *Biochim. Biophys. Acta* 139:217-220, 1967.
Kutzbach et al., "Mammalian Methylenetetrahydrofolate Reductase. Partial Purification, Properties, and Inhibition by S-Adenosylmethionine," *Biochim. Biophys. Acta* 250:459-477, Jun. 23, 1971.
Levine et al., "Adenoviral-Mediated Gene Transfer to Human Adipocytes in Vitro, and Human Adipose Tissue Ex Vivo and Rabbit Femoral Adipose Tissue in Vivo," *J Nutr. Sci. Vitaminol.* 44:569-572, Mar. 16, 1998.
Lodha et al., "Investigation of residues Lys112, Glu136, His138, Gly247, Tyr248, and Asp249 in the active site of yeast cystathionine β-synthase," *Biochem. Cell Biol.* 87:531-540, 2009.
Maclean et al., "Transsulfuration in *Saccharomyces cerevisiae* is not dependent on heme: purification and characterization of recombinant yeast cystathionine β-synthase." *Journal of Inorganic Biochemistry* 81:161-171, Apr. 12, 2000.
Majtan et al., "Behavior, body composition, and vascular phenotype of homocystinuric mice on methionine-restricted diet or enzyme replacement therapy," *FASEB J.* 33:12477-12486, Nov. 2019.
Majtan et al., "Engineering and Characterization of an Enzyme Replacement Therapy for Classical Homocystinuria," *Biomacromolecules* 18:1747-1761, 2017.
Majtan et al., "Enzyme replacement prevents neonatal death, liver damage, and osteoporosis in murine homocystinuria," *FASEB J.* 31:5495-5506, Dec. 2017.
Majtan et al., "Enzyme Replacement Therapy Ameliorates Multiple Symptoms of Murine Homocystinuria," *Molecular Therapy* 26(3):834-844, Mar. 2018.
Majtan et al., "Purification and characterization of cystathionine β-synthase bearing a cobalt protoporphyrin," *Archives of Biochemistry and Biophysics* 508:25-30, Jan. 22, 2011.
Maurice et al., "Enhancement of cardiac function after adenoviral-mediated in vivo intracoronary $β_2$-adrenergic receptor gene delivery," *J Clin. Invest.* 104:21-29, Jul. 1999.
Millecamps et al., "Neuron-restrictive silencer elements mediate neuron specificity of adenoviral gene expression" *Nature Biotechnology* 17:865-869, Sep. 1999.
Nozaki et al., "Characterization of Transsulfuration and Cysteine Biosynthetic Pathways in the Protozoan Hemoflagellate, *Trypanosoma cruzi.* Isolation and Molecular Characterization of Cystathionine β-Synthase and Serine Acetyltransferase from Trypanosoma," *The Journal of Biological Chemistry* 276(9):6516-6523, Mar. 2, 2001.
Office Action dated Oct. 23, 2020 in Japanese application No. 2019-187777, entitled, "Purification of Cystathionine Beta-Synthase," 11 pages (with English translation).
Office Action dated Oct. 25, 2018 in Japanese application No. 2017-078808, entitled "Purification of Cystathionine Beta-Synthase," 13 pages (with English Translation).
Office Action dated Sep. 11, 2020 in Japanese application No. 2017-078808, entitled "Purification of Cystathionine Beta-Synthase," 3 pages (with English Translation).
Office Action received in Israel Application No. 234635, dated Aug. 21, 2017, 3 pages (with English Translation).
Official Action dated Feb. 27, 2018 received in Japan Application No. 2017-78808, 10 pages (with English Translation).
Official Action dated May 21, 2018 received in Israel application No. 234635, 3 pages (with English Translation).
Oligino et al., "Intra-articular delivery of a herpes simplex virus IL-1Ra gene vector reduces inflammation in a rabbit model of arthritis," *Gene Therapy* 6:1713-1720, Jun. 16, 1999.
O'Shannessy et al. "Determination of Rate and Equilibrium Binding Constants for Macromolecular Interactions Using Surface Plasmon Resonance: Use of Nonlinear Least Squares Analysis Methods," *Analytical Biochemistry* 212:457-468, 1993.
Park et al., "Hypermethioninemia Leads to Fatal Bleeding and Increased Mortality in a Transgenic I278T Mouse Model of Homocystinuria," *Biomedicines* 8:244, Jul. 24, 2020 (15 pages).
Park et al., "Interplay of Enzyme Therapy and Dietary Management of Murine Homocystinuria," *Nutrients* 12:2895, Sep. 22, 2020 (13 pages).
Park et al., "Long-term uninterrupted enzyme replacement therapy prevents liver disease in murine model of severe homocystinuria," *Human Mutation* 41:1662-1670, Jul. 2, 2020.
Park et al., "Recombinant adeno-associated virus mediated gene transfer in a mouse model for homocystinuria," *Exp. Mol. Med.* 38(6):652-661, Dec. 2006.
Robert et al., "Cystathionine β Synthase Deficiency Promotes Oxidative Stress, Fibrosis, and Steatosis in Mice Liver," *Gastroenterology* 128:1405-1415, 2005.
Robichon et al., "Engineering *Escherichia coli* BL21(DE3) Derivative Strains To Minimize *E. coli* Protein Contamination after Purification by Immobilized Metal Affinity Chromatography," *Applied and Environmental Microbiology* 77(13):4634-4646, Jul. 2011.
Rolland et al., "O-Acetylserine(thiol)lyase from Spinach (*Spinacia oleracea* L.) Leaf: cDNA Cloning, Characterization, and Overexpression in *Escherichia coli* of the Chloroplast Isoform," *Archives of Biochemistry and Biophysics* 300(1):213-222, Jan. 1993.
Sacharow et al., "Homocystinuria Caused by Cystathionine Beta-Synthase Deficiency," *GeneReviews*:1-21, Jan. 4, 2004.
Saluta et al., "Troubleshooting GST fusion protein expression in *E. coli,*" Life Science News 1: 1-3, 1998.
Salzmann et al., "Rates of Evolution of Pyridoxal-5'-Phosphate-Dependent Enzymes," *Biochemical and Biophysical Research Communications* 270(2):576-580, Feb. 10, 2000.

(56) References Cited

OTHER PUBLICATIONS

Schuster et al., "Assembly and function of a quaternary signal transduction complex monitored by surface plasmon resonance," *Letters to Nature* 365:343-347, Sep. 23, 1993.

Sen et al., "Cystathionine-β-synthase gene transfer and 3-deazaadenosine ameliorate inflammatory response in endothelial cell," *Am J Physiol Cell Physiol* 293: C1779-C1787, Sep. 13, 2007.

Shan et al., "Correction of disease-causing CBS mutation in yeast," *Nature Genetics* 19:91-93, May 1998.

Shan et al., "Mutations in the regulatory domain of cystathionine β-synthase can functionally suppress patient-derived mutations in cis." *Human Molecular Genetics* 10(6):635-643, Jan. 9, 2001.

Singh et al., "Functional Rescue of Mutant Human Cystathionine β-Synthase by Manipulation of Hsp26 and Hsp70 Levels in *Saccharomyces*," *The Journal of Biological Chemistry* 284(7):4238-4245, Feb. 13, 2009.

Singh et al., "Modulation of the Heme Electronic Structure and Cystathionine β-synthase Activity by Second Coordination Sphere Ligands: The Role of Heme Ligand Switching in Redox Regulation," *J Inorg Biochem* 103(5):689-697, May 2009 (NIH Public Access Author Manuscript, available in PMC May 1, 2010) (23 pages).

Stribling et al., "Aerosol gene delivery in vivo," *Proc. Natl. Acad. Sci. USA* 89:11277-11281, Dec. 1992.

Taoka et al., "Characterization of NO binding to human cystathionine β-synthase: Possible implications of the effects of CO and NO binding to the human enzyme," *Journal of Inorganic Biochemistry* 87:245-251, Jul. 10, 2001.

Taoka et al., "Characterization of the Heme and Pyridoxal Phosphate Cofactors of Human Cystathionine β-Synthase Reveals Nonequivalent Active Sites," *Biochemistry* 38:2738-2744, Feb. 5, 1999.

Taoka et al., "Evidence for Heme-mediated Redox Regulation of Human Cystathionine β-Synthase Activity," *The Journal of Biological Chemistry* 273(39):25179-25184, Sep. 25, 1998.

Taoka et al., "Stopped-flow Kinetic Analysis of the Reaction Catalyzed by the Full-Length Yeast Cystathionine β-Synthase," *The Journal of Biological Chemistry* 277(25):22421-22425, Jun. 21, 2002.

Van Guldener et al., "Homocysteine-lowering treatment: an overview," *Expert Opin Pharmacother.* 2(9): 1449-1460, 2001.

Von der Leyen et al., "Gene therapy inhibiting neointimal vascular lesion: In vivo transfer of endothelial cell nitric oxide synthase gene," *Proc. Natl. Acad. Sci. USA* 92:1137-1141, Feb. 1995.

Wang et al., "Expression of mutant human cystathionine β-synthase rescues neonatal lethality but not homocystinuria in a mouse model," *Human Molecular Genetics* 14(15):2201-2208, Jun. 22, 2005.

Wang et al., "Expression, Purification and Characterization of Recombinant Human CBS in *Escherichia coli*," *Progress in Modern Biomedicine* 11(5):830-833, Mar. 2011 (with English Abstract).

Whisstock et al., "Prediction of protein function from protein sequence and structure," *Quarterly Reviews of Biophysics* 36(3):301-340, 2003.

Yamanishi et al., "Structural insights into pathogenic mutations in heme-dependent cystathionine-β-synthase," *Journal of Inorganic Biochemistry* 100:1988-1995, Sep. 20, 2006.

Yap, "Classical homocystinuria: Vascular risk and its prevention," *J. Inherit. Metab. Dis.* 26:259-265, 2003.

Zhang et al., "Characteristics and Crystal Structure of Bacterial Inosine-5'-monophosphate Dehydrogenase," *Biochemistry* 35(15):4691-4700, Mar. 26, 1999.

Zou et al., "Tumor Necrosis Factor-α-induced Targeted Proteolysis of Cystathionine β-Synthase Modulates Redox Homeostasis," *The Journal of Biological Chemistry* 278(19):16802-16808, May 9, 2003.

Arai, "Applications of the capillary electrophoresis in the development process and quality control of the monoclonal antibody for clinical use," *Biophysical Chemistry* 52:139-144, 2008 (with English Abstract).

Bell et al., "Formulation and PEGylation optimization of the therapeutic PEGylated phenylalanine ammonia lyase for the treatment of phenylketonuria," *PLoS ONE* 12(3):e0173269, Mar. 10, 2017 (17 pages).

\* cited by examiner

OPTIMIZATION OF ENZYME REPLACEMENT THERAPY FOR TREATMENT OF HOMOCYSTINURIA

CROSS REFERENCE TO RELATED APPLICATIONS

This application is a 35 U.S.C. § 371 U.S. National Stage Entry of International Application No. PCT/US2018/027854 filed Apr. 17, 2018, entitled "OPTIMIZATION OF ENZYME REPLACEMENT THERAPY FOR TREATMENT OF HOMOCYSTINURIA," which claims the benefit of priority of U.S. Provisional Patent Application No. 62/486,246, filed Apr. 17, 2017, entitled "OPTIMIZATION OF ENZYME REPLACEMENT THERAPY FOR TREATMENT OF HOMOCYSTINURIA," the contents of each of which are herein incorporated by reference in their entirety.

SEQUENCE LISTING

The present application is being filed along with a Sequence Listing in electronic format. The Sequence Listing file, entitled 20891004US371 SL.txt, was created on Oct. 17, 2019, and is 10,892 bytes in size. The information in electronic format of the Sequence Listing is incorporated herein by reference in its entirety.

FIELD OF THE INVENTION

The invention relates to characterizing PEGylated human truncated cystathionine beta-synthase (htCBS) conjugates to identify their suitability for reproducible manufacturing and further clinical development as an enzyme replacement therapy for classical homocystinuria.

BACKGROUND OF THE INVENTION

Human cystathionine beta-synthase (CBS, KEGG enzyme identifier: EC 4.2.1.22) is an important enzyme of the sulfur amino acid metabolism, whose activity determines either recycling of the sulfur in the methionine (Met) cycle or its diversion into synthesis of cysteine through the transsulfuration pathway. See, Finkelstein, J. D., *J. Nutr. Biochem.* 1990, 1, 228-237, which is hereby incorporated by reference in its entirety. The critical intermediate of sulfur amino acid metabolism is the non-proteinogenic amino acid homocysteine (Hcy), which can be either converted back to Met by an action of Met synthase or betaine homocysteine methyltransferase or redirected by CBS to cysteine biosynthesis via the transsulfuration pathway. CBS is a pyridoxal 5'-phosphate-dependent homotetrameric hemeprotein, which catalyzes the condensation of Hcy with serine forming cystathionine (Cth) and water. Cth is subsequently hydrolyzed by the action of cystathionine gamma-lyase to cysteine (Cys), alpha-ketobutyrate and ammonia, what completes the conversion of the essential amino acid Met to Cys. Activity of CBS, and thus the flux of sulfur through the transsulfuration pathway, is attenuated by the autoinhibitory function of the enzyme's C-terminal regulatory domain. Binding of S-adenosylmethionine to this domain results in a conformational rearrangement of the regulatory domain, subsequent release of the autoinhibitory block and 4-5-fold activation of the enzyme. See, Ereno-Orbea et al., *Proc Natl Acad Sci USA* 2014, 111, (37), E3845-52, which is hereby incorporated by reference in its entirety. Similar level of CBS activation can be achieved by removal of the C-terminal regulatory domain and consequent formation of a dimeric, permanently activated human truncated enzyme (htCBS). See, Kery et al., *Arch Biochem Biophys* 1998, 355, (2), 222-32, which is hereby incorporated by reference in its entirety.

Lack of CBS activity results in classical homocystinuria (HCU), an autosomal recessively inherited rare metabolic disorder. See, Mudd et al., Disorders of transsulfuration. In *The Metabolic and Molecular Bases of Inherited Disease*, 8 ed.; Scriver, C. R.; Beaudet, A. L.; Sly, W. S.; Valle, D.; Childs, B.; Kinzler, K.; Vogelstein, B., Eds. McGraw-Hill: New York, 2001; pp 2007-2056 which is hereby incorporated by reference in its entirety. The inactivation of CBS, chiefly due to the presence of missense pathogenic mutations, yields severe elevation of Hcy, Met, and S-adenosylhomocysteine and conversely lack of Cth and decrease of Cys in plasma samples of HCU patients. These biochemical sequelae are accompanied with connective tissue disorders, such as dislocated optic lenses, long and thin limbs and osteoporosis, thromboembolism, cognitive impairment and other clinical symptoms. See, Mudd et al. Present treatment of HCU is mostly symptomatic aimed at reduction of Hcy concentration in the plasma and tissues by protein-restricted diet with Met-free L-amino acid supplementation. See, Komrower et al., *Arch Dis Child* 1966, 41, (220), 666-71, which is hereby incorporated by reference in its entirety. This dietary intervention is often combined with betaine, which promotes the remethylation of Hcy back to Met. See, Smolin et al. *J Pediatr* 99(3), 467-472 (1981), which is hereby incorporated by reference in its entirety. In addition, supplementation with the pyridoxal 5'-phosphate precursor pyridoxine (vitamin B6) was shown to be effective in roughly 50% of HCU patients by stimulating the residual CBS activity and thus relieving the clinical manifestation and relaxing the dietary regime. See, Barber et al. *J Pediatr* 75(3), 463-778 (1969), which is hereby incorporated by reference in its entirety. Although Met restriction is generally effective in lowering plasma Hcy levels, a compliance of the HCU patients with the diet is quite poor with consequent manifestation of the symptoms. See, Walter et al., *Eur. Pediatr.* 1998, 157 (Suppl 2), S71-S76, which is hereby incorporated by reference in its entirety. Thus, there is a need in the art for an alternative therapy that would not require a stringent diet but would achieve similar reduction of Hcy levels and prevent onset and/or escalation of the clinical symptoms.

Enzyme replacement therapy (ERT) for HCU has recently been described using PEGylated htCBS. See, Bublil et al., *J Clin Invest* 2016, 126, (6), 2372-84 and International application PCT/2016/061050, which are hereby incorporated by reference in their entireties. PEGylation is conjugation of protein of interest to one or more polyethylene glycol (PEG) moieties or molecules and is a well-recognized and accepted strategy to alter pharmacokinetic profiles of a variety of drugs to improve their therapeutic potential. See, Fishburn et al., *J Pharm Sci* 2008, 97, (10), 4167-83, which is hereby incorporated by reference in its entirety. Unmodified htCBS exhibited rapid clearance from the circulation of the mouse model of the disease (elimination half-life after IV administration was 2.7 h). PEGylation of htCBS has been observed to lengthen the elimination half-life of PEGylated htCBS after IV administration by 6-11-fold, improve the plasma metabolic profile of murine homocystinuria in "Human Only" (HO) mice, and rescue the CBS knock-out (KO) mice from neonatal lethality by preventing liver damage. See, Bublil et al., *J Clin Invest* 2016, 126, (6), 2372-84; each of which is herein incorporated by reference in its entirety.

There is a long-felt need in the art to design and characterize a PEGylated htCBS conjugate that exhibits high reproducibility and control during manufacturing as well as having long-term efficacy. In previous studies, introduction of the C15S point mutation to htCBS was observed to diminish formation of protein aggregates and higher order oligomers and improved PEGylation profile for 20 kDa linear maleimide-activated PEG molecule. See, Bublil et al. Various htCBS C15S conjugate PEGylated with either maleimide (MA) or N-hydroxysuccinimide (NHS) ester-activated PEG molecule (further referred as PEG-htCBS C15S) are characterized herein for their potency to correct metabolic profile of murine homocystinuria after a single administration or multiple rounds of repeated administration interrupted with washout periods. The PEG-htCBS C15S conjugates were ranked based on their pharmacodynamics. In addition, insight was gained into reproducibility and consistency of PEG-htCBS preparation and characterization of the sites modified by the PEG molecules. Assays were identified to monitor and evaluate the extent of htCBS C15S PEGylation.

SUMMARY OF THE INVENTION

Various embodiments of the invention herein provide a method of PEGylating a human truncated cystathionine β-synthase (CBS) protein containing a mutation of a cysteine to a serine at amino acid position 15 of SEQ ID NO: 1 or a variant thereof (htCBS C15S), the method comprising: (a) conjugating the htCBS C15S with one or a plurality of NHS ester PEG molecules in solution at a molar excess of the NHS ester PEG molecules up to about 40-fold to create a batch, wherein the plurality of NHS ester PEG molecules are 5 kDa, 10 kDa, or 20 kDa NHS ester PEG molecules; (b) comparing a retention time from a chromatographic profile from Size Exclusion Chromatography-High Performance Liquid Chromatography (SEC-HPLC) analysis of the batch to a retention time from a chromatographic profile from SEC-HPLC analysis of htCBS C15S with acceptable PEGylation to identify insufficient PEGylation, wherein the batch with insufficient PEGylation has a retention time greater than the retention time of the htCBS C15S with acceptable PEGylation; and (c) adding additional NHS ester PEG molecules to the batch to reduce the amount of insufficient PEGylation in the batch, thereby PEGylating the htCBS C15S.

Various embodiments of the invention herein provide a method of PEGylating a human truncated cystathionine β-synthase (CBS) protein containing a mutation of a cysteine to a serine at amino acid position 15 of SEQ ID NO: 1 or a variant thereof (htCBS C15S), the method comprising: (a) conjugating the htCBS C15S with one or a plurality of NHS ester PEG molecules in solution at a molar excess of the NHS ester PEG molecules less than about 40-fold to create a batch, wherein the plurality of NHS ester PEG molecules are 5 kDa, 10 kDa, or 20 kDa NHS ester PEG molecules; (b) comparing a retention time from non-reduced capillary electrophoresis (NR-CE) analysis of the batch to a retention time from NR-CE analysis of htCBS C15S with acceptable PEGylation to identify insufficient PEGylation, wherein the batch with insufficient PEGylation has a retention time less than the retention time of the htCBS C15S with acceptable PEGylation; and (c) adding additional NHS ester PEG molecules to the batch to reduce the amount of insufficient PEGylation in the batch, thereby PEGylating the htCBS C15S.

In certain embodiments, NHS ester PEG molecules are present in a molar excess of about 10-fold. In certain embodiments, the NHS ester PEG molecules are present in a molar excess of about 20-fold. Alternatively, the NHS ester PEG molecules are present in a molar excess less than 20-fold, less than 10-fold, less than 5-fold, or less than 2-fold. Certain embodiments provide that the plurality of NHS ester PEG molecules consists of about 5 kDa. NHS ester (5NHS) PEG molecules. In certain embodiments, the plurality of NHS ester PEG molecules consists of about 20 kDa NHS ester (20NHS) PEG molecules. In certain embodiments, the plurality of NHS ester PEG molecules is less than about 20 kDa. For example, the plurality of NHS ester PEG molecules consists of about 10 kDa NHS ester (10NHS) PEG molecules. In certain embodiments, htCBS C15S with insufficient PEGylation comprises fewer than 15, fewer than 10, fewer than 5, or fewer than 1 PEGylated amino acids. In certain embodiments, htCBS C15S with acceptable PEGylation comprises at least 1 PEGylated amino acid.

In certain embodiments, the retention time of the batch of htCBS C15S with insufficient PEGylation is greater than about 9.50 minutes, about 9.75 minutes, about 10.00 minutes, and about 10.25 minutes. In certain embodiments, the retention time of the batch of htCBS C15S with insufficient PEGylation is between about 9.60 minutes and about 9.70 minutes. In certain embodiments, the retention time htCBS C15S with acceptable PEGylation is within a range from about 9.50 to about 9.60 minutes. In certain embodiments, the retention time htCBS C15S with acceptable PEGylation is less than about 9.53 minutes. For example, a PEGylated htCBS C15S with insufficient PEGylation comprises zero (0) PEGylated amino acids.

Various embodiments of the invention herein provides a method of maintaining efficacy of a treatment for homocystinuria in a subject throughout the duration of the treatment, the method including the steps of: administering to the subject a therapeutically effective amount of human truncated cystathionine β-synthase (CBS) protein containing a mutation of a cysteine to a serine at amino acid position 15 of SEQ ID NO: 1 or a variant thereof (htCBS C15S) PEGylated using the method above. In certain embodiments, the efficacy of the treatment is maintained for up to 2 weeks, up to 1 month, up to 6 months, or up to 1 year. Alternatively, the efficacy of the treatment is maintained for longer than 1 year.

Various embodiments of the invention herein provide a method of reducing the level of homocysteine (Hcy) in a subject with homocystinuria, the method including: administering to the subject a therapeutically effective amount of human truncated cystathionine β-synthase (CBS) protein containing a mutation of a cysteine to a serine at amino acid position 15 of SEQ ID NO: 1 or a variant thereof (htCBS C15S) PEGylated using the method above. In certain embodiments, the level of Hcy is reduced in a range selected from the group of ranges selected from about 5% to about 10%, about 10% to about 20% about 20% to about 30%, about 30% to about 40%, about 40% to about 50%, about 60% to about 70%, about 70% to about 80%, about 80% to about 90%, and about 90% to about 100%.

Various embodiments of the invention herein provide a method of increasing the level of cysteine (Cys) in a subject with homocystinuria, the method including the steps of: administering to the subject a therapeutically effective amount of human truncated cystathionine β-synthase (CBS) protein containing a mutation of a cysteine to a serine at amino acid position 15 of SEQ ID NO: 1 or a variant thereof (htCBS C15S) PEGylated using the method above. In certain embodiments, the variant shares at least 80%, 85%, 90%, 91%, 92%, 93%, 94%, 95%, 96%, 97%, 98%, or 99% sequence identity with SEQ ID NO: 1. In certain embodiments, a therapeutic effect resulting from the administering step is maintained for at least 6 hours, at least 12 hours, at least 18 hours, or at least 24 hours.

Various embodiments of the invention herein provide a pharmaceutical composition including a human truncated cystathionine (i-synthase (CBS) protein containing a mutation of a cysteine to a serine at amino acid position 15 of SEQ ID NO: 1 or a variant thereof (htCBS C15S) PEGylated using the method above: and a pharmaceutically acceptable carrier, diluent, or excipient. In certain embodiments, the variant in the pharmaceutical composition shares at least 80%, 85%, 90%, 91%, 92%, 93%, 94%, 95%, 96%, 97%, 98%, or 99% sequence identity with SEQ ID NO: 1.

BRIEF DESCRIPTION OF THE DRAWINGS

FIG. 8A shows metabolite concentrations in weaned (day 21) 1278T mice (n=3) that were treated 3× a week with 20NHS PEG-htCBS C15S (SC, 7.5 mg/kg) for about 9 months. Day 21 shows plasma levels of Hcy (solid line and squares), Cth (dashed line and circles), and Cys (dashed line and diamonds) prior the treatment commencement, while days 28 and 63 illustrate the plasma levels 72 hours after the 3rd and 18th injection, respectively (i.e. weekend washout). All subsequent time points show plasma sulfur amino acids 24 hours after dosing. FIG. 8B shows results for the adult, fully symptomatic 1278T mice (n=10) injected 3 times per week with 20NHS PEG-htCBS C15S (SC, 7.5 mg/kg) from age of 26 weeks for a period of about 6 months. Day 182 shows initial levels prior treatment and all the subsequent time points represent plasma metabolites 24 hours after dosing. Symbols represent an average value from individual mice and error bars indicate standard error of the means (SEMs).

FIG. 9A shows a semi-log plot of CBS specific activity in plasma of male (black squares, n=11 each group) and female rats (gray circles, n=8 each group) after a single SC administration of 8 mg/kg (solid lines) or 24 mg/kg 20NHS PEG-htCBS C15S (dashed lines). CBS specific activity in plasma of male (black, n=8) and female rats (gray, n=8) after repeated SC injections of 4 mg/kg (FIG. 9B) or 24 mg/kg 20NHS PEG-htCBS C15S (FIG. 9C). The gray arrows designate a dosing time point for a total of 9 doses administered every 2 days. Data points in all plots represent average values and error bars show SEMs.

DETAILED DESCRIPTION OF THE INVENTION

I. Introduction

Figure 1:
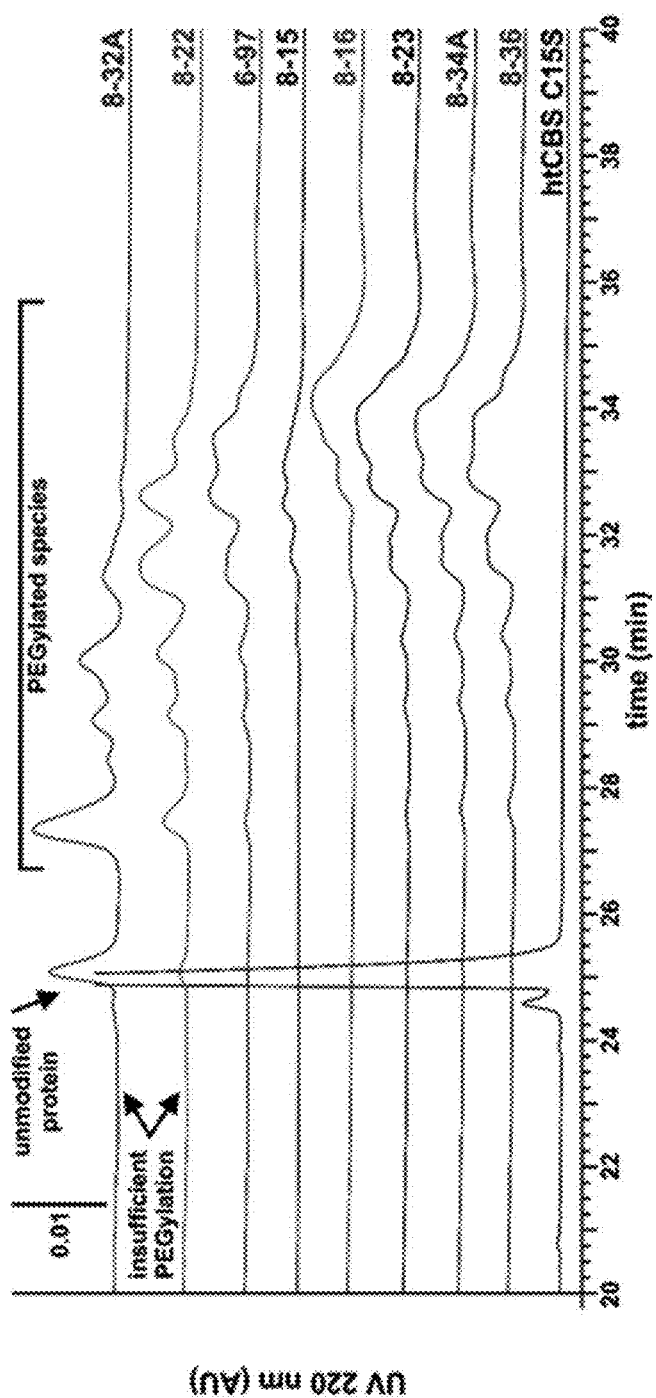
FIG. 1 shows non-reduced capillary electrophoresis (NR-CE) profiles of multiple 20NHS PEG-htCBS C15S batches compared to an unmodified htCBS C15S protein.

Homocystinuna (HCU) due to loss of CBS causes accumulation of homocysteine (Hcy) and depletion of cysteine (Cys). There is a long felt need in the art for an optimized targeted treatment, which would address the underlying enzyme deficiency, thus the development of an enzyme replacement therapy based on PEGylated human truncated CBS (PEG-htCBS) has been explored herein. Attenuation of potency was observed, which warranted screening of several different PEG-htCBS C15S conjugates. The PEG-htCBS C15S conjugates were ranked based on their efficacy to correct plasma metabolite profile of murine homocystinuria after repeated administrations interrupted with washouts. CBS was observed to couple with maleimide PEG molecules inconsistently. In contrast, the PEG-htCBS C15S conjugate with 20 kDa linear NHS-PEG showed very little loss of potency likely due to reproducible PEGylation resulting in species modified with an average of 5 PEGylation sites per peptide. In addition, assays were developed to monitor the extent of CBS PEGylation. These results identified the PEG-htCBS C15S conjugate of those analyzed most suitable for manufacturing and clinical development.

An integral part of any novel therapeutic development effort, whether it is a small molecule drug or a biologic, is the selection, optimization and characterization of a lead candidate to enter the clinical trials. Although effective, treatment of HCU to reduce methionine (Met) intake through dietary restrictions is very difficult to follow and results in serious patient compliancy issues. See, Walter et al., *Eur. J. Pediatr.* 1998, 157 (Suppl 2), S71-S76, which is hereby incorporated by reference in its entirety. The therapeutic goal of the currently available treatments for HCU, i.e., a restricted diet, pyridoxine, and/or betaine supplementation, is to reduce or normalize plasma Hcy levels because fluctuations and high levels of Hcy are often associated with serious complications, particularly thromboembolic events. See, Morris et al., Guidelines for the diagnosis and management of cystathionine beta-synthase deficiency. *J Inherit Metab Dis* 2016, which is hereby incorporated by reference in its entirety. Development of an alternative treatment, such as ERT, would reduce or eliminate reliance on dietary restrictions, which would allow HCU patients and their families access to a better quality of life. To achieve this therapeutic goal (i.e. the reduction or normalization of plasma levels of Hcy), the htCBS C15S variant has been previously modified with 20 kDa linear maleimide-activated PEG molecule and proof of concept was provided using murine models of HCU. See, Bublil et al., *J Clin Invest* 2016, 126, (6), 2372-84 and International application PCT/2016/061050, which are hereby incorporated by reference in their entireties.

There is a trend in PEGylation of therapeutic macromolecules from heterogeneous mixtures of conjugate isomers towards a single modified form, such as characterization/identification of the product and reproducibility of the manufacturing process. See, Pasut et al., *J Control Release* 2012, 161, (2), 461-72, which is hereby incorporated by reference in its entirety. Modification of accessible Cys residues using maleimide PEG molecules is one of the most commonly used approaches for site selective PEGylation. Despite the mutagenesis of the most accessible cysteine residue 15 into serine (C15S) in htCBS, multiple PEGylated species were observed in addition to a fraction of an unmodified enzyme. See, Frank et al., *Biochemistry* 2006, 45, (36), 11021-9, which is hereby incorporated by reference in its entirety. Although the individual species were chromatographically separable, such operation would certainly result in substantial losses and/or would likely render the process economically non-viable. Maleimide PEGylation of htCBS C15S was mapped to a peptide containing residues C272 and C275 with the former residue being a primary site for modification. Mutagenesis of either Cys residue would most likely increased reproducibility of PEGylation; however, substantial reduction in heme saturation and catalytic activity was anticipated. See, Taoka et al., *Biochemistry* 2002, 41, (33), 10454-61, which is hereby incorporated by reference in its entirety.

Similar strategy for PEGylation was employed in the development of an ERT for phenylketonuria based on phenylalanine ammonia-lyase (PAL). Unlike CBS described herein, the PAL is a tetrameric non-mammalian enzyme originating from cyanobacterial and fungal species. See, Sarkissian et al., *Proc Natl Acad Sci USA* 2008, 105. (52), 20894-9, which is hereby incorporated by reference in its entirety. Therefore, immunogenicity of such a foreign protein represented a substantial concern and various PEGylation protocols were tested with PAL. See, Gamez et al., *Molecular therapy: the journal of the American Society of Gene Therapy* 2005, 11, (6), 986-9, which is hereby incorporated by reference in its entirety. PAL was conjugated with NHS ester PEGs ranging from a linear 5 kDa up to a branched 40 kDa in size with linear 20 kDa PEG-PAL conjugates demonstrating increased performance and masking immunogenicity the best. Reduction of the PEG-PAL immunogenicity was directly proportional to the number of PEGs attached to the PAL subunit with gel-based estimate of 6-8 PEGs per PAL monomer suppressing the immune response most efficiently. See, Gamez et al.

When PEG-PAL was administered to the PKU mouse model, plasma phenylalanine levels were brought down to zero in short-term study and after overcoming an initial immune response also in a long-term study. See, Sarkissian et al., *Proc Natl Acad Sci USA* 2008, 105, (52), 20894-9, which is hereby incorporated by reference in its entirety. The Hcy metabolism and pathophysiology need to be taken into an account. Unlike phenylalanine, Hcy is a redox-active thiol group-containing molecule existing in plasma in a variety of chemical forms (as fractions of total Hcy pool): thiolactone (<1%), free reduced (about 2%0/), disulfide (about 18%), and protein-bound (about 80%). Refsum et al., *Clin Chem* 1985, 31, 624-628; Rasmussen et al. *Ann Clin Biochem* 2000, 37 (Pt 5), 627-48; Jakubowski. H., *Anal Biochem* 2002, 308, (1), 112-9, each of which are hereby incorporated by reference in their entireties.

Free Hcy is increased substantially to a 10-25% of total plasma Hcy in HCU. See, Mansoor et al., *Metabolism* 1993, 42, 1481-1485. In addition, Hcy, in homocystinuria, substantially replaces Cys bound to plasma albumin, what may contribute to decreased levels of plasma Cys found in HCU. See, Bar-Or et al., *Biochem Biophys Res Commun* 2004, 325, (4), 1449-53, which is hereby incorporated by reference in its entirety. Albumin is synthesized exclusively in the liver and its plasma concentration of 33-52 g/l in healthy human represents only about 40%, while the remaining about 60% of albumin stays in extravascular space. See, Boldt et al., *Br J Anaesth* 2010, 104, (3), 276-84, which is hereby incorporated by reference in its entirety. In theory, only a free Hcy represents a substrate for CBS. Thus, the 50-80% decrease of total Hcy in HO mice upon continuous administration of 20NHS PEG-htCBS C15S may be explained by shifting the balance of metabolites in favor of free Hcy compared to other forms (disulfides and protein-bound). See, Bublil et al., *J Clin Invest* 2016, 126, (6), 2372-84 and International application PCT/2016/061050, which are hereby incorporated by reference in their entireties. 20NHS PEG-htCBS C15S in circulation serves as a "sink" for excess of Hcy to improve the Hcy plasma levels. Possible reasons for failing to normalize levels could be the constant flux of intracellular Hcy (particularly from the liver as Hcy bound to a newly synthesized albumin), dynamic balance between intra- and extra-vascular Hcy pools (mediated mostly by albumin), and homocystinuria-induced pro-oxidative environment favoring disulfides and protein-bound forms of total Hcy pool. Nevertheless, recently published guidelines for diagnosis and management of HCU recommend keeping the plasma total of Hcy below 100 µM to prevent progress and/or occurrence of serious complications. See, Morris et al., Guidelines for the diagnosis and management of cystathionine beta-synthase deficiency. *J Inherit Metab Dis* 2016, which is hereby incorporated by reference in its entirety. Values are extrapolated from the results herein from homocystinuric HO mice fed with standard unrestricted chow containing 4-5 g Met per kg of diet (corresponds to 18-19% of protein). Administration of 20NHS PEG-htCBS C15S to human HCU patients results in guideline-recommended total Hcy levels in plasma without any additional treatment. Based on the results herein, a GLP-toxicology (GLP-tox) study in humans using 20NHS PEG-htCBS C15S as an ERT for HCU has been initiated.

II. Methods of Characterizing Pegylated HtCBS C15S

A. Extent of PEGylation of htCBS C15S (PEG-htCBS C15S)

In certain embodiments, the extent of PEGylation of htCBS C15S may be used to define acceptance criteria for individual PEG-htCBS C15S. In some embodiments, the PEG molecule is ME-200GS (also know n as 20NHS).

In certain embodiments, size exclusion chromatography (SEC)-high performance liquid chromatography (HPLC) is used to compare a batch of PEG-htCBS C15S during processing to unmodified htCBS C15S. Insufficiently PEGylated htCBS batches are identified by longer retention times than the retention times for acceptable PEGylation. In certain embodiments, a retention time of greater than about 9.5 minutes, about 9.75 minutes, about 10 minutes, and about 10.25 minutes indicates insufficient PEGylation (<1 PEG/protein or <5 PEGs/protein). For example, a retention time between 9.6 and 9.7 minutes, such as 9.67 minutes, may indicate insufficient PEGylation.

In certain embodiments, a retention time of less than about 9.6 minutes, about 9.4 minutes, about 9.2 minutes, and about 9 minutes was determined to indicate acceptable PEGylation (at least 1 PEG/protein). For example, a retention time between 9.5 and 9.6 minutes, such as 9.53 minutes, may indicate acceptable PEGylation.

In some embodiments, additional PEG molecules may be added to the reaction mixture for insufficiently PEGylated batches to potentially rescue the extent of PEGylation. The comparison by SEC-HPLC may be performed multiple times during the PEGylation process. Alternatively, the comparison by SEC-HPLC may be performed once during the PEGylation process.

In certain embodiments, non-capillary electrophoresis is used to quantify multiple PEG-htCBS C15S species. Insufficiently PEGylated batches of PEG-htCBS C15S were identified by the presence of unmodified enzyme and an increased occurrence of low molecular weight PEG-htCBS C15S species. In certain embodiments, liquid chromatography-mass spectrometry (LC-MS) is used to estimate the number of PEG molecules per peptide. In certain embodiments, at least seven PEGylated lysines are observed to be modified in an PEGylated htCBS C15S with acceptable PEGylation. For example, K25, K30, K211, K247, K271, K405, and K406 of htCBS C15S may be PEGylated. The lysines may have varying degrees of PEGylation. More specifically, K25 and K30 of htCBS C15S may be PEGylated to the full extent, while other lysines may be partially PEGylated.

In certain embodiments, acceptable PEGylation is defined as about 5 PEGylated sites per htCBS C15S protein. Alternatively, acceptable PEGylation may be selected from at least one range of between 1-5 PEGylated sites, between 3-7 PEGylated sites, and between 5-9 PEGylated sites per htCBS CBS protein. For example, acceptable PEGylation of htCBS C15S may include one PEGylated lysine per protein. Alternatively, acceptable PEGylation of htCBS C15S may include about 5 PEGylated lysines per protein.

B. Optimizing PEG Conjugation

Various approaches such as reduction of accessible cysteines with tris(2-carboxyethyl)phosphine (TCEP) prior to PEGylation to enhance the yield of the modified enzyme or multiple PEGylation schemes to gain consistency in the process have been previously observed to partially improve the consistency of PEGylation.

Maleimide PEGylation of htCBS may be site-specific. In certain embodiments, htCBS C15S is first PEGylated at C272 during maleimide PEGylation. Alternatively, htCBS C15S is PEGylated at C272 and C275 during maleimide PEGylation.

Alternatively, htCBS C15S may be PEGylated by at least one of 5, 10, or 20 kDa linear NHS ester PEG molecules. In certain embodiments, PEGylation of htCBS C15S by a NHS ester PEG molecule results in a reproducible pattern. In certain embodiments, PEGylation is performed with up to 20-fold excess of PEG molecule to the CBS protein. For example, PEGylation of htCBS C15S is performed with between about 10-fold and 20-fold excess of 5 kDa NHS ester PEG (5NHS), 10 kDa NHS ester PEG (10NHS), or 20 kDa NHS ester PEG (20NHS) molecules.

Alternatively, PEGylation is performed with about 40-fold to about 60-fold excess of PEG molecule to the CBS protein. In one aspect, PEGylation of htCBS C15S is performed with about 40-fold excess of 5 kDa NHS ester PEG (5NHS), 10 kDa NHS ester PEG (10NHS), or 20 kDa NHS ester PEG (20NHS) molecules. Alternatively. PEGylation of htCBS C15S is performed with less than about 40-fold excess of 5 kDa NHS ester PEG (5NHS), 10 kDa NHS ester PEG (10NHS), or 20 kDa NHS ester PEG (20NHS) molecules.

In certain embodiments, residual ammonium sulfate from chromatographic purification is removed from an unmodified batch of CBS protein, such as unmodified htCBS C15S, to increase reproducibility of the PEGylation pattern as compared to the reproducibility of the PEGylation pattern of htCBS C15S in a mixture containing the residual ammonium sulfate. For example, the ammonium sulfate may be removed using a buffer exchange technique.

Following PEGylation, unreacted PEG molecules are removed from the PEGylation mixture to reduce its viscosity by increasing the surface area of the diafiltration membrane. For example, the surface area is increased by about 2-fold, about 3-fold, or about 4-fold. Alternatively, viscosity may be reduced by diluting the PEGylation mixture. For example, the PEGylation mixture is diluted by about 2-fold. In certain embodiments, the unreacted PEG molecules or unmodified htCBS C15S is removed from the mixture to reduce immunogenicity.

III. Treatment with PEGylated HtCBS C15S

In certain embodiments, a mammal may be administered htCBS C15S PEGylated with a 5 kDa ester NHS PEG molecule or a 20 kDa ester NHS PEG molecule. For example, 5NHS PEG-htCBS C15S or 20NHS PEG-htCBS C15S. Administration of 5NHS PEG-htCBS C15S or 20NHS PEG-htCBS C15S reduces levels of Hcy in plasma or in kidney, liver, or brain tissue by at least 40%. For example, Hcy levels are reduced by more than 40%, such as at least 50%, at least 60%, at least 70%, at least 80%, at least 90%, or at least 99%. Administration of 5NHS PEG-htCBS C15S or 20NHS PEG-htCBS C15S increases levels of Cth in plasma or in kidney, liver, or brain tissue by at least 70%. For example, Cth levels are increased by at least 80%, at least 90%, or at least 99%. Administration of 5NHS PEG-htCBS C15S or 20NHS PEG-htCBS C15S increases levels of Cys in plasma or in kidney, liver, or brain tissue by at least 30%. For example, Cys levels are increased by at least 40%, at least 50%, at least 60%, at least 70%, at least 80%, at least 90%, or at least 99%.

Administration of 20NHS PEG-htCBS C15S may reduce levels of homolanthionine (Hlth) in plasma or in kidney, liver, or brain tissue by at least 50%. For example, Hlth levels are reduced by at least 60%, at least 70%, at least 80%, at least 90%, or at least 99%.

The therapeutic effects of administration of 20NHS PEG-htCBS C15S may continue for at least 12 hours of at least 24 hours, at least 48 hours, or at least 72 hours. Specifically, the therapeutic effects may continue for about 24 hours.

S-Adenosylmethionine (SAM) and S-Adenosylhomocysteine (SAH) are metabolites involved in the conversion of methionine to homocysteine during the proximal portion of the methionine cycle. See, Krijt, et al. J Chromatogr B Analyt Technol Biomed Life Sci. 2009 Jul. 15: 877(22-3): 2061-2066, which is hereby incorporated by reference herein in its entirety. In certain embodiments, homocystinuria results in reduction of the ratio of S-adenosylmethionine (SAM) to S-adenosylhomocysteine (SAH) (SAM/SAH), which indicates a decrease in methylation capacity. In certain embodiments, the SAM/SAH ratio may be increased or normalized by administration of a PEG-htCBS C15S to a subject. For example, administration of a 20NHS PEG-htCBS C15S conjugate reduces SAH accumulation, thus increasing the SAM/SAH ratio, thereby normalizing the balance of metabolites in a subject.

IV. Dosing and Administration

In certain embodiments, PEG-htCBS C15S may be administered to a subject by parenteral administration.

In certain embodiments, PEG-htCBS C15S may be administered to a subject by subcutaneous (SC), intravenous (IV) or intraperitoneal (IP) injection. As a non-limiting example, PEG-htCBS C15S may be administered to a subject by subcutaneous administration. As a non-limiting example, PEG-htCBS C15S may be administered to a subject by intravenous administration. As a non-limiting example, PEG-htCBS C15S may be administered to a subject by intraperitoneal administration.

In certain embodiments, PEG-htCBS C15S may be administered to a subject at least 1, 2, 3, 4, 5, 6, 7, 8, 9, 10, 11, 12, 13, 14, 15, 16, 17, 18, 19, 20 or more than 20 times.

In certain embodiments, the administration of the PEG-htCBS C15S may be repeated every minute, 2 minutes, 3 minutes, 4 minutes, 5 minutes, six 6, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, hourly, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, daily, 2 days, 3 days, 4 days, 5 days, 6 days, weekly, biweekly, 3 weeks, monthly, 2 months, quarterly, 4 months, 5 months, 6 months, 7 months, 8 months, 9 months, 10 months, 11 months, yearly, 13 months, 14 months, 15 months, 16 months, 17 months, or 18 months.

In certain embodiments, the administration of the PEG-htCBS C15S may be a series of doses which are minutes, hours, days or weeks apart. The number of doses in a series may be 2, 3, 4, 5 or 6. As a non-limiting example, a subject is administered 3 doses 24 hours apart. As another non-limiting example, a subject is administered 5 doses 12 hours apart.

In certain embodiments, the administration of the PEG-htCBS C15S may follow a dosing schedule of a series of doses that has a gap between the first series and the second series of doses. The gap between the doses may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. The number of doses in a series may be 2, 3, 4, 5 or 6. As a non-limiting example, a subject may be administered a first series of 5 doses 12 hours apart and then 14 days after the first dose a subject is administered a second series of 5 doses 12 hours apart. As another non-limiting example, a subject is administered two series of doses over a period of 8 weeks where the first series is one dose twice a week for two weeks and the second series of doses is three times a week for 6 weeks.

In one embodiment, PEG-htCBS C15S may be administered at least once after a subject has been administered betaine. The time between the betaine administration the PEG-htCBS C15S may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. As a non-limiting example, the PEG-htCBS C15S may be administered 14 days after the subject was administered betaine. As another non-limiting example, a subject may be administered two doses after the subject was administered betaine. The PEG-htCBS C15S mutant may be administered 14 and 15 days after betaine administration.

In one embodiment, PEG-htCBS C15S mutant may be administered in combination with betaine to a subject. The combination may be administered at least 1, 2, 3, 4, 5, 6, 7, 8, 9, 10, 11, 12, 13, 14, 15 or more than 15 times.

In one embodiment. PEG-htCBS C15S mutant may be administered in combination with betaine to a subject after the subject has initially received betaine. The time between the combination treatment and the original betaine administration may be 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, day, 2 days, 3 days, 4 days, 5 days, 6 days, week, 2 weeks, 3 weeks, monthly, 2 months, quarterly, 4 months, 5 months, 6 months, 7 months, 8 months, 9 months, 10 months, 11 months, 12 months, 13 months, 14 months, 15 months, 16 months, 17 months, or 18 months. As a non-limiting example, the combination may be administered 14 days after the subject was first administered betaine. As another non-limiting example, a subject may be administered two doses after the subject was first administered betaine. The combination may be administered 14 and 15 days after betaine administration.

In one embodiment, the dose of PEG-htCBS C15S mutant administered to a subject may be between 0.01 mg/kg and 1 mg/kg such as 0.05 mg/kg, 0.1 mg/kg, 0.5 mg/kg or 1 mg/kg, or between 5 and 8 mg/kg such as 5 mg/kg, 5.5 mg/kg, 6 mg/kg, 6.5 mg/kg, 7 mg/kg, 7.5 mg/kg or 8 mg/kg. Alternatively, the dose of PEG-htCBS C15S mutant administered to a subject may be between about 2 mg/kg and about 8 mg/kg, about 4 mg/kg and about 16 mg/kg, about 6 mg/kg and 24 mg/kg. For example, the dose is about 24 mg/kg or about 8 mg/kg.

In one embodiment, the PEG-htCBS C15S may be co-administered with another therapeutic for treating CBSDH.

As used herein, "co-administered" means the administration of two or more components. Components for co-administration include, but are not limited to PEG-htCBS C15S, betaine or Vitamin B6. Co-administration refers to the administration of two or more components simultaneously or with a time lapse between administration such as 1 second, 5 seconds, 10 seconds, 15 seconds, 30 seconds, 45 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, 1 hour, 1.5 hours, 2 hours, 2.5 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 1.5 days, 2 days, or more than 3 days.

V. Definitions

As used in this specification, the singular forms "a", "an", and "the" include plural referents unless the context clearly dictates otherwise. Thus, for example, reference to a "polymer" includes a single polymer as well as two or more of the same or different polymers, or a reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure and specifically disclosed. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

"Recombinant," when used to reference, e.g., a cell, nucleic acid, polypeptide, expression cassette or vector, refers to a material, or a material corresponding to the natural or native form of the material, that has been modified by the introduction of a new moiety or alteration of an existing moiety, or is identical thereto but produced or derived from synthetic materials. For example, recombinant cells express genes that are not found within the native (non-recombinant) form of the cell (i.e., "exogenous nucleic acids") or express native genes that are otherwise expressed at a different level, typically, under-expressed or not expressed at all.

Recombinant techniques can include, e.g., use of a recombinant nucleic acid, such as a cDNA encoding a protein or an antisense sequence, for insertion into an expression system, such as an expression vector: the resultant construct is introduced into a cell, and the cell expresses the nucleic acid, and the protein, if appropriate. Recombinant techniques also encompass the ligation of nucleic acids to coding or promoter sequences from different sources into one expression cassette or vector for expression of a fusion protein, constitutive expression of a protein, or inducible expression of a protein.

The terms "subject", "individual" or "patient" are used interchangeably herein and refer to a vertebrate, preferably a mammal. Mammals include, but are not limited to, humans.

"Associated" refers to coincidence with the development or manifestation of a disease, condition or phenotype. Association may be due to, but is not limited to, genes responsible for housekeeping functions whose alteration can provide the foundation for a variety of diseases and conditions, those that are part of a pathway that is involved in a specific disease, condition or phenotype and those that indirectly contribute to the manifestation of a disease, condition or phenotype.

"Physiological conditions" or "physiological solution" refers to an aqueous environment having an ionic strength, pH, and temperature substantially similar to conditions in an intact mammalian cell or in a tissue space or organ of a living mammal. Typically, physiological conditions comprise an aqueous solution having about 150 mM NaCl, pH 6.5-7.6, and a temperature of approximately 22-37° C. Generally, physiological conditions are suitable binding conditions for intermolecular association of biological macromolecules. For example, physiological conditions of 150 mM NaCl, pH 7.4, at 37° C. are generally suitable.

"Pharmaceutically acceptable excipient or carrier" refers to an excipient that may optionally be included in the compositions of the invention and that causes no significant adverse toxicological effects to the patient. The term refers to an excipient that can be taken into the mammalian subject's body in association with an active compound (e.g. PEG-htCBS C15S) with no significant adverse toxicological effects to the subject.

The term "excipient" or "vehicle" as used herein means any substance, not itself a therapeutic agent, used as a carrier for delivery of a therapeutic agent and suitable for administration to a subject, e.g. a mammal or added to a pharmaceutical composition to improve its handling or storage properties or to permit or facilitate formation of a dose unit of the composition into a discrete article such as a capsule or tablet suitable for oral administration. Excipients and vehicles include any such materials known in the art, e.g., any liquid, gel, solvent, liquid diluent, solubilizer, or the like, which is nontoxic, and which does not interact with other components of the composition in a deleterious manner. Administration can mean oral administration, inhalation, enteral administration, feeding or inoculation by intravenous injection. The excipients may include standard pharmaceutical excipients and may also include any components that may be used to prepare foods and beverages for human and/or animal consumption, feed or bait formulations or other foodstuffs.

"Permeant", "drug", and "pharmacologically active agent" or any other similar term means any chemical or biological material or compound, inclusive of peptides, suitable for administration by the methods previously known in the art and/or by the methods taught in the present disclosure, that induces a desired biological or pharmacological effect, which may include, but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anesthetic effect, or it may be systemic. This disclosure is not drawn to novel permeants or to new classes of active agents. Rather it is limited to the mode of delivery of agents or permeants which exist in the state of the art or which may later be established as active agents and which are suitable for delivery by the present disclosure.

The term "about", particularly in reference to a given quantity, is meant to encompass deviations of plus or minus five percent.

"Optional" or "optionally" means that the subsequently described circumstance may or may not be present or occur, so that the description includes instances where the circumstance is present or occurs and instances where it is not present or does not occur.

"Substantially absent" or "substantially free" of a certain feature or entity means nearly totally or completely absent the feature or entity. For example, for a subject administered PEG-htCBS C15S, the substantial absence of an observable side effect means that such side effect is either non-detectable, or occurs only to a negligible degree, e.g., to an extent or frequency that is reduced by about 50% or more when compared to either the frequency or intensity of the same side effect observed in an untreated patient.

The terms "pharmacologically effective amount" or "therapeutically effective amount" as related to the present composition refer to a non-toxic, but sufficient amount of the active agent (or composition containing the active agent) to provide the desired level in the bloodstream or at the site of action (e.g. intracellularly) in the subject to be treated, and/or to provide a desired physiological, biophysical, biochemical, pharmacological or therapeutic response, such as amelioration of the manifestations of homocystinuria. The exact amount required will vary from subject to subject, and will depend on numerous factors, such as the active agent, the activity of the composition, the delivery device employed, the physical characteristics of the composition, intended patient use (i.e., the number of doses administered per day), as well as patient considerations, such as species, age, and general condition of the subject, the severity of the condition being treated, additional drugs being taken by the subject, mode of administration, and the like. These factors and considerations can readily be determined by one skilled in the art, based upon the information provided herein. An appropriate "effective" amount in any individual case may be determined by one of ordinary skill in the art using routine experimentation, based upon the information provided herein.

The term "biological activity" refers to any biological activity typically attributed to a nucleic acid or protein by those skilled in the art. Examples of biological activities are enzymatic activity, ability to dimerize, fold or bind another protein or nucleic acid molecule, etc.

The term "nucleic acid" may be in the form of RNA or in the form of DNA, and include messenger RNA, synthetic RNA and DNA, cDNA, and genomic DNA. The DNA may be double-stranded or single-stranded, and if single-stranded may be the coding strand or the non-coding (anti-sense, complementary) strand.

As used herein, a "variant" is a nucleic acid, protein or polypeptide which is not identical to, but has significant homology (for example, 80%, 85%, 90%, 91%, 92%, 93%, 94%, 95%, 96%, 97%, 98% or 99% sequence identity) over the entire length of the wild type nucleic acid or amino acid sequence, as exemplified by sequences in the public sequence databases, such as GenBank. As used herein, a "protein, polypeptide or peptide fragment thereof" means the full-length protein or a portion of it having an amino acid sequence usually at least 5, 6, 7, 8. 9, 10, 11, 12, 13, 14 or 15 amino acids in length, although dipeptides, tripeptides and tetrapeptides are also contemplated and encompassed by the present disclosure.

As used herein, a "mutant" is a mutated protein designed or engineered to alter properties or functions relating to glycosylation, protein stabilization and % or ligand binding.

As used herein, the terms "native" or "wild-type" relative to a given cell, polypeptide, nucleic acid, trait or phenotype, refers to the form in which that is typically found in nature.

As used herein, the terms "protein", "polypeptide", "oligopeptide", and "peptide" have their conventional meaning and are used interchangeably to denote a polymer of at least two amino acids covalently linked by an amide bond, regardless of length or post-translational modification (e.g., glycosylation, phosphorylation, lipidation, myristylation, ubiquitination, etc.). Furthermore, the polypeptides described herein are not limited to a specific length. Included within this definition are D- and L-amino acids, and mixtures ofD- and L-amino acids. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Polypeptides can also refer to amino acid subsequences comprising epitopes, i.e., antigenic determinants substantially responsible for the immunogenic properties of a polypeptide and being capable of evoking an immune response.

"Position corresponding to" refers to a position of interest (i.e., base number or residue number) in a nucleic acid molecule or protein relative to the position in another reference nucleic acid molecule or protein. Corresponding positions can be determined by comparing and aligning sequences to maximize the number of matching nucleotides or residues, for example, such that identity between the sequences is greater than 90%, greater than 95%, greater than 96%, greater than 97%, greater than 98% or greater than 99%. The position of interest is then given the number assigned in the reference nucleic acid molecule. For example, if a particular polymorphism in Gene-X occurs at nucleotide 2073 of SEQ ID No. X, to identify the corresponding nucleotide in another allele or isolate, the sequences are aligned and then the position that lines up with 2073 is identified. Since various alleles may be of different length, the position designated 2073 may not be nucleotide 2073, but instead is at a position that "corresponds" to the position in the reference sequence.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted. e.g., by the local homology algorithm of Smith & Waterman, *Adv. Appl. Math.* 2:482 (1981), by the homology alignment algorithm of Needleman & Wunsch, *J. Mol. Biol,* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length "W" in the query sequence, which either match or satisfy some positive-valued threshold score "T" when aligned with a word of the same length in a database sequence. T is referred to as, the neighborhood word score threshold (Altschul et al, supra). These initial neighborhood word hits act as "seeds" for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues: always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments: or the end of either sequence is reached. The BLAST algorithm parameters W, T. and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff& Henikoff. *Proc. Natl. Acad Sci. USA* 89:10915 (1989)).

While all the above-mentioned algorithms and programs are suitable for a determination of sequence alignment and % sequence identity, for purposes of the disclosure herein, determination of % sequence identity will typically be performed using the BESTFIT or GAP programs in the GCG Wisconsin Software package (ACCELRYS®, Madison Wis.), using default parameters provided.

The term "L or D form amino acids" may be used in relation to the peptide described herein. As will be recognized by skilled artisans, the various $X^n$ residues comprising the compounds of the invention may be in either the L- or D-configuration about their $C_\alpha$ carbons. In one embodiment, all the $C_\alpha$ carbons of a particular compound are in the same configuration. In some embodiments of the invention, the compounds comprise specific chiralities about one or more $C_\alpha$ carbon(s) and/or include non-peptide linkages at specified locations to impart the compound with specified properties. For example, it is well-known that peptides composed in whole or in part of D-amino acids are more resistant to proteases than their corresponding L-peptide counterparts. Thus, in one embodiment, the compounds are peptides composed in whole or in part of D-amino acids. Alternatively, compounds having good stability against proteases may include peptide analogs including peptide linkages of reversed polarity at specified positions. For example, compounds having stability against tryptic-like proteases include peptide analogs having peptide linkages of reversed polarity before each L-Arg or L-Lys residue: compounds having stability against chymotrypsin-like proteases include peptide analogs having peptide linkages of reversed polarity before each small and medium-sized L-aliphatic residue or L-nonpolar residue. In another embodiment, compounds having stability against proteases include peptide analogs composed wholly of peptide bonds of reversed polarity. Other embodiments having stability against proteases will be apparent to those of skill in the art. Additional specific embodiments of the compounds are described herein.

Described herein are compositions, methods, processes, kits and devices for the design, preparation, manufacture and/or formulation of PEG-htCBS C15S proteins. The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

The present invention is further illustrated by the following non-limiting examples.

VI. Examples

Example 1. Experimental Procedures

A. Chemicals

Unless stated otherwise, all materials were purchased from SIGMA-ALDRICH® or FISHER SCIENTIFIC™. L-[$^{14}$C]-serine was obtained from PERKIN ELMER®, Life Sciences.

B. Animals

All animal procedures were approved under animal protocol #B-49414(03)1E by the University of Colorado Denver Institutional Animal Care and Use Committee (IACUC), which is an AAALAC INTERNATIONAL®-accredited (#00235), Public Health Service-assured (#A 3269-01) and USDA-licensed (#84-R-0059) institution. "Human Only" (HO) mice were previously generated and propagated and genotyped as described in Maclean et al., *Mol. Genet. Metab.* 2010, 101, (2-3), 153-62; Bublil et al., *J Clin Invest* 2016, 126, (6), 2372-84: and International application PCT/2016/061050, which are hereby incorporated by reference in their entireties. Animals were maintained on extruded standard diet 2918, 2919, or 2920X from TEKLAD GLOBAL RODENT DIETS® (Harlan. Livermore, Calif., USA). A single-use lancet for submandibular bleeding was used for blood collection into CAPIJECT®, T-MLHG lithium heparin (12.5 IU) tubes with gel (Terumo Medical Corporation, NJ, USA). Tubes were then centrifuged at 1,200×g for 10 minutes, followed by transfer of plasma to 1.5 ml tubes and storage at −80° C.

C. Determination of Metabolite Concentrations

Plasma metabolites were determined by stable-isotope-dilution gas chromatography mass spectrometry as previously described. See, Allen et al., *Metabolism* 1993, 42, 1448-1460. The analysis was performed in a blinded fashion without knowing the animal genotype and/or treatment regimen.

D. Size Exclusion Chromatography-High Performance Liquid Chromatography (SEC-HPLC)

CBS and PEG-htCBS C15S preparations were separated on BioSEC-5 7.8×300 mm, 1000 Å pore size column (Agilent, CA, USA). Column was equilibrated and operated in 100 mM sodium phosphate, pH 6.8, 150 mM NaCl at a flow rate of 1 ml/min at room temperature. Protein samples diluted in mobile phase to a final concentration of 2 mg/ml were loaded on a column via 10 µl sample loop and detected using UV detector at wavelength of 225 nm. Chromatograms were recorded and analyzed using 32 karat software (BECKMAN COULTER®), CA, USA).

E. Non-Reduced Capillary Electrophoresis (NR-CE)

CBS and PEG-htCBS C15S preparations were analyzed on PA800 capillary electrophoresis system (BECKMAN COULTER®, CA. USA) equipped with 30 cm long, 50 µm ID bare-fused silica capillary. The capillary was cut to provide a total length of 30 cm with a distance of approximately 20 cm from sample introduction inlet to detection window and installed in a cartridge with a 100×800 µm aperture. The capillary was preconditioned with 0, 1 M NaOH wash followed by 0.1 M HCl wash before rinsing it with water and final equilibration with SDS MW sample buffer. Protein samples of concentrations less than 10 mg/ml and in a formulation containing high salt were buffer exchanged in water twice (about 7-fold dilution each time) to remove matrix interference, diluted to 1 mg/ml final concentration, and denatured by heating at 80° C. for 5 minutes. The sample was loaded by a high-resolution method using electrokinetic injection (5 kV) for a duration of 20 seconds and separated for 50 minutes under voltage of 15 kV. Electropherograms were recorded at a UV wavelength of 220 nm and analyzed using 32 karat software (BECKMAN COULTER®, CA, USA).

F. Protein Purification and PEGylation

Human truncated CBS carrying the C15S mutation (htCBS C15S) was expressed and purified as described in Bublil et al., *J Clin Invest* 2016, 126, (6), 2372-84, International application PCT/2016/061050, which are hereby incorporated by reference in their entireties. The purified enzyme was formulated and concentrated using the LABSCALE™ Tangential Flow Filter (TFF) system (EMD Millipore, MA, USA) equipped with PELLICON®, XL 50 ULTRAcel 30 cartridge (regenerated cellulose 30 kDa molecular weight cut-off (MWCO) membrane) into 200 mM potassium phosphate pH 6.5 or 100 mM sodium phosphate pH 7.2. Activated PEG molecules with either a maleimide or a NHS ester coupling group were purchased from NOF Corporation (Japan). PEGylation of htCBS C15S with maleimide and NHS ester PEG molecules was carried out in 100 mM potassium phosphate pH 6.5 and 50 mM sodium phosphate pH 7.2, respectively, by adding PEG molecules dissolved in MILLIQ®, purified water in the desired molar ratio (typically CBS protein:PEG=1:10) to a final protein concentration of 5 mg/ml. Reaction was carried out at 4° C. overnight. Subsequently, reaction mixture was diluted twice with MILLIQ® purified water, buffer exchanged into Gibco 1×PBS (Thermo Fisher Scientific, MA. USA) and concentrated using LABSCALE™ TFF system with PELLICON® XL 50 Biomax 100 cartridge (polyether sulfone 100 kDa MWCO membrane). The final PEG-htCBS C15S conjugates were filter sterilized (Millipore's 0.2 µm PVDF membrane filter), aliquoted, flash frozen in liquid nitrogen and stored at −80° C.

G. Protein Gel Electrophoresis

Protein concentrations were determined by the Bradford assay (Thermo Pierce, MA, USA) using bovine serum albumin (BSA) as a standard per the manufacturer's recommendations. Denatured proteins were separated by SDS-PAGE using a 10% Mini-PROTEAN®. Tris-glycine extended (TGX) gels (BIORAD®, CA, USA), while native samples were resolved by native PAGE in 4-15% Mini-PROTEAN® TGX gels. For visualization, the gels were stained with Simple Blue (Invitrogen, CA, USA). Free PEG molecules and PEGylated htCBS C15S were visualized using barium iodide staining as described in Kurfurst et al., *Anal Biochem* 1992, 200, (2), 244-8, which is hereby incorporated by reference in its entirety.

H. CBS Activity Assays

The CBS activity was determined by a previously described radioisotope assay using L-[$^{14}$C]-serine as the labeled substrate with the following modification. See, Kraus et al., *Methods Enzymol* 1987, 143, 388-94: Bublil et al., *J Clin Invest* 2016, 126, (6), 2372-84, each of which are hereby incorporated by reference in their entireties. Four or five µl of undiluted plasma was assayed in a total volume of 100 µl for 30 minutes. The reaction was terminated by mixing of 20 µl of a reaction mixture with 5 µL of chilled performic acid (30% $H_2O_2$:100% formic acid=1:9) and further processed as described in the original protocol.

I. PEGylation Mapping

Mapping of maleimide and NHS ester PEGylation of htCBS C15S was performed using ESI-QTOF mass spectrometer model 6538 (Agilent, CA, USA). Unmodified enzyme was used as a control and PEGylated CBS were used as is (unmodified htCBS C15S, 20NHS PEG htCBS-C15S, and 400MA PEG-htCBS C15S) or dePEGylated by incubating the sample at pH 11.5 for 22 hours at 37° C. (20NHS PEG-htCBS C15S). All samples were buffer exchanged, denatured, reduced with 10 mM DTT and alkylated with 30 mM iodoacetamide prior digestion. The 400MA PEG-htCBS C15S and 20NHS PEG-htCBS C15S were digested overnight with Lys-C and Asp-N (1:50 (w/w) ratio, 37° C.), respectively. The 20NHS PEG-htCBS C15S conjugates were also chemically digested using 2-nitro-5-thiocyanobenzoic acid (NTCB) to further differentiate which cysteine residues had been modified. Peptides were separated on a C18 column (Xbridge BEH130 3.5 µm, 4.6×150 mm) using RP-HPLC with UV detection (Agilent), and LC/UV/MS/MS chromatograms were analyzed using MassHunter software (Agilent. CA, USA). Peptide mapping and sequence matching was performed using BioConfirm package (Agilent, CA, USA) with manual validation to ensure correct assignment.

J. Statistical Analysis

All data are presented as mean±standard error of the mean (SEM). Statistical comparisons of 2 groups were conducted using an unpaired, two tailed Students t-test. Statistical analysis of 3 or more factor levels was conducted by ANOVA followed by Tukey's multiple comparison test to determine significance. The p value of less than 0.05 was determined to correspond to statistical significance.

Example 2. Optimizing PEGylation of htCBS C15S

Figure 2:
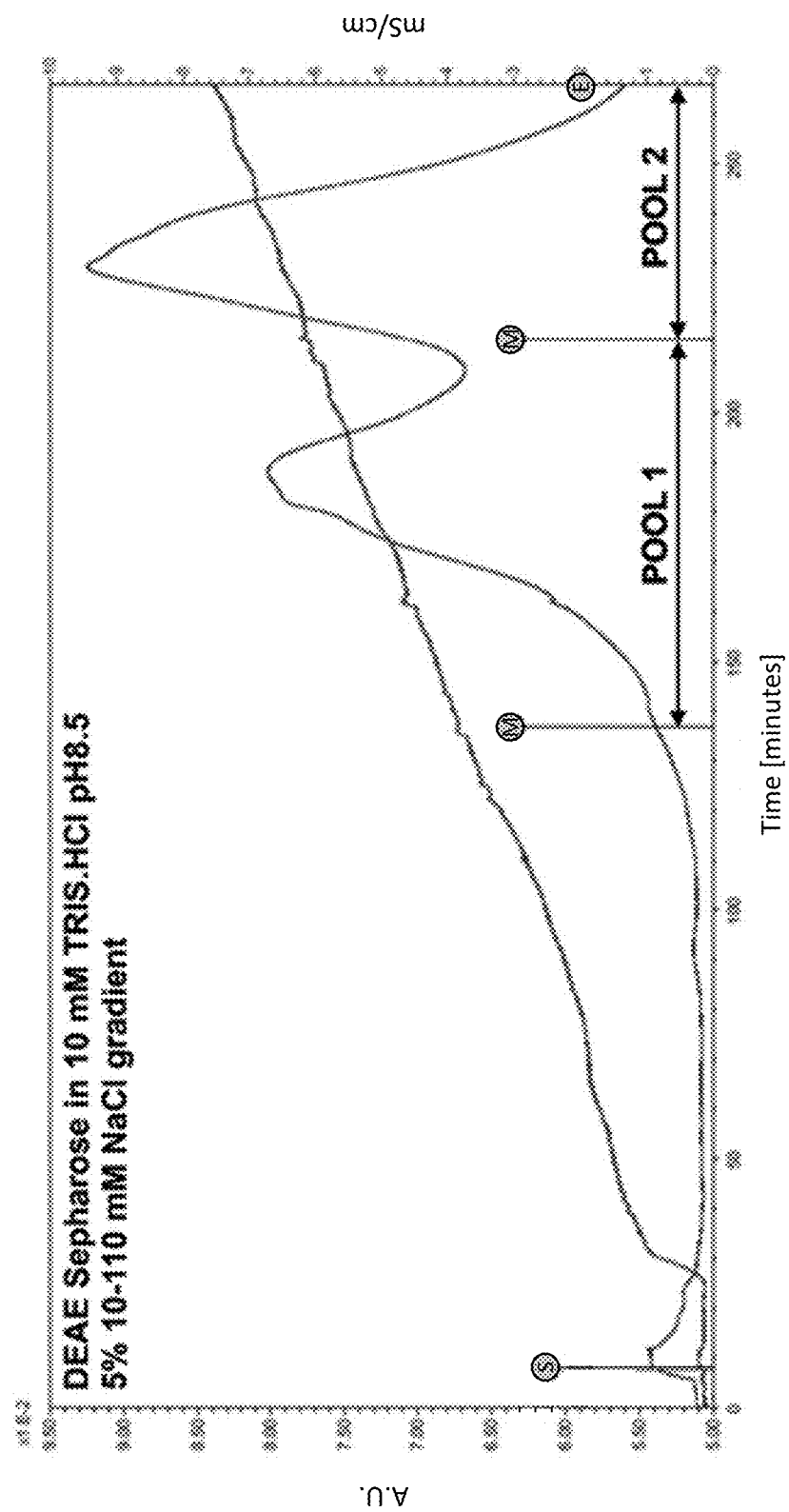
FIG. 2 shows chromatographic separation of 400MA PEG-htCBS C15S species on DEAE Sepharose using a shallow salt gradient (5%, 10-110 mM NaCl). The straight line represents absorbance at 280 nm, while the peaks show changes in conductivity of the mobile phase. Both lines were generated using BIO-RAD® Biologic LP chromatographic system with BIO-RAD® Biologic LP Data View Software version 1.03. "S" represents the time point of the start of the pump and recording by the software program, and "E" represents the time point of the end of operation of the pump and recording by the software program. "M" represents a manually designated points of the beginning of the monitoring of Pool 1 and Pool 2 as indicated by the labels in the figure.

To understand the PEGylation patterns and to optimize the conjugation reaction to yield a more uniform modification, the individual PEG-htCBS C15S species were separated and the residues targeted with the ME-400MA maleimide PEG molecules were later identified (FIG. 2). First, the PEGylation reaction was loaded onto a DEAE Sepharose column equilibrated in a buffer with low conductivity and higher pH (10 mM TRIS.HCl pH 8.5) to enhance binding of all 400MA PEG-htCBS C15S species and ran on a shallow salt gradient (5%, 10-110 mM NaCl) to elute the protein. FIG. 2 shows a chromatogram of such a run and the recovery of two pools, which were subsequently analyzed along with an unmodified htCBS C15S and 400MA PEG-htCBS C15S reaction mixture on SDS-PAGE and native PAGE. Gel analysis of the pools provided evidence that the 400MA PEG-htCBS C15S consisted of at least 3 different PEG-htCBS C15S species.

Pool 1 (P1) was enriched in forms which had a weaker negative charge (FIG. 2) and more PEG moieties attached than those recovered in pool 2 (P2). The predominant 400MA PEG-htCBS C15S conjugate in P1 consisted of a dimeric htCBS C15S, where each protein was modified with ME-400MA to the same extent, most likely 2 PEGs per CBS dimer (homoPEGylated dimer). Moreover, P1 contained a minor 400MA PEG-htCBS C15S species with an additional 1 or 2 PEG moieties. On the other hand, the major 400MA PEG-htCBS C15S form of P2 contained a dimeric enzyme, where just one of the proteins was modified with PEG, i.e. 1 PEG per CBS dimer (hemiPEGylated dimer). Separation of individual 400MA PEG-htCBS C15S species enabled the identification of the sites of maleimide PEGylation using LC-MS.

Figure 3A:
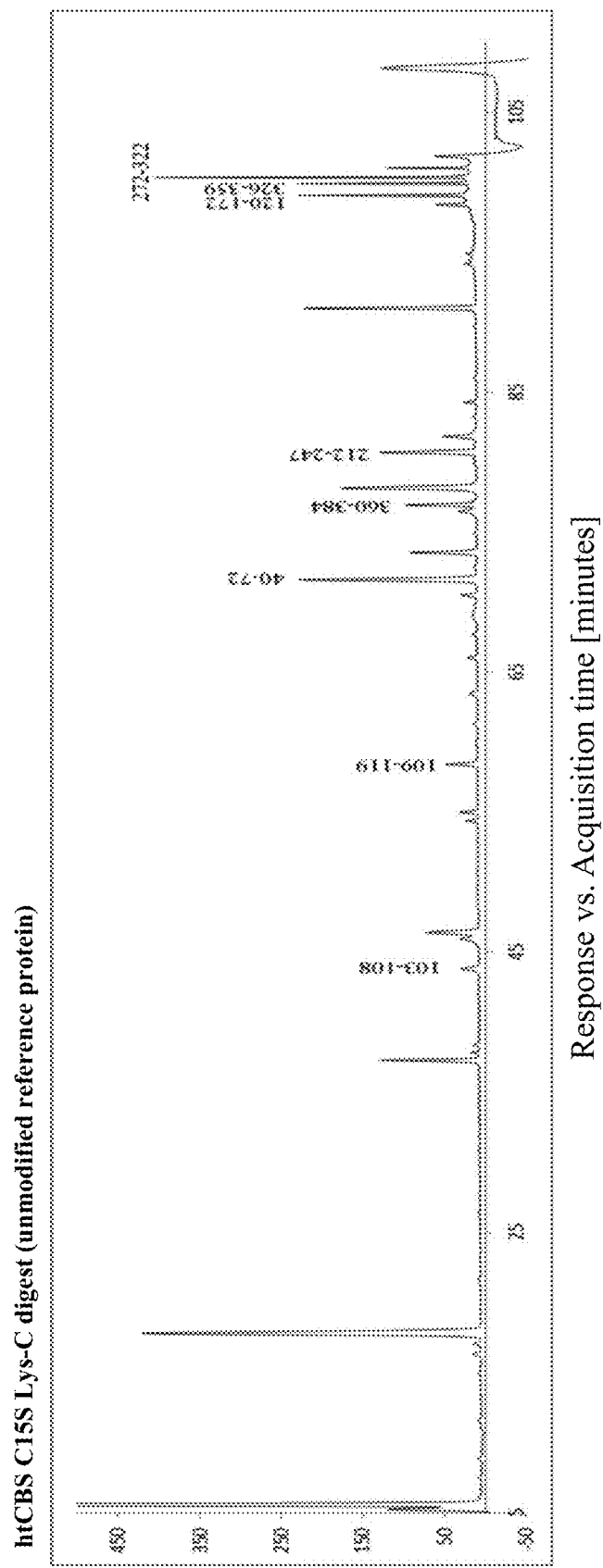
FIG. 3A-3C show maleimide PEGylation mapping using a Lys-C digest. These figures show reduced alkylated LC-MS peptide maps after a Lys-C digest of unmodified htCBS C15S as a reference (FIG. 3A), homoPEGylated 400MA PEG-htCBS C15S (P1) (FIG. 3B), and hemiPEGylated 400MA PEG-htCBS C15S (P2) (FIG. 3C) proteins.
Figure 3B:
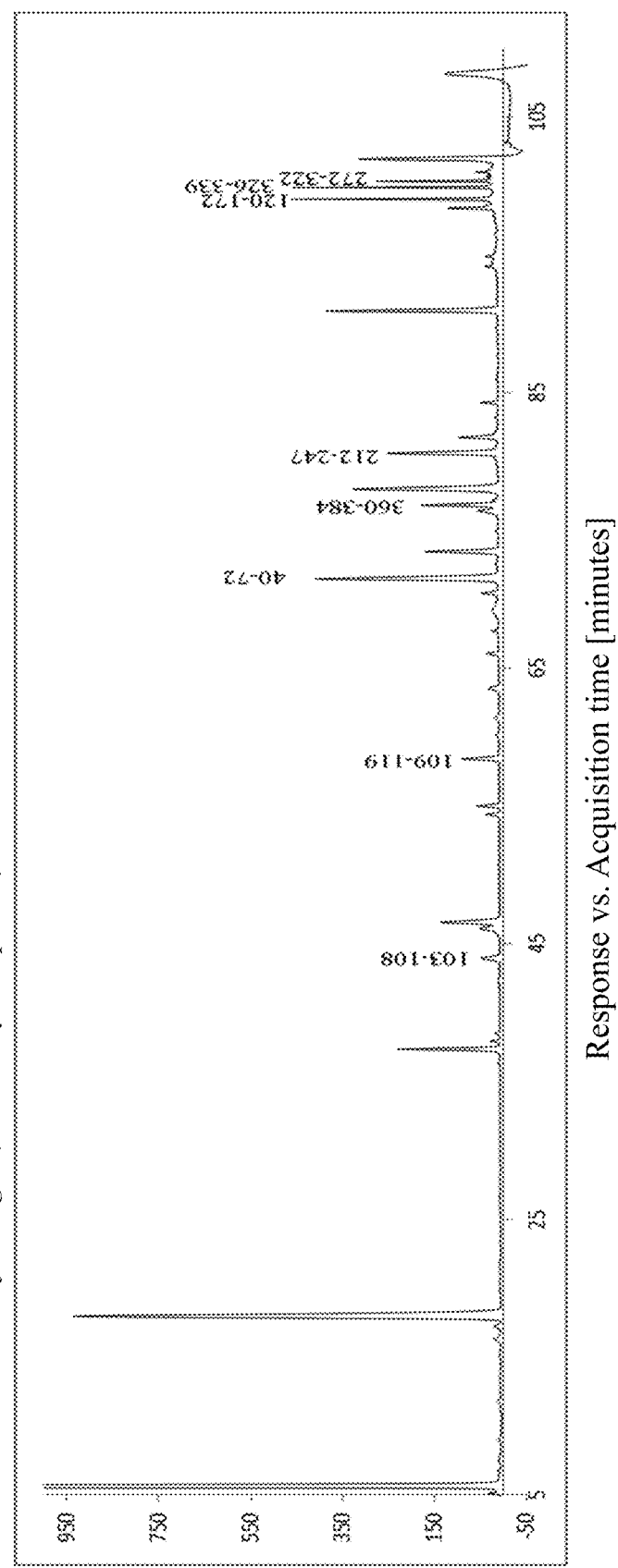
Figure 3C:
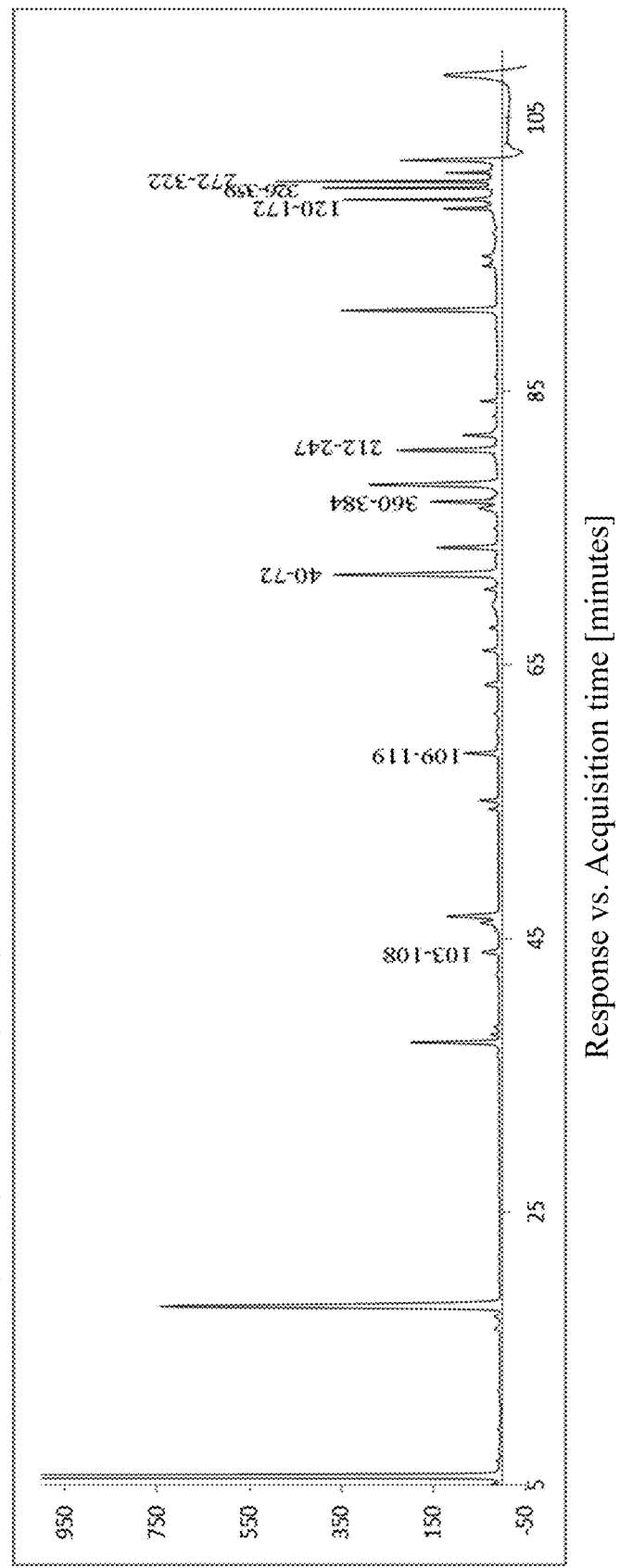

For phase I, the unmodified htCBS C15S, P1 and P2 were digested with Lys-C. Results of LC-MS are shown in FIG. 3A, FIG. 3B, and FIG. 3C. Out of eight cysteine-containing peptides identified from the reduced/alkylated LC-MS peptide map, seven such peptides yielded similar relative abundances in all three samples indicating that these peptides were unlikely to have been PEGylated. Only one peptide (272-322; SEQ ID NO: 31) containing two cysteine residues (C272 and C275) showed a significant decrease in each of the two 400MA PEG-htCBS C15S species (P1 and P2).

Figure 4A:
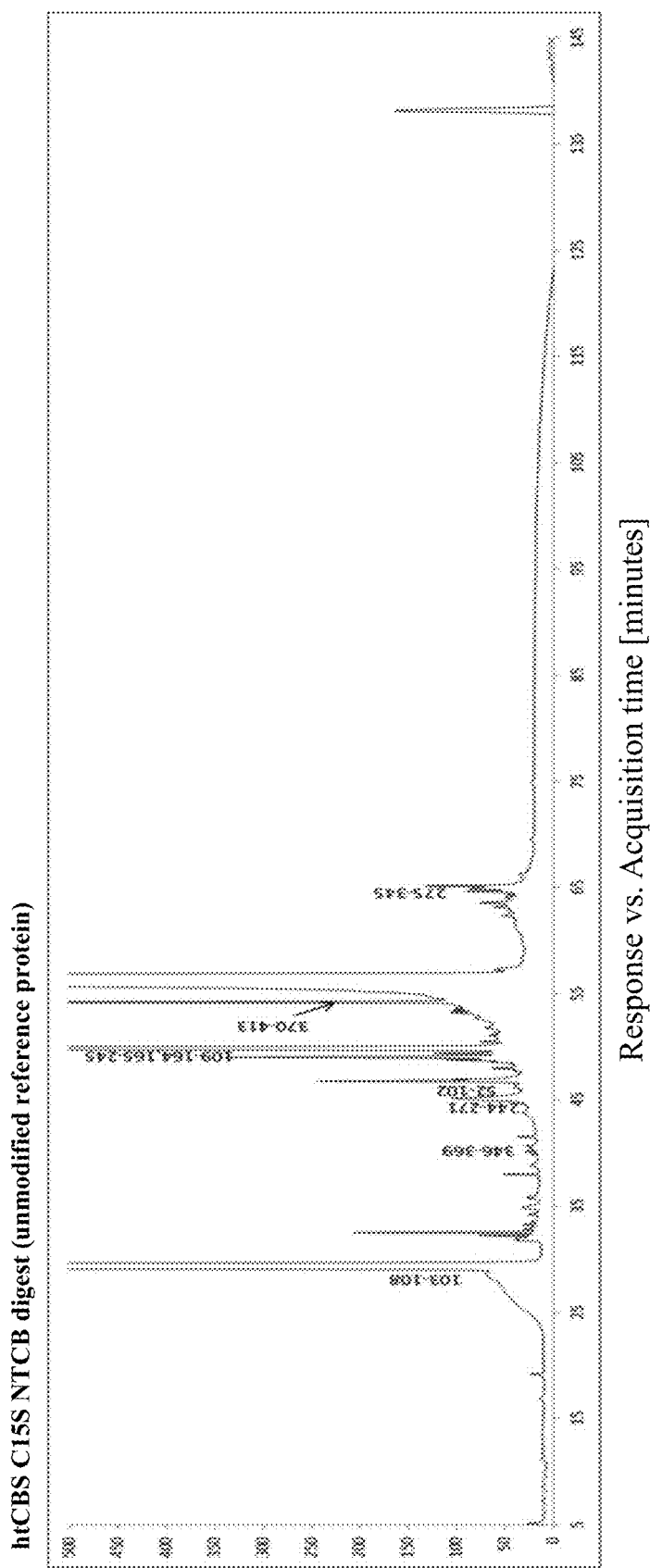
FIG. 4A-4C show maleimide PEGylation mapping using a NTCB digest. These figures show LC-MS peptide maps after NTCB treatment of unmodified htCBS C15S as a reference (FIG. 4A), homoPEGylated 400MA PEG-htCBS C15S (P) (FIG. 4B), and hemiPEGylated 400MA PEG-htCBS C15S (P2) (FIG. 4C) protein samples.
Figure 4B:
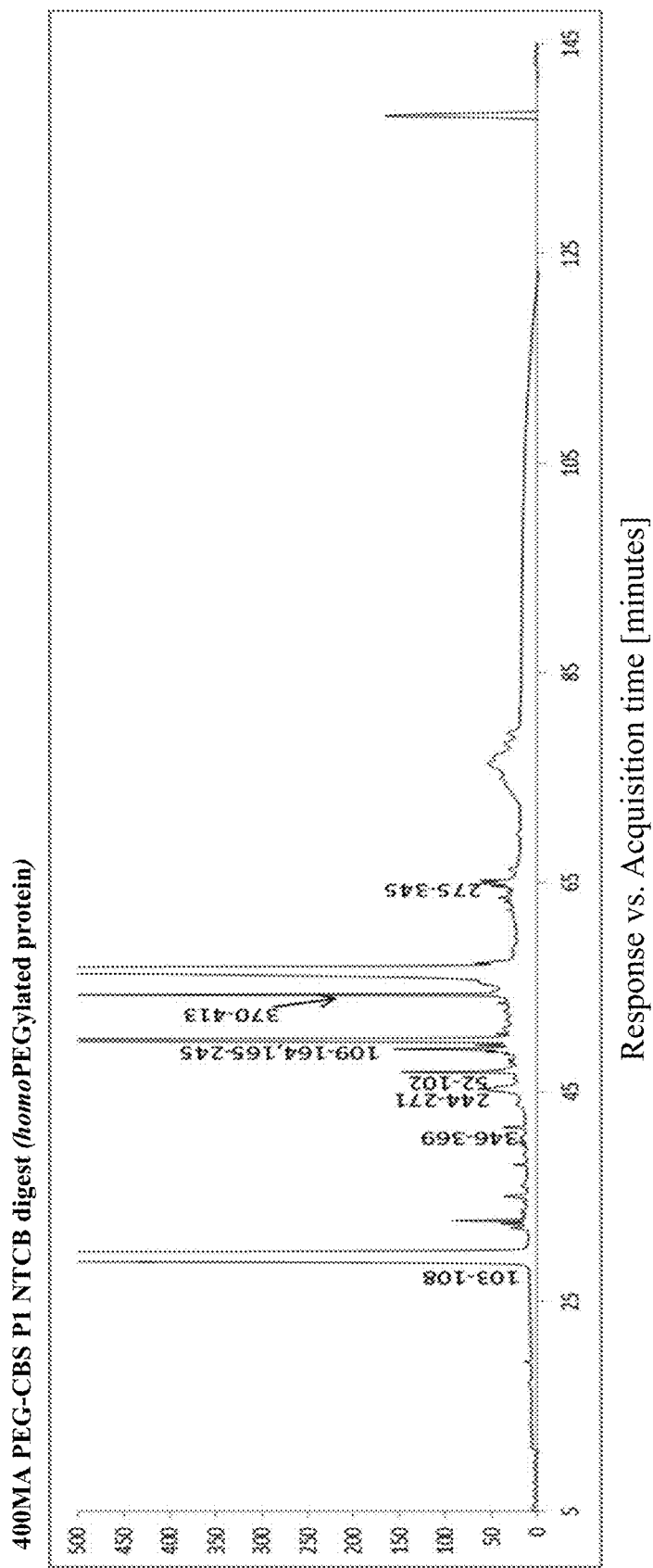
Figure 4C:
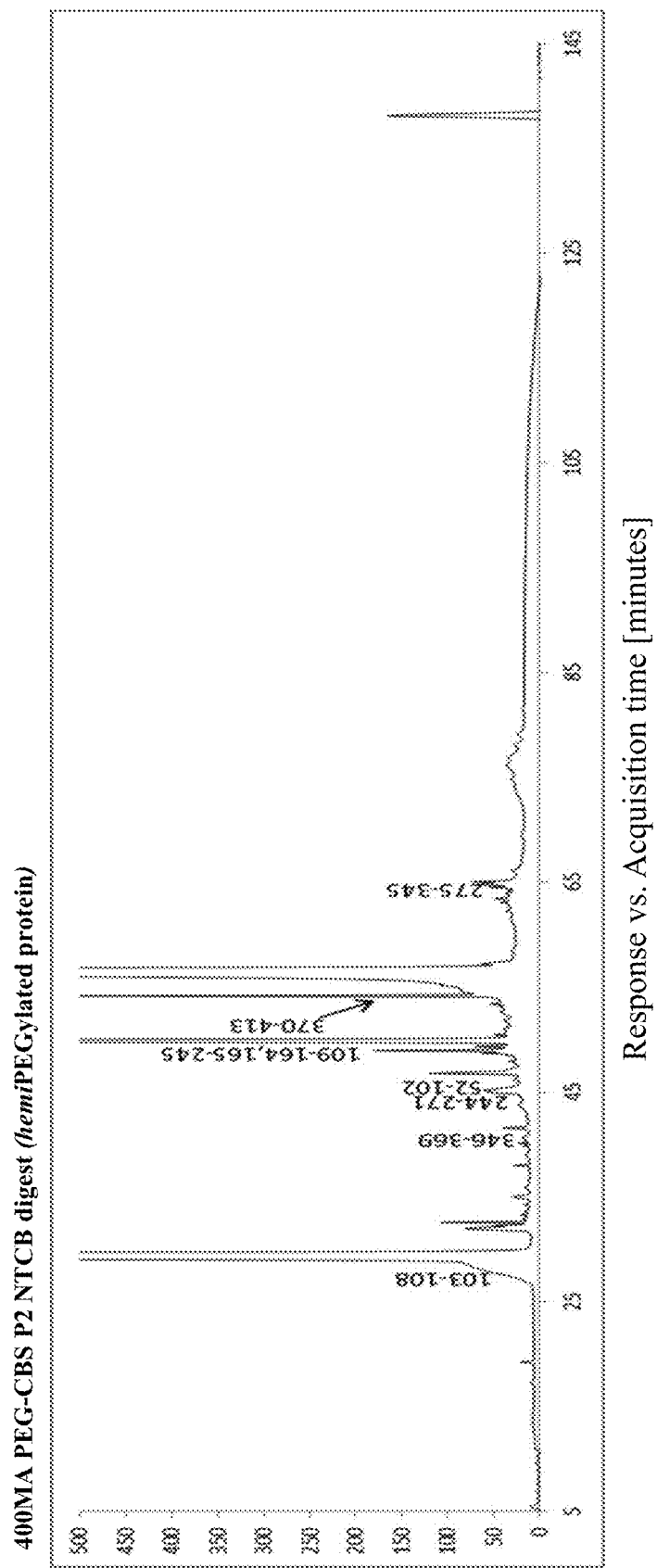

To further differentiate whether C272 and/or C275 were modified in phase II, the two residues would need to be separated into different peptides. Reagent NTCB cleaves N-terminally to a free cysteine residue. Results of LC-MS of an unmodified reference, homoPEGylated, and hemiPEGylated proteins are shown in FIG. 4A. FIG. 4B, and FIG. 4C.

Only one peptide (244-271; SEQ ID NO: 32) showed a significant decrease in 400MA PEG-htCBS C15S forms (more in P1 than for P2) compared to similarly treated unmodified htCBS C15S. The yield for the 244-271 peptide was lowered in the homoPEGylated 400MA PEG-htCBS C15S P1 sample and to a lesser extent in the hemiPEGylated 400MA PEG-htCBS C15S P2.

The peptide recovery signifies that C272 is blocked, thus the lower yield of the 244-271 peptide in 400MA PEG-htCBS C15S forms signifies that C272 is the primary site for maleimide PEGylation. It is possible that both cysteine residues C272 and C275 are involved in the PEGylation of higher molecular weight species present in the low abundance in P1. Low NTCB digestion efficiency resulted in low abundance of the recovered peptides.

Example 3. Reproducibility of PEGylation of htCBS C15S with NHS Ester PEG Molecules The issues with reproducibility of htCBS C15S PEGylation with maleimide PEGs led to analysis of other PEGylation chemistries, particularly the use of NHS ester-activated PEGs. First, modification of htCBS C15S was assessed with three NHS ester PEG molecules to determine their impact on enzyme activity. Four, three and two different PEG:CBS molar ratios were tested in PEGylations with 5, 10 and 20 kDa linear NHS ester PEG molecules, respectively. Unlike the site-selective maleimide PEGylation, the NHS ester PEG molecules yielded a reproducible mixture of highly modified isomers that were practically inseparable using SDS-PAGE as well as by native PAGE or SEC-HPLC.

For example, htCBS C15S modified by three linear 5, 10, and 20 kDa NHS ester PEG molecules (5NHS, 10NHS, and 20NHS) in different molar excesses of PEG molecules to the CBS protein were separated on SDS-PAGE (BIORAD® 10% Mini-PROTEAN® TGX gel) or native PAGE (BIO-RAD® 4-15% Mini-PROTEAN® TGX gel) and stained with Safe Stain (Invitrogen) per manufacturer's recommendation. Partial separation was achieved only using NR-CE (FIG. 1), which served as a method for "fingerprinting" of the 20NHS PEG-htCBS C15S production batches.

Figure 5:
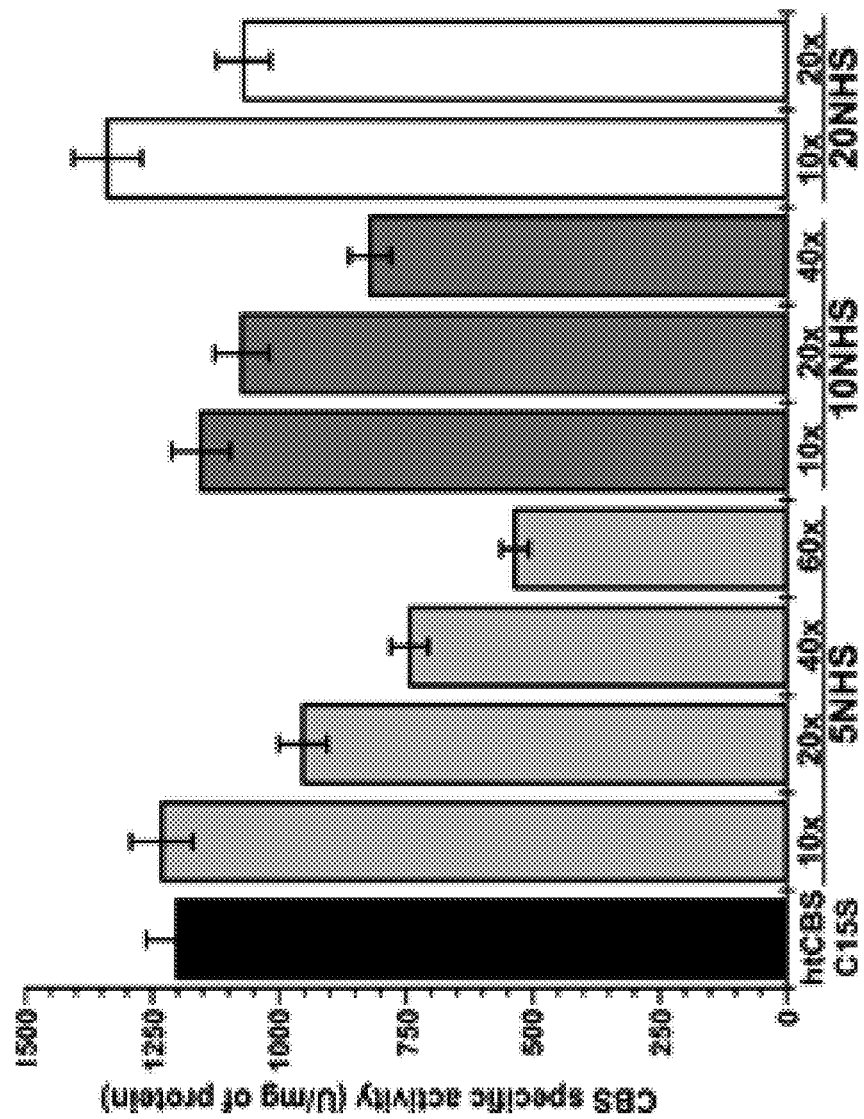
FIG. 5 shows CBS specific activity of various NHS PEG-htCBS C15S conjugates compared to unmodified htCBS C15S. Bars represent the average from 3 separate measurements and error bars designate standard error of the means (SEMs).

While a 10-20-fold molar excess of PEG molecules to the CBS protein yielded NHS PEG-htCBS C15S species with only a slight effect on CBS activity, higher excess of PEG, such as 40- and 60-fold for 5 kDa and 40-fold for 10 kDa NHS PEG, resulted in a markedly reduced activity of the respective NHS PEG-htCBS C15S conjugates (FIG. 5). Thus, conjugation of htCBS C15S with either NHS PEG molecules in a PEGylation reaction with no more than 20-fold PEG:CBS molar excess yielded highly modified, bulky NHS PEG-htCBS C15S conjugates with essentially fully retained activity. PEGylation of htCBS C15S with lysine-targeting 5, 10 or 20 kDa NHS ester PEGs used in up to a 20-fold molar excess to htCBS C15S protein did not significantly affect the enzyme's specific activity (FIG. 5), a property shared with the maleimide PEGs (maleimide PEGylation data shown in Bublil et al., *J Clin Invest* 2016, 126, (6), 2372-84 and International application PCT/2016/061050, which are hereby incorporated by reference in their entireties).

PEGylation of htCBS C15S with 20NHS ester PEG molecules showed reproducibility. Similarly, as done for the maleimide PEGs, the reproducibility of htCBS C15S PEGylation with 20NHS PEG (10-fold PEG:CBS molar excess) was assessed. Initial batches had a highly variable extent of PEGylation (data not shown). However, the main culprit of variability was identified as the residual ammonium sulfate in unmodified htCBS C15S. An extensive buffer exchange scheme was employed at the end of the chromatographic purification (15-20 diavolumes) to formulate the enzyme into the pre-PEGylation buffer, which resulted in a reproducible PEGylating pattern.

Four batches of purified unmodified htCBS C15S were PEGylated with 20NHS PEG molecules yielding four 20NHS PEG-htCBS C15S conjugates. The respective 4 pairs of unmodified enzyme (pre) and 20NHS PEG-htCBS C15S conjugate (post) were designated as LAB, 10L, TR1 and TR2. The protein samples were resolved in SDS-PAGE (BIORAD® 10% Mini-PROTEAN® TGX gel) or native PAGE (BIORAD® 4-15% Mini-PROTEAN® TGX gel) and stained with Safe Stain (Invitrogen) per manufacturer's recommendation or iodine stained to detect PEG. Unmodified htCBS C15S and free unreacted PEG molecules were also observed.

Compared to all the previous PEG-htCBS C15S conjugates, the 20NHS PEG-htCBS C15S showed increased viscosity (data not shown) and thus there was a concern of sufficient free, unreacted PEG molecule removal during the final (post PEGylation) buffer exchange. Indeed, processing of the initial batches (for example LAB and 10L) yielded a large amount of unreacted PEG molecules carried over to the final product. Corrective measures, which included removal of 20% DMSO from the mixture, higher MWCO membrane cartridge for TFF unit (100 versus 30 kDa), 3-fold larger surface area and 2-fold dilution of the PEGylation mixture prior buffer exchange, all helped to reduce the viscosity and assisted in better clearance of free PEG molecules during the final formulation (TR1 and TR2).

Example 4. Characterizing the Extent of PEGylation Using NHS Ester PEG Molecules SDS and native PAGE were not observed to sufficiently resolve individual 20NHS PEG-htCBS C15S species. Two additional methods were developed for characterization of the extent to which the htCBS C15S was modified with 20NHS PEG molecules allowing for a quick assessment of PEGylation in production and providing a definition of acceptance criteria for the product (FIG. 1).

One method relied on comparison of SEC-HPLC chromatographic profiles of individual 20NHS PEG-htCBS C15S batches compared with that of unmodified htCBS C15S as shown in Table 1.

TABLE 1

UV 225 nm Absorbance [AU] values for different batches

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 0.00 | 2.30E−05 | 2.00E−06 | 1.00E−05 | 1.00E−06 | 1.30E−05 | 8.00E−06 | −1.20E−05 | −3.30E−05 | −1.00E−06 | 1.00E−05 |
| 0.02 | 2.70E−05 | 4.00E−06 | 5.00E−06 | 2.00E−06 | 4.00E−06 | −1.20E−05 | 1.00E−06 | −1.50E−05 | −3.20E−05 | 6.00E−06 |
| 0.03 | 2.10E−05 | −1.00E−06 | 1.80E−05 | 6.00E−06 | 1.80E−05 | 5.00E−06 | −1.60E−05 | −2.30E−05 | −1.30E−05 | 1.50E−05 |
| 0.05 | 1.40E−05 | −6.00E−06 | 1.50E−05 | 4.00E−06 | 5.00E−06 | 5.00E−06 | −6.00E−06 | −1.50E−05 | −2.40E−05 | 6.00E−06 |
| 0.07 | 1.20E−05 | 1.60E−05 | 3.30E−05 | 8.00E−06 | 5.00E−06 | 8.00E−06 | 3.00E−06 | −2.10E−05 | −1.80E−05 | 6.00E−06 |
| 0.08 | 1.20E−05 | 1.20E−05 | 7.00E−06 | 4.00E−06 | −5.00E−06 | 1.40E−05 | 6.00E−06 | 6.00E−06 | −7.00E−06 | 4.00E−06 |
| 0.10 | 1.30E−05 | −8.00E−06 | 1.70E−05 | 1.20E−05 | 7.00E−06 | −1.00E−06 | 1.00E−06 | −1.50E−05 | −2.30E−05 | 6.00E−06 |
| 0.12 | 3.10E−05 | 1.30E−05 | 4.00E−06 | 1.00E−06 | 1.50E−05 | 8.00E−06 | 2.00E−06 | 5.00E−06 | −1.30E−05 | 1.00E−05 |
| 0.13 | 2.70E−05 | 4.00E−06 | 1.00E−05 | 2.70E−05 | 1.40E−05 | 1.80E−05 | 1.20E−05 | −6.00E−06 | −2.50E−05 | 1.10E−05 |
| 0.15 | 2.20E−05 | 1.00E−06 | 2.40E−05 | 1.30E−05 | −1.00E−06 | 2.30E−05 | 2.00E−06 | 0.00E+00 | −1.80E−05 | 7.00E−06 |
| 0.17 | 1.60E−05 | 1.40E−05 | 1.20E−05 | 2.20E−05 | 1.20E−05 | 1.00E−06 | −3.00E−06 | 5.00E−06 | −1.20E−05 | 1.80E−05 |
| 0.18 | 1.10E−05 | −4.00E−06 | 1.30E−05 | 1.00E−05 | −1.00E−06 | −3.00E−06 | 3.00E−06 | 6.00E−06 | −1.80E−05 | 1.50E−05 |
| 0.20 | 1.40E−05 | 2.00E−06 | 1.50E−05 | 3.00E−06 | 1.60E−05 | 1.60E−05 | −8.00E−06 | 1.20E−05 | −2.30E−05 | 1.80E−05 |
| 0.22 | 2.10E−05 | 1.30E−05 | 1.00E−05 | 3.40E−05 | 1.00E−05 | 7.00E−06 | 0.00E+00 | 5.00E−06 | −2.70E−05 | 1.60E−05 |
| 0.23 | 1.70E−05 | 5.00E−06 | 8.00E−06 | 1.00E−06 | 1.00E−06 | 1.70E−05 | 1.10E−05 | 1.00E−06 | −2.30E−05 | 1.80E−05 |
| 0.25 | 1.70E−05 | 1.20E−05 | 2.50E−05 | 1.00E−05 | 6.00E−06 | 5.00E−06 | −1.30E−05 | −7.00E−06 | −3.20E−05 | 2.50E−05 |
| 0.27 | 8.00E−06 | −1.00E−06 | 2.70E−05 | 1.20E−05 | 1.40E−05 | 1.30E−05 | −1.20E−05 | −4.00E−06 | −2.70E−05 | 2.40E−05 |
| 0.28 | 2.20E−05 | 2.00E−06 | 8.00E−06 | 2.10E−05 | −3.00E−06 | 2.00E−06 | 7.00E−06 | 1.30E−05 | −2.80E−05 | 3.10E−05 |
| 0.30 | 2.60E−05 | −3.00E−06 | 1.80E−05 | 2.60E−05 | 5.00E−06 | 1.40E−05 | −6.00E−06 | 7.00E−06 | −3.10E−05 | 2.00E−05 |
| 0.32 | 1.70E−05 | 7.00E−06 | 2.40E−05 | −4.00E−06 | 5.00E−06 | 1.00E−05 | 2.00E−06 | −7.00E−06 | −3.10E−05 | 1.50E−05 |
| 0.33 | 1.40E−05 | 5.00E−06 | 2.20E−05 | 3.10E−05 | 1.30E−05 | 1.00E−05 | 2.00E−06 | 8.00E−06 | −3.00E−05 | 1.50E−05 |
| 0.35 | 1.50E−05 | 6.00E−06 | 1.10E−05 | 2.00E−06 | 6.00E−06 | 6.00E−06 | −5.00E−06 | 7.00E−06 | −1.80E−05 | 2.30E−05 |
| 0.37 | 8.00E−06 | 1.00E−06 | 4.00E−06 | 1.80E−05 | 0.00E+00 | 2.80E−05 | −3.00E−06 | 4.00E−06 | −3.80E−05 | 2.40E−05 |
| 0.38 | 2.00E−06 | 0.00E+00 | 4.40E−05 | 2.70E−05 | 1.00E−05 | 1.60E−05 | 2.00E−06 | 3.00E−06 | −3.40E−05 | 3.10E−05 |
| 0.40 | 1.00E−05 | 1.30E−05 | 4.00E−05 | 7.00E−06 | 4.00E−06 | 1.00E−06 | 1.10E−05 | 1.70E−05 | −3.50E−05 | 3.40E−05 |
| 0.42 | 1.40E−05 | −3.00E−06 | 1.80E−05 | 4.00E−06 | 5.00E−06 | 2.00E−05 | 1.00E−05 | 0.00E+00 | −3.40E−05 | 3.40E−05 |
| 0.43 | 6.00E−06 | −4.00E−06 | 2.20E−05 | 1.00E−05 | 1.60E−05 | 2.10E−05 | 5.00E−06 | −3.00E−06 | −3.80E−05 | 2.70E−05 |
| 0.45 | 1.00E−05 | −1.00E−05 | 1.80E−05 | 1.20E−05 | 3.30E−05 | 1.10E−05 | 1.10E−05 | −8.00E−06 | −2.60E−05 | 3.30E−05 |
| 0.47 | 6.00E−06 | −1.10E−05 | 2.00E−05 | 2.00E−06 | 0.00E+00 | 1.10E−05 | 2.40E−05 | −1.20E−05 | −2.80E−05 | 2.50E−05 |
| 0.48 | 1.20E−05 | 1.10E−05 | 2.00E−05 | 1.60E−05 | 2.20E−05 | 1.80E−05 | 6.00E−06 | −4.00E−06 | −3.00E−05 | 3.70E−05 |
| 0.50 | 6.00E−06 | 2.00E−06 | 2.10E−05 | 1.60E−05 | 4.00E−06 | 1.20E−05 | 3.20E−05 | −7.00E−06 | −3.30E−05 | 3.10E−05 |
| 0.52 | 3.20E−05 | 1.20E−05 | 1.70E−05 | 4.00E−06 | 0.00E+00 | 6.00E−06 | 1.00E−05 | −1.10E−05 | −3.50E−05 | 2.40E−05 |
| 0.53 | 1.50E−05 | 7.00E−06 | 2.50E−05 | 2.30E−05 | 4.00E−06 | 0.00E+00 | 2.30E−05 | 0.00E+00 | −3.30E−05 | 2.40E−05 |
| 0.55 | 1.10E−05 | 7.00E−06 | 2.80E−05 | 2.60E−05 | 4.00E−06 | 1.60E−05 | 3.60E−05 | −2.00E−05 | −4.00E−05 | 2.70E−05 |
| 0.57 | 8.00E−06 | −4.00E−06 | 5.20E−05 | 1.00E−05 | 3.00E−06 | 8.00E−06 | 1.50E−05 | −2.00E−05 | −2.10E−05 | 5.40E−05 |
| 0.58 | 1.50E−05 | 1.20E−05 | 3.00E−05 | 6.00E−06 | 1.00E−05 | 5.00E−06 | 1.80E−05 | −1.60E−05 | −2.50E−05 | 2.30E−05 |
| 0.60 | 1.20E−05 | 1.00E−05 | 4.50E−05 | 5.00E−06 | −2.00E−06 | 2.00E+05 | 2.30E−05 | −1.80E−05 | −1.30E−05 | 2.00E−05 |
| 0.62 | 2.00E−06 | 2.70E−05 | 3.50E−05 | 3.20E−05 | 7.00E−06 | 2.00E−05 | 3.10E−05 | −1.80E−05 | −3.20E−05 | 3.10E−05 |
| 0.63 | 1.40E−05 | −8.00E−06 | 4.30E−05 | 1.10E−05 | 1.40E−05 | 1.30E−05 | 2.80E−05 | −2.80E−05 | −3.80E−05 | 3.00E−05 |
| 0.65 | 7.00E−06 | −7.00E−06 | 3.80E−05 | 1.30E−05 | 3.00E−06 | 1.40E−05 | 2.60E−05 | −2.10E−05 | −3.10E−05 | 2.70E−05 |
| 0.67 | 1.00E−06 | −1.60E−05 | 4.20E−05 | 2.80E−05 | −1.00E−06 | 8.00E−06 | 2.10E−05 | −2.70E−05 | −1.70E−05 | 4.10E−05 |
| 0.68 | 2.30E−05 | 0.00E+00 | 3.80E−05 | 2.20E−05 | 4.00E−06 | 1.60E−05 | 2.40E−05 | −2.10E−05 | −2.30E−05 | 3.10E−05 |
| 0.70 | 1.50E−05 | −1.00E−06 | 3.30E−05 | 2.60E−05 | 3.00E−06 | 1.20E−05 | 2.80E−05 | −3.10E−05 | −3.40E−05 | 2.70E−05 |
| 0.72 | −1.00E−06 | −4.00E−06 | 2.00E−05 | 1.50E−05 | 1.10E−05 | 3.50E−05 | 1.50E−05 | −2.60E−05 | −3.20E−05 | 3.80E−05 |
| 0.73 | 7.00E−06 | 3.00E−06 | 4.00E−05 | 1.60E−05 | 1.40E−05 | 1.10E−05 | 3.20E−05 | −2.30E−05 | −2.30E−05 | 4.50E−05 |
| 0.75 | 1.80E−05 | 4.00E−06 | 4.50E−05 | 3.00E−05 | 1.30E−05 | 1.40E−05 | 2.80E−05 | −3.30E−05 | −1.50E−05 | 3.20E−05 |
| 0.77 | 1.60E−05 | 3.00E−06 | 3.40E−05 | 1.30E−05 | 1.00E−05 | 7.00E−06 | 4.00E−05 | −2.00E−05 | −3.80E−05 | 2.70E−05 |
| 0.78 | 3.10E−05 | −1.20E−05 | 3.60E−05 | 1.10E−05 | 5.00E−06 | 5.00E−06 | 3.70E−05 | −3.20E−05 | −2.80E−05 | 3.40E−05 |
| 0.80 | 5.00E−06 | −1.00E−05 | 3.60E−05 | 1.80E−05 | 6.00E−06 | 1.30E−05 | 2.40E−05 | −2.20E−05 | −2.10E−05 | 3.00E−05 |
| 0.82 | 8.00E−06 | −1.00E−05 | 3.10E−05 | 2.20E−05 | 1.00E−05 | 7.00E−06 | 2.70E−05 | −2.10E−05 | −3.10E−05 | 4.30E−05 |
| 0.83 | 3.80E−05 | −1.00E−06 | 3.70E−05 | 2.30E−05 | 3.00E−06 | 1.10E−05 | 3.40E−05 | −3.00E−05 | −3.50E−05 | 2.40E−05 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 0.85 | 1.60E−05 | 2.00E−06 | 5.10E−05 | 2.20E−05 | 1.50E−05 | 2.20E−05 | 2.50E−05 | −2.80E−05 | −2.80E−05 | 4.00E−05 |
| 0.87 | 4.00E−06 | 1.00E−06 | 3.60E−05 | 1.40E−05 | 3.00E−06 | 1.40E−05 | 3.40E−05 | −3.70E−05 | −2.30E−05 | 4.80E−05 |
| 0.88 | 3.50E−05 | 7.00E−06 | 4.60E−05 | 3.80E−05 | 1.70E−05 | 1.20E−05 | 3.40E−05 | −3.00E−05 | −1.40E−05 | 3.70E−05 |
| 0.90 | 3.10E−05 | 6.00E−06 | 4.70E−05 | 2.60E−05 | 1.70E−05 | 5.00E−06 | 3.40E−05 | −3.60E−05 | −2.10E−05 | 3.30E−05 |
| 0.92 | 1.80E−05 | −1.10E−05 | 5.10E−05 | 2.20E−05 | 1.20E−05 | −2.00E−06 | 3.30E−05 | −2.50E−05 | −1.40E−05 | 3.40E−05 |
| 0.93 | 2.20E−05 | −7.00E−06 | 4.20E−05 | 2.00E−05 | 2.00E−05 | 1.60E−05 | 3.80E−05 | −2.50E−05 | −1.20E−05 | 7.50E−05 |
| 0.95 | 1.10E−05 | 2.00E−06 | 3.50E−05 | 2.10E−05 | 1.40E−05 | 4.00E−06 | 3.20E−05 | −2.80E−05 | −1.20E−05 | 4.20E−05 |
| 0.97 | 1.70E−05 | 4.00E−06 | 3.60E−05 | 4.60E−05 | −3.00E−06 | −1.00E−06 | 3.40E−05 | −4.40E−05 | −1.50E−05 | 4.20E−05 |
| 0.98 | 1.50E−05 | 1.20E−05 | 5.50E−05 | 3.30E−05 | 1.60E−05 | 2.50E−05 | 3.80E−05 | −3.60E−05 | −1.00E−06 | 4.50E−05 |
| 1.00 | 1.30E−05 | 7.00E−06 | 5.10E−05 | 3.50E−05 | 1.60E−05 | 3.60E−05 | 4.00E−05 | −3.80E−05 | −2.00E−05 | 3.80E−05 |
| 1.02 | 6.00E−06 | −1.00E−06 | 3.40E−05 | 3.00E−05 | 6.00E−06 | 7.00E−06 | 3.40E−05 | −5.00E−06 | −1.50E−05 | 2.60E−05 |
| 1.03 | 1.30E−05 | 2.00E−06 | 3.70E−05 | 5.20E−05 | 1.30E−05 | 2.00E−05 | 3.50E−05 | −4.30E−05 | −3.00E−06 | 2.10E−05 |
| 1.05 | 1.60E−05 | −5.00E−06 | 4.60E−05 | 2.60E−05 | 1.20E−05 | 1.40E−05 | 5.40E−05 | −3.40E−05 | −2.10E−05 | 4.10E−05 |
| 1.07 | 2.20E−05 | −1.00E−06 | 4.20E−05 | 3.10E−05 | 1.30E−05 | 8.00E−06 | 4.50E−05 | −3.60E−05 | −2.40E−05 | 4.40E−05 |
| 1.08 | 3.20E−05 | −1.00E−05 | 3.50E−05 | 4.50E−05 | 1.20E−05 | 4.00E−06 | 4.60E−05 | −4.30E−05 | −1.80E−05 | 3.70E−05 |
| 1.10 | 2.10E−05 | −1.10E−05 | 2.80E−05 | 3.00E−05 | 2.60E−05 | 8.00E−06 | 4.10E−05 | −4.00E−05 | −1.50E−05 | 2.80E−05 |
| 1.12 | 2.70E−05 | 2.00E−06 | 5.40E−05 | 2.40E−05 | 3.00E−06 | 1.10E−05 | 6.10E−05 | −3.20E−05 | −2.50E−05 | 3.60E−05 |
| 1.13 | 8.00E−06 | −1.10E−05 | 4.30E−05 | 3.60E−05 | 6.00E−06 | 1.20E−05 | 4.10E−05 | −3.60E−05 | −2.10E−05 | 2.30E−05 |
| 1.15 | 3.00E−05 | −1.20E−05 | 5.40E−05 | 2.70E−05 | 2.50E−05 | 1.80E−05 | 4.00E−05 | −4.20E−05 | −3.50E−05 | 2.80E−05 |
| 1.17 | 2.60E−05 | 3.00E−06 | 6.30E−05 | 2.20E−05 | 2.60E−05 | 1.40E−05 | 4.20E−05 | −3.60E−05 | −2.70E−05 | 3.40E−05 |
| 1.18 | 3.00E−05 | 8.00E−06 | 3.70E−05 | 2.30E−05 | 1.40E−05 | 1.50E−05 | 5.10E−05 | −4.50E−05 | −3.60E−05 | 4.20E−05 |
| 1.20 | 2.60E−05 | −2.00E−06 | 4.40E−05 | 2.10E−05 | 2.00E−05 | 2.00E−05 | 4.10E−05 | −4.10E−05 | −2.50E−05 | 3.00E−05 |
| 1.22 | 1.70E−05 | 1.00E−06 | 5.50E−05 | 3.10E−05 | 6.00E−06 | 5.00E−06 | 4.00E−05 | −2.30E−05 | −2.20E−05 | 3.40E−05 |
| 1.23 | 1.60E−05 | 7.00E−06 | 6.20E−05 | 2.60E−05 | 3.10E−05 | 4.00E−06 | 6.30E−05 | −3.80E−05 | −2.40E−05 | 2.80E−05 |
| 1.25 | −1.00E−06 | −1.10E−05 | 5.10E−05 | 3.10E−05 | 3.00E−06 | 1.60E−05 | 5.50E−05 | −3.80E−05 | −2.50E−05 | 3.10E−05 |
| 1.27 | 5.00E−06 | −1.00E−06 | 5.00E−05 | 3.00E−05 | 1.50E−05 | 2.20E−05 | 6.10E−05 | −3.40E−05 | −1.70E−05 | 2.60E−05 |
| 1.28 | 1.10E−05 | −1.10E−05 | 4.20E−05 | 1.20E−05 | 1.60E−05 | 1.40E−05 | 6.40E−05 | −3.60E−05 | −2.20E−05 | 3.00E−05 |
| 1.30 | 1.80E−05 | −3.00E−06 | 5.70E−05 | 2.10E−05 | 1.40E−05 | 1.20E−05 | 5.20E−05 | −3.10E−05 | −1.10E−05 | 3.00E−05 |
| 1.32 | 2.70E−05 | −1.00E−05 | 5.00E−05 | 2.10E−05 | 2.20E−05 | 1.50E−05 | 4.60E−05 | −2.00E−05 | −3.00E−05 | 3.40E−05 |
| 1.33 | 2.50E−05 | −7.00E−06 | 4.30E−05 | 3.10E−05 | 2.00E−05 | 1.20E−05 | 6.50E−05 | −3.40E−05 | −3.40E−05 | 2.10E−05 |
| 1.35 | 1.20E−05 | −1.00E−05 | 5.40E−05 | 2.30E−05 | 2.80E−05 | 1.80E−05 | 6.40E−05 | −2.00E−05 | −2.40E−05 | 2.30E−05 |
| 1.37 | 1.60E−05 | 2.00E−06 | 5.00E−05 | 2.30E−05 | 4.30E−05 | 0.00E−00 | 7.50E−05 | −4.20E−05 | −1.40E−05 | 2.40E−05 |
| 1.38 | 1.60E−05 | −3.00E−06 | 4.70E−05 | 1.40E−05 | 1.00E−05 | 1.20E−05 | 7.30E−05 | −3.50E−05 | −2.00E−05 | 2.70E−05 |
| 1.40 | 2.80E−05 | 5.00E−06 | 5.00E−05 | 2.40E−05 | 1.70E−05 | 3.30E−05 | 7.00E−05 | −3.10E−05 | −1.60E−05 | 4.00E−05 |
| 1.42 | 8.00E−06 | 3.00E−06 | 5.20E−05 | 1.20E−05 | 2.30E−05 | 2.00E−05 | 7.10E−05 | −4.50E−05 | −2.30E−05 | 3.50E−05 |
| 1.43 | 2.60E−05 | 6.00E−06 | 6.30E−05 | 3.00E−06 | 2.40E−05 | 2.80E−05 | 6.50E−05 | −4.10E−05 | −1.80E−05 | 2.40E−05 |
| 1.45 | 3.70E−05 | −4.00E−06 | 4.60E−05 | 2.60E−05 | 2.20E−05 | 2.30E−05 | 7.20E−05 | −1.80E−05 | −3.30E−05 | 2.60E−05 |
| 1.47 | 1.70E−05 | −1.10E−05 | 5.50E−05 | 1.70E−05 | 2.50E−05 | 1.10E−05 | 6.30E−05 | −3.00E−05 | −2.10E−05 | 2.80E−05 |
| 1.48 | 1.80E−05 | 2.10E−05 | 6.60E−05 | 2.60E−05 | 2.80E−05 | 3.70E−05 | 6.60E−05 | −4.30E−05 | −1.30E−05 | 1.20E−05 |
| 1.50 | 3.50E−05 | 0.00E+00 | 5.30E−05 | 2.30E−05 | 2.70E−05 | 2.40E−05 | 5.40E−05 | −3.30E−05 | −8.00E−06 | 3.50E−05 |
| 1.52 | 2.80E−05 | 1.10E−05 | 6.10E−05 | 1.70E−05 | 2.20E−05 | 4.50E−05 | 7.30E−05 | −3.40E−05 | −3.10E−05 | 3.20E−05 |
| 1.53 | 2.80E−05 | 1.00E−06 | 5.70E−05 | 8.00E−06 | 2.10E−05 | 4.30E−05 | 4.30E−05 | −4.50E−05 | −1.30E−05 | 2.40E−05 |
| 1.55 | 1.80E−05 | 1.00E−06 | 4.50E−05 | 1.50E−05 | 1.80E−05 | 4.60E−05 | 5.20E−05 | −2.40E−05 | −3.50E−05 | 3.70E−05 |
| 1.57 | 6.00E−06 | 1.00E−06 | 5.10E−05 | 1.70E−05 | 1.10E−05 | 5.20E−05 | 4.40E−05 | −2.40E−05 | −1.00E−05 | 1.00E−05 |
| 1.58 | 4.30E−06 | 2.00E−06 | 6.60E−05 | 1.80E−05 | 1.80E−05 | 4.40E−05 | 3.50E−05 | −4.10E−05 | −1.70E−05 | 3.20E−05 |
| 1.60 | 3.70E−05 | 1.00E−06 | 5.20E−05 | 5.00E−06 | 2.30E−05 | 5.00E−05 | 4.60E−05 | −2.80E−05 | −1.70E−05 | 2.80E−05 |
| 1.62 | 1.70E−05 | 7.00E−06 | 5.20E−05 | 6.00E−06 | 1.50E−05 | 5.10E−05 | 4.10E−05 | −3.70E−05 | −3.00E−06 | 1.40E−05 |
| 1.63 | 3.50E−05 | 1.40E−05 | 4.50E−05 | 7.00E−06 | 4.10E−05 | 5.30E−05 | 3.40E−05 | −3.80E−05 | −1.00E−05 | 3.50E−05 |
| 1.65 | 2.20E−05 | 4.00E−06 | 4.40E−05 | 1.40E−05 | 2.60E−05 | 5.10E−05 | 4.70E−05 | −5.00E−05 | −2.10E−05 | 1.30E−05 |
| 1.67 | 1.20E−05 | 2.10E−05 | 5.50E−05 | 2.40E−05 | 2.00E−05 | 4.60E−05 | 4.10E−05 | −3.10E−05 | −2.10E−05 | 2.10E−05 |
| 1.68 | 2.30E−05 | 1.40E−05 | 5.20E−05 | 4.00E−06 | 4.00E−05 | 7.60E−05 | 3.70E−05 | −2.80E−05 | −6.00E−06 | 3.10E−05 |
| 1.70 | 3.00E−06 | 1.80E−05 | 4.50E−05 | 1.70E−05 | 1.60E−05 | 5.30E−05 | 3.80E−05 | −2.50E−05 | −1.80E−05 | 1.50E−05 |
| 1.72 | 1.70E−05 | 1.70E−05 | 5.00E−05 | 2.10E−05 | 1.60E−05 | 6.10E−05 | 4.00E−05 | −3.40E−05 | −1.40E−05 | 1.30E−05 |
| 1.73 | 3.50E−05 | 8.00E−06 | 5.60E−05 | 1.30E−05 | 3.00E−05 | 5.00E−05 | 4.70E−05 | −3.60E−05 | −2.20E−05 | 7.00E−06 |
| 1.75 | 2.60E−05 | 7.00E−06 | 5.00E−05 | 2.00E−05 | 1.30E−05 | 5.70E−05 | 4.10E−05 | −3.20E−05 | −1.00E−05 | 2.50E−05 |
| 1.77 | 1.70E−05 | 1.10E−05 | 5.00E−05 | 2.40E−05 | 3.00E−05 | 5.60E−05 | 2.10E−05 | −3.40E−05 | −2.00E−05 | 7.00E−06 |
| 1.78 | 3.10E−05 | 8.00E−06 | 4.60E−05 | 2.40E−05 | 3.40E−05 | 4.20E−05 | 3.50E−05 | −3.00E−05 | −3.10E−05 | 7.00E−06 |
| 1.80 | 4.00E−05 | 1.10E−05 | 4.50E−05 | 3.70E−05 | 4.00E−05 | 4.30E−05 | 3.20E−05 | −3.40E−05 | −3.10E−05 | 2.70E−05 |
| 1.82 | 1.80E−05 | 1.10E−05 | 4.00E−05 | 1.70E−05 | 2.60E−05 | 6.00E−05 | 4.00E−05 | −2.20E−05 | −2.70E−06 | 3.30E−05 |
| 1.83 | 7.00E−06 | 1.30E−05 | 5.30E−05 | 2.00E−05 | 1.30E−05 | 4.80E−05 | 4.60E−05 | −4.10E−05 | −5.00E−06 | 1.80E−05 |
| 1.85 | 2.10E−05 | 1.40E−05 | 6.10E−05 | 1.70E−05 | 1.70E−05 | 4.10E−05 | 5.50E−05 | −4.00E−05 | −6.00E−06 | 1.70E−05 |
| 1.87 | 1.80E−05 | 1.80E−05 | 4.60E−05 | 2.70E−05 | 3.50E−05 | 3.60E−05 | 4.00E−05 | −2.60E−05 | −1.20E−05 | 2.10E−05 |
| 1.88 | 4.30E−05 | 2.50E−05 | 4.30E−05 | 1.80E−05 | 2.70E−05 | 5.00E−05 | 2.70E−05 | −5.30E−05 | −2.30E−05 | 3.10E−05 |
| 1.90 | 5.00E−05 | 2.20E−05 | 4.50E−05 | 2.40E−05 | 3.20E−05 | 5.50E−05 | 4.00E−05 | −3.70E−05 | −1.80E−05 | 1.30E−05 |
| 1.92 | 2.20E−05 | 1.70E−05 | 6.10E−05 | 2.40E−05 | 2.50E−05 | 4.60E−05 | 2.50E−05 | −2.70E−05 | −1.80E−05 | 2.60E−05 |
| 1.93 | 3.10E−05 | 2.50E−05 | 6.70E−05 | 2.80E−05 | 2.60E−05 | 4.10E−05 | 2.80E−05 | −4.00E−05 | −2.50E−05 | 3.00E−05 |
| 1.95 | 2.70E−05 | 1.70E−05 | 6.30E−05 | 3.60E−05 | 2.50E−05 | 2.40E−05 | 3.00E−05 | −4.70E−05 | −2.80E−05 | 1.80E−05 |
| 1.97 | 2.40E−05 | 1.60E−05 | 4.60E−05 | 2.50E−05 | 2.70E−05 | 3.70E−05 | 1.80E−05 | −4.20E−05 | −3.00E−05 | 1.80E−05 |
| 1.98 | 3.20E−05 | 1.80E−05 | 3.30E−05 | 1.20E−05 | 1.80E−05 | 4.50E−05 | 4.00E−05 | −4.60E−05 | −1.10E−05 | 5.00E−05 |
| 2.00 | 3.10E−05 | 2.30E−05 | 5.10E−05 | 1.80E−05 | 2.30E−05 | 4.10E−05 | 3.60E−05 | −4.00E−05 | −1.20E−05 | 2.40E−05 |
| 2.02 | 2.70E−05 | 2.30E−05 | 4.10E−05 | 2.20E−05 | 1.70E−05 | 5.10E−05 | 2.40E−05 | −3.30E−05 | −1.60E−05 | 3.60E−05 |
| 2.03 | 2.30E−05 | 2.00E−05 | 5.00E−05 | 2.00E−05 | 2.30E−05 | 5.10E−05 | 2.60E−05 | −4.30E−05 | −6.00E−06 | 3.20E−05 |
| 2.05 | 1.20E−05 | 2.20E−05 | 3.00E−05 | 2.80E−05 | 2.30E−05 | 4.70E−05 | 3.60E−05 | −3.80E−05 | −1.70E−05 | 3.60E−05 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 2.07 | 2.70E−05 | 1.70E−05 | 5.00E−05 | 1.40E−05 | 2.60E−05 | 4.30E−05 | 3.80E−05 | −3.10E−05 | −2.70E−05 | 3.70E−05 |
| 2.08 | 2.20E−05 | 2.70E−05 | 5.00E−05 | 1.30E−05 | 2.30E−05 | 5.50E−05 | 2.10E−05 | −2.30E−05 | −1.20E−05 | 3.30E−05 |
| 2.10 | 3.50E−05 | 2.30E−05 | 5.20E−05 | 1.70E−05 | 3.30E−05 | 3.40E−05 | 3.40E−05 | −4.00E−05 | −2.50E−05 | 4.80E−05 |
| 2.12 | 2.20E−05 | 2.80E−05 | 3.80E−05 | 2.10E−05 | 2.40E−05 | 4.20E−05 | 2.50E−05 | −3.40E−05 | −2.50E−05 | 3.80E−05 |
| 2.13 | 1.70E−05 | 1.80E−05 | 5.30E−05 | 1.80E−05 | 2.40E−05 | 5.70E−05 | 2.10E−05 | −6.00E−05 | −2.30E−05 | 3.50E−05 |
| 2.15 | 2.20E−05 | 1.20E−05 | 5.40E−05 | 1.40E−05 | 2.80E−05 | 4.80E−05 | 2.50E−05 | −4.30E−05 | −1.60E−05 | 6.70E−05 |
| 2.17 | 3.40E−05 | 2.00E−05 | 4.60E−05 | 6.00E−06 | 2.80E−05 | 2.70E−05 | 2.00E−05 | −4.00E−05 | −1.10E−05 | 4.40E−05 |
| 2.18 | 3.20E−05 | 2.70E−05 | 6.10E−05 | 1.60E−05 | 2.70E−05 | 4.80E−05 | 3.20E−05 | −4.80E−05 | 2.00E−06 | 4.50E−05 |
| 2.20 | 2.30E−05 | 2.40E−05 | 5.30E−05 | 1.80E−05 | 2.80E−05 | 5.00E−05 | 1.80E−05 | −4.50E−05 | −1.40E−05 | 3.10E−05 |
| 2.22 | 1.20E−05 | 2.10E−05 | 3.80E−05 | 7.00E−06 | 2.60E−05 | 5.20E−05 | 2.70E−05 | −4.00E−05 | −1.80E−05 | 3.20E−05 |
| 2.23 | 1.80E−05 | 7.00E−06 | 3.30E−05 | −1.00E−06 | 4.70E−05 | 4.40E−05 | 2.10E−05 | −4.00E−05 | −2.80E−05 | 3.60E−05 |
| 2.25 | 2.60E−05 | 2.80E−05 | 4.20E−05 | −3.00E−06 | 3.20E−05 | 4.80E−05 | 2.40E−05 | −4.20E−05 | −1.70E−05 | 4.60E−05 |
| 2.27 | 2.50E−05 | 1.40E−05 | 5.00E−05 | 2.00E−05 | 3.20E−05 | 3.80E−05 | 5.00E−06 | −2.60E−05 | −1.50E−05 | 4.10E−05 |
| 2.28 | 2.40E−05 | 1.30E−05 | 4.30E−05 | 8.00E−06 | 8.00E−06 | 5.70E−05 | 2.00E−05 | −4.20E−05 | −6.00E−06 | 3.10E−05 |
| 2.30 | 3.20E−05 | 3.00E−05 | 4.60E−05 | −1.00E−06 | 3.40E−05 | 4.40E−05 | 2.30E−05 | −3.80E−05 | −2.60E−05 | 1.60E−05 |
| 2.32 | 2.60E−05 | 2.70E−05 | 3.00E−05 | 1.10E−05 | 4.10E−05 | 5.30E−05 | 1.60E−05 | −1.80E−05 | −1.60E−05 | 2.10E−05 |
| 2.33 | 1.60E−05 | 2.00E−05 | 4.00E−05 | 2.00E−05 | 3.40E−05 | 4.60E−05 | 2.20E−05 | −3.70E−05 | −1.30E−05 | 2.20E−05 |
| 2.35 | 1.80E−05 | 2.80E−05 | 3.80E−05 | 5.00E−06 | 3.60E−05 | 5.00E−05 | 2.40E−05 | −2.60E−05 | −2.10E−05 | 2.30E−05 |
| 2.37 | 2.50E−05 | 3.30E−05 | 3.80E−05 | 1.70E−05 | 3.70E−05 | 5.00E−05 | 2.50E−05 | −4.20E−05 | −8.00E−06 | 1.70E−05 |
| 2.38 | 3.20E−05 | 2.80E−05 | 4.00E−05 | 1.30E−05 | 4.60E−05 | 6.20E−05 | 2.50E−05 | −5.60E−05 | −2.50E−05 | 2.30E−05 |
| 2.40 | 2.40E−05 | 2.20E−05 | 4.50E−05 | 7.00E−06 | 4.00E−05 | 5.50E−05 | 3.50E−05 | −3.30E−05 | −2.00E−05 | 3.00E−05 |
| 2.42 | 1.60E−05 | 2.40E−05 | 4.80E−05 | −1.60E−05 | 3.10E−05 | 5.50E−05 | 2.50E−05 | −3.70E−05 | −6.00E−06 | 2.40E−05 |
| 2.43 | 4.00E−05 | 2.20E−05 | 3.30E−05 | 1.00E−05 | 3.00E−05 | 5.80E−05 | 1.70E−05 | −3.20E−05 | −1.60E−05 | 2.00E−05 |
| 2.45 | 3.00E−05 | 1.30E−05 | 4.70E−05 | 1.50E−05 | 2.40E−05 | 5.00E−05 | 3.70E−05 | −3.20E−05 | −7.00E−06 | 3.70E−05 |
| 2.47 | 2.80E−05 | 2.50E−05 | 3.80E−05 | 4.00E−06 | 5.20E−05 | 6.20E−05 | 3.40E−05 | −3.40E−05 | 0.00E+00 | 2.20E−05 |
| 2.48 | 1.70E−05 | 1.80E−05 | 4.50E−05 | 2.00E−05 | 3.80E−05 | 6.60E−05 | 1.80E−05 | −4.70E−05 | −1.30E−05 | 2.00E−05 |
| 2.50 | 1.80E−05 | 7.00E−06 | 3.30E−05 | 1.70E−05 | 3.80E−05 | 5.20E−05 | 2.50E−05 | −4.80E−05 | −8.00E−06 | 2.40E−05 |
| 2.52 | 2.60E−05 | 2.60E−05 | 5.10E−05 | 2.00E−06 | 2.50E−05 | 6.40E−05 | 2.30E−05 | −4.60E−05 | −7.00E−06 | 2.50E−05 |
| 2.53 | 4.50E−05 | 2.20E−05 | 3.60E−05 | 4.00E−06 | 3.10E−05 | 4.10E−05 | 3.00E−05 | −3.70E−05 | −2.20E−05 | 1.50E−05 |
| 2.55 | 2.10E−05 | 1.60E−05 | 3.80E−05 | 4.00E−06 | 5.30E−05 | 4.80E−05 | 1.70E−05 | −3.40E−05 | −5.00E−06 | 2.20E−05 |
| 2.57 | 3.00E−05 | 1.80E−05 | 3.30E−05 | −6.00E−06 | 4.50E−05 | 4.20E−05 | 2.60E−05 | −4.50E−05 | 8.00E−06 | 1.30E−05 |
| 2.58 | 2.80E−05 | 2.70E−05 | 3.60E−05 | −1.00E−06 | 4.30E−05 | 4.40E−05 | 2.20E−05 | −3.10E−05 | 1.30E−05 | 2.00E−05 |
| 2.60 | 3.40E−05 | 1.80E−05 | 4.70E−05 | 3.00E−06 | 4.70E−05 | 5.30E−05 | 2.70E−05 | −3.30E−05 | 1.00E−05 | 2.30E−05 |
| 2.62 | 3.60E−05 | 2.60E−05 | 4.40E−05 | −1.00E−05 | 4.80E−05 | 5.10E−05 | 2.50E−05 | −4.10E−05 | 1.60E−05 | 2.20E−05 |
| 2.63 | 2.30E−05 | 2.10E−05 | 3.30E−05 | 1.00E−05 | 4.50E−05 | 3.70E−05 | 1.20E−05 | −3.40E−05 | −6.00E−06 | 2.30E−05 |
| 2.65 | 2.00E−05 | 3.00E−05 | 2.40E−05 | −1.00E−06 | 4.50E−05 | 4.30E−05 | 1.80E−05 | −5.20E−05 | 2.00E−06 | 1.70E−05 |
| 2.67 | 1.40E−05 | 3.00E−05 | 3.30E−05 | 8.00E−06 | 3.40E−05 | 5.80E−05 | 2.00E−06 | −5.70E−05 | 1.20E−05 | 1.00E−05 |
| 2.68 | 4.00E−05 | 1.40E−05 | 4.40E−05 | −1.40E−05 | 3.00E−05 | 4.30E−05 | 1.50E−05 | −3.50E−05 | 4.80E−05 | 2.30E−05 |
| 2.70 | 2.20E−05 | 2.60E−05 | 3.70E−05 | −6.00E−06 | 5.70E−05 | 4.60E−05 | 8.00E−06 | −4.50E−05 | 4.00E−05 | 1.80E−05 |
| 2.72 | 2.50E−05 | 1.70E−05 | 3.40E−05 | 1.00E−06 | 4.50E−05 | 3.70E−05 | 5.00E−06 | −4.30E−05 | 1.40E−05 | 1.50E−05 |
| 2.73 | 3.10E−05 | 2.40E−05 | 5.40E−05 | −1.40E−05 | 3.10E−05 | 4.50E−05 | 2.00E−05 | −5.00E−05 | −4.00E−06 | 2.50E−05 |
| 2.75 | 1.10E−05 | 1.80E−05 | 3.10E−05 | −2.00E−06 | 4.00E−05 | 4.20E−05 | 1.20E−05 | −2.80E−05 | 1.50E−05 | 1.10E−05 |
| 2.77 | 1.70E−05 | 2.70E−05 | 4.80E−05 | −1.10E−05 | 3.60E−05 | 2.80E−05 | 1.60E−05 | −3.40E−05 | 1.10E−05 | 2.00E−05 |
| 2.78 | 2.00E−05 | 4.40E−05 | 4.80E−05 | 1.10E−05 | 4.60E−05 | 4.70E−05 | 1.10E−05 | −4.70E−05 | −3.00E−06 | 1.80E−05 |
| 2.80 | 3.80E−05 | 2.00E−05 | 4.60E−05 | −7.00E−06 | 3.80E−05 | 3.40E−05 | 1.50E−05 | −3.60E−05 | 1.80E−05 | 8.00E−06 |
| 2.82 | 3.50E−05 | 3.70E−05 | 3.20E−05 | −5.00E−06 | 4.00E−05 | 3.60E−05 | 1.50E−05 | −3.40E−05 | 1.40E−05 | 1.70E−05 |
| 2.83 | 4.80E−05 | 1.60E−05 | 4.00E−05 | −8.00E−06 | 3.40E−05 | 3.40E−05 | 1.30E−05 | −3.20E−05 | 1.10E−05 | 8.00E−06 |
| 2.85 | 1.50E−05 | 1.30E−05 | 4.10E−05 | −7.00E−06 | 5.70E−05 | 2.40E−05 | 1.60E−05 | −3.70E−05 | 4.00E−06 | 2.00E−05 |
| 2.87 | 1.50E−05 | 4.70E−05 | 3.70E−05 | −1.00E−05 | 3.60E−05 | 3.50E−05 | 8.00E−06 | −4.10E−05 | 1.00E−05 | 2.00E−05 |
| 2.88 | 3.00E−05 | 2.70E−05 | 3.60E−05 | −1.80E−05 | 3.10E−05 | 4.00E−05 | 1.10E−05 | −4.80E−05 | −3.00E−06 | 2.20E−05 |
| 2.90 | 2.60E−05 | 2.00E−05 | 3.80E−05 | −6.00E−06 | 5.30E−05 | 7.70E−05 | 4.00E−05 | −3.00E−05 | −1.40E−05 | 3.20E−05 |
| 2.92 | 1.10E−05 | 2.40E−05 | 3.60E−05 | −1.60E−05 | 4.60E−05 | 2.70E−05 | 5.00E−06 | −4.50E−05 | 3.00E−06 | 1.30E−05 |
| 2.93 | 2.70E−05 | 8.00E−06 | 3.20E−05 | 0.00E+00 | 5.50E−05 | 3.20E−05 | 5.00E−06 | −3.30E−05 | 3.00E−06 | 3.00E−05 |
| 2.95 | 3.50E−05 | 1.40E−05 | 3.70E−05 | −1.20E−05 | 4.10E−05 | 3.80E−05 | 1.10E−05 | −4.40E−05 | 2.00E−06 | 1.40E−05 |
| 2.97 | 5.10E−05 | 1.40E−05 | 4.10E−05 | −1.20E−05 | 2.80E−05 | 5.70E−05 | 5.00E−06 | −4.10E−05 | −1.10E−05 | 1.70E−05 |
| 2.98 | 1.70E−05 | 1.70E−05 | 3.50E−05 | −1.10E−05 | 5.00E−05 | 5.60E−05 | 7.00E−06 | −3.80E−05 | 4.00E−06 | 7.00E−06 |
| 3.00 | 2.50E−05 | 1.50E−05 | 3.60E−05 | −1.50E−05 | 4.50E−05 | 3.20E−05 | 1.00E−05 | −4.50E−05 | −1.80E−05 | 8.00E−06 |
| 3.02 | 3.30E−05 | 1.60E−05 | 4.60E−05 | 4.00E−06 | 4.10E−05 | 4.20E−05 | −1.20E−05 | −4.50E−05 | −1.00E−06 | 2.20E−05 |
| 3.03 | 1.50E−05 | 1.30E−05 | 5.70E−05 | −1.10E−05 | 5.00E−05 | 3.10E−05 | 1.00E−05 | −5.00E−05 | 1.00E−06 | 3.60E−05 |
| 3.05 | 2.20E−05 | 1.40E−05 | 2.20E−05 | −1.00E−05 | 5.20E−05 | 3.20E−05 | −1.00E−06 | −4.20E−05 | −1.20E−05 | 1.00E−05 |
| 3.07 | 2.60E−05 | 2.40E−05 | 4.50E−05 | −1.20E−05 | 4.20E−05 | 3.20E−05 | 1.00E−06 | −2.70E−05 | −1.10E−05 | 1.80E−05 |
| 3.08 | 1.00E−05 | 1.20E−05 | 2.60E−05 | −1.00E−06 | 4.30E−05 | 3.80E−05 | 8.00E−06 | −4.50E−05 | −6.00E−06 | 2.10E−05 |
| 3.10 | 7.00E−06 | 1.70E−05 | 3.20E−05 | −5.00E−06 | 5.70E−05 | 4.00E−05 | 1.30E−05 | −5.30E−05 | −1.20E−05 | 2.70E−05 |
| 3.12 | 1.00E−05 | 1.60E−05 | 3.10E−05 | −2.20E−05 | 4.20E−05 | 4.50E−05 | −4.00E−06 | −4.60E−05 | −3.00E−06 | 1.50E−05 |
| 3.13 | 2.40E−05 | 1.00E−05 | 3.80E−05 | −1.50E−05 | 4.30E−05 | 3.20E−05 | 1.60E−05 | −4.30E−05 | 0.00E+00 | 2.80E−05 |
| 3.15 | 2.60E−05 | 2.40E−05 | 3.40E−05 | 1.00E−06 | 4.80E−05 | 3.10E−05 | 5.00E−06 | −2.50E−05 | −1.20E−05 | 2.20E−05 |
| 3.17 | 8.00E−06 | 3.20E−05 | 2.80E−05 | 0.00E+00 | 4.80E−05 | 5.00E−05 | 1.00E−06 | −4.20E−05 | −1.30E−05 | 7.00E−06 |
| 3.18 | 1.80E−05 | 1.80E−05 | 3.10E−05 | −1.70E−05 | 4.60E−05 | 4.60E−05 | 0.00E+00 | −4.10E−05 | −8.00E−06 | 1.50E−05 |
| 3.20 | 1.30E−05 | 2.20E−05 | 3.10E−05 | −7.00E−06 | 4.20E−05 | 4.00E−05 | 1.40E−05 | −4.40E−05 | −7.00E−06 | 2.00E−05 |
| 3.22 | 3.50E−05 | 2.60E−05 | 5.30E−05 | 3.00E−06 | 5.30E−05 | 3.40E−05 | −1.00E−06 | −3.70E−05 | −1.40E−05 | 1.80E−05 |
| 3.23 | 2.40E−05 | 2.20E−05 | 4.50E−05 | −1.10E−05 | 4.10E−05 | 3.70E−05 | 1.10E−05 | −4.00E−05 | −1.00E−06 | 3.00E−05 |
| 3.25 | 1.80E−05 | 1.10E−05 | 3.60E−05 | −5.00E−06 | 7.40E−05 | 3.80E−05 | 1.80E−05 | −2.80E−05 | −6.00E−06 | 2.80E−05 |
| 3.27 | 2.50E−05 | 1.50E−05 | 2.60E−05 | −5.00E−06 | 4.80E−05 | 5.10E−05 | 6.00E−06 | −4.30E−05 | −7.00E−06 | 1.40E−05 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 3.28 | 1.40E−05 | 0.00E+00 | 5.00E−05 | −1.00E−05 | 4.10E−05 | 4.30E−05 | 7.00E−06 | −3.80E−05 | −2.00E−06 | 1.80E−05 |
| 3.30 | 3.10E−05 | 1.10E−05 | 2.70E−05 | −1.40E−05 | 3.10E−05 | 5.20E−05 | 1.20E−05 | −4.40E−05 | −8.00E−06 | 3.20E−05 |
| 3.32 | 2.30E−05 | 7.00E−06 | 3.20E−05 | −1.00E−06 | 3.50E−05 | 3.70E−05 | 1.20E−05 | −5.10E−05 | −1.00E−06 | 3.60E−05 |
| 3.33 | 2.60E−05 | 4.00E−06 | 2.70E−05 | −2.00E−06 | 3.60E−05 | 5.00E−05 | −2.00E−06 | −5.20E−05 | −4.00E−06 | 3.10E−05 |
| 3.35 | 2.60E−05 | 1.80E−05 | 3.50E−05 | −1.00E−05 | 4.30E−05 | 5.50E−05 | 2.00E−05 | −5.80E−05 | 7.00E−06 | 2.10E−05 |
| 3.37 | 8.00E−06 | 2.70E−05 | 5.00E−05 | −1.50E−05 | 3.60E−05 | 4.20E−05 | 1.10E−05 | −5.50E−05 | 1.80E−05 | 1.80E−05 |
| 3.38 | 2.80E−05 | 1.80E−05 | 3.40E−05 | −1.80E−05 | 2.80E−05 | 3.20E−05 | −1.30E−05 | −4.00E−05 | −1.50E−05 | 2.80E−05 |
| 3.40 | 2.40E−05 | 1.30E−05 | 3.40E−05 | 0.00E+00 | 2.50E−05 | 3.50E−05 | 1.80E−05 | −3.70E−05 | −3.00E−06 | 2.00E−05 |
| 3.42 | 1.70E−05 | 3.10E−05 | 4.10E−05 | −4.00E−06 | 3.60E−05 | 4.10E−05 | 2.00E−06 | −4.00E−05 | 0.00E+00 | 3.00E−05 |
| 3.43 | 1.60E−05 | 5.00E−06 | 3.70E−05 | −1.00E−05 | 5.10E−05 | 5.60E−05 | 1.20E−05 | −1.80E−05 | 8.00E−06 | 2.70E−05 |
| 3.45 | 2.60E−05 | 2.00E−05 | 4.00E−05 | −3.00E−06 | 3.20E−05 | 3.50E−05 | 7.00E−06 | −4.30E−05 | 8.00E−06 | 2.40E−05 |
| 3.47 | 2.30E−05 | 7.00E−06 | 3.20E−05 | 1.00E−06 | 3.20E−05 | 2.60E−05 | −2.00E−06 | −5.00E−05 | 0.00E+00 | 4.60E−05 |
| 3.48 | 1.80E−05 | 3.00E−06 | 3.50E−05 | 6.00E−06 | 5.80E−05 | 3.60E−05 | 5.00E−06 | −5.50E−05 | 7.00E−06 | 3.20E−05 |
| 3.50 | 2.20E−05 | 1.10E−05 | 3.50E−05 | −4.00E−06 | 4.60E−05 | 4.40E−05 | 1.10E−05 | −5.70E−05 | 1.00E−05 | 2.50E−05 |
| 3.52 | 2.00E−05 | 2.10E−05 | 3.60E−05 | 1.50E−05 | 5.10E−05 | 3.40E−05 | 5.00E−06 | −3.20E−05 | 7.00E−06 | 3.30E−05 |
| 3.53 | 1.50E−05 | 3.20E−05 | 4.30E−05 | 1.00E−05 | 2.80E−05 | 5.10E−05 | 1.00E−06 | −4.80E−05 | −8.00E−06 | 3.30E−05 |
| 3.55 | 2.00E−05 | 1.80E−05 | 3.10E−05 | 1.80E−05 | 3.70E−05 | 3.30E−05 | −5.00E−06 | −5.80E−05 | 1.00E−06 | 3.30E−05 |
| 3.57 | 2.20E−05 | 1.20E−05 | 4.60E−05 | 8.00E−06 | 2.50E−05 | 4.50E−05 | 1.50E−05 | −3.50E−05 | 1.00E−05 | 1.80E−05 |
| 3.58 | 1.50E−05 | 8.00E−06 | 3.30E−05 | 2.70E−05 | 3.30E−05 | 4.40E−05 | 8.00E−06 | −4.40E−05 | 4.00E−06 | 3.60E−05 |
| 3.60 | 2.10E−05 | 6.00E−06 | 4.50E−05 | 2.60E−05 | 4.50E−05 | 3.40E−05 | 6.00E−06 | −4.20E−05 | 3.00E−06 | 3.60E−05 |
| 3.62 | 1.20E−05 | 1.30E−05 | 4.40E−05 | 3.00E−05 | 4.40E−05 | 4.20E−05 | 6.00E−06 | −4.30E−05 | −1.30E−05 | 2.10E−05 |
| 3.63 | 1.70E−05 | 2.50E−05 | 3.60E−05 | 3.50E−05 | 3.40E−05 | 4.80E−05 | −1.00E−05 | −4.30E−05 | −3.00E−06 | 2.60E−05 |
| 3.65 | 1.80E−05 | 2.20E−05 | 4.20E−05 | 6.50E−05 | 3.00E−05 | 4.30E−05 | 1.50E−05 | −4.80E−05 | 2.00E−06 | 3.30E−05 |
| 3.67 | 2.20E−05 | 1.80E−05 | 3.60E−05 | 4.70E−05 | 3.70E−05 | 3.00E−05 | 1.10E−05 | −4.30E−05 | 0.00E+00 | 3.20E−05 |
| 3.68 | 6.00E−06 | 2.00E−06 | 2.60E−05 | 4.60E−05 | 3.30E−05 | 3.30E−05 | 3.00E−06 | −4.40E−05 | 1.30E−05 | 4.20E−05 |
| 3.70 | 2.00E−06 | 2.20E−05 | 3.10E−05 | 6.10E−05 | 5.00E−05 | 3.30E−05 | 1.00E−05 | −4.10E−05 | −5.00E−06 | 1.30E−05 |
| 3.72 | 1.80E−05 | 1.60E−05 | 2.80E−05 | 6.40E−05 | 3.00E−05 | 4.70E−05 | 8.00E−06 | −5.10E−05 | 2.00E−06 | 3.60E−05 |
| 3.73 | 2.30E−05 | 2.40E−05 | 2.70E−05 | 6.90E−05 | 3.30E−05 | 4.80E−05 | 5.00E−06 | −4.40E−05 | 8.00E−06 | 2.50E−05 |
| 3.75 | 2.20E−05 | 1.30E−05 | 4.10E−05 | 7.20E−05 | 3.10E−05 | 4.10E−05 | 1.00E−05 | 0.00E+00 | 3.40E−05 | 3.40E−05 |
| 3.77 | 2.40E−05 | 2.00E−06 | 4.10E−05 | 7.00E−05 | 4.30E−05 | 4.50E−05 | 1.00E−05 | −5.20E−05 | 4.00E−05 | 4.10E−05 |
| 3.78 | −1.00E−06 | 2.30E−05 | 3.10E−05 | 1.10E−04 | 2.40E−05 | 4.40E−05 | 1.70E−05 | −5.80E−05 | 3.20E−05 | 4.50E−05 |
| 3.80 | 2.60E−05 | 1.10E−05 | 3.40E−05 | 7.20E−05 | 4.00E−05 | 4.10E−05 | 1.30E−05 | −4.80E−05 | 1.00E−05 | 4.30E−05 |
| 3.82 | 2.40E−05 | 2.80E−05 | 3.00E−05 | 6.20E−05 | 3.40E−05 | 4.80E−05 | 1.00E−05 | −6.10E−05 | 2.00E−06 | 2.40E−05 |
| 3.83 | 1.40E−05 | 1.80E−05 | 3.30E−05 | 5.20E−05 | 2.30E−05 | 4.00E−05 | 1.80E−05 | −2.80E−05 | 6.00E−06 | 3.60E−05 |
| 3.85 | 2.00E−05 | 8.00E−06 | 3.20E−05 | 6.20E−05 | 3.40E−05 | 5.00E−05 | 1.40E−05 | −4.30E−05 | 2.00E−05 | 4.30E−05 |
| 3.87 | 1.30E−05 | 5.00E−06 | 3.80E−05 | 4.40E−05 | 1.70E−05 | 4.60E−05 | 5.00E−06 | −5.00E−05 | 2.20E−05 | 4.00E−05 |
| 3.88 | 1.40E−05 | 7.00E−06 | 4.20E−05 | 4.50E−05 | 2.60E−05 | 4.70E−05 | 2.10E−05 | −5.50E−05 | 1.30E−05 | 2.80E−05 |
| 3.90 | 2.30E−05 | 1.40E−05 | 4.10E−05 | 3.70E−05 | 2.50E−05 | 6.00E−05 | 2.00E−06 | −4.80E−05 | 1.20E−05 | 4.00E−05 |
| 3.92 | 1.40E−05 | 1.60E−05 | 3.80E−05 | 4.60E−05 | 3.00E−05 | 6.70E−05 | 2.80E−05 | −6.00E−05 | 1.20E−05 | 4.40E−05 |
| 3.93 | 1.40E−05 | 1.40E−05 | 3.80E−05 | 3.40E−05 | 1.70E−05 | 7.40E−05 | 1.70E−05 | −4.30E−05 | 2.30E−05 | 3.20E−05 |
| 3.95 | 1.80E−05 | 2.60E−05 | 3.50E−05 | 3.70E−05 | 3.40E−05 | 7.20E−05 | 3.10E−05 | −5.60E−05 | 1.80E−05 | 3.10E−05 |
| 3.97 | 2.30E−05 | 2.30E−05 | 4.20E−05 | 3.30E−05 | 3.80E−05 | 8.00E−05 | 2.80E−05 | −5.70E−05 | 1.20E−05 | 4.40E−05 |
| 3.98 | 1.30E−05 | 1.70E−05 | 3.70E−05 | 4.20E−05 | 3.30E−05 | 9.00E−05 | 3.30E−05 | −6.30E−05 | 1.70E−05 | 3.50E−05 |
| 4.00 | 4.10E−05 | 1.20E−05 | 4.30E−05 | 2.00E−05 | 2.30E−05 | 1.01E−04 | 4.50E−05 | −4.70E−05 | 3.50E−05 | 3.60E−05 |
| 4.02 | 8.00E−06 | 6.00E−06 | 3.30E−05 | 3.00E−05 | 4.00E−05 | 1.06E−04 | 5.40E−05 | −5.20E−05 | 1.10E−05 | 3.50E−05 |
| 4.03 | 2.20E−05 | 8.00E−06 | 2.40E−05 | 1.00E−05 | 2.30E−05 | 1.09E−04 | 6.20E−05 | −6.50E−05 | 2.20E−05 | 5.00E−05 |
| 4.05 | 1.70E−05 | 3.00E−06 | 4.00E−05 | 2.10E−05 | 3.30E−05 | 1.07E−04 | 7.90E−05 | −3.00E−05 | 1.00E−05 | 3.20E−05 |
| 4.07 | 2.40E−05 | 1.00E−05 | 4.10E−05 | 1.70E−05 | 3.10E−05 | 1.11E−04 | 8.00E−05 | −5.30E−05 | 1.50E−05 | 2.40E−05 |
| 4.08 | 2.40E−05 | 1.00E−05 | 3.60E−05 | 1.20E−05 | 1.80E−05 | 1.19E−04 | 9.00E−05 | −5.30E−05 | 2.20E−05 | 3.70E−05 |
| 4.10 | 2.50E−05 | 2.30E−05 | 1.70E−05 | 2.10E−05 | 1.60E−05 | 1.11E−04 | 1.16E−04 | −3.40E−05 | 1.70E−05 | 3.80E−05 |
| 4.12 | 1.70E−05 | 2.30E−05 | 4.40E−05 | 8.00E−06 | 3.30E−05 | 1.21E−04 | 9.90E−05 | −5.40E−05 | 1.00E−05 | 4.00E−05 |
| 4.13 | 1.80E−05 | 1.40E−05 | 2.80E−05 | 2.50E−05 | 2.20E−05 | 1.05E−04 | 1.06E−04 | −6.70E−05 | 1.80E−05 | 4.00E−05 |
| 4.15 | 2.30E−05 | 1.40E−05 | 3.80E−05 | 2.40E−05 | 2.10E−05 | 1.17E−04 | 1.07E−04 | −3.60E−05 | 2.00E−06 | 4.80E−05 |
| 4.17 | 5.00E−06 | 7.00E−06 | 3.10E−05 | 1.30E−05 | 1.80E−05 | 1.11E−04 | 1.19E−04 | −4.20E−05 | 1.10E−05 | 5.20E−05 |
| 4.18 | 2.50E−05 | 2.40E−05 | 3.20E−05 | −5.00E−06 | 1.40E−05 | 1.10E−04 | 1.16E−04 | −4.50E−05 | 8.00E−06 | 4.50E−05 |
| 4.20 | 2.30E−05 | 4.00E−05 | 2.10E−05 | 1.10E−05 | 3.20E−05 | 1.26E−04 | 1.26E−04 | −5.00E−05 | 8.00E−06 | 5.00E−05 |
| 4.22 | 2.60E−05 | 8.00E−06 | 4.70E−05 | 2.00E−05 | 2.80E−05 | 9.40E−05 | 1.36E−04 | −5.40E−05 | 2.10E−05 | 4.80E−05 |
| 4.23 | 2.30E−05 | 4.00E−06 | 2.70E−05 | 5.00E−06 | 3.00E−05 | 1.01E−04 | 1.33E−04 | −5.50E−05 | 1.30E−05 | 4.60E−05 |
| 4.25 | 2.80E−05 | 7.00E−06 | 3.60E−05 | −6.00E−06 | 2.50E−05 | 9.40E−05 | 1.32E−04 | −5.80E−05 | 2.40E−05 | 5.20E−05 |
| 4.27 | 1.00E−05 | 5.00E−06 | 3.30E−05 | 7.00E−06 | 2.20E−05 | 7.40E−05 | 1.26E−04 | −5.00E−05 | 1.50E−05 | 4.10E−05 |
| 4.28 | 1.60E−05 | 5.00E−06 | 3.00E−05 | 2.00E−06 | 2.10E−05 | 8.50E−05 | 1.39E−04 | −6.50E−05 | 2.20E−05 | 3.70E−05 |
| 4.30 | 2.10E−05 | 3.00E−06 | 3.70E−05 | 2.00E−06 | 1.80E−05 | 6.70E−05 | 9.70E−05 | −5.20E−05 | 1.60E−05 | 2.50E−05 |
| 4.32 | 2.30E−05 | 1.10E−05 | 3.70E−05 | −8.00E−06 | 2.60E−05 | 8.20E−05 | 9.70E−05 | −4.70E−05 | 1.80E−05 | 5.80E−05 |
| 4.33 | 3.30E−05 | −2.00E−06 | 4.70E−05 | −3.00E−06 | 2.60E−05 | 6.60E−05 | 8.60E−05 | −5.50E−05 | 1.10E−05 | 4.20E−05 |
| 4.35 | 2.40E−05 | 7.00E−06 | 5.00E−05 | −7.00E−06 | 2.20E−05 | 6.10E−05 | 9.40E−05 | −6.30E−05 | 4.00E−06 | 4.60E−05 |
| 4.37 | 1.50E−05 | 1.40E−05 | 3.10E−05 | 0.00E+00 | 3.20E−05 | 5.60E−05 | 8.20E−05 | −5.70E−05 | 1.30E−05 | 4.40E−05 |
| 4.38 | 2.80E−05 | 5.00E−06 | 4.70E−05 | 1.40E−05 | 1.10E−05 | 5.40E−05 | 7.70E−05 | −5.60E−05 | 8.00E−06 | 2.70E−05 |
| 4.40 | 1.60E−05 | 1.00E−05 | 5.20E−05 | −5.00E−06 | 3.70E−05 | 4.70E−05 | 7.50E−05 | −4.70E−05 | 1.10E−05 | 5.00E−05 |
| 4.42 | 2.70E−05 | 1.20E−05 | 4.40E−05 | −6.00E−06 | 1.70E−05 | 6.00E−05 | 7.40E−05 | −4.80E−05 | 1.60E−05 | 4.10E−05 |
| 4.43 | 3.10E−05 | 2.40E−05 | 4.60E−05 | 0.00E+00 | 1.70E−05 | 3.60E−05 | 6.20E−05 | −6.20E−05 | 7.00E−06 | 3.50E−05 |
| 4.45 | 2.40E−05 | 1.30E−05 | 4.70E−05 | 7.00E−06 | 1.00E−05 | 3.70E−05 | 6.20E−05 | −6.10E−05 | −1.00E−06 | 3.10E−05 |
| 4.47 | 4.40E−05 | 5.00E−06 | 4.80E−05 | −3.00E−06 | 1.30E−05 | 5.10E−05 | 5.50E−05 | −4.10E−05 | 3.70E−05 | 3.40E−05 |
| 4.48 | 2.10E−05 | −1.00E−06 | 4.50E−05 | −1.20E−05 | 1.60E−05 | 4.50E−05 | 5.60E−05 | −5.10E−05 | 3.00E−06 | 4.50E−05 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 4.50 | 2.50E−05 | 1.20E−05 | 4.30E−05 | −7.00E−06 | 1.20E−05 | 4.50E−05 | 6.00E−05 | −5.00E−05 | 1.30E−05 | 5.40E−05 |
| 4.52 | 2.40E−05 | 2.30E−05 | 5.60E−05 | −1.00E−05 | 1.70E−05 | 3.20E−05 | 5.30E−05 | −5.80E−05 | 2.20E−05 | 5.00E−05 |
| 4.53 | 3.60E−05 | 6.00E−06 | 5.80E−05 | −1.00E−05 | 1.20E−05 | 4.60E−05 | 5.10E−05 | −5.80E−05 | 8.00E−06 | 5.10E−05 |
| 4.55 | 3.20E−05 | 2.50E−05 | 4.10E−05 | 3.00E−06 | 1.60E−05 | 2.80E−05 | 4.50E−05 | −5.50E−05 | 2.00E−05 | 4.80E−05 |
| 4.57 | 2.70E−05 | 4.00E−06 | 5.50E−05 | −1.00E−05 | 4.00E−06 | 1.70E−05 | 5.10E−05 | −5.00E−05 | 2.00E−05 | 6.00E−05 |
| 4.58 | 3.80E−05 | 0.00E+00 | 4.80E−05 | 1.00E−06 | 1.50E−05 | 7.20E−05 | 4.10E−05 | −3.80E−05 | 1.00E−05 | 3.70E−05 |
| 4.60 | 1.80E−05 | −3.00E−06 | 5.50E−05 | −5.00E−06 | 6.00E−06 | 3.10E−05 | 5.40E−05 | −5.30E−05 | 4.00E−06 | 4.10E−05 |
| 4.62 | 1.40E−05 | 3.00E−06 | 5.10E−05 | −1.00E−06 | 5.00E−06 | 1.80E−05 | 4.40E−05 | −6.10E−05 | 1.30E−05 | 4.70E−05 |
| 4.63 | 1.20E−05 | 1.30E−05 | 5.10E−05 | −1.10E−05 | 6.00E−06 | 3.00E−05 | 4.30E−05 | −6.00E−05 | 1.00E−06 | 5.60E−05 |
| 4.65 | 2.40E−05 | 2.40E−05 | 4.30E−05 | −7.00E−06 | 2.10E−05 | 2.40E−05 | 2.80E−05 | −6.70E−05 | 1.10E−05 | 5.30E−05 |
| 4.67 | 2.20E−05 | 2.30E−05 | 5.40E−05 | −1.60E−05 | 3.10E−05 | 2.20E−05 | 4.70E−05 | −6.00E−05 | 1.00E−05 | 4.20E−05 |
| 4.68 | 1.60E−05 | 8.00E−06 | 5.40E−05 | −1.20E−05 | 1.50E−05 | 2.20E−05 | 4.60E−05 | −6.90E−05 | 1.50E−05 | 3.80E−05 |
| 4.70 | 2.60E−05 | 1.70E−05 | 4.30E−05 | −2.00E−06 | 5.00E−06 | 5.00E−06 | 4.00E−05 | −5.50E−05 | 5.00E−06 | 4.70E−05 |
| 4.72 | 2.00E−05 | −5.00E−06 | 5.80E−05 | 4.00E−06 | −1.00E−06 | 2.10E−05 | 2.40E−05 | −5.30E−05 | 1.10E−05 | 4.70E−05 |
| 4.73 | 2.50E−05 | 1.80E−05 | 6.10E−05 | −1.60E−05 | 1.30E−05 | 2.00E−05 | 4.00E−05 | −4.10E−05 | 1.60E−05 | 4.10E−05 |
| 4.75 | 2.00E−05 | −2.00E−06 | 5.70E−05 | −1.10E−05 | 4.00E−06 | 8.00E−06 | 2.30E−05 | −5.00E−05 | 1.10E−05 | 3.70E−05 |
| 4.77 | 2.30E−05 | 0.00E+00 | 5.70E−05 | 2.00E−06 | 1.80E−05 | −3.00E−06 | 3.30E−05 | −5.40E−05 | 7.00E−06 | 6.00E−05 |
| 4.78 | 1.50E−05 | 1.50E−05 | 5.20E−05 | −2.00E−06 | 1.20E−05 | 7.00E−06 | 2.80E−05 | −5.40E−05 | 4.00E−06 | 4.60E−05 |
| 4.80 | 2.10E−05 | 2.10E−05 | 4.70E−05 | 0.00E+00 | 1.30E−05 | 2.20E−05 | 3.10E−05 | −3.50E−05 | 1.20E−05 | 4.10E−05 |
| 4.82 | 2.50E−05 | 3.00E−05 | 6.40E−05 | 1.00E−06 | 7.00E−06 | 1.60E−05 | 1.50E−05 | −5.00E−05 | 1.60E−05 | 4.10E−05 |
| 4.83 | 7.00E−06 | 2.00E−05 | 6.50E−05 | −5.00E−06 | 2.30E−05 | 1.00E−05 | 2.60E−05 | −5.60E−05 | 2.00E−05 | 4.30E−05 |
| 4.85 | 2.10E−05 | 1.00E−05 | 5.60E−05 | −3.00E−06 | 1.10E−05 | 8.00E−06 | 3.50E−05 | −6.10E−05 | 5.00E−06 | 4.40E−05 |
| 4.87 | 2.70E−05 | 8.00E−06 | 5.50E−05 | 3.00E−06 | −4.00E−06 | 1.10E−05 | 2.40E−05 | −5.70E−05 | 8.00E−06 | 4.80E−05 |
| 4.88 | 1.70E−05 | 2.00E−06 | 5.40E−05 | −3.00E−06 | 0.00E+00 | 1.40E−05 | 2.00E−05 | −5.00E−05 | −2.00E−06 | 5.10E−05 |
| 4.90 | 1.20E−05 | 7.00E−06 | 5.10E−05 | 3.00E−06 | 1.40E−05 | −4.00E−06 | 1.80E−05 | −6.20E−05 | 1.60E−05 | 3.80E−05 |
| 4.92 | 3.50E−05 | 1.30E−05 | 5.20E−05 | 1.00E−06 | 1.10E−05 | 1.10E−05 | 3.70E−05 | −5.30E−05 | 6.00E−06 | 5.60E−05 |
| 4.93 | 3.20E−05 | 1.60E−05 | 6.00E−05 | −1.20E−05 | 3.00E−06 | −2.00E−06 | 1.30E−05 | −6.30E−05 | −1.00E−06 | 5.10E−05 |
| 4.95 | 2.30E−05 | 8.00E−06 | 6.30E−05 | 0.00E+00 | 1.50E−05 | −1.00E−06 | 1.30E−05 | −2.60E−05 | 1.20E−05 | 4.10E−05 |
| 4.97 | 1.50E−05 | 7.00E−06 | 7.00E−05 | 1.00E−05 | 8.00E−06 | 8.00E−06 | 2.20E−05 | −5.60E−05 | 1.00E−05 | 4.80E−05 |
| 4.98 | 1.70E−05 | 3.00E−06 | 4.60E−05 | 1.00E−05 | 1.80E−05 | −1.00E−06 | 1.80E−05 | −7.30E−05 | 3.00E−06 | 5.70E−05 |
| 5.00 | 2.20E−05 | 1.70E−05 | 5.20E−05 | −1.00E−06 | 0.00E+00 | 1.20E−05 | 2.20E−05 | −5.70E−05 | 1.40E−05 | 5.50E−05 |
| 5.02 | 1.80E−05 | 1.20E−05 | 6.00E−05 | 1.30E−05 | 7.00E−06 | 3.00E−06 | 2.20E−05 | −5.30E−05 | −2.00E−06 | 5.20E−05 |
| 5.03 | 2.00E−05 | 1.50E−05 | 5.10E−05 | 2.00E−06 | 1.30E−05 | 2.00E−06 | 1.70E−05 | −4.60E−05 | 7.00E−06 | 4.70E−05 |
| 5.05 | 1.70E−05 | 1.00E−05 | 5.40E−05 | 1.00E−05 | 1.30E−05 | 5.00E−06 | 2.60E−05 | −5.80E−05 | 1.10E−05 | 6.30E−05 |
| 5.07 | 3.30E−05 | 2.00E−05 | 6.10E−05 | −2.00E−06 | 3.00E−06 | 7.00E−06 | 1.60E−05 | −5.30E−05 | 1.80E−05 | 6.00E−05 |
| 5.08 | 2.70E−05 | 2.10E−05 | 5.00E−05 | 1.20E−05 | 1.00E−06 | −1.60E−05 | 1.50E−05 | −6.20E−05 | −3.00E−06 | 5.50E−05 |
| 5.10 | 1.70E−05 | 2.20E−05 | 4.50E−05 | 3.00E−06 | 1.20E−05 | −1.00E−06 | 4.00E−05 | −6.00E−05 | 5.00E−06 | 6.50E−05 |
| 5.12 | 1.50E−05 | 6.00E−06 | 6.40E−05 | 0.00E+00 | 1.00E−05 | −1.40E−05 | 1.70E−05 | −4.80E−05 | −2.00E−06 | 5.70E−05 |
| 5.13 | 2.30E−05 | 7.00E−06 | 5.80E−05 | 1.10E−05 | 7.00E−06 | 4.00E−06 | 1.60E−05 | −8.50E−05 | 8.00E−06 | 4.80E−05 |
| 5.15 | 2.10E−05 | 1.10E−05 | 7.00E−05 | 4.00E−06 | 1.80E−05 | −1.00E−06 | 1.50E−05 | −5.40E−05 | 6.00E−06 | 5.40E−05 |
| 5.17 | 2.00E−05 | 1.40E−05 | 5.30E−05 | 2.60E−05 | 1.60E−05 | 0.00E+00 | 2.40E−05 | −7.00E−05 | −1.40E−05 | 5.50E−05 |
| 5.18 | 1.60E−05 | 6.00E−06 | 7.10E−05 | 5.00E−06 | 5.00E−06 | 0.00E+00 | 1.70E−05 | −6.50E−05 | 3.00E−06 | 5.80E−05 |
| 5.20 | 3.00E−06 | 6.00E−06 | 6.40E−05 | 5.00E−06 | 2.00E−06 | 4.00E−06 | 1.40E−05 | −6.10E−05 | 1.40E−05 | 5.70E−05 |
| 5.22 | 2.50E−05 | 2.80E−05 | 5.50E−05 | 2.40E−05 | 1.30E−05 | 3.00E−06 | 1.40E−05 | −5.30E−05 | 0.00E+00 | 4.60E−05 |
| 5.23 | 1.20E−05 | 2.70E−05 | 6.70E−05 | 8.00E−06 | 1.30E−05 | 1.30E−05 | 1.60E−05 | −5.10E−05 | 1.00E−05 | 6.20E−05 |
| 5.25 | 2.80E−05 | 1.80E−05 | 6.00E−05 | 3.00E−06 | −3.00E−06 | −5.00E−06 | 1.80E−05 | −6.90E−05 | 1.10E−05 | 5.80E−05 |
| 5.27 | 1.20E−05 | 1.10E−05 | 6.50E−05 | 2.60E−05 | 5.00E−06 | 5.00E−06 | 2.80E−05 | −6.50E−05 | 1.30E−05 | 5.30E−05 |
| 5.28 | 1.30E−05 | 4.00E−06 | 7.60E−05 | 1.10E−05 | 1.40E−05 | 1.10E−05 | 1.60E−05 | −5.00E−05 | 4.00E−06 | 6.10E−05 |
| 5.30 | 2.10E−05 | 8.00E−06 | 5.20E−05 | 1.20E−05 | −1.00E−06 | −5.00E−06 | 1.20E−05 | −5.80E−05 | 8.00E−06 | 4.20E−05 |
| 5.32 | 2.60E−05 | 1.00E−05 | 6.30E−05 | 2.80E−05 | 1.50E−05 | 4.00E−06 | 2.30E−05 | −5.30E−05 | 0.00E+00 | 5.40E−05 |
| 5.33 | 1.80E−05 | 2.10E−05 | 6.50E−05 | 2.00E−05 | 1.10E−05 | −3.00E−06 | 1.40E−05 | −5.30E−05 | 1.10E−05 | 4.50E−05 |
| 5.35 | 1.70E−05 | 1.20E−05 | 6.70E−05 | 1.20E−05 | −8.00E−06 | 7.00E−06 | 1.40E−05 | −5.60E−05 | −8.00E−06 | 6.50E−05 |
| 5.37 | 1.80E−05 | 3.00E−06 | 6.40E−05 | 3.10E−05 | 7.00E−06 | −4.00E−06 | 2.10E−05 | −7.70E−05 | −2.00E−06 | 4.40E−05 |
| 5.38 | 1.60E−05 | 2.00E−05 | 6.50E−05 | 1.40E−05 | 2.40E−05 | −2.00E−06 | 2.50E−05 | −7.00E−05 | −4.00E−06 | 6.60E−05 |
| 5.40 | 1.30E−05 | 1.20E−05 | 5.10E−05 | 5.00E−06 | 7.00E−06 | −2.00E−06 | 1.50E−05 | −6.60E−05 | 6.00E−06 | 4.50E−05 |
| 5.42 | 3.80E−05 | 2.40E−05 | 7.60E−05 | 1.10E−05 | −1.00E−06 | −7.00E−06 | 6.00E−06 | −5.80E−05 | 7.00E−06 | 5.10E−05 |
| 5.43 | 6.00E−06 | 7.00E−06 | 7.70E−05 | 2.00E−06 | 8.00E−06 | 2.00E−06 | 2.10E−05 | −6.20E−05 | −5.00E−06 | 4.50E−05 |
| 5.45 | 1.30E−05 | 1.20E−05 | 7.00E−05 | 1.30E−05 | 1.20E−05 | −1.00E−06 | 2.60E−05 | −4.70E−05 | 1.40E−05 | 6.00E−05 |
| 5.47 | 1.80E−05 | 1.30E−05 | 7.50E−05 | 8.00E−06 | 1.30E−05 | 2.00E−06 | 2.40E−05 | −5.40E−05 | 7.00E−06 | 5.50E−05 |
| 5.48 | 1.20E−05 | 2.20E−05 | 6.30E−05 | 1.30E−05 | 7.00E−06 | −7.00E−06 | 2.00E−05 | −6.00E−05 | 8.00E−06 | 5.00E−05 |
| 5.50 | 1.60E−05 | 3.20E−05 | 7.40E−05 | 2.60E−05 | 8.00E−06 | 4.00E−06 | 2.00E−05 | −5.20E−05 | 1.40E−05 | 6.30E−05 |
| 5.52 | 1.80E−05 | 2.40E−05 | 4.80E−05 | 8.00E−06 | 5.00E−06 | −4.00E−06 | 1.80E−05 | −5.80E−05 | 1.40E−05 | 4.70E−05 |
| 5.53 | 2.30E−05 | 2.00E−05 | 6.00E−05 | 3.00E−06 | 5.00E−06 | 7.00E−06 | 1.80E−05 | −3.60E−05 | 1.00E−06 | 5.00E−05 |
| 5.55 | 2.40E−05 | 1.30E−05 | 7.50E−05 | 2.20E−05 | 7.00E−06 | 3.00E−06 | 2.20E−05 | −5.40E−05 | 1.00E−06 | 6.00E−05 |
| 5.57 | 2.80E−05 | 1.60E−05 | 6.90E−05 | 1.50E−05 | 1.20E−05 | 1.80E−05 | 1.30E−05 | −5.40E−05 | 4.00E−06 | 4.40E−05 |
| 5.58 | 3.00E−06 | 2.40E−05 | 7.10E−05 | 2.50E−05 | 2.00E−06 | −8.00E−06 | 2.10E−05 | −6.50E−05 | 1.00E−05 | 6.50E−05 |
| 5.60 | 2.00E−05 | 2.30E−05 | 5.40E−05 | 2.10E−05 | −1.00E−05 | 5.00E−06 | 1.70E−05 | −5.40E−05 | 0.00E+00 | 5.50E−05 |
| 5.62 | 1.70E−05 | 2.00E−05 | 6.90E−05 | 1.60E−05 | 5.00E−06 | 1.00E−06 | 2.20E−05 | −5.10E−05 | 6.00E−06 | 5.80E−05 |
| 5.63 | 2.00E−05 | 1.30E−05 | 5.50E−05 | 3.00E−05 | −6.00E−06 | −1.10E−05 | 3.50E−05 | −3.40E−05 | −4.00E−06 | 5.30E−05 |
| 5.65 | 2.00E−05 | 1.40E−05 | 7.70E−05 | 1.10E−05 | 0.00E+00 | −4.00E−06 | 1.30E−05 | −4.20E−05 | 2.00E−06 | 4.50E−05 |
| 5.67 | 4.00E−06 | 3.10E−05 | 7.20E−05 | 2.50E−05 | −1.00E−06 | −4.00E−06 | 2.80E−05 | −5.20E−05 | 8.00E−06 | 4.60E−05 |
| 5.68 | 1.30E−05 | 2.10E−05 | 6.10E−05 | 8.00E−06 | 2.00E−06 | 0.00E+00 | 2.40E−05 | −3.60E−05 | 5.00E−06 | 5.50E−05 |
| 5.70 | 1.10E−05 | 2.50E−05 | 7.30E−05 | 1.70E−05 | 6.00E−06 | −6.00E−06 | 1.80E−05 | −4.30E−05 | 8.00E−06 | 4.20E−05 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 5.72 | 3.50E−05 | 5.00E−06 | 6.40E−05 | 1.70E−05 | 5.00E−06 | −1.00E−06 | 2.00E−05 | −4.10E−05 | −2.00E−06 | 5.00E−05 |
| 5.73 | 1.30E−05 | 2.20E−05 | 6.20E−05 | 2.10E−05 | 8.00E−06 | −1.00E−05 | 2.30E−05 | −5.00E−05 | 4.00E−06 | 7.30E−05 |
| 5.75 | 2.20E−05 | 1.70E−05 | 7.20E−05 | 2.60E−05 | 1.00E−06 | 2.00E−05 | 1.80E−05 | −5.10E−05 | −1.20E−05 | 4.00E−05 |
| 5.77 | 6.00E−06 | 2.80E−05 | 6.20E−05 | 1.00E−05 | 1.00E−06 | −2.00E−06 | 2.40E−05 | −4.40E−05 | −1.00E−06 | 4.10E−05 |
| 5.78 | 2.00E−05 | 2.50E−05 | 4.80E−05 | 2.20E−05 | 8.00E−06 | 2.00E−06 | 2.20E−05 | −3.10E−05 | 0.00E+00 | 4.50E−05 |
| 5.80 | 2.00E−05 | 1.80E−05 | 6.50E−05 | 1.30E−05 | 8.00E−06 | 1.00E−06 | 1.10E−05 | −5.10E−05 | −8.00E−06 | 3.80E−05 |
| 5.82 | 1.10E−05 | 1.80E−05 | 5.50E−05 | 8.00E−06 | 4.00E−06 | 0.00E+00 | 1.40E−05 | −4.10E−05 | 2.00E−06 | 4.00E−05 |
| 5.83 | 2.00E−05 | 1.70E−05 | 5.30E−05 | 1.70E−05 | 1.70E−05 | 3.00E−06 | 2.20E−05 | −4.30E−05 | −4.00E−06 | 3.60E−05 |
| 5.85 | 1.80E−05 | 2.50E−05 | 7.30E−05 | 2.00E−05 | 2.30E−05 | −1.00E−06 | 2.00E−05 | −3.60E−05 | −8.00E−06 | 5.00E−05 |
| 5.87 | 6.00E−06 | 2.20E−05 | 7.30E−05 | 1.80E−05 | −1.00E−06 | 1.10E−05 | 8.00E−06 | −3.00E−05 | 4.00E−06 | 2.80E−05 |
| 5.88 | 1.00E−05 | 2.70E−05 | 5.50E−05 | 1.80E−05 | 1.40E−05 | 1.50E−05 | 1.20E−05 | −3.30E−05 | 0.00E+00 | 4.10E−05 |
| 5.90 | 1.00E−06 | 4.30E−05 | 6.40E−05 | 6.00E−06 | 1.00E−06 | 7.00E−06 | 7.00E−06 | −4.50E−05 | 2.00E−06 | 4.20E−05 |
| 5.92 | 2.10E−05 | 2.70E−05 | 6.30E−05 | 2.70E−05 | 7.00E−06 | −1.00E−06 | 2.40E−05 | −3.80E−05 | −1.00E−06 | 5.70E−05 |
| 5.93 | 2.00E−05 | 3.80E−05 | 7.50E−05 | 1.80E−05 | 1.40E−05 | 5.00E−06 | 7.00E−06 | −3.10E−05 | −5.00E−06 | 3.30E−05 |
| 5.95 | 3.10E−05 | 3.40E−05 | 8.00E−05 | 1.50E−05 | 1.70E−05 | 1.00E−06 | 1.30E−05 | −2.40E−05 | −6.00E−06 | 4.00E−05 |
| 5.97 | 1.00E−05 | 3.20E−05 | 6.90E−05 | 6.00E−06 | 1.20E−05 | 6.00E−06 | 1.20E−05 | −3.50E−05 | 1.00E−06 | 4.50E−05 |
| 5.98 | 3.30E−05 | 4.70E−05 | 6.30E−05 | 3.10E−05 | 0.00E+00 | 1.00E−06 | 1.50E−05 | −4.20E−05 | 8.00E−06 | 4.40E−05 |
| 6.00 | 1.30E−05 | 4.40E−05 | 7.00E−05 | 2.00E−05 | 4.00E−06 | 4.00E−06 | −1.00E−06 | −2.70E−05 | −1.60E−05 | 4.30E−05 |
| 6.02 | 2.30E−05 | 3.50E−05 | 6.50E−05 | 2.50E−05 | 1.60E−05 | −7.00E−06 | 1.20E−05 | −2.30E−05 | 1.50E−05 | 3.10E−05 |
| 6.03 | 1.50E−05 | 5.00E−05 | 6.50E−05 | 1.20E−05 | 1.00E−05 | 1.10E−05 | 6.00E−06 | −1.40E−05 | −1.00E−06 | 4.10E−05 |
| 6.05 | 1.80E−05 | 3.00E−05 | 7.00E−05 | 2.00E−05 | 7.00E−06 | 7.00E−06 | −6.00E−06 | −2.10E−05 | 2.00E−05 | 2.80E−05 |
| 6.07 | 2.10E−05 | 3.50E−05 | 7.60E−05 | 1.70E−05 | 4.00E−06 | 1.30E−05 | 6.00E−06 | −2.70E−05 | −4.00E−06 | 4.60E−05 |
| 6.08 | 1.50E−05 | 3.20E−05 | 7.70E−05 | 2.50E−05 | −4.00E−06 | 4.00E−06 | 1.30E−05 | −3.50E−05 | −1.40E−05 | 5.20E−05 |
| 6.10 | 1.60E−05 | 2.50E−05 | 7.20E−05 | 3.60E−05 | 1.80E−05 | 7.00E−06 | 1.10E−05 | −2.60E−05 | −1.60E−05 | 4.50E−05 |
| 6.12 | 1.70E−05 | 5.70E−05 | 7.60E−05 | 6.00E−06 | 1.00E−06 | 6.00E−06 | 6.00E−06 | −2.20E−05 | −1.80E−05 | 4.40E−05 |
| 6.13 | 1.20E−05 | 3.40E−05 | 6.90E−05 | 1.70E−05 | −1.10E−05 | 3.00E−06 | 4.00E−06 | −2.50E−05 | −1.20E−05 | 6.00E−05 |
| 6.15 | 1.60E−05 | 3.60E−05 | 6.70E−05 | 1.50E−05 | −1.00E−06 | −2.00E−06 | 6.00E−06 | −2.60E−05 | −2.00E−06 | 3.50E−05 |
| 6.17 | 4.20E−05 | 3.10E−05 | 7.10E−05 | 1.20E−05 | 1.40E−05 | 3.00E−06 | 1.10E−05 | −1.80E−05 | −1.00E−05 | 4.80E−05 |
| 6.18 | 2.00E−05 | 3.00E−05 | 8.70E−05 | 1.40E−05 | 1.20E−05 | −3.00E−06 | 7.00E−06 | −1.10E−05 | −1.00E−05 | 4.10E−05 |
| 6.20 | −7.00E−06 | 3.20E−05 | 8.00E−05 | 1.60E−05 | −4.00E−06 | −7.00E−06 | 1.80E−05 | −1.30E−05 | −8.00E−06 | 4.10E−05 |
| 6.22 | 1.60E−05 | 2.30E−05 | 5.40E−05 | 1.30E−05 | 1.00E−06 | 6.00E−06 | 3.00E−06 | −1.60E−05 | 7.00E−06 | 5.20E−05 |
| 6.23 | 1.60E−05 | 4.00E−05 | 8.00E−05 | 2.40E−05 | 3.00E−06 | 4.00E−06 | 5.00E−06 | −1.00E−05 | −1.00E−05 | 3.50E−05 |
| 6.25 | 1.80E−05 | 4.00E−05 | 4.80E−05 | 7.00E−06 | 1.20E−05 | 1.00E−06 | 7.00E−06 | −1.80E−05 | −6.00E−06 | 4.30E−05 |
| 6.27 | 2.10E−05 | 4.40E−05 | 7.40E−05 | 1.80E−05 | −1.10E−05 | −3.00E−06 | −6.00E−06 | −2.40E−05 | −2.00E−06 | 4.10E−05 |
| 6.28 | 2.00E−05 | 3.30E−05 | 6.60E−05 | 1.70E−05 | 2.20E−05 | −3.00E−06 | 2.30E−05 | −8.00E−06 | −3.00E−06 | 2.70E−05 |
| 6.30 | 1.70E−05 | 3.20E−05 | 8.30E−05 | 1.30E−05 | 1.00E−05 | 4.00E−06 | 0.00E+00 | −1.40E−05 | −1.00E−05 | 4.60E−05 |
| 6.32 | 6.00E−06 | 4.50E−05 | 7.10E−05 | 1.60E−05 | 3.00E−06 | 1.00E−05 | 8.00E−06 | −5.00E−06 | 5.00E−06 | 3.40E−05 |
| 6.33 | 1.50E−05 | 3.20E−05 | 7.60E−05 | 2.60E−05 | 6.00E−06 | 2.00E−06 | 1.20E−05 | −2.70E−05 | −1.00E−06 | 2.30E−05 |
| 6.35 | 3.00E−05 | 4.30E−05 | 6.60E−05 | 2.30E−05 | 7.00E−06 | −3.00E−06 | 1.60E−05 | −2.40E−05 | −8.00E−06 | 3.00E−05 |
| 6.37 | 2.70E−05 | 4.60E−05 | 6.20E−05 | 2.00E−05 | 1.30E−05 | 0.00E+00 | 8.00E−06 | −1.40E−05 | 1.00E−06 | 3.40E−05 |
| 6.38 | 2.30E−05 | 4.20E−05 | 7.50E−05 | 1.80E−05 | −2.00E−06 | −2.00E−06 | 5.00E−06 | −2.10E−05 | −7.00E−06 | 4.40E−05 |
| 6.40 | 3.00E−06 | 2.50E−05 | 6.60E−05 | 2.70E−05 | 6.00E−06 | −5.00E−06 | 1.40E−05 | −1.40E−05 | −1.50E−05 | 4.20E−05 |
| 6.42 | 1.80E−05 | 3.40E−05 | 8.10E−05 | 4.00E−06 | 1.60E−05 | −4.00E−06 | −4.00E−06 | −1.20E−05 | −1.20E−05 | 3.10E−05 |
| 6.43 | 5.00E−06 | 4.70E−05 | 6.70E−05 | 2.50E−05 | 1.50E−05 | 1.00E−05 | 1.50E−05 | −7.00E−06 | 1.00E−06 | 3.70E−05 |
| 6.45 | 1.20E−05 | 3.40E−05 | 7.10E−05 | 1.40E−05 | 1.80E−05 | 6.00E−06 | 7.00E−06 | −1.30E−05 | −8.00E−06 | 3.00E−05 |
| 6.47 | 2.30E−05 | 4.70E−05 | 7.30E−05 | 5.00E−06 | 5.00E−06 | 1.10E−05 | 2.00E−06 | −1.10E−05 | −1.40E−05 | 3.80E−05 |
| 6.48 | 2.40E−05 | 4.20E−05 | 6.90E−05 | 1.80E−05 | 6.00E−06 | −2.00E−06 | 2.00E−06 | −5.00E−06 | 5.00E−06 | 3.30E−05 |
| 6.50 | 2.50E−05 | 4.50E−05 | 6.20E−05 | 1.60E−05 | 4.00E−06 | 8.00E−06 | 1.70E−05 | −7.00E−06 | 0.00E+00 | 2.70E−05 |
| 6.52 | 2.10E−05 | 4.40E−05 | 7.30E−05 | 6.00E−06 | 1.80E−05 | 2.00E−06 | 7.00E−06 | −1.00E−06 | −6.00E−06 | 3.20E−05 |
| 6.53 | 2.00E−05 | 4.40E−05 | 6.00E−05 | 3.30E−05 | 4.00E−06 | 1.40E−05 | 0.00E+00 | −1.80E−05 | 1.00E−06 | 3.40E−05 |
| 6.55 | 1.60E−05 | 5.60E−05 | 5.20E−05 | 2.30E−05 | 7.00E−06 | −5.00E−06 | 1.00E−05 | −1.60E−05 | 2.00E−06 | 4.10E−05 |
| 6.57 | 1.10E−05 | 3.00E−05 | 7.50E−05 | 1.70E−05 | 1.00E−06 | 1.50E−05 | 1.00E−05 | −1.70E−05 | −1.00E−06 | 4.20E−05 |
| 6.58 | 2.10E−05 | 4.70E−05 | 6.50E−05 | 1.00E−05 | 1.70E−05 | 6.00E−06 | 6.00E−06 | −1.00E−05 | −7.00E−06 | 4.00E−05 |
| 6.60 | 2.30E−05 | 4.20E−05 | 8.10E−05 | 1.80E−05 | 1.00E−05 | 1.40E−05 | 1.00E−05 | −1.30E−05 | −6.00E−06 | 3.80E−05 |
| 6.62 | 1.20E−05 | 3.60E−05 | 7.70E−05 | 2.20E−05 | 1.10E−05 | −1.00E−05 | 8.00E−06 | −3.00E−06 | 3.00E−06 | 4.60E−05 |
| 6.63 | 8.00E−06 | 4.00E−05 | 6.20E−05 | 2.30E−05 | −2.00E−06 | 3.00E−06 | −5.00E−06 | −4.00E−06 | 2.00E−06 | 3.80E−05 |
| 6.65 | 1.10E−05 | 4.20E−05 | 8.00E−05 | 2.80E−05 | 1.70E−05 | 4.00E−06 | 1.20E−05 | −2.70E−05 | 4.00E−06 | 4.80E−05 |
| 6.67 | 1.60E−05 | 4.80E−05 | 7.60E−05 | 2.70E−05 | 1.00E−06 | 7.00E−06 | 1.20E−05 | −7.00E−06 | −1.10E−05 | 4.10E−05 |
| 6.68 | 2.20E−05 | 3.30E−05 | 8.50E−05 | 1.50E−05 | 1.00E−05 | −3.00E−06 | 1.10E−05 | −2.70E−05 | −2.00E−06 | 3.10E−05 |
| 6.70 | 1.30E−05 | 3.30E−05 | 7.00E−05 | 2.60E−05 | 1.10E−05 | −1.00E−05 | 6.00E−06 | −8.00E−06 | 2.00E−06 | 5.60E−05 |
| 6.72 | 2.00E−05 | 3.00E−05 | 8.10E−05 | 2.50E−05 | 1.10E−05 | 2.00E−06 | 2.40E−05 | 1.00E−06 | 7.00E−06 | 5.10E−05 |
| 6.73 | 2.60E−05 | 4.80E−05 | 6.70E−05 | 1.70E−05 | 1.20E−05 | 4.00E−06 | 1.80E−05 | −2.10E−05 | −2.00E−06 | 4.20E−05 |
| 6.75 | 2.70E−05 | 3.80E−05 | 7.20E−05 | 3.10E−05 | 1.00E−05 | 2.40E−05 | 2.00E−06 | −2.00E−05 | 3.00E−06 | 4.30E−05 |
| 6.77 | 2.50E−05 | 4.50E−05 | 8.30E−05 | 3.10E−05 | 2.00E−05 | 5.00E−06 | 2.10E−05 | −2.20E−05 | −1.20E−05 | 3.80E−05 |
| 6.78 | 2.10E−05 | 3.80E−05 | 7.70E−05 | 1.80E−05 | 1.50E−05 | −5.00E−06 | 7.00E−06 | −1.00E−05 | −1.10E−05 | 4.40E−05 |
| 6.80 | 1.40E−05 | 3.10E−05 | 6.60E−05 | 1.40E−05 | 7.00E−06 | 1.20E−05 | 6.00E−06 | −1.60E−05 | 2.00E−06 | 3.50E−05 |
| 6.82 | 2.60E−05 | 4.10E−05 | 7.50E−05 | 8.00E−06 | 6.00E−06 | 1.10E−05 | 1.10E−05 | −1.80E−05 | 5.00E−06 | 4.80E−05 |
| 6.83 | 2.80E−05 | 3.60E−05 | 6.90E−05 | 2.20E−05 | 1.00E−05 | 1.80E−05 | 6.00E−06 | −1.40E−05 | −4.00E−06 | 5.40E−05 |
| 6.85 | 2.20E−05 | 3.70E−05 | 7.60E−05 | 2.30E−05 | 1.70E−05 | 2.00E−05 | 6.00E−06 | −1.40E−05 | −1.30E−05 | 5.50E−05 |
| 6.87 | 3.40E−05 | 5.30E−05 | 7.70E−05 | 3.30E−05 | 1.60E−05 | 1.00E−05 | 1.20E−05 | −2.10E−05 | 7.00E−06 | 5.50E−05 |
| 6.88 | 3.30E−05 | 3.80E−05 | 7.00E−05 | 1.20E−05 | 3.50E−05 | 1.40E−05 | 6.00E−06 | −1.20E−05 | −2.00E−06 | 6.20E−05 |
| 6.90 | 1.80E−05 | 4.20E−05 | 8.10E−05 | 2.20E−05 | 1.30E−05 | 1.20E−05 | 2.00E−06 | −4.00E−06 | 5.00E−06 | 5.20E−05 |
| 6.92 | 1.60E−05 | 3.60E−05 | 7.10E−05 | 2.60E−05 | 1.00E−05 | 2.70E−05 | −2.00E−06 | −1.00E−05 | 1.60E−05 | 5.70E−05 |

TABLE 1-continued

UV 225 nm Absorbance [AU] values for different batches

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 6.93 | 4.00E−05 | 3.80E−05 | 7.60E−05 | 1.40E−05 | 4.00E−06 | 2.50E−05 | −2.00E−06 | −1.60E−05 | 2.70E−05 | 5.70E−05 |
| 6.95 | 3.30E−05 | 4.40E−05 | 7.60E−05 | 1.60E−05 | 1.70E−05 | 1.50E−05 | 7.00E−06 | −1.00E−06 | −5.00E−06 | 5.10E−05 |
| 6.97 | 2.80E−05 | 3.00E−05 | 6.10E−05 | 1.70E−05 | 7.00E−06 | 2.10E−05 | 4.00E−06 | −3.00E−06 | 1.30E−05 | 6.60E−05 |
| 6.98 | 2.50E−05 | 3.20E−05 | 7.40E−05 | 2.80E−05 | 1.80E−05 | 3.40E−05 | 6.00E−06 | −1.00E−06 | 8.00E−06 | 4.30E−05 |
| 7.00 | 3.30E−05 | 3.80E−05 | 7.90E−05 | 2.70E−05 | 1.40E−05 | 2.30E−05 | 3.00E−06 | 0.00E+00 | 1.30E−05 | 6.50E−05 |
| 7.02 | 3.60E−05 | 5.30E−05 | 9.40E−05 | 6.00E−05 | 1.30E−05 | 1.80E−05 | 1.10E−05 | −2.00E−06 | 1.10E−05 | 6.60E−05 |
| 7.03 | 3.50E−05 | 4.10E−05 | 7.50E−05 | 2.70E−05 | 1.70E−05 | 3.00E−05 | 1.00E−05 | −1.00E−05 | 1.00E−05 | 6.20E−05 |
| 7.05 | 3.20E−05 | 3.70E−05 | 7.60E−05 | 3.20E−05 | 1.70E−05 | 3.10E−05 | 1.70E−05 | −7.00E−06 | 1.30E−05 | 5.50E−05 |
| 7.07 | 3.70E−05 | 4.60E−05 | 7.50E−05 | 3.20E−05 | 1.10E−05 | 2.30E−05 | 4.00E−06 | −1.10E−05 | 1.40E−05 | 5.40E−05 |
| 7.08 | 3.20E−05 | 4.20E−05 | 8.50E−05 | 3.30E−05 | 1.70E−05 | 5.00E−05 | −1.00E−06 | 7.00E−06 | 4.00E−05 | 5.80E−05 |
| 7.10 | 2.70E−05 | 4.00E−05 | 8.40E−05 | 3.80E−05 | 2.10E−05 | 4.70E−05 | −4.00E−06 | −2.20E−05 | 1.70E−05 | 6.20E−05 |
| 7.12 | 3.30E−05 | 3.80E−05 | 7.00E−05 | 4.70E−05 | 5.00E−06 | 4.20E−05 | 2.00E−06 | −7.00E−06 | 1.80E−05 | 6.30E−05 |
| 7.13 | 1.80E−05 | 3.80E−05 | 7.70E−05 | 4.40E−05 | 1.60E−05 | 5.50E−05 | −6.00E−06 | −5.00E−06 | 1.50E−05 | 6.20E−05 |
| 7.15 | 4.40E−05 | 4.80E−05 | 7.70E−05 | 4.20E−05 | 2.30E−05 | 4.70E−05 | −2.00E−06 | −4.00E−06 | 2.20E−05 | 7.20E−05 |
| 7.17 | 5.40E−05 | 5.60E−05 | 8.20E−05 | 4.50E−05 | 3.20E−05 | 5.40E−05 | 1.20E−05 | −1.30E−05 | 4.30E−05 | 7.00E−05 |
| 7.18 | 2.50E−05 | 5.00E−05 | 7.60E−05 | 5.80E−05 | 2.40E−05 | 4.60E−05 | 1.40E−05 | −1.40E−05 | 5.10E−05 | 7.00E−05 |
| 7.20 | 3.40E−05 | 3.60E−05 | 7.90E−05 | 5.30E−05 | 1.00E−05 | 6.90E−05 | 1.20E−05 | −1.00E−05 | 2.80E−05 | 8.70E−05 |
| 7.22 | 3.00E−05 | 5.10E−05 | 7.60E−05 | 5.30E−05 | 3.10E−05 | 7.50E−05 | −2.00E−06 | −1.00E−05 | 3.30E−05 | 9.30E−05 |
| 7.23 | 2.50E−05 | 5.80E−05 | 7.60E−05 | 7.30E−05 | 3.70E−05 | 8.50E−05 | −7.00E−06 | −1.30E−05 | 5.00E−05 | 9.00E−05 |
| 7.25 | 3.50E−05 | 5.70E−05 | 8.00E−05 | 9.40E−05 | 1.50E−05 | 9.60E−05 | 0.00E+00 | 1.10E−05 | 5.60E−05 | 8.00E−05 |
| 7.27 | 2.30E−05 | 7.00E−05 | 9.00E−05 | 9.30E−05 | 2.00E−05 | 9.40E−05 | 2.10E−05 | 4.00E−06 | 5.40E−05 | 8.70E−05 |
| 7.28 | 3.60E−05 | 6.20E−05 | 8.00E−05 | 8.00E−05 | 3.20E−05 | 1.31E−04 | 8.00E−06 | −2.00E−06 | 5.80E−05 | 1.14E−04 |
| 7.30 | 5.30E−05 | 7.00E−05 | 1.01E−04 | 1.01E−04 | 2.10E−05 | 1.21E−04 | −3.00E−06 | 2.40E−05 | 6.90E−05 | 1.13E−04 |
| 7.32 | 4.30E−05 | 6.50E−05 | 7.90E−05 | 1.06E−04 | 2.20E−05 | 1.39E−04 | −1.10E−05 | 2.00E−05 | 8.20E−05 | 1.19E−04 |
| 7.33 | 5.00E−05 | 7.50E−05 | 8.60E−05 | 1.44E−04 | 3.10E−05 | 1.44E−04 | 1.20E−05 | 6.00E−06 | 8.60E−05 | 1.15E−04 |
| 7.35 | 4.10E−05 | 8.20E−05 | 7.10E−05 | 1.31E−04 | 2.50E−05 | 1.69E−04 | 1.50E−05 | 2.50E−05 | 9.10E−05 | 1.26E−04 |
| 7.37 | 4.10E−05 | 7.10E−05 | 8.50E−05 | 1.51E−04 | 2.60E−05 | 1.98E−04 | −3.00E−06 | 2.20E−05 | 1.15E−04 | 1.35E−04 |
| 7.38 | 3.70E−05 | 8.30E−05 | 8.50E−05 | 1.74E−04 | 1.70E−05 | 2.11E−04 | 2.00E−06 | 3.50E−05 | 1.23E−04 | 1.59E−04 |
| 7.40 | 4.80E−05 | 9.50E−05 | 8.30E−05 | 1.92E−04 | 1.80E−05 | 2.24E−04 | 1.40E−05 | 1.50E−05 | 1.35E−04 | 1.59E−04 |
| 7.42 | 5.50E−05 | 1.04E−04 | 9.40E−05 | 2.07E−04 | 3.30E−05 | 2.59E−04 | 1.20E−05 | 3.10E−05 | 1.62E−04 | 1.76E−04 |
| 7.43 | 3.30E−05 | 1.11E−04 | 9.10E−05 | 2.40E−04 | 1.70E−05 | 2.82E−04 | 1.00E−05 | 2.30E−05 | 1.74E−04 | 1.92E−04 |
| 7.45 | 2.30E−05 | 1.14E−04 | 9.90E−05 | 2.48E−04 | 2.80E−05 | 3.18E−04 | 1.50E−05 | 5.00E−05 | 1.86E−04 | 2.02E−04 |
| 7.47 | 2.70E−05 | 1.31E−04 | 9.20E−05 | 2.63E−04 | 2.40E−05 | 3.33E−04 | 1.50E−05 | 5.10E−05 | 2.12E−04 | 2.34E−04 |
| 7.48 | 4.60E−05 | 1.45E−04 | 1.10E−04 | 3.00E−04 | 2.80E−05 | 3.75E−04 | 1.00E−05 | 5.50E−05 | 2.29E−04 | 2.41E−04 |
| 7.50 | 4.00E−05 | 1.46E−04 | 8.60E−05 | 3.46E−04 | 3.20E−05 | 4.00E−04 | 7.00E−06 | 5.40E−05 | 2.43E−04 | 2.64E−04 |
| 7.52 | 4.30E−05 | 1.64E−04 | 8.60E−05 | 3.68E−04 | 2.20E−05 | 4.37E−04 | 8.00E−06 | 8.40E−05 | 2.64E−04 | 2.92E−04 |
| 7.53 | 5.10E−05 | 1.79E−04 | 8.20E−05 | 3.80E−04 | 1.80E−05 | 4.73E−04 | 8.00E−06 | 9.20E−05 | 3.12E−04 | 3.18E−04 |
| 7.55 | 4.80E−05 | 1.86E−04 | 9.70E−05 | 4.24E−04 | 3.10E−05 | 5.15E−04 | 1.30E−05 | 1.09E−04 | 3.25E−04 | 3.57E−04 |
| 7.57 | 3.70E−05 | 1.93E−04 | 1.01E−04 | 4.75E−04 | 1.70E−05 | 5.44E−04 | 3.40E−05 | 1.10E−04 | 3.69E−04 | 3.79E−04 |
| 7.58 | 3.60E−05 | 2.21E−04 | 1.16E−04 | 5.29E−04 | 3.50E−05 | 6.16E−04 | 2.80E−05 | 1.29E−04 | 3.94E−04 | 4.00E−04 |
| 7.60 | 4.40E−05 | 2.39E−04 | 1.04E−04 | 5.69E−04 | 3.40E−05 | 6.60E−04 | 2.30E−05 | 1.69E−04 | 4.26E−04 | 4.35E−04 |
| 7.62 | 5.20E−05 | 2.62E−04 | 1.17E−04 | 6.03E−04 | 5.00E−06 | 7.52E−04 | 2.10E−05 | 1.68E−04 | 4.74E−04 | 4.70E−04 |
| 7.63 | 6.30E−05 | 2.82E−04 | 1.05E−04 | 6.71E−04 | 3.20E−05 | 8.04E−04 | 1.60E−05 | 1.83E−04 | 5.19E−04 | 5.18E−04 |
| 7.65 | 2.60E−05 | 3.06E−04 | 1.07E−04 | 7.42E−04 | 3.00E−05 | 8.93E−04 | 4.70E−05 | 1.99E−04 | 5.94E−04 | 5.65E−04 |
| 7.67 | 3.10E−05 | 3.25E−04 | 1.15E−04 | 8.13E−04 | 2.20E−05 | 9.87E−04 | 2.60E−05 | 2.28E−04 | 6.40E−04 | 6.02E−04 |
| 7.68 | 4.10E−05 | 3.45E−04 | 1.22E−04 | 8.99E−04 | 2.40E−05 | 1.10E−03 | 3.20E−05 | 2.71E−04 | 7.25E−04 | 6.81E−04 |
| 7.70 | 4.80E−05 | 3.84E−04 | 1.11E−04 | 9.95E−04 | 3.50E−05 | 1.21E−03 | 3.50E−05 | 3.00E−04 | 8.04E−04 | 7.36E−04 |
| 7.72 | 4.00E−05 | 4.27E−04 | 1.39E−04 | 1.11E−03 | 2.50E−05 | 1.35E−03 | 3.60E−05 | 3.26E−04 | 9.01E−04 | 8.00E−04 |
| 7.73 | 3.70E−05 | 4.69E−04 | 1.31E−04 | 1.22E−03 | 3.10E−05 | 1.49E−03 | 3.70E−05 | 3.48E−04 | 9.98E−04 | 9.03E−04 |
| 7.75 | 4.30E−05 | 5.12E−04 | 1.28E−04 | 1.35E−03 | 4.50E−05 | 1.62E−03 | 3.60E−05 | 3.94E−04 | 1.12E−03 | 1.01E−03 |
| 7.77 | 4.50E−05 | 5.73E−04 | 1.29E−04 | 1.47E−03 | 3.20E−05 | 1.79E−03 | 4.30E−05 | 4.46E−04 | 1.23E−03 | 1.10E−03 |
| 7.78 | 4.30E−05 | 6.21E−04 | 1.56E−04 | 1.62E−03 | 4.40E−05 | 1.95E−03 | 2.80E−05 | 5.04E−04 | 1.36E−03 | 1.23E−03 |
| 7.80 | 4.40E−05 | 6.95E−04 | 1.43E−04 | 1.80E−03 | 3.30E−05 | 2.10E−03 | 4.30E−05 | 5.59E−04 | 1.50E−03 | 1.35E−03 |
| 7.82 | 5.20E−05 | 7.66E−04 | 1.58E−04 | 1.94E−03 | 4.00E−05 | 2.25E−03 | 6.00E−05 | 6.26E−04 | 1.63E−03 | 1.49E−03 |
| 7.83 | 4.80E−05 | 8.43E−04 | 1.62E−04 | 2.10E−03 | 3.10E−05 | 2.42E−03 | 6.30E−05 | 7.29E−04 | 1.78E−03 | 1.63E−03 |
| 7.85 | 6.00E−05 | 9.28E−04 | 1.70E−04 | 2.25E−03 | 4.60E−05 | 2.59E−03 | 7.40E−05 | 8.02E−04 | 1.94E−03 | 1.77E−03 |
| 7.87 | 4.00E−05 | 1.02E−03 | 1.85E−04 | 2.40E−03 | 5.20E−05 | 2.74E−03 | 5.60E−05 | 8.84E−04 | 2.07E−03 | 1.93E−03 |
| 7.88 | 4.40E−05 | 1.13E−03 | 2.02E−04 | 2.58E−03 | 4.60E−05 | 2.89E−03 | 5.30E−05 | 9.70E−04 | 2.22E−03 | 2.09E−03 |
| 7.90 | 5.60E−05 | 1.22E−03 | 1.93E−04 | 2.70E−03 | 6.60E−05 | 3.01E−03 | 7.90E−05 | 1.10E−03 | 2.35E−03 | 2.23E−03 |
| 7.92 | 5.10E−05 | 1.32E−03 | 2.30E−04 | 2.85E−03 | 6.90E−05 | 3.14E−03 | 8.40E−05 | 1.20E−03 | 2.47E−03 | 2.38E−03 |
| 7.93 | 4.40E−05 | 1.44E−03 | 2.35E−04 | 2.96E−03 | 6.50E−05 | 3.23E−03 | 9.50E−05 | 1.33E−03 | 2.58E−03 | 2.52E−03 |
| 7.95 | 6.00E−05 | 1.57E−03 | 2.47E−04 | 3.10E−03 | 7.00E−05 | 3.33E−03 | 9.50E−05 | 1.44E−03 | 2.71E−03 | 2.66E−03 |
| 7.97 | 5.40E−05 | 1.64E−03 | 2.62E−04 | 3.18E−03 | 1.01E−04 | 3.43E−03 | 1.04E−04 | 1.57E−03 | 2.82E−03 | 2.77E−03 |
| 7.98 | 5.40E−05 | 1.74E−03 | 2.92E−04 | 3.28E−03 | 1.12E−04 | 3.49E−03 | 1.26E−04 | 1.69E−03 | 2.92E−03 | 2.89E−03 |
| 8.00 | 6.10E−05 | 1.84E−03 | 3.10E−04 | 3.36E−03 | 1.22E−04 | 3.59E−03 | 1.29E−04 | 1.83E−03 | 3.00E−03 | 3.00E−03 |
| 8.02 | 5.20E−05 | 1.92E−03 | 3.45E−04 | 3.43E−03 | 1.42E−04 | 3.67E−03 | 1.30E−04 | 1.96E−03 | 3.11E−03 | 3.11E−03 |
| 8.03 | 5.00E−05 | 2.02E−03 | 3.52E−04 | 3.53E−03 | 1.68E−04 | 3.74E−03 | 1.52E−04 | 2.07E−03 | 3.20E−03 | 3.20E−03 |
| 8.05 | 4.80E−05 | 2.08E−03 | 3.81E−04 | 3.61E−03 | 2.12E−04 | 3.87E−03 | 1.73E−04 | 2.16E−03 | 3.29E−03 | 3.29E−03 |
| 8.07 | 5.20E−05 | 2.16E−03 | 4.22E−04 | 3.73E−03 | 2.38E−04 | 4.02E−03 | 1.75E−04 | 2.28E−03 | 3.42E−03 | 3.38E−03 |
| 8.08 | 6.20E−05 | 2.24E−03 | 4.54E−04 | 3.87E−03 | 2.63E−04 | 4.19E−03 | 1.86E−04 | 2.37E−03 | 3.54E−03 | 3.48E−03 |
| 8.10 | 6.60E−05 | 2.28E−03 | 5.04E−04 | 3.98E−03 | 3.48E−04 | 4.42E−03 | 2.27E−04 | 2.48E−03 | 3.73E−03 | 3.59E−03 |
| 8.12 | 4.00E−05 | 2.36E−03 | 5.34E−04 | 4.16E−03 | 4.08E−04 | 4.69E−03 | 2.34E−04 | 2.56E−03 | 3.91E−03 | 3.73E−03 |
| 8.13 | 6.30E−05 | 2.40E−03 | 5.76E−04 | 4.41E−03 | 5.00E−04 | 5.03E−03 | 2.50E−04 | 2.66E−03 | 4.17E−03 | 3.89E−03 |

TABLE 1-continued

UV 225 nm Absorbance [AU] values for different batches

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 8.15 | 5.50E−05 | 2.48E−03 | 6.08E−04 | 4.70E−03 | 6.16E−04 | 5.45E−03 | 2.97E−04 | 2.76E−03 | 4.46E−03 | 4.07E−03 |
| 8.17 | 6.00E−05 | 2.57E−03 | 6.50E−04 | 5.08E−03 | 7.59E−04 | 5.95E−03 | 3.32E−04 | 2.87E−03 | 4.83E−03 | 4.32E−03 |
| 8.18 | 6.20E−05 | 2.68E−03 | 6.96E−04 | 5.52E−03 | 9.38E−04 | 6.55E−03 | 3.60E−04 | 2.98E−03 | 5.27E−03 | 4.60E−03 |
| 8.20 | 6.10E−05 | 2.80E−03 | 7.39E−04 | 6.04E−03 | 1.18E−03 | 7.26E−03 | 4.00E−04 | 3.12E−03 | 5.78E−03 | 4.97E−03 |
| 8.22 | 5.30E−05 | 2.95E−03 | 7.71E−04 | 6.65E−03 | 1.43E−03 | 8.06E−03 | 4.39E−04 | 3.26E−03 | 6.38E−03 | 5.41E−03 |
| 8.23 | 6.30E−05 | 3.15E−03 | 8.21E−04 | 7.37E−03 | 1.76E−03 | 8.95E−03 | 4.74E−04 | 3.47E−03 | 7.08E−03 | 5.91E−03 |
| 8.25 | 6.00E−05 | 3.38E−03 | 8.80E−04 | 8.20E−03 | 2.17E−03 | 9.97E−03 | 5.56E−04 | 3.69E−03 | 7.87E−03 | 6.49E−03 |
| 8.27 | 6.20E−05 | 3.69E−03 | 9.03E−04 | 9.12E−03 | 2.66E−03 | 1.11E−02 | 5.47E−04 | 3.99E−03 | 8.76E−03 | 7.19E−03 |
| 8.28 | 7.10E−05 | 4.02E−03 | 9.68E−04 | 1.01E−02 | 3.25E−03 | 1.22E−02 | 6.06E−04 | 4.31E−03 | 9.71E−03 | 7.99E−03 |
| 8.30 | 6.50E−05 | 4.42E−03 | 1.01E−03 | 1.12E−02 | 3.91E−03 | 1.35E−02 | 6.33E−04 | 4.69E−03 | 1.07E−02 | 8.84E−03 |
| 8.32 | 6.00E−05 | 4.89E−03 | 1.05E−03 | 1.24E−02 | 4.68E−03 | 1.48E−02 | 6.86E−04 | 5.15E−03 | 1.19E−02 | 9.83E−03 |
| 8.33 | 7.00E−05 | 5.45E−03 | 1.12E−03 | 1.37E−02 | 5.53E−03 | 1.62E−02 | 7.53E−04 | 5.67E−03 | 1.30E−02 | 1.09E−02 |
| 8.35 | 6.20E−05 | 6.08E−03 | 1.20E−03 | 1.50E−02 | 6.49E−03 | 1.75E−02 | 7.94E−04 | 6.28E−03 | 1.42E−02 | 1.20E−02 |
| 8.37 | 6.50E−05 | 6.74E−03 | 1.25E−03 | 1.63E−02 | 7.48E−03 | 1.89E−02 | 8.62E−04 | 6.97E−03 | 1.54E−02 | 1.32E−02 |
| 8.38 | 5.60E−05 | 7.49E−03 | 1.33E−03 | 1.76E−02 | 8.52E−03 | 2.02E−02 | 9.40E−04 | 7.76E−03 | 1.67E−02 | 1.44E−02 |
| 8.40 | 6.70E−05 | 8.33E−03 | 1.44E−03 | 1.89E−02 | 9.59E−03 | 2.14E−02 | 9.87E−04 | 8.60E−03 | 1.79E−02 | 1.57E−02 |
| 8.42 | 8.40E−05 | 9.21E−03 | 1.53E−03 | 2.02E−02 | 1.07E−02 | 2.26E−02 | 1.05E−03 | 9.53E−03 | 1.90E−02 | 1.69E−02 |
| 8.43 | 6.40E−05 | 1.01E−02 | 1.67E−03 | 2.14E−02 | 1.18E−02 | 2.37E−02 | 1.15E−03 | 1.05E−02 | 2.01E−02 | 1.81E−02 |
| 8.45 | 6.30E−05 | 1.11E−02 | 1.82E−03 | 2.25E−02 | 1.29E−02 | 2.46E−02 | 1.24E−03 | 1.15E−02 | 2.11E−02 | 1.93E−02 |
| 8.47 | 6.00E−05 | 1.21E−02 | 1.99E−03 | 2.35E−02 | 1.39E−02 | 2.54E−02 | 1.35E−03 | 1.26E−02 | 2.20E−02 | 2.05E−02 |
| 8.48 | 5.50E−05 | 1.31E−02 | 2.17E−03 | 2.44E−02 | 1.48E−02 | 2.61E−02 | 1.46E−03 | 1.38E−02 | 2.28E−02 | 2.15E−02 |
| 8.50 | 6.20E−05 | 1.40E−02 | 2.40E−03 | 2.52E−02 | 1.56E−02 | 2.66E−02 | 1.61E−03 | 1.49E−02 | 2.34E−02 | 2.24E−02 |
| 8.52 | 4.70E−05 | 1.50E−02 | 2.66E−03 | 2.58E−02 | 1.63E−02 | 2.69E−02 | 1.74E−03 | 1.60E−02 | 2.39E−02 | 2.33E−02 |
| 8.53 | 5.70E−05 | 1.59E−02 | 2.94E−03 | 2.63E−02 | 1.69E−02 | 2.71E−02 | 1.91E−03 | 1.71E−02 | 2.43E−02 | 2.40E−02 |
| 8.55 | 5.60E−05 | 1.67E−02 | 3.27E−03 | 2.65E−02 | 1.74E−02 | 2.70E−02 | 2.12E−03 | 1.81E−02 | 2.45E−02 | 2.46E−02 |
| 8.57 | 6.00E−05 | 1.75E−02 | 3.63E−03 | 2.67E−02 | 1.78E−02 | 2.69E−02 | 2.34E−03 | 1.91E−02 | 2.46E−02 | 2.50E−02 |
| 8.58 | 6.10E−05 | 1.82E−02 | 4.01E−03 | 2.66E−02 | 1.81E−02 | 2.65E−02 | 2.58E−03 | 2.01E−02 | 2.45E−02 | 2.52E−02 |
| 8.60 | 6.60E−05 | 1.88E−02 | 4.43E−03 | 2.65E−02 | 1.82E−02 | 2.61E−02 | 2.87E−03 | 2.08E−02 | 2.43E−02 | 2.53E−02 |
| 8.62 | 5.10E−05 | 1.93E−02 | 4.90E−03 | 2.61E−02 | 1.83E−02 | 2.55E−02 | 3.18E−03 | 2.16E−02 | 2.40E−02 | 2.53E−02 |
| 8.63 | 6.00E−05 | 1.97E−02 | 5.35E−03 | 2.57E−02 | 1.82E−02 | 2.48E−02 | 3.52E−03 | 2.22E−02 | 2.36E−02 | 2.51E−02 |
| 8.65 | 5.70E−05 | 2.00E−02 | 5.88E−03 | 2.51E−02 | 1.81E−02 | 2.40E−02 | 3.90E−03 | 2.27E−02 | 2.30E−02 | 2.48E−02 |
| 8.67 | 5.70E−05 | 2.02E−02 | 6.39E−03 | 2.44E−02 | 1.79E−02 | 2.32E−02 | 4.31E−03 | 2.31E−02 | 2.24E−02 | 2.44E−02 |
| 8.68 | 5.50E−05 | 2.02E−02 | 6.91E−03 | 2.37E−02 | 1.76E−02 | 2.23E−02 | 4.75E−03 | 2.33E−02 | 2.17E−02 | 2.39E−02 |
| 8.70 | 5.60E−05 | 2.02E−02 | 7.45E−03 | 2.29E−02 | 1.72E−02 | 2.14E−02 | 5.22E−03 | 2.34E−02 | 2.10E−02 | 2.33E−02 |
| 8.72 | 6.10E−05 | 2.00E−02 | 8.01E−03 | 2.20E−02 | 1.69E−02 | 2.05E−02 | 5.72E−03 | 2.34E−02 | 2.03E−02 | 2.26E−02 |
| 8.73 | 5.80E−05 | 1.98E−02 | 8.54E−03 | 2.11E−02 | 1.65E−02 | 1.96E−02 | 6.24E−03 | 2.33E−02 | 1.95E−02 | 2.18E−02 |
| 8.75 | 6.60E−05 | 1.94E−02 | 9.07E−03 | 2.02E−02 | 1.61E−02 | 1.87E−02 | 6.80E−03 | 2.31E−02 | 1.87E−02 | 2.11E−02 |
| 8.77 | 6.10E−05 | 1.90E−02 | 9.58E−03 | 1.94E−02 | 1.57E−02 | 1.78E−02 | 7.36E−03 | 2.27E−02 | 1.80E−02 | 2.03E−02 |
| 8.78 | 5.10E−05 | 1.85E−02 | 1.01E−02 | 1.85E−02 | 1.53E−02 | 1.70E−02 | 7.93E−03 | 2.23E−02 | 1.72E−02 | 1.95E−02 |
| 8.80 | 6.90E−05 | 1.79E−02 | 1.05E−02 | 1.77E−02 | 1.49E−02 | 1.63E−02 | 8.51E−03 | 2.18E−02 | 1.65E−02 | 1.87E−02 |
| 8.82 | 4.70E−05 | 1.73E−02 | 1.09E−02 | 1.69E−02 | 1.46E−02 | 1.56E−02 | 9.08E−03 | 2.12E−02 | 1.59E−02 | 1.79E−02 |
| 8.83 | 5.30E−05 | 1.67E−02 | 1.13E−02 | 1.63E−02 | 1.43E−02 | 1.50E−02 | 9.66E−03 | 2.06E−02 | 1.53E−02 | 1.72E−02 |
| 8.85 | 5.70E−05 | 1.61E−02 | 1.17E−02 | 1.56E−02 | 1.40E−02 | 1.45E−02 | 1.02E−02 | 1.99E−02 | 1.48E−02 | 1.65E−02 |
| 8.87 | 5.60E−05 | 1.54E−02 | 1.20E−02 | 1.51E−02 | 1.38E−02 | 1.41E−02 | 1.08E−02 | 1.92E−02 | 1.43E−02 | 1.58E−02 |
| 8.88 | 4.40E−05 | 1.47E−02 | 1.22E−02 | 1.46E−02 | 1.36E−02 | 1.38E−02 | 1.13E−02 | 1.85E−02 | 1.39E−02 | 1.53E−02 |
| 8.90 | 5.70E−05 | 1.41E−02 | 1.24E−02 | 1.42E−02 | 1.35E−02 | 1.35E−02 | 1.18E−02 | 1.78E−02 | 1.36E−02 | 1.48E−02 |
| 8.92 | 7.10E−05 | 1.34E−02 | 1.26E−02 | 1.39E−02 | 1.34E−02 | 1.34E−02 | 1.22E−02 | 1.71E−02 | 1.34E−02 | 1.43E−02 |
| 8.93 | 5.70E−05 | 1.28E−02 | 1.27E−02 | 1.37E−02 | 1.35E−02 | 1.34E−02 | 1.27E−02 | 1.64E−02 | 1.33E−02 | 1.40E−02 |
| 8.95 | 6.10E−05 | 1.22E−02 | 1.27E−02 | 1.36E−02 | 1.36E−02 | 1.36E−02 | 1.30E−02 | 1.58E−02 | 1.33E−02 | 1.37E−02 |
| 8.97 | 6.40E−05 | 1.17E−02 | 1.27E−02 | 1.37E−02 | 1.39E−02 | 1.39E−02 | 1.34E−02 | 1.52E−02 | 1.34E−02 | 1.36E−02 |
| 8.98 | 6.20E−05 | 1.13E−02 | 1.27E−02 | 1.39E−02 | 1.42E−02 | 1.44E−02 | 1.37E−02 | 1.47E−02 | 1.38E−02 | 1.35E−02 |
| 9.00 | 6.50E−05 | 1.09E−02 | 1.26E−02 | 1.43E−02 | 1.48E−02 | 1.52E−02 | 1.39E−02 | 1.42E−02 | 1.43E−02 | 1.36E−02 |
| 9.02 | 7.00E−05 | 1.06E−02 | 1.25E−02 | 1.49E−02 | 1.55E−02 | 1.61E−02 | 1.41E−02 | 1.38E−02 | 1.51E−02 | 1.39E−02 |
| 9.03 | 7.20E−05 | 1.03E−02 | 1.23E−02 | 1.57E−02 | 1.66E−02 | 1.75E−02 | 1.43E−02 | 1.35E−02 | 1.61E−02 | 1.43E−02 |
| 9.05 | 5.30E−05 | 1.02E−02 | 1.21E−02 | 1.68E−02 | 1.78E−02 | 1.92E−02 | 1.44E−02 | 1.34E−02 | 1.75E−02 | 1.50E−02 |
| 9.07 | 7.50E−05 | 1.03E−02 | 1.19E−02 | 1.83E−02 | 1.96E−02 | 2.15E−02 | 1.45E−02 | 1.33E−02 | 1.93E−02 | 1.60E−02 |
| 9.08 | 6.10E−05 | 1.05E−02 | 1.17E−02 | 2.03E−02 | 2.17E−02 | 2.42E−02 | 1.46E−02 | 1.35E−02 | 2.16E−02 | 1.72E−02 |
| 9.10 | 4.80E−05 | 1.09E−02 | 1.15E−02 | 2.27E−02 | 2.44E−02 | 2.76E−02 | 1.46E−02 | 1.38E−02 | 2.45E−02 | 1.89E−02 |
| 9.12 | 6.50E−05 | 1.16E−02 | 1.12E−02 | 2.57E−02 | 2.77E−02 | 3.18E−02 | 1.46E−02 | 1.44E−02 | 2.80E−02 | 2.11E−02 |
| 9.13 | 5.80E−05 | 1.26E−02 | 1.10E−02 | 2.94E−02 | 3.18E−02 | 3.68E−02 | 1.46E−02 | 1.53E−02 | 3.23E−02 | 2.38E−02 |
| 9.15 | 6.90E−05 | 1.39E−02 | 1.08E−02 | 3.39E−02 | 3.67E−02 | 4.27E−02 | 1.45E−02 | 1.65E−02 | 3.74E−02 | 2.71E−02 |
| 9.17 | 6.10E−05 | 1.56E−02 | 1.06E−02 | 3.93E−02 | 4.26E−02 | 4.96E−02 | 1.45E−02 | 1.82E−02 | 4.33E−02 | 3.12E−02 |
| 9.18 | 7.20E−05 | 1.78E−02 | 1.05E−02 | 4.56E−02 | 4.94E−02 | 5.75E−02 | 1.45E−02 | 2.03E−02 | 5.03E−02 | 3.62E−02 |
| 9.20 | 5.60E−05 | 2.06E−02 | 1.05E−02 | 5.29E−02 | 5.72E−02 | 6.66E−02 | 1.45E−02 | 2.29E−02 | 5.83E−02 | 4.20E−02 |
| 9.22 | 6.90E−05 | 2.40E−02 | 1.05E−02 | 6.13E−02 | 6.62E−02 | 7.70E−02 | 1.45E−02 | 2.62E−02 | 6.73E−02 | 4.87E−02 |
| 9.23 | 7.30E−05 | 2.81E−02 | 1.06E−02 | 7.09E−02 | 7.63E−02 | 8.84E−02 | 1.46E−02 | 3.01E−02 | 7.73E−02 | 5.65E−02 |
| 9.25 | 7.00E−05 | 3.30E−02 | 1.09E−02 | 8.15E−02 | 8.74E−02 | 1.01E−01 | 1.47E−02 | 3.48E−02 | 8.84E−02 | 6.54E−02 |
| 9.27 | 6.50E−05 | 3.87E−02 | 1.13E−02 | 9.33E−02 | 9.96E−02 | 1.14E−01 | 1.50E−02 | 4.03E−02 | 1.00E−01 | 7.54E−02 |
| 9.28 | 6.10E−05 | 4.54E−02 | 1.19E−02 | 1.06E−01 | 1.13E−01 | 1.29E−01 | 1.53E−02 | 4.68E−02 | 1.13E−01 | 8.64E−02 |
| 9.30 | 6.50E−05 | 5.28E−02 | 1.27E−02 | 1.20E−01 | 1.26E−01 | 1.45E−01 | 1.58E−02 | 5.41E−02 | 1.27E−01 | 9.83E−02 |
| 9.32 | 6.60E−05 | 6.12E−02 | 1.39E−02 | 1.35E−01 | 1.41E−01 | 1.61E−01 | 1.65E−02 | 6.23E−02 | 1.41E−01 | 1.11E−01 |
| 9.33 | 7.20E−05 | 7.05E−02 | 1.53E−02 | 1.51E−01 | 1.56E−01 | 1.78E−01 | 1.73E−02 | 7.15E−02 | 1.56E−01 | 1.25E−01 |
| 9.35 | 5.70E−05 | 8.08E−02 | 1.71E−02 | 1.67E−01 | 1.71E−01 | 1.94E−01 | 1.85E−02 | 8.15E−02 | 1.71E−01 | 1.39E−01 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 9.37 | 6.70E−05 | 9.19E−02 | 1.94E−02 | 1.83E−01 | 1.86E−01 | 2.12E−01 | 1.98E−02 | 9.25E−02 | 1.86E−01 | 1.54E−01 |
| 9.38 | 8.50E−05 | 1.04E−01 | 2.21E−02 | 2.00E−01 | 2.01E−01 | 2.29E−01 | 2.16E−02 | 1.04E−01 | 2.01E−01 | 1.69E−01 |
| 9.40 | 8.90E−05 | 1.16E−01 | 2.54E−02 | 2.17E−01 | 2.15E−01 | 2.45E−01 | 2.37E−02 | 1.17E−01 | 2.15E−01 | 1.85E−01 |
| 9.42 | 7.70E−05 | 1.29E−01 | 2.92E−02 | 2.34E−01 | 2.29E−01 | 2.61E−01 | 2.62E−02 | 1.30E−01 | 2.28E−01 | 2.00E−01 |
| 9.43 | 7.30E−05 | 1.43E−01 | 3.36E−02 | 2.50E−01 | 2.41E−01 | 2.75E−01 | 2.93E−02 | 1.43E−01 | 2.41E−01 | 2.15E−01 |
| 9.45 | 7.90E−05 | 1.56E−01 | 3.87E−02 | 2.65E−01 | 2.52E−01 | 2.89E−01 | 3.28E−02 | 1.57E−01 | 2.52E−01 | 2.29E−01 |
| 9.47 | 6.70E−05 | 1.70E−01 | 4.45E−02 | 2.79E−01 | 2.62E−01 | 3.01E−01 | 3.69E−02 | 1.71E−01 | 2.62E−01 | 2.43E−01 |
| 9.48 | 6.90E−05 | 1.83E−01 | 5.09E−02 | 2.91E−01 | 2.69E−01 | 3.10E−01 | 4.16E−02 | 1.85E−01 | 2.70E−01 | 2.55E−01 |
| 9.50 | 7.00E−05 | 1.96E−01 | 5.80E−02 | 3.02E−01 | 2.75E−01 | 3.18E−01 | 4.70E−02 | 1.98E−01 | 2.76E−01 | 2.66E−01 |
| 9.52 | 7.10E−05 | 2.09E−01 | 6.56E−02 | 3.11E−01 | 2.79E−01 | 3.24E−01 | 5.30E−02 | 2.11E−01 | 2.81E−01 | 2.75E−01 |
| 9.53 | 7.00E−05 | 2.21E−01 | 7.39E−02 | 3.18E−01 | 2.80E−01 | 3.27E−01 | 5.96E−02 | 2.24E−01 | 2.83E−01 | 2.82E−01 |
| 9.55 | 6.50E−05 | 2.32E−01 | 8.29E−02 | 3.23E−01 | 2.79E−01 | 3.28E−01 | 6.69E−02 | 2.35E−01 | 2.83E−01 | 2.87E−01 |
| 9.57 | 4.80E−05 | 2.41E−01 | 9.23E−02 | 3.25E−01 | 2.76E−01 | 3.26E−01 | 7.49E−02 | 2.46E−01 | 2.81E−01 | 2.90E−01 |
| 9.58 | 6.20E−05 | 2.50E−01 | 1.02E−01 | 3.25E−01 | 2.71E−01 | 3.22E−01 | 8.35E−02 | 2.55E−01 | 2.77E−01 | 2.91E−01 |
| 9.60 | 8.30E−05 | 2.57E−01 | 1.12E−01 | 3.22E−01 | 2.64E−01 | 3.15E−01 | 9.26E−02 | 2.63E−01 | 2.71E−01 | 2.90E−01 |
| 9.62 | 6.40E−05 | 2.62E−01 | 1.23E−01 | 3.17E−01 | 2.55E−01 | 3.06E−01 | 1.02E−01 | 2.69E−01 | 2.63E−01 | 2.87E−01 |
| 9.63 | 6.40E−05 | 2.66E−01 | 1.33E−01 | 3.10E−01 | 2.45E−01 | 2.96E−01 | 1.12E−01 | 2.74E−01 | 2.54E−01 | 2.82E−01 |
| 9.65 | 7.70E−05 | 2.67E−01 | 1.44E−01 | 3.00E−01 | 2.34E−01 | 2.83E−01 | 1.23E−01 | 2.77E−01 | 2.43E−01 | 2.74E−01 |
| 9.67 | 7.90E−05 | 2.68E−01 | 1.54E−01 | 2.89E−01 | 2.21E−01 | 2.69E−01 | 1.33E−01 | 2.78E−01 | 2.32E−01 | 2.65E−01 |
| 9.68 | 7.10E−05 | 2.66E−01 | 1.65E−01 | 2.76E−01 | 2.08E−01 | 2.55E−01 | 1.44E−01 | 2.77E−01 | 2.19E−01 | 2.55E−01 |
| 9.70 | 6.60E−05 | 2.63E−01 | 1.74E−01 | 2.62E−01 | 1.95E−01 | 2.39E−01 | 1.55E−01 | 2.75E−01 | 2.06E−01 | 2.43E−01 |
| 9.72 | 6.70E−05 | 2.58E−01 | 1.84E−01 | 2.47E−01 | 1.81E−01 | 2.23E−01 | 1.66E−01 | 2.71E−01 | 1.93E−01 | 2.31E−01 |
| 9.73 | 9.40E−05 | 2.51E−01 | 1.93E−01 | 2.32E−01 | 1.68E−01 | 2.07E−01 | 1.76E−01 | 2.65E−01 | 1.79E−01 | 2.18E−01 |
| 9.75 | 8.60E−05 | 2.43E−01 | 2.01E−01 | 2.16E−01 | 1.54E−01 | 1.91E−01 | 1.87E−01 | 2.58E−01 | 1.66E−01 | 2.04E−01 |
| 9.77 | 7.90E−05 | 2.35E−01 | 2.09E−01 | 2.00E−01 | 1.42E−01 | 1.75E−01 | 1.96E−01 | 2.50E−01 | 1.53E−01 | 1.90E−01 |
| 9.78 | 8.60E−05 | 2.25E−01 | 2.15E−01 | 1.85E−01 | 1.29E−01 | 1.60E−01 | 2.06E−01 | 2.40E−01 | 1.41E−01 | 1.77E−01 |
| 9.80 | 6.70E−05 | 2.15E−01 | 2.21E−01 | 1.70E−01 | 1.18E−01 | 1.45E−01 | 2.15E−01 | 2.30E−01 | 1.29E−01 | 1.63E−01 |
| 9.82 | 6.90E−05 | 2.04E−01 | 2.25E−01 | 1.55E−01 | 1.07E−01 | 1.32E−01 | 2.23E−01 | 2.19E−01 | 1.18E−01 | 1.50E−01 |
| 9.83 | 7.20E−05 | 1.92E−01 | 2.29E−01 | 1.41E−01 | 9.70E−02 | 1.19E−01 | 2.30E−01 | 2.08E−01 | 1.07E−01 | 1.37E−01 |
| 9.85 | 8.60E−05 | 1.81E−01 | 2.31E−01 | 1.28E−01 | 8.79E−02 | 1.08E−01 | 2.36E−01 | 1.96E−01 | 9.71E−02 | 1.26E−01 |
| 9.87 | 5.80E−05 | 1.69E−01 | 2.33E−01 | 1.16E−01 | 7.95E−02 | 9.70E−02 | 2.42E−01 | 1.84E−01 | 8.81E−02 | 1.15E−01 |
| 9.88 | 9.10E−05 | 1.58E−01 | 2.33E−01 | 1.05E−01 | 7.17E−02 | 8.73E−02 | 2.46E−01 | 1.73E−01 | 7.99E−02 | 1.04E−01 |
| 9.90 | 8.00E−05 | 1.47E−01 | 2.33E−01 | 9.47E−02 | 6.47E−02 | 7.85E−02 | 2.50E−01 | 1.61E−01 | 7.22E−02 | 9.44E−02 |
| 9.92 | 7.30E−05 | 1.36E−01 | 2.31E−01 | 8.53E−02 | 5.85E−02 | 7.06E−02 | 2.52E−01 | 1.50E−01 | 6.53E−02 | 8.55E−02 |
| 9.93 | 7.10E−05 | 1.25E−01 | 2.28E−01 | 7.69E−02 | 5.29E−02 | 6.34E−02 | 2.53E−01 | 1.39E−01 | 5.90E−02 | 7.74E−02 |
| 9.95 | 6.90E−05 | 1.16E−01 | 2.25E−01 | 6.91E−02 | 4.78E−02 | 5.69E−02 | 2.54E−01 | 1.28E−01 | 5.34E−02 | 7.00E−02 |
| 9.97 | 8.60E−05 | 1.06E−01 | 2.21E−01 | 6.22E−02 | 4.33E−02 | 5.12E−02 | 2.53E−01 | 1.18E−01 | 4.83E−02 | 6.33E−02 |
| 9.98 | 7.60E−05 | 9.74E−02 | 2.16E−01 | 5.60E−02 | 3.92E−02 | 4.62E−02 | 2.51E−01 | 1.09E−01 | 4.37E−02 | 5.72E−02 |
| 10.00 | 6.60E−05 | 8.92E−02 | 2.10E−01 | 5.05E−02 | 3.57E−02 | 4.17E−02 | 2.49E−01 | 1.00E−01 | 3.97E−02 | 5.17E−02 |
| 10.02 | 8.10E−05 | 8.16E−02 | 2.04E−01 | 4.56E−02 | 3.25E−02 | 3.77E−02 | 2.45E−01 | 9.19E−02 | 3.61E−02 | 4.68E−02 |
| 10.03 | 8.00E−05 | 7.46E−02 | 1.97E−01 | 4.12E−02 | 2.97E−02 | 3.42E−02 | 2.41E−01 | 8.42E−02 | 3.29E−02 | 4.25E−02 |
| 10.05 | 7.90E−05 | 6.81E−02 | 1.90E−01 | 3.73E−02 | 2.72E−02 | 3.12E−02 | 2.36E−01 | 7.71E−02 | 3.00E−02 | 3.86E−02 |
| 10.07 | 6.30E−05 | 6.21E−02 | 1.82E−01 | 3.39E−02 | 2.50E−02 | 2.84E−02 | 2.31E−01 | 7.06E−02 | 2.74E−02 | 3.51E−02 |
| 10.08 | 6.50E−05 | 5.66E−02 | 1.75E−01 | 3.09E−02 | 2.31E−02 | 2.61E−02 | 2.25E−01 | 6.46E−02 | 2.52E−02 | 3.20E−02 |
| 10.10 | 6.90E−05 | 5.17E−02 | 1.67E−01 | 2.83E−02 | 2.14E−02 | 2.40E−02 | 2.19E−01 | 5.90E−02 | 2.32E−02 | 2.92E−02 |
| 10.12 | 8.10E−05 | 4.72E−02 | 1.59E−01 | 2.59E−02 | 1.99E−02 | 2.21E−02 | 2.12E−01 | 5.40E−02 | 2.14E−02 | 2.68E−02 |
| 10.13 | 7.40E−05 | 4.31E−02 | 1.51E−01 | 2.39E−02 | 1.85E−02 | 2.05E−02 | 2.04E−01 | 4.94E−02 | 1.99E−02 | 2.46E−02 |
| 10.15 | 7.20E−05 | 3.94E−02 | 1.44E−01 | 2.20E−02 | 1.73E−02 | 1.91E−02 | 1.97E−01 | 4.53E−02 | 1.84E−02 | 2.27E−02 |
| 10.17 | 6.60E−05 | 3.60E−02 | 1.36E−01 | 2.04E−02 | 1.63E−02 | 1.79E−02 | 1.89E−01 | 4.15E−02 | 1.72E−02 | 2.11E−02 |
| 10.18 | 7.10E−05 | 3.30E−02 | 1.29E−01 | 1.91E−02 | 1.53E−02 | 1.68E−02 | 1.81E−01 | 3.81E−02 | 1.61E−02 | 1.96E−02 |
| 10.20 | 7.90E−05 | 3.04E−02 | 1.21E−01 | 1.78E−02 | 1.45E−02 | 1.58E−02 | 1.72E−01 | 3.50E−02 | 1.52E−02 | 1.83E−02 |
| 10.22 | 6.30E−05 | 2.79E−02 | 1.14E−01 | 1.67E−02 | 1.37E−02 | 1.50E−02 | 1.64E−01 | 3.22E−02 | 1.43E−02 | 1.70E−02 |
| 10.23 | 6.50E−05 | 2.57E−02 | 1.07E−01 | 1.57E−02 | 1.31E−02 | 1.42E−02 | 1.57E−01 | 2.97E−02 | 1.35E−02 | 1.60E−02 |
| 10.25 | 8.50E−05 | 2.37E−02 | 1.01E−01 | 1.49E−02 | 1.25E−02 | 1.35E−02 | 1.49E−01 | 2.74E−02 | 1.28E−02 | 1.51E−02 |
| 10.27 | 7.70E−05 | 2.20E−02 | 9.45E−02 | 1.42E−02 | 2.97E−02 | 3.42E−02 | 1.42E−01 | 2.53E−02 | 1.22E−02 | 1.42E−02 |
| 10.28 | 5.40E−05 | 2.04E−02 | 8.85E−02 | 1.35E−02 | 1.14E−02 | 1.24E−02 | 1.35E−01 | 2.35E−02 | 1.16E−02 | 1.35E−02 |
| 10.30 | 8.30E−05 | 1.90E−02 | 8.29E−02 | 1.28E−02 | 1.09E−02 | 1.19E−02 | 1.28E−01 | 2.18E−02 | 1.11E−02 | 1.28E−02 |
| 10.32 | 6.70E−05 | 1.77E−02 | 7.76E−02 | 1.23E−02 | 1.05E−02 | 1.14E−02 | 1.22E−01 | 2.04E−02 | 1.07E−02 | 1.22E−02 |
| 10.33 | 7.30E−05 | 1.65E−02 | 7.27E−02 | 1.18E−02 | 1.01E−02 | 1.10E−02 | 1.16E−01 | 1.90E−02 | 1.02E−02 | 1.17E−02 |
| 10.35 | 6.40E−05 | 1.55E−02 | 6.82E−02 | 1.13E−02 | 9.79E−03 | 1.06E−02 | 1.09E−01 | 1.78E−02 | 9.86E−03 | 1.12E−02 |
| 10.37 | 8.10E−05 | 1.47E−02 | 6.38E−02 | 1.09E−02 | 9.42E−03 | 1.03E−02 | 1.03E−01 | 1.68E−02 | 9.51E−03 | 1.07E−02 |
| 10.38 | 7.10E−05 | 1.38E−02 | 5.97E−02 | 1.05E−02 | 9.10E−03 | 9.97E−03 | 9.67E−02 | 1.58E−02 | 9.16E−03 | 1.03E−02 |
| 10.40 | 6.60E−05 | 1.31E−02 | 5.59E−02 | 1.02E−02 | 8.84E−03 | 9.64E−03 | 9.06E−02 | 1.49E−02 | 8.86E−03 | 9.93E−03 |
| 10.42 | 7.70E−05 | 1.24E−02 | 5.22E−02 | 9.82E−03 | 8.54E−03 | 9.39E−03 | 8.47E−02 | 1.41E−02 | 8.58E−03 | 9.58E−03 |
| 10.43 | 6.70E−05 | 1.18E−02 | 4.87E−02 | 9.53E−03 | 8.32E−03 | 9.09E−03 | 7.90E−02 | 1.34E−02 | 8.31E−03 | 9.30E−03 |
| 10.45 | 5.80E−05 | 1.12E−02 | 4.53E−02 | 9.23E−03 | 8.02E−03 | 8.82E−03 | 7.38E−02 | 1.27E−02 | 8.05E−03 | 8.93E−03 |
| 10.47 | 7.00E−05 | 1.07E−02 | 4.22E−02 | 8.94E−03 | 7.80E−03 | 8.60E−03 | 6.91E−02 | 1.21E−02 | 7.80E−03 | 8.65E−03 |
| 10.48 | 6.30E−05 | 1.02E−02 | 3.92E−02 | 8.68E−03 | 7.58E−03 | 8.31E−03 | 6.48E−02 | 1.16E−02 | 7.56E−03 | 8.39E−03 |
| 10.50 | 6.00E−05 | 9.80E−03 | 3.65E−02 | 8.42E−03 | 7.35E−03 | 8.12E−03 | 6.11E−02 | 1.10E−02 | 7.36E−03 | 8.13E−03 |
| 10.52 | 5.70E−05 | 9.39E−03 | 3.40E−02 | 8.20E−03 | 7.15E−03 | 7.89E−03 | 5.77E−02 | 1.06E−02 | 7.15E−03 | 7.87E−03 |
| 10.53 | 6.90E−05 | 9.04E−03 | 3.17E−02 | 8.00E−03 | 6.96E−03 | 7.68E−03 | 5.47E−02 | 1.01E−02 | 6.98E−03 | 7.63E−03 |
| 10.55 | 6.50E−05 | 8.70E−03 | 2.98E−02 | 7.73E−03 | 6.78E−03 | 7.49E−03 | 5.20E−02 | 9.71E−03 | 6.75E−03 | 7.42E−03 |
| 10.57 | 7.40E−05 | 8.38E−03 | 2.80E−02 | 7.52E−03 | 6.60E−03 | 7.29E−03 | 4.94E−02 | 9.39E−03 | 6.57E−03 | 7.22E−03 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 10.58 | 6.30E−05 | 8.07E−03 | 2.63E−02 | 7.31E−03 | 6.41E−03 | 7.10E−03 | 4.70E−02 | 9.03E−03 | 6.40E−03 | 7.03E−03 |
| 10.60 | 6.20E−05 | 7.80E−03 | 2.49E−02 | 7.11E−03 | 6.25E−03 | 6.91E−03 | 4.45E−02 | 8.71E−03 | 6.24E−03 | 6.80E−03 |
| 10.62 | 7.10E−05 | 7.58E−03 | 2.35E−02 | 6.93E−03 | 6.09E−03 | 6.74E−03 | 4.20E−02 | 8.42E−03 | 6.05E−03 | 6.61E−03 |
| 10.63 | 5.80E−05 | 7.34E−03 | 2.23E−02 | 6.73E−03 | 5.93E−03 | 6.58E−03 | 3.95E−02 | 8.15E−03 | 5.90E−03 | 6.46E−03 |
| 10.65 | 5.50E−05 | 7.11E−03 | 2.11E−02 | 6.56E−03 | 5.78E−03 | 6.42E−03 | 3.70E−02 | 7.91E−03 | 5.75E−03 | 6.29E−03 |
| 10.67 | 6.10E−05 | 6.89E−03 | 2.00E−02 | 6.40E−03 | 5.65E−03 | 6.24E−03 | 3.45E−02 | 7.66E−03 | 5.60E−03 | 6.16E−03 |
| 10.68 | 5.50E−05 | 6.68E−03 | 1.89E−02 | 6.24E−03 | 5.49E−03 | 6.10E−03 | 3.20E−02 | 7.40E−03 | 5.47E−03 | 5.95E−03 |
| 10.70 | 6.30E−05 | 6.51E−03 | 1.79E−02 | 6.06E−03 | 5.35E−03 | 5.95E−03 | 2.97E−02 | 7.18E−03 | 5.30E−03 | 5.81E−03 |
| 10.72 | 8.40E−05 | 6.30E−03 | 1.69E−02 | 5.89E−03 | 5.21E−03 | 5.78E−03 | 2.76E−02 | 6.96E−03 | 5.16E−03 | 5.67E−03 |
| 10.73 | 7.00E−05 | 6.12E−03 | 1.59E−02 | 5.74E−03 | 5.12E−03 | 5.67E−03 | 2.57E−02 | 6.78E−03 | 5.02E−03 | 5.51E−03 |
| 10.75 | 6.90E−05 | 5.93E−03 | 1.49E−02 | 5.63E−03 | 4.98E−03 | 5.50E−03 | 2.38E−02 | 6.57E−03 | 4.92E−03 | 5.36E−03 |
| 10.77 | 7.20E−05 | 5.78E−03 | 1.41E−02 | 5.48E−03 | 4.84E−03 | 5.35E−03 | 2.23E−02 | 6.38E−03 | 4.78E−03 | 5.22E−03 |
| 10.78 | 5.80E−05 | 5.63E−03 | 1.32E−02 | 5.31E−03 | 4.72E−03 | 5.21E−03 | 2.11E−02 | 6.18E−03 | 4.64E−03 | 5.09E−03 |
| 10.80 | 7.60E−05 | 5.46E−03 | 1.25E−02 | 5.16E−03 | 4.60E−03 | 5.08E−03 | 2.00E−02 | 6.00E−03 | 4.52E−03 | 4.94E−03 |
| 10.82 | 7.60E−05 | 5.31E−03 | 1.19E−02 | 5.01E−03 | 4.49E−03 | 4.95E−03 | 1.90E−02 | 5.85E−03 | 4.39E−03 | 4.83E−03 |
| 10.83 | 5.80E−05 | 5.15E−03 | 1.13E−02 | 4.91E−03 | 4.40E−03 | 4.83E−03 | 1.83E−02 | 5.69E−03 | 4.29E−03 | 4.68E−03 |
| 10.85 | 6.50E−05 | 5.00E−03 | 1.08E−02 | 4.78E−03 | 4.26E−03 | 4.70E−03 | 1.77E−02 | 5.53E−03 | 4.19E−03 | 4.57E−03 |
| 10.87 | 7.20E−05 | 4.86E−03 | 1.03E−02 | 4.64E−03 | 4.14E−03 | 4.56E−03 | 1.71E−02 | 5.37E−03 | 4.05E−03 | 4.45E−03 |
| 10.88 | 6.90E−05 | 4.72E−03 | 9.95E−03 | 4.51E−03 | 4.02E−03 | 4.44E−03 | 1.66E−02 | 5.22E−03 | 3.94E−03 | 4.35E−03 |
| 10.90 | 7.70E−05 | 4.59E−03 | 9.60E−03 | 4.39E−03 | 3.91E−03 | 4.33E−03 | 1.60E−02 | 5.09E−03 | 3.85E−03 | 4.24E−03 |
| 10.92 | 7.30E−05 | 4.45E−03 | 9.30E−03 | 4.26E−03 | 3.83E−03 | 4.20E−03 | 1.55E−02 | 4.94E−03 | 3.76E−03 | 4.11E−03 |
| 10.93 | 7.40E−05 | 4.35E−03 | 8.99E−03 | 4.15E−03 | 3.71E−03 | 4.09E−03 | 1.49E−02 | 4.82E−03 | 3.63E−03 | 4.00E−03 |
| 10.95 | 9.30E−05 | 4.24E−03 | 8.73E−03 | 4.04E−03 | 3.62E−03 | 3.99E−03 | 1.43E−02 | 4.67E−03 | 3.52E−03 | 3.90E−03 |
| 10.97 | 8.10E−05 | 4.11E−03 | 8.46E−03 | 3.92E−03 | 3.52E−03 | 3.86E−03 | 1.37E−02 | 4.55E−03 | 3.42E−03 | 3.78E−03 |
| 10.98 | 1.40E−04 | 4.00E−03 | 8.20E−03 | 3.80E−03 | 3.44E−03 | 3.76E−03 | 1.30E−02 | 4.45E−03 | 3.34E−03 | 3.67E−03 |
| 11.00 | 8.40E−05 | 3.89E−03 | 7.93E−03 | 3.71E−03 | 3.32E−03 | 3.67E−03 | 1.24E−02 | 4.33E−03 | 3.24E−03 | 3.59E−03 |
| 11.02 | 9.60E−05 | 3.80E−03 | 7.67E−03 | 3.60E−03 | 3.23E−03 | 3.57E−03 | 1.17E−02 | 4.20E−03 | 3.16E−03 | 3.48E−03 |
| 11.03 | 9.90E−05 | 3.69E−03 | 7.41E−03 | 3.50E−03 | 3.20E−03 | 3.45E−03 | 1.11E−02 | 4.09E−03 | 3.06E−03 | 3.40E−03 |
| 11.05 | 1.01E−04 | 3.59E−03 | 7.15E−03 | 3.42E−03 | 3.07E−03 | 3.36E−03 | 1.05E−02 | 3.99E−03 | 2.99E−03 | 3.30E−03 |
| 11.07 | 1.06E−04 | 3.48E−03 | 6.87E−03 | 3.31E−03 | 2.98E−03 | 3.26E−03 | 9.82E−03 | 3.87E−03 | 2.88E−03 | 3.21E−03 |
| 11.08 | 1.20E−04 | 3.37E−03 | 6.63E−03 | 3.20E−03 | 2.89E−03 | 3.17E−03 | 9.29E−03 | 3.77E−03 | 2.81E−03 | 3.12E−03 |
| 11.10 | 1.11E−04 | 3.31E−03 | 6.36E−03 | 3.12E−03 | 2.81E−03 | 3.08E−03 | 8.81E−03 | 3.65E−03 | 2.72E−03 | 3.03E−03 |
| 11.12 | 1.48E−04 | 3.20E−03 | 6.12E−03 | 3.02E−03 | 2.74E−03 | 2.99E−03 | 8.38E−03 | 3.55E−03 | 2.63E−03 | 2.93E−03 |
| 11.13 | 1.54E−04 | 3.11E−03 | 5.90E−03 | 2.94E−03 | 2.68E−03 | 2.89E−03 | 7.99E−03 | 3.44E−03 | 2.58E−03 | 2.85E−03 |
| 11.15 | 1.66E−04 | 3.01E−03 | 5.68E−03 | 2.86E−03 | 2.59E−03 | 2.81E−03 | 7.59E−03 | 3.35E−03 | 2.51E−03 | 2.78E−03 |
| 11.17 | 1.69E−04 | 2.92E−03 | 5.49E−03 | 2.77E−03 | 2.52E−03 | 2.74E−03 | 7.31E−03 | 3.24E−03 | 2.42E−03 | 2.71E−03 |
| 11.18 | 2.24E−04 | 2.84E−03 | 5.27E−03 | 2.68E−03 | 2.44E−03 | 2.66E−03 | 7.03E−03 | 3.14E−03 | 2.35E−03 | 2.63E−03 |
| 11.20 | 2.51E−04 | 2.74E−03 | 5.09E−03 | 2.61E−03 | 2.39E−03 | 2.57E−03 | 6.80E−03 | 3.05E−03 | 2.28E−03 | 2.55E−03 |
| 11.22 | 2.89E−04 | 2.65E−03 | 4.92E−03 | 2.53E−03 | 2.30E−03 | 2.49E−03 | 6.59E−03 | 2.96E−03 | 2.22E−03 | 2.50E−03 |
| 11.23 | 3.41E−04 | 2.59E−03 | 4.76E−03 | 2.44E−03 | 2.23E−03 | 2.42E−03 | 6.38E−03 | 2.86E−03 | 2.15E−03 | 2.40E−03 |
| 11.25 | 3.80E−04 | 2.48E−03 | 4.63E−03 | 2.37E−03 | 2.17E−03 | 2.36E−03 | 6.22E−03 | 2.78E−03 | 2.10E−03 | 2.33E−03 |
| 11.27 | 4.58E−04 | 2.41E−03 | 4.49E−03 | 2.32E−03 | 2.11E−03 | 2.27E−03 | 6.09E−03 | 2.69E−03 | 2.03E−03 | 2.27E−03 |
| 11.28 | 5.44E−04 | 2.34E−03 | 4.37E−03 | 2.23E−03 | 2.06E−03 | 2.22E−03 | 5.94E−03 | 2.61E−03 | 1.98E−03 | 2.22E−03 |
| 11.30 | 6.34E−04 | 2.26E−03 | 4.24E−03 | 2.17E−03 | 1.99E−03 | 2.15E−03 | 5.79E−03 | 2.55E−03 | 1.92E−03 | 2.14E−03 |
| 11.32 | 7.64E−04 | 2.20E−03 | 4.11E−03 | 2.10E−03 | 1.94E−03 | 2.07E−03 | 5.68E−03 | 2.47E−03 | 1.86E−03 | 2.08E−03 |
| 11.33 | 8.98E−04 | 2.14E−03 | 4.02E−03 | 2.05E−03 | 1.91E−03 | 2.02E−03 | 5.55E−03 | 2.41E−03 | 1.81E−03 | 2.02E−03 |
| 11.35 | 1.04E−03 | 2.08E−03 | 3.91E−03 | 1.99E−03 | 1.84E−03 | 1.98E−03 | 5.41E−03 | 2.32E−03 | 1.76E−03 | 1.98E−03 |
| 11.37 | 1.25E−03 | 2.02E−03 | 3.81E−03 | 1.92E−03 | 1.78E−03 | 1.91E−03 | 5.27E−03 | 2.26E−03 | 1.71E−03 | 1.92E−03 |
| 11.38 | 1.48E−03 | 1.96E−03 | 3.70E−03 | 1.89E−03 | 1.76E−03 | 1.88E−03 | 5.11E−03 | 2.20E−03 | 1.67E−03 | 1.88E−03 |
| 11.40 | 1.76E−03 | 1.89E−03 | 3.62E−03 | 1.82E−03 | 1.71E−03 | 1.81E−03 | 4.96E−03 | 2.14E−03 | 1.63E−03 | 1.83E−03 |
| 11.42 | 2.09E−03 | 1.84E−03 | 3.51E−03 | 1.78E−03 | 1.67E−03 | 1.76E−03 | 4.79E−03 | 2.08E−03 | 1.61E−03 | 1.80E−03 |
| 11.43 | 2.51E−03 | 1.79E−03 | 3.43E−03 | 1.72E−03 | 1.63E−03 | 1.72E−03 | 4.64E−03 | 2.03E−03 | 1.55E−03 | 1.74E−03 |
| 11.45 | 3.05E−03 | 1.74E−03 | 3.34E−03 | 1.68E−03 | 1.59E−03 | 1.67E−03 | 4.46E−03 | 1.96E−03 | 1.51E−03 | 1.69E−03 |
| 11.47 | 3.70E−03 | 1.70E−03 | 3.25E−03 | 1.63E−03 | 1.55E−03 | 1.65E−03 | 4.30E−03 | 1.90E−03 | 1.47E−03 | 1.65E−03 |
| 11.48 | 4.53E−03 | 1.65E−03 | 3.16E−03 | 1.58E−03 | 1.50E−03 | 1.59E−03 | 4.16E−03 | 1.87E−03 | 1.43E−03 | 1.63E−03 |
| 11.50 | 5.54E−03 | 1.62E−03 | 3.08E−03 | 1.55E−03 | 1.46E−03 | 1.55E−03 | 4.00E−03 | 1.83E−03 | 1.41E−03 | 1.57E−03 |
| 11.52 | 6.73E−03 | 1.59E−03 | 2.99E−03 | 1.52E−03 | 1.44E−03 | 1.51E−03 | 3.86E−03 | 1.77E−03 | 1.38E−03 | 1.52E−03 |
| 11.53 | 8.12E−03 | 1.53E−03 | 2.92E−03 | 1.48E−03 | 1.41E−03 | 1.48E−03 | 3.74E−03 | 1.73E−03 | 1.33E−03 | 1.49E−03 |
| 11.55 | 9.72E−03 | 1.51E−03 | 2.83E−03 | 1.45E−03 | 1.37E−03 | 1.46E−03 | 3.61E−03 | 1.69E−03 | 1.30E−03 | 1.47E−03 |
| 11.57 | 1.15E−02 | 1.50E−03 | 2.77E−03 | 1.41E−03 | 1.35E−03 | 1.44E−03 | 3.50E−03 | 1.64E−03 | 1.26E−03 | 1.44E−03 |
| 11.58 | 1.33E−02 | 1.48E−03 | 2.71E−03 | 1.38E−03 | 1.33E−03 | 1.43E−03 | 3.40E−03 | 1.62E−03 | 1.25E−03 | 1.40E−03 |
| 11.60 | 1.52E−02 | 1.48E−03 | 2.65E−03 | 1.37E−03 | 1.30E−03 | 1.42E−03 | 3.33E−03 | 1.58E−03 | 1.24E−03 | 1.38E−03 |
| 11.62 | 1.70E−02 | 1.49E−03 | 2.60E−03 | 1.33E−03 | 1.28E−03 | 1.44E−03 | 3.26E−03 | 1.56E−03 | 1.23E−03 | 1.36E−03 |
| 11.63 | 1.87E−02 | 1.49E−03 | 2.60E−03 | 1.33E−03 | 1.29E−03 | 1.44E−03 | 3.19E−03 | 1.55E−03 | 1.19E−03 | 1.37E−03 |
| 11.65 | 2.03E−02 | 1.54E−03 | 2.59E−03 | 1.32E−03 | 1.27E−03 | 1.50E−03 | 3.15E−03 | 1.54E−03 | 1.19E−03 | 1.36E−03 |
| 11.67 | 2.17E−02 | 1.60E−03 | 2.61E−03 | 1.33E−03 | 1.27E−03 | 1.55E−03 | 3.09E−03 | 1.53E−03 | 1.16E−03 | 1.35E−03 |
| 11.68 | 2.30E−02 | 1.68E−03 | 2.64E−03 | 1.33E−03 | 1.28E−03 | 1.60E−03 | 3.08E−03 | 1.52E−03 | 1.15E−03 | 1.36E−03 |
| 11.70 | 2.44E−02 | 1.75E−03 | 2.68E−03 | 1.32E−03 | 1.24E−03 | 1.66E−03 | 3.01E−03 | 1.52E−03 | 1.12E−03 | 1.36E−03 |
| 11.72 | 2.63E−02 | 1.80E−03 | 2.72E−03 | 1.35E−03 | 1.24E−03 | 1.72E−03 | 2.96E−03 | 1.50E−03 | 1.10E−03 | 1.36E−03 |
| 11.73 | 2.92E−02 | 1.88E−03 | 2.76E−03 | 1.35E−03 | 1.23E−03 | 1.77E−03 | 2.90E−03 | 1.48E−03 | 1.09E−03 | 1.35E−03 |
| 11.75 | 3.40E−02 | 1.91E−03 | 2.78E−03 | 1.36E−03 | 1.21E−03 | 1.79E−03 | 2.82E−03 | 1.44E−03 | 1.05E−03 | 1.35E−03 |
| 11.77 | 4.19E−02 | 1.92E−03 | 2.81E−03 | 1.34E−03 | 1.20E−03 | 1.80E−03 | 2.73E−03 | 1.43E−03 | 1.04E−03 | 1.33E−03 |
| 11.78 | 5.41E−02 | 1.90E−03 | 2.79E−03 | 1.33E−03 | 1.17E−03 | 1.79E−03 | 2.64E−03 | 1.38E−03 | 1.01E−03 | 1.31E−03 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 11.80 | 7.29E-02 | 1.87E-03 | 2.73E-03 | 1.31E-03 | 1.13E-03 | 1.74E-03 | 2.51E-03 | 1.33E-03 | 9.67E-04 | 1.26E-03 |
| 11.82 | 9.97E-02 | 1.80E-03 | 2.66E-03 | 1.26E-03 | 1.09E-03 | 1.68E-03 | 2.42E-03 | 1.29E-03 | 9.61E-04 | 1.23E-03 |
| 11.83 | 1.36E-01 | 1.71E-03 | 2.57E-03 | 1.24E-03 | 1.05E-03 | 1.61E-03 | 2.31E-03 | 1.23E-03 | 9.10E-04 | 1.18E-03 |
| 11.85 | 1.81E-01 | 1.61E-03 | 2.43E-03 | 1.17E-03 | 1.03E-03 | 1.51E-03 | 2.21E-03 | 1.17E-03 | 8.75E-04 | 1.14E-03 |
| 11.87 | 2.34E-01 | 1.48E-03 | 2.31E-03 | 1.13E-03 | 9.87E-04 | 1.42E-03 | 2.12E-03 | 1.13E-03 | 8.54E-04 | 1.09E-03 |
| 11.88 | 2.94E-01 | 1.37E-03 | 2.18E-03 | 1.07E-03 | 9.50E-04 | 1.32E-03 | 2.03E-03 | 1.08E-03 | 8.39E-04 | 1.04E-03 |
| 11.90 | 3.55E-01 | 1.28E-03 | 2.03E-03 | 1.03E-03 | 8.93E-04 | 1.22E-03 | 1.95E-03 | 1.05E-03 | 8.43E-04 | 1.01E-03 |
| 11.92 | 4.11E-01 | 1.18E-03 | 1.91E-03 | 9.81E-04 | 8.73E-04 | 1.15E-03 | 1.87E-03 | 1.01E-03 | 7.94E-04 | 9.87E-04 |
| 11.93 | 4.57E-01 | 1.09E-03 | 1.80E-03 | 9.33E-04 | 8.72E-04 | 1.09E-03 | 1.83E-03 | 9.66E-04 | 7.86E-04 | 9.47E-04 |
| 11.95 | 4.88E-01 | 1.02E-03 | 1.70E-03 | 8.88E-04 | 8.44E-04 | 1.03E-03 | 1.74E-03 | 9.40E-04 | 7.79E-04 | 9.16E-04 |
| 11.97 | 5.02E-01 | 9.48E-04 | 1.62E-03 | 8.68E-04 | 8.29E-04 | 9.85E-04 | 1.69E-03 | 9.11E-04 | 7.62E-04 | 8.29E-04 |
| 11.98 | 4.96E-01 | 8.99E-04 | 1.54E-03 | 8.37E-04 | 8.11E-04 | 9.34E-04 | 1.65E-03 | 8.93E-04 | 7.50E-04 | 8.88E-04 |
| 12.00 | 4.73E-01 | 8.71E-04 | 1.46E-03 | 8.22E-04 | 8.00E-04 | 9.07E-04 | 1.60E-03 | 8.77E-04 | 7.27E-04 | 8.65E-04 |
| 12.02 | 4.37E-01 | 8.32E-04 | 1.40E-03 | 7.96E-04 | 7.76E-04 | 8.98E-04 | 1.54E-03 | 8.30E-04 | 7.12E-04 | 8.43E-04 |
| 12.03 | 3.91E-01 | 7.88E-04 | 1.34E-03 | 7.82E-04 | 7.71E-04 | 8.54E-04 | 1.51E-03 | 8.18E-04 | 7.04E-04 | 8.30E-04 |
| 12.05 | 3.40E-01 | 7.63E-04 | 1.31E-03 | 7.70E-04 | 7.47E-04 | 8.29E-04 | 1.47E-03 | 8.06E-04 | 6.91E-04 | 8.23E-04 |
| 12.07 | 2.89E-01 | 7.49E-04 | 1.27E-03 | 7.45E-04 | 7.42E-04 | 8.25E-04 | 1.43E-03 | 7.78E-04 | 6.77E-04 | 8.08E-04 |
| 12.08 | 2.42E-01 | 7.05E-04 | 1.22E-03 | 7.42E-04 | 7.17E-04 | 8.32E-04 | 1.37E-03 | 7.73E-04 | 6.63E-04 | 7.96E-04 |
| 12.10 | 2.00E-01 | 7.00E-04 | 1.18E-03 | 7.32E-04 | 6.98E-04 | 7.89E-04 | 1.35E-03 | 7.50E-04 | 6.42E-04 | 7.55E-04 |
| 12.12 | 1.64E-01 | 6.83E-04 | 1.16E-03 | 7.12E-04 | 6.98E-04 | 7.74E-04 | 1.31E-03 | 7.51E-04 | 6.43E-04 | 7.61E-04 |
| 12.13 | 1.33E-01 | 6.62E-04 | 1.14E-03 | 7.00E-04 | 6.78E-04 | 7.45E-04 | 1.28E-03 | 7.22E-04 | 6.29E-04 | 7.47E-04 |
| 12.15 | 1.09E-01 | 6.55E-04 | 1.12E-03 | 6.73E-04 | 6.58E-04 | 7.26E-04 | 1.23E-03 | 7.14E-04 | 6.08E-04 | 7.29E-04 |
| 12.17 | 9.03E-02 | 6.27E-04 | 1.07E-03 | 6.50E-04 | 6.44E-04 | 7.09E-04 | 1.21E-03 | 6.84E-04 | 6.03E-04 | 7.07E-04 |
| 12.18 | 7.53E-02 | 6.11E-04 | 1.05E-03 | 6.42E-04 | 6.40E-04 | 6.85E-04 | 1.17E-03 | 6.77E-04 | 5.84E-04 | 6.95E-04 |
| 12.20 | 6.33E-02 | 5.86E-04 | 1.02E-03 | 6.19E-04 | 6.26E-04 | 6.74E-04 | 1.14E-03 | 6.70E-04 | 5.89E-04 | 6.92E-04 |
| 12.22 | 5.38E-02 | 5.96E-04 | 1.01E-03 | 6.09E-04 | 6.14E-04 | 6.47E-04 | 1.12E-03 | 6.42E-04 | 5.82E-04 | 6.76E-04 |
| 12.23 | 4.63E-02 | 5.75E-04 | 9.96E-04 | 5.95E-04 | 6.05E-04 | 6.54E-04 | 1.09E-03 | 6.42E-04 | 5.58E-04 | 6.48E-04 |
| 12.25 | 4.03E-02 | 5.82E-04 | 9.61E-04 | 5.84E-04 | 5.97E-04 | 6.26E-04 | 1.07E-03 | 6.28E-04 | 5.38E-04 | 6.46E-04 |
| 12.27 | 3.54E-02 | 5.48E-04 | 9.48E-04 | 5.66E-04 | 5.96E-04 | 6.17E-04 | 1.04E-03 | 6.19E-04 | 5.48E-04 | 6.29E-04 |
| 12.28 | 3.12E-02 | 5.46E-04 | 9.21E-04 | 5.86E-04 | 5.69E-04 | 6.06E-04 | 1.03E-03 | 6.23E-04 | 5.33E-04 | 6.36E-04 |
| 12.30 | 2.79E-02 | 5.29E-04 | 9.29E-04 | 5.48E-04 | 5.78E-04 | 5.94E-04 | 1.00E-03 | 5.97E-04 | 5.47E-04 | 6.26E-04 |
| 12.32 | 2.50E-02 | 5.26E-04 | 8.78E-04 | 5.38E-04 | 5.73E-04 | 5.82E-04 | 9.77E-04 | 5.94E-04 | 5.37E-04 | 6.26E-04 |
| 12.33 | 2.26E-02 | 5.14E-04 | 8.58E-04 | 5.26E-04 | 5.63E-04 | 5.81E-04 | 9.56E-04 | 5.86E-04 | 5.30E-04 | 6.15E-04 |
| 12.35 | 2.05E-02 | 5.06E-04 | 8.44E-04 | 5.37E-04 | 5.52E-04 | 5.64E-04 | 9.34E-04 | 5.58E-04 | 5.05E-04 | 6.13E-04 |
| 12.37 | 1.87E-02 | 5.01E-04 | 8.27E-04 | 5.28E-04 | 5.55E-04 | 5.53E-04 | 9.18E-04 | 5.63E-04 | 5.07E-04 | 5.98E-04 |
| 12.38 | 1.71E-02 | 4.78E-04 | 8.21E-04 | 5.14E-04 | 5.49E-04 | 5.69E-04 | 9.09E-04 | 5.47E-04 | 5.00E-04 | 6.04E-04 |
| 12.40 | 1.58E-02 | 4.73E-04 | 7.93E-04 | 5.35E-04 | 5.38E-04 | 5.74E-04 | 8.75E-04 | 5.63E-04 | 5.13E-04 | 5.86E-04 |
| 12.42 | 1.47E-02 | 4.56E-04 | 7.81E-04 | 5.09E-04 | 5.53E-04 | 5.55E-04 | 8.63E-04 | 5.55E-04 | 4.86E-04 | 5.87E-04 |
| 12.43 | 1.36E-02 | 4.58E-04 | 7.59E-04 | 5.06E-04 | 5.28E-04 | 5.53E-04 | 8.29E-04 | 5.45E-04 | 4.89E-04 | 5.81E-04 |
| 12.45 | 1.27E-02 | 4.46E-04 | 7.54E-04 | 5.09E-04 | 5.34E-04 | 5.48E-04 | 8.25E-04 | 5.14E-04 | 4.88E-04 | 5.77E-04 |
| 12.47 | 1.20E-02 | 4.35E-04 | 7.31E-04 | 5.04E-04 | 5.20E-04 | 5.53E-04 | 7.98E-04 | 5.06E-04 | 4.89E-04 | 5.66E-04 |
| 12.48 | 1.13E-02 | 4.42E-04 | 7.31E-04 | 4.98E-04 | 5.26E-04 | 5.38E-04 | 7.99E-04 | 5.13E-04 | 4.75E-04 | 5.60E-04 |
| 12.50 | 1.08E-02 | 4.47E-04 | 7.19E-04 | 4.90E-04 | 4.95E-04 | 5.13E-04 | 7.84E-04 | 4.98E-04 | 4.57E-04 | 5.55E-04 |
| 12.52 | 1.02E-02 | 4.24E-04 | 7.13E-04 | 4.84E-04 | 5.14E-04 | 5.22E-04 | 7.64E-04 | 4.81E-04 | 4.56E-04 | 5.47E-04 |
| 12.53 | 9.83E-03 | 4.32E-04 | 7.04E-04 | 5.04E-04 | 4.96E-04 | 4.97E-04 | 7.49E-04 | 4.88E-04 | 4.70E-04 | 5.37E-04 |
| 12.55 | 9.51E-03 | 4.31E-04 | 6.85E-04 | 4.79E-04 | 4.81E-04 | 4.98E-04 | 7.54E-04 | 4.83E-04 | 4.75E-04 | 5.12E-04 |
| 12.57 | 9.23E-03 | 4.07E-04 | 6.95E-04 | 4.56E-04 | 4.75E-04 | 4.79E-04 | 7.30E-04 | 4.74E-04 | 4.51E-04 | 5.19E-04 |
| 12.58 | 9.00E-03 | 4.10E-04 | 6.95E-04 | 4.54E-04 | 4.61E-04 | 4.69E-04 | 7.34E-04 | 4.89E-04 | 4.46E-04 | 5.18E-04 |
| 12.60 | 8.86E-03 | 4.09E-04 | 6.94E-04 | 4.55E-04 | 4.71E-04 | 4.71E-04 | 7.35E-04 | 4.81E-04 | 4.58E-04 | 5.16E-04 |
| 12.62 | 8.75E-03 | 4.18E-04 | 6.96E-04 | 4.65E-04 | 4.76E-04 | 4.71E-04 | 7.30E-04 | 4.70E-04 | 4.50E-04 | 5.07E-04 |
| 12.63 | 8.66E-03 | 4.32E-04 | 6.73E-04 | 4.50E-04 | 5.05E-04 | 4.81E-04 | 7.42E-04 | 4.75E-04 | 4.67E-04 | 5.14E-04 |
| 12.65 | 8.57E-03 | 4.30E-04 | 6.80E-04 | 4.90E-04 | 5.35E-04 | 4.99E-04 | 7.52E-04 | 4.68E-04 | 4.79E-04 | 5.15E-04 |
| 12.67 | 8.45E-03 | 4.48E-04 | 6.86E-04 | 4.95E-04 | 5.74E-04 | 5.08E-04 | 7.45E-04 | 4.84E-04 | 4.81E-04 | 5.24E-04 |
| 12.68 | 8.32E-03 | 4.75E-04 | 6.66E-04 | 5.36E-04 | 6.29E-04 | 5.30E-04 | 7.75E-04 | 4.81E-04 | 4.96E-04 | 5.19E-04 |
| 12.70 | 8.18E-03 | 4.90E-04 | 6.60E-04 | 6.02E-04 | 6.98E-04 | 5.95E-04 | 8.27E-04 | 5.07E-04 | 5.30E-04 | 5.27E-04 |
| 12.72 | 7.99E-03 | 5.04E-04 | 6.47E-04 | 6.74E-04 | 8.18E-04 | 6.28E-04 | 8.83E-04 | 5.39E-04 | 5.69E-04 | 5.24E-04 |
| 12.73 | 7.81E-03 | 5.40E-04 | 6.51E-04 | 7.56E-04 | 9.43E-04 | 7.43E-04 | 9.81E-04 | 5.86E-04 | 6.21E-04 | 5.48E-04 |
| 12.75 | 7.62E-03 | 5.92E-04 | 6.46E-04 | 8.87E-04 | 1.13E-03 | 8.59E-04 | 1.09E-03 | 6.54E-04 | 7.01E-04 | 5.59E-04 |
| 12.77 | 7.41E-03 | 6.31E-04 | 6.62E-04 | 1.08E-03 | 1.36E-03 | 1.01E-03 | 1.18E-03 | 7.36E-04 | 7.65E-04 | 5.84E-04 |
| 12.78 | 7.25E-03 | 7.09E-04 | 6.93E-04 | 1.31E-03 | 1.58E-03 | 1.21E-03 | 1.26E-03 | 8.28E-04 | 8.28E-04 | 6.17E-04 |
| 12.80 | 7.09E-03 | 8.28E-04 | 7.25E-04 | 1.60E-03 | 1.78E-03 | 1.42E-03 | 1.32E-03 | 9.03E-04 | 8.75E-04 | 6.71E-04 |
| 12.82 | 6.92E-03 | 9.60E-04 | 7.52E-04 | 1.86E-03 | 1.88E-03 | 1.57E-03 | 1.32E-03 | 9.68E-04 | 8.98E-04 | 7.22E-04 |
| 12.83 | 6.74E-03 | 1.11E-03 | 7.75E-04 | 2.09E-03 | 1.91E-03 | 1.67E-03 | 1.31E-03 | 1.00E-03 | 9.29E-04 | 7.72E-04 |
| 12.85 | 6.57E-03 | 1.29E-03 | 8.22E-04 | 2.21E-03 | 1.81E-03 | 1.67E-03 | 1.27E-03 | 1.01E-03 | 9.01E-04 | 8.45E-04 |
| 12.87 | 6.41E-03 | 1.44E-03 | 8.53E-04 | 2.21E-03 | 1.68E-03 | 1.62E-03 | 1.22E-03 | 1.01E-03 | 8.54E-04 | 8.67E-04 |
| 12.88 | 6.25E-03 | 1.60E-03 | 8.67E-04 | 2.08E-03 | 1.50E-03 | 1.48E-03 | 1.13E-03 | 9.89E-04 | 8.11E-04 | 8.84E-04 |
| 12.90 | 6.08E-03 | 1.68E-03 | 8.64E-04 | 1.89E-03 | 1.29E-03 | 1.31E-03 | 1.05E-03 | 9.43E-04 | 7.65E-04 | 8.94E-04 |
| 12.92 | 5.89E-03 | 1.72E-03 | 8.62E-04 | 1.64E-03 | 1.14E-03 | 1.14E-03 | 9.62E-04 | 8.68E-04 | 7.10E-04 | 8.51E-04 |
| 12.93 | 5.72E-03 | 1.66E-03 | 8.22E-04 | 1.40E-03 | 9.86E-04 | 9.82E-04 | 8.67E-04 | 7.85E-04 | 6.31E-04 | 8.13E-04 |
| 12.95 | 5.56E-03 | 1.55E-03 | 7.74E-04 | 1.18E-03 | 8.51E-04 | 8.54E-04 | 8.00E-04 | 7.16E-04 | 5.95E-04 | 7.69E-04 |
| 12.97 | 5.41E-03 | 1.39E-03 | 7.31E-04 | 1.00E-03 | 7.71E-04 | 7.56E-04 | 7.19E-04 | 6.35E-04 | 5.44E-04 | 7.11E-04 |
| 12.98 | 5.21E-03 | 1.21E-03 | 6.86E-04 | 8.58E-04 | 6.95E-04 | 6.82E-04 | 6.71E-04 | 5.96E-04 | 5.19E-04 | 6.46E-04 |
| 13.00 | 5.06E-03 | 1.04E-03 | 6.38E-04 | 7.49E-04 | 6.29E-04 | 6.28E-04 | 6.07E-04 | 5.18E-04 | 4.79E-04 | 5.98E-04 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 13.02 | 4.94E-03 | 8.82E-04 | 5.93E-04 | 6.71E-04 | 5.79E-04 | 5.77E-04 | 5.77E-04 | 4.89E-04 | 4.50E-04 | 5.70E-04 |
| 13.03 | 4.81E-03 | 7.54E-04 | 5.60E-04 | 6.28E-04 | 5.78E-04 | 5.42E-04 | 5.47E-04 | 4.44E-04 | 4.42E-04 | 5.44E-04 |
| 13.05 | 4.67E-03 | 6.65E-04 | 5.32E-04 | 5.76E-04 | 5.35E-04 | 5.22E-04 | 5.25E-04 | 4.00E-04 | 4.20E-04 | 4.90E-04 |
| 13.07 | 4.52E-03 | 5.75E-04 | 5.12E-04 | 5.58E-04 | 5.06E-04 | 4.90E-04 | 5.08E-04 | 3.95E-04 | 3.98E-04 | 4.84E-04 |
| 13.08 | 4.41E-03 | 5.03E-04 | 5.00E-04 | 5.13E-04 | 5.06E-04 | 4.78E-04 | 4.88E-04 | 3.77E-04 | 3.75E-04 | 4.85E-04 |
| 13.10 | 4.30E-03 | 4.68E-04 | 4.68E-04 | 4.88E-04 | 4.91E-04 | 4.63E-04 | 4.80E-04 | 3.68E-04 | 3.57E-04 | 4.59E-04 |
| 13.12 | 4.21E-03 | 4.36E-04 | 4.67E-04 | 4.58E-04 | 4.54E-04 | 4.40E-04 | 4.42E-04 | 3.42E-04 | 3.50E-04 | 4.45E-04 |
| 13.13 | 4.14E-03 | 4.05E-04 | 4.40E-04 | 4.49E-04 | 4.60E-04 | 4.38E-04 | 4.30E-04 | 3.42E-04 | 3.48E-04 | 4.36E-04 |
| 13.15 | 3.99E-03 | 3.86E-04 | 4.32E-04 | 4.30E-04 | 4.41E-04 | 4.01E-04 | 4.20E-04 | 3.14E-04 | 3.36E-04 | 4.32E-04 |
| 13.17 | 3.91E-03 | 3.55E-04 | 4.28E-04 | 4.26E-04 | 4.29E-04 | 3.96E-04 | 4.18E-04 | 3.13E-04 | 3.36E-04 | 3.98E-04 |
| 13.18 | 3.83E-03 | 3.38E-04 | 4.15E-04 | 4.02E-04 | 4.27E-04 | 3.91E-04 | 4.00E-04 | 2.91E-04 | 3.20E-04 | 4.16E-04 |
| 13.20 | 3.76E-03 | 3.40E-04 | 4.25E-04 | 3.97E-04 | 4.28E-04 | 3.89E-04 | 4.06E-04 | 2.90E-04 | 3.22E-04 | 4.07E-04 |
| 13.22 | 3.66E-03 | 3.19E-04 | 4.10E-04 | 3.89E-04 | 4.21E-04 | 3.97E-04 | 3.88E-04 | 2.91E-04 | 3.11E-04 | 4.05E-04 |
| 13.23 | 3.57E-03 | 3.04E-04 | 4.17E-04 | 3.72E-04 | 4.22E-04 | 3.68E-04 | 3.86E-04 | 2.86E-04 | 3.09E-04 | 3.96E-04 |
| 13.25 | 3.47E-03 | 3.00E-04 | 3.98E-04 | 3.87E-04 | 4.10E-04 | 3.72E-04 | 3.73E-04 | 2.73E-04 | 3.12E-04 | 3.96E-04 |
| 13.27 | 3.41E-03 | 2.92E-04 | 3.88E-04 | 3.55E-04 | 4.11E-04 | 3.68E-04 | 3.77E-04 | 2.63E-04 | 2.92E-04 | 3.89E-04 |
| 13.28 | 3.34E-03 | 2.93E-04 | 3.75E-04 | 3.55E-04 | 4.15E-04 | 3.59E-04 | 3.58E-04 | 2.69E-04 | 3.06E-04 | 4.01E-04 |
| 13.30 | 3.24E-03 | 3.00E-04 | 3.72E-04 | 3.67E-04 | 3.94E-04 | 3.55E-04 | 3.70E-04 | 2.66E-04 | 3.02E-04 | 3.97E-04 |
| 13.32 | 3.21E-03 | 2.76E-04 | 3.68E-04 | 3.65E-04 | 3.95E-04 | 3.67E-04 | 3.51E-04 | 2.54E-04 | 2.84E-04 | 3.92E-04 |
| 13.33 | 3.11E-03 | 2.67E-04 | 3.78E-04 | 3.47E-04 | 3.72E-04 | 3.46E-04 | 3.47E-04 | 2.48E-04 | 3.03E-04 | 3.98E-04 |
| 13.35 | 3.04E-03 | 2.67E-04 | 3.63E-04 | 3.55E-04 | 3.76E-04 | 3.29E-04 | 3.36E-04 | 2.45E-04 | 2.90E-04 | 3.73E-04 |
| 13.37 | 2.97E-03 | 2.68E-04 | 3.61E-04 | 3.20E-04 | 3.58E-04 | 3.21E-04 | 3.32E-04 | 2.43E-04 | 2.76E-04 | 3.82E-04 |
| 13.38 | 2.88E-03 | 2.77E-04 | 3.50E-04 | 3.30E-04 | 3.49E-04 | 3.70E-04 | 3.13E-04 | 2.21E-04 | 2.69E-04 | 3.71E-04 |
| 13.40 | 2.80E-03 | 2.62E-04 | 3.42E-04 | 3.11E-04 | 3.52E-04 | 3.26E-04 | 3.22E-04 | 2.20E-04 | 2.77E-04 | 3.77E-04 |
| 13.42 | 2.73E-03 | 2.52E-04 | 3.53E-04 | 2.99E-04 | 3.31E-04 | 3.08E-04 | 3.17E-04 | 2.18E-04 | 2.78E-04 | 3.66E-04 |
| 13.43 | 2.68E-03 | 2.39E-04 | 3.38E-04 | 3.10E-04 | 3.47E-04 | 3.12E-04 | 3.03E-04 | 2.28E-04 | 2.77E-04 | 3.63E-04 |
| 13.45 | 2.59E-03 | 2.41E-04 | 3.36E-04 | 2.84E-04 | 3.38E-04 | 2.92E-04 | 3.08E-04 | 2.14E-04 | 2.56E-04 | 3.65E-04 |
| 13.47 | 2.50E-03 | 2.47E-04 | 3.35E-04 | 2.88E-04 | 3.19E-04 | 3.08E-04 | 3.03E-04 | 2.14E-04 | 2.58E-04 | 3.65E-04 |
| 13.48 | 2.43E-03 | 2.47E-04 | 3.25E-04 | 2.98E-04 | 3.27E-04 | 2.94E-04 | 3.03E-04 | 2.00E-04 | 2.59E-04 | 3.70E-04 |
| 13.50 | 2.37E-03 | 2.42E-04 | 3.03E-04 | 2.82E-04 | 3.18E-04 | 2.94E-04 | 2.97E-04 | 2.01E-04 | 2.63E-04 | 3.49E-04 |
| 13.52 | 2.29E-03 | 2.47E-04 | 2.96E-04 | 2.81E-04 | 3.29E-04 | 2.82E-04 | 3.03E-04 | 2.01E-04 | 2.58E-04 | 3.58E-04 |
| 13.53 | 2.23E-03 | 2.45E-04 | 3.01E-04 | 2.71E-04 | 3.18E-04 | 2.79E-04 | 2.82E-04 | 1.92E-04 | 2.62E-04 | 3.56E-04 |
| 13.55 | 2.14E-03 | 2.30E-04 | 3.03E-04 | 2.86E-04 | 3.28E-04 | 2.78E-04 | 2.76E-04 | 1.89E-04 | 2.45E-04 | 3.52E-04 |
| 13.57 | 2.07E-03 | 2.25E-04 | 3.11E-04 | 2.70E-04 | 2.96E-04 | 2.87E-04 | 2.87E-04 | 1.75E-04 | 2.45E-04 | 3.59E-04 |
| 13.58 | 2.01E-03 | 2.37E-04 | 3.03E-04 | 2.69E-04 | 3.17E-04 | 2.79E-04 | 2.66E-04 | 1.81E-04 | 2.54E-04 | 3.42E-04 |
| 13.60 | 1.94E-03 | 2.27E-04 | 3.00E-04 | 2.81E-04 | 3.16E-04 | 2.82E-04 | 2.63E-04 | 1.82E-04 | 2.56E-04 | 3.50E-04 |
| 13.62 | 1.86E-03 | 2.14E-04 | 3.10E-04 | 2.76E-04 | 2.92E-04 | 2.86E-04 | 2.87E-04 | 1.68E-04 | 2.53E-04 | 3.40E-04 |
| 13.63 | 1.80E-03 | 2.25E-04 | 2.77E-04 | 2.63E-04 | 2.89E-04 | 2.71E-04 | 2.49E-04 | 1.91E-04 | 2.57E-04 | 3.53E-04 |
| 13.65 | 1.75E-03 | 2.21E-04 | 2.87E-04 | 2.68E-04 | 2.98E-04 | 2.83E-04 | 2.59E-04 | 1.71E-04 | 2.57E-04 | 3.27E-04 |
| 13.67 | 1.68E-03 | 2.29E-04 | 2.80E-04 | 2.43E-04 | 3.02E-04 | 2.74E-04 | 2.53E-04 | 1.71E-04 | 2.44E-04 | 3.26E-04 |
| 13.68 | 1.65E-03 | 2.37E-04 | 2.83E-04 | 2.50E-04 | 2.98E-04 | 2.79E-04 | 2.41E-04 | 1.53E-04 | 2.57E-04 | 3.32E-04 |
| 13.70 | 1.60E-03 | 2.17E-04 | 2.73E-04 | 2.41E-04 | 2.91E-04 | 2.60E-04 | 2.35E-04 | 1.62E-04 | 2.43E-04 | 3.31E-04 |
| 13.72 | 1.54E-03 | 2.07E-04 | 2.60E-04 | 2.52E-04 | 2.82E-04 | 2.66E-04 | 2.37E-04 | 1.65E-04 | 2.31E-04 | 3.25E-04 |
| 13.73 | 1.47E-03 | 2.03E-04 | 2.67E-04 | 2.43E-04 | 2.91E-04 | 2.82E-04 | 2.32E-04 | 1.62E-04 | 2.58E-04 | 3.26E-04 |
| 13.75 | 1.43E-03 | 2.12E-04 | 2.64E-04 | 2.43E-04 | 2.91E-04 | 2.58E-04 | 2.27E-04 | 1.66E-04 | 2.37E-04 | 3.22E-04 |
| 13.77 | 1.39E-03 | 2.05E-04 | 2.59E-04 | 2.30E-04 | 2.81E-04 | 2.82E-04 | 2.20E-04 | 1.62E-04 | 2.41E-04 | 3.26E-04 |
| 13.78 | 1.33E-03 | 2.18E-04 | 2.63E-04 | 2.25E-04 | 2.73E-04 | 2.50E-04 | 2.17E-04 | 1.46E-04 | 2.32E-04 | 3.12E-04 |
| 13.80 | 1.30E-03 | 2.13E-04 | 2.49E-04 | 2.30E-04 | 2.82E-04 | 2.59E-04 | 2.28E-04 | 1.59E-04 | 2.42E-04 | 3.27E-04 |
| 13.82 | 1.25E-03 | 2.09E-04 | 2.42E-04 | 2.35E-04 | 2.72E-04 | 2.54E-04 | 2.24E-04 | 1.60E-04 | 2.32E-04 | 3.13E-04 |
| 13.83 | 1.25E-03 | 2.11E-04 | 2.50E-04 | 2.34E-04 | 2.70E-04 | 2.66E-04 | 2.05E-04 | 1.42E-04 | 2.34E-04 | 3.11E-04 |
| 13.85 | 1.20E-03 | 1.98E-04 | 2.44E-04 | 2.24E-04 | 2.53E-04 | 2.59E-04 | 2.02E-04 | 1.40E-04 | 2.30E-04 | 3.20E-04 |
| 13.87 | 1.14E-03 | 2.03E-04 | 2.34E-04 | 2.25E-04 | 2.61E-04 | 2.61E-04 | 2.07E-04 | 1.52E-04 | 2.29E-04 | 3.31E-04 |
| 13.88 | 1.10E-03 | 1.89E-04 | 2.30E-04 | 2.22E-04 | 2.72E-04 | 2.63E-04 | 2.01E-04 | 1.45E-04 | 2.30E-04 | 3.10E-04 |
| 13.90 | 1.07E-03 | 1.97E-04 | 2.39E-04 | 2.11E-04 | 2.61E-04 | 2.49E-04 | 2.03E-04 | 1.45E-04 | 2.28E-04 | 3.02E-04 |
| 13.92 | 1.04E-03 | 1.99E-04 | 2.23E-04 | 2.09E-04 | 2.51E-04 | 2.45E-04 | 1.86E-04 | 1.46E-04 | 2.25E-04 | 3.22E-04 |
| 13.93 | 1.02E-03 | 2.00E-04 | 2.32E-04 | 2.19E-04 | 2.58E-04 | 2.38E-04 | 1.94E-04 | 1.49E-04 | 2.28E-04 | 3.02E-04 |
| 13.95 | 9.71E-04 | 1.90E-04 | 2.22E-04 | 2.13E-04 | 2.52E-04 | 2.52E-04 | 1.90E-04 | 1.38E-04 | 2.31E-04 | 3.20E-04 |
| 13.97 | 9.52E-04 | 1.80E-04 | 2.20E-04 | 2.02E-04 | 2.60E-04 | 2.50E-04 | 2.05E-04 | 1.39E-04 | 2.37E-04 | 3.03E-04 |
| 13.98 | 9.27E-04 | 1.89E-04 | 2.25E-04 | 2.20E-04 | 2.61E-04 | 2.44E-04 | 1.83E-04 | 1.38E-04 | 2.32E-04 | 3.01E-04 |
| 14.00 | 9.02E-04 | 1.80E-04 | 2.23E-04 | 1.92E-04 | 2.71E-04 | 2.34E-04 | 1.83E-04 | 1.36E-04 | 2.29E-04 | 2.99E-04 |
| 14.02 | 8.91E-04 | 1.70E-04 | 2.20E-04 | 1.95E-04 | 2.45E-04 | 2.47E-04 | 1.80E-04 | 1.36E-04 | 2.35E-04 | 3.09E-04 |
| 14.03 | 8.64E-04 | 1.90E-04 | 2.18E-04 | 2.01E-04 | 2.51E-04 | 2.29E-04 | 1.75E-04 | 1.19E-04 | 2.27E-04 | 2.96E-04 |
| 14.05 | 8.38E-04 | 1.93E-04 | 2.19E-04 | 2.05E-04 | 2.31E-04 | 2.42E-04 | 1.86E-04 | 1.36E-04 | 2.35E-04 | 2.99E-04 |
| 14.07 | 8.18E-04 | 1.73E-04 | 2.23E-04 | 2.10E-04 | 2.42E-04 | 2.35E-04 | 1.68E-04 | 1.25E-04 | 2.22E-04 | 3.00E-04 |
| 14.08 | 7.92E-04 | 1.81E-04 | 2.05E-04 | 2.01E-04 | 2.14E-04 | 2.24E-04 | 1.65E-04 | 1.21E-04 | 2.24E-04 | 3.00E-04 |
| 14.10 | 7.82E-04 | 1.69E-04 | 2.07E-04 | 1.94E-04 | 2.25E-04 | 2.44E-04 | 1.69E-04 | 1.32E-04 | 2.35E-04 | 3.02E-04 |
| 14.12 | 7.61E-04 | 1.86E-04 | 2.02E-04 | 1.90E-04 | 2.37E-04 | 2.47E-04 | 1.81E-04 | 1.26E-04 | 2.49E-04 | 2.93E-04 |
| 14.13 | 7.49E-04 | 1.78E-04 | 2.22E-04 | 1.86E-04 | 2.35E-04 | 2.23E-04 | 1.81E-04 | 1.15E-04 | 2.23E-04 | 2.93E-04 |
| 14.15 | 7.32E-04 | 1.73E-04 | 2.03E-04 | 2.00E-04 | 2.42E-04 | 2.42E-04 | 1.83E-04 | 1.23E-04 | 2.21E-04 | 2.97E-04 |
| 14.17 | 7.13E-04 | 1.66E-04 | 2.00E-04 | 1.82E-04 | 2.28E-04 | 2.28E-04 | 1.69E-04 | 1.15E-04 | 2.21E-04 | 2.90E-04 |
| 14.18 | 7.03E-04 | 1.66E-04 | 2.07E-04 | 1.93E-04 | 2.39E-04 | 2.35E-04 | 1.66E-04 | 1.16E-04 | 2.37E-04 | 2.83E-04 |
| 14.20 | 6.75E-04 | 1.68E-04 | 2.05E-04 | 1.90E-04 | 2.32E-04 | 2.32E-04 | 1.55E-04 | 1.49E-04 | 2.40E-04 | 2.89E-04 |
| 14.22 | 6.70E-04 | 1.70E-04 | 2.05E-04 | 1.92E-04 | 2.33E-04 | 2.29E-04 | 1.69E-04 | 1.20E-04 | 2.17E-04 | 2.86E-04 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 14.23 | 6.54E-04 | 1.81E-04 | 1.86E-04 | 1.89E-04 | 2.23E-04 | 2.29E-04 | 1.69E-04 | 1.16E-04 | 2.27E-04 | 2.82E-04 |
| 14.25 | 6.41E-04 | 1.95E-04 | 2.12E-04 | 1.84E-04 | 2.40E-04 | 2.29E-04 | 1.65E-04 | 1.35E-04 | 2.22E-04 | 2.89E-04 |
| 14.27 | 6.28E-04 | 1.68E-04 | 1.91E-04 | 1.83E-04 | 2.22E-04 | 2.30E-04 | 1.55E-04 | 1.11E-04 | 2.11E-04 | 2.81E-04 |
| 14.28 | 6.40E-04 | 1.75E-04 | 1.90E-04 | 1.90E-04 | 2.25E-04 | 2.42E-04 | 1.69E-04 | 1.07E-04 | 2.35E-04 | 2.83E-04 |
| 14.30 | 6.06E-04 | 1.72E-04 | 1.84E-04 | 1.84E-04 | 2.22E-04 | 2.37E-04 | 1.55E-04 | 1.25E-04 | 2.21E-04 | 2.84E-04 |
| 14.32 | 5.98E-04 | 1.81E-04 | 1.89E-04 | 1.76E-04 | 2.28E-04 | 2.15E-04 | 1.79E-04 | 1.07E-04 | 2.32E-04 | 2.98E-04 |
| 14.33 | 5.91E-04 | 1.82E-04 | 1.88E-04 | 1.82E-04 | 2.24E-04 | 2.19E-04 | 1.56E-04 | 1.05E-04 | 2.24E-04 | 2.81E-04 |
| 14.35 | 5.75E-04 | 1.80E-04 | 2.00E-04 | 1.73E-04 | 2.32E-04 | 2.25E-04 | 1.52E-04 | 1.11E-04 | 2.27E-04 | 2.92E-04 |
| 14.37 | 5.62E-04 | 1.58E-04 | 1.93E-04 | 1.79E-04 | 2.24E-04 | 2.21E-04 | 1.66E-04 | 1.12E-04 | 2.20E-04 | 2.69E-04 |
| 14.38 | 5.57E-04 | 1.76E-04 | 2.02E-04 | 1.81E-04 | 2.25E-04 | 2.34E-04 | 1.61E-04 | 1.10E-04 | 2.25E-04 | 2.86E-04 |
| 14.40 | 5.42E-04 | 1.69E-04 | 1.83E-04 | 1.82E-04 | 2.20E-04 | 2.24E-04 | 1.49E-04 | 1.15E-04 | 2.29E-04 | 2.91E-04 |
| 14.42 | 5.25E-04 | 1.88E-04 | 1.90E-04 | 1.78E-04 | 2.37E-04 | 2.20E-04 | 1.53E-04 | 1.09E-04 | 2.21E-04 | 2.70E-04 |
| 14.43 | 5.26E-04 | 1.69E-04 | 1.95E-04 | 1.71E-04 | 2.10E-04 | 2.08E-04 | 1.59E-04 | 9.30E-05 | 2.20E-04 | 2.71E-04 |
| 14.45 | 5.26E-04 | 1.64E-04 | 1.97E-04 | 1.80E-04 | 2.08E-04 | 2.19E-04 | 1.53E-04 | 1.03E-04 | 2.14E-04 | 2.73E-04 |
| 14.47 | 5.19E-04 | 1.74E-04 | 2.00E-04 | 1.84E-04 | 2.13E-04 | 2.08E-04 | 1.71E-04 | 1.11E-04 | 2.35E-04 | 2.64E-04 |
| 14.48 | 5.06E-04 | 1.76E-04 | 1.78E-04 | 1.75E-04 | 2.22E-04 | 2.18E-04 | 1.58E-04 | 1.13E-04 | 2.23E-04 | 2.74E-04 |
| 14.50 | 4.93E-04 | 1.68E-04 | 1.88E-04 | 1.59E-04 | 2.02E-04 | 2.17E-04 | 1.62E-04 | 9.90E-04 | 2.31E-04 | 2.77E-04 |
| 14.52 | 4.95E-04 | 1.63E-04 | 1.98E-04 | 1.72E-04 | 2.11E-04 | 2.05E-04 | 1.60E-04 | 1.05E-04 | 2.30E-04 | 3.02E-04 |
| 14.53 | 4.78E-04 | 1.60E-04 | 2.00E-04 | 1.69E-04 | 1.98E-04 | 2.04E-04 | 1.49E-04 | 1.01E-04 | 2.17E-04 | 2.79E-04 |
| 14.55 | 4.78E-04 | 1.80E-04 | 1.99E-04 | 1.98E-04 | 2.15E-04 | 2.17E-04 | 1.69E-04 | 1.03E-04 | 2.24E-04 | 2.74E-04 |
| 14.57 | 4.81E-04 | 1.73E-04 | 1.78E-04 | 1.59E-04 | 2.13E-04 | 1.93E-04 | 1.56E-04 | 1.00E-04 | 2.25E-04 | 2.63E-04 |
| 14.58 | 4.65E-04 | 1.52E-04 | 1.86E-04 | 1.72E-04 | 1.97E-04 | 2.09E-04 | 1.58E-04 | 9.60E-05 | 2.33E-04 | 2.73E-04 |
| 14.60 | 4.83E-04 | 1.58E-04 | 1.84E-04 | 1.61E-04 | 2.12E-04 | 2.03E-04 | 1.65E-04 | 9.60E-05 | 2.32E-04 | 2.66E-04 |
| 14.62 | 4.46E-04 | 1.48E-04 | 1.92E-04 | 1.53E-04 | 2.02E-04 | 2.10E-04 | 1.55E-04 | 1.17E-04 | 2.29E-04 | 2.73E-04 |
| 14.63 | 4.54E-04 | 1.72E-04 | 1.89E-04 | 1.63E-04 | 2.07E-04 | 2.01E-04 | 1.62E-04 | 1.03E-04 | 2.38E-04 | 2.63E-04 |
| 14.65 | 4.41E-04 | 1.83E-04 | 1.85E-04 | 1.42E-04 | 1.99E-04 | 2.03E-04 | 1.68E-04 | 9.90E-05 | 2.39E-04 | 2.69E-04 |
| 14.67 | 4.37E-04 | 1.65E-04 | 1.91E-04 | 1.66E-04 | 2.19E-04 | 2.05E-04 | 1.79E-04 | 1.12E-04 | 2.51E-04 | 2.82E-04 |
| 14.68 | 4.35E-04 | 1.54E-04 | 1.95E-04 | 1.60E-04 | 2.03E-04 | 1.99E-04 | 1.66E-04 | 1.02E-04 | 2.68E-04 | 2.68E-04 |
| 14.70 | 4.22E-04 | 1.72E-04 | 1.86E-04 | 1.53E-04 | 2.10E-04 | 1.91E-04 | 1.73E-04 | 1.03E-04 | 2.60E-04 | 2.73E-04 |
| 14.72 | 4.18E-04 | 1.66E-04 | 2.10E-04 | 1.51E-04 | 2.21E-04 | 2.12E-04 | 1.80E-04 | 1.07E-04 | 2.53E-04 | 2.70E-04 |
| 14.73 | 4.24E-04 | 1.64E-04 | 1.98E-04 | 1.59E-04 | 2.17E-04 | 2.04E-04 | 1.81E-04 | 1.21E-04 | 2.71E-04 | 2.79E-04 |
| 14.75 | 4.18E-04 | 1.68E-04 | 2.04E-04 | 1.59E-04 | 2.20E-04 | 2.11E-04 | 1.85E-04 | 1.23E-04 | 2.61E-04 | 2.84E-04 |
| 14.77 | 4.54E-04 | 1.63E-04 | 1.89E-04 | 1.42E-04 | 2.39E-04 | 2.12E-04 | 1.81E-04 | 1.23E-04 | 2.67E-04 | 2.86E-04 |
| 14.78 | 4.14E-04 | 1.79E-04 | 2.04E-04 | 1.62E-04 | 2.15E-04 | 2.11E-04 | 1.75E-04 | 1.28E-04 | 2.62E-04 | 2.80E-04 |
| 14.80 | 3.79E-04 | 1.72E-04 | 1.90E-04 | 1.60E-04 | 2.24E-04 | 2.10E-04 | 1.93E-04 | 1.12E-04 | 2.66E-04 | 2.77E-04 |
| 14.82 | 3.91E-04 | 1.82E-04 | 1.95E-04 | 1.68E-04 | 2.30E-04 | 2.09E-04 | 1.75E-04 | 1.15E-04 | 2.60E-04 | 2.87E-04 |
| 14.83 | 3.87E-04 | 1.74E-04 | 2.02E-04 | 1.65E-04 | 2.17E-04 | 2.05E-04 | 1.78E-04 | 1.11E-04 | 2.30E-04 | 2.94E-04 |
| 14.85 | 3.76E-04 | 1.76E-04 | 2.12E-04 | 1.65E-04 | 2.03E-04 | 2.09E-04 | 1.75E-04 | 1.12E-04 | 2.43E-04 | 2.86E-04 |
| 14.87 | 3.68E-04 | 1.75E-04 | 2.01E-04 | 1.53E-04 | 2.12E-04 | 2.07E-04 | 1.84E-04 | 9.90E-05 | 2.38E-04 | 2.64E-04 |
| 14.88 | 3.77E-04 | 1.63E-04 | 1.92E-04 | 1.70E-04 | 2.21E-04 | 1.98E-04 | 1.65E-04 | 1.05E-04 | 2.45E-04 | 2.66E-04 |
| 14.90 | 3.65E-04 | 1.52E-04 | 1.85E-04 | 1.51E-04 | 1.97E-04 | 1.99E-04 | 1.85E-04 | 1.09E-04 | 2.34E-04 | 2.61E-04 |
| 14.92 | 3.69E-04 | 1.63E-04 | 1.99E-04 | 1.56E-04 | 1.90E-04 | 1.82E-04 | 1.89E-04 | 1.01E-04 | 2.42E-04 | 2.60E-04 |
| 14.93 | 3.56E-04 | 1.65E-04 | 1.80E-04 | 1.52E-04 | 1.97E-04 | 2.03E-04 | 1.66E-04 | 9.50E-05 | 2.25E-04 | 2.57E-04 |
| 14.95 | 3.46E-04 | 1.58E-04 | 1.85E-04 | 1.41E-04 | 2.07E-04 | 2.00E-04 | 1.83E-04 | 9.10E-05 | 2.48E-04 | 2.53E-04 |
| 14.97 | 3.39E-04 | 1.54E-04 | 1.76E-04 | 1.69E-04 | 2.00E-04 | 1.85E-04 | 1.90E-04 | 8.20E-05 | 2.29E-04 | 2.50E-04 |
| 14.98 | 3.47E-04 | 1.44E-04 | 1.84E-04 | 1.29E-04 | 1.93E-04 | 1.91E-04 | 1.86E-04 | 9.70E-05 | 2.42E-04 | 2.54E-04 |
| 15.00 | 3.52E-04 | 1.41E-04 | 1.82E-04 | 1.38E-04 | 1.91E-04 | 1.86E-04 | 1.82E-04 | 1.02E-04 | 2.30E-04 | 2.43E-04 |
| 15.02 | 3.30E-04 | 1.51E-04 | 1.81E-04 | 1.39E-04 | 1.97E-04 | 2.01E-04 | 1.76E-04 | 1.02E-04 | 2.32E-04 | 2.51E-04 |
| 15.03 | 3.35E-04 | 1.53E-04 | 1.90E-04 | 1.45E-04 | 1.92E-04 | 1.86E-04 | 1.71E-04 | 8.50E-05 | 2.32E-04 | 2.57E-04 |
| 15.05 | 3.42E-04 | 1.40E-04 | 1.73E-04 | 1.46E-04 | 1.93E-04 | 1.91E-04 | 1.81E-04 | 7.60E-05 | 2.21E-04 | 2.56E-04 |
| 15.07 | 3.18E-04 | 1.34E-04 | 1.76E-04 | 1.36E-04 | 2.02E-04 | 1.89E-04 | 1.64E-04 | 9.10E-05 | 2.35E-04 | 2.62E-04 |
| 15.08 | 3.30E-04 | 1.40E-04 | 1.83E-04 | 1.30E-04 | 1.94E-04 | 1.83E-04 | 1.85E-04 | 9.30E-05 | 2.37E-04 | 2.38E-04 |
| 15.10 | 3.27E-04 | 1.31E-04 | 1.76E-04 | 1.35E-04 | 1.85E-04 | 1.79E-04 | 1.74E-04 | 9.00E-05 | 2.15E-04 | 2.60E-04 |
| 15.12 | 3.12E-04 | 1.32E-04 | 1.81E-04 | 1.40E-04 | 1.88E-04 | 1.92E-04 | 1.88E-04 | 8.10E-05 | 2.35E-04 | 2.49E-04 |
| 15.13 | 3.14E-04 | 1.44E-04 | 1.89E-04 | 1.43E-04 | 1.89E-04 | 1.85E-04 | 1.65E-04 | 8.60E-05 | 2.23E-04 | 2.51E-04 |
| 15.15 | 3.13E-04 | 1.19E-04 | 1.85E-04 | 1.51E-04 | 1.85E-04 | 1.95E-04 | 1.74E-04 | 7.60E-05 | 2.28E-04 | 2.31E-04 |
| 15.17 | 3.02E-04 | 1.25E-04 | 1.85E-04 | 1.34E-04 | 1.78E-04 | 1.83E-04 | 1.79E-04 | 1.02E-04 | 2.39E-04 | 2.34E-04 |
| 15.18 | 3.12E-04 | 1.39E-04 | 1.83E-04 | 1.28E-04 | 1.78E-04 | 1.73E-04 | 2.04E-04 | 8.70E-05 | 2.35E-04 | 2.39E-04 |
| 15.20 | 3.12E-04 | 1.22E-04 | 1.61E-04 | 1.24E-04 | 1.70E-04 | 1.85E-04 | 1.75E-04 | 8.40E-05 | 2.25E-04 | 2.57E-04 |
| 15.22 | 3.08E-04 | 1.23E-04 | 1.69E-04 | 1.29E-04 | 1.70E-04 | 1.65E-04 | 1.91E-04 | 8.10E-05 | 2.25E-04 | 2.35E-04 |
| 15.23 | 3.11E-04 | 1.29E-04 | 1.80E-04 | 1.39E-04 | 1.80E-04 | 1.74E-04 | 1.73E-04 | 9.10E-05 | 2.23E-04 | 2.37E-04 |
| 15.25 | 3.00E-04 | 1.26E-04 | 1.78E-04 | 1.35E-04 | 1.70E-04 | 1.73E-04 | 1.73E-04 | 7.40E-05 | 2.23E-04 | 2.40E-04 |
| 15.27 | 2.98E-04 | 1.14E-04 | 1.86E-04 | 1.29E-04 | 1.75E-04 | 1.84E-04 | 1.74E-04 | 9.10E-05 | 2.20E-04 | 2.69E-04 |
| 15.28 | 2.89E-04 | 1.11E-04 | 1.62E-04 | 1.09E-04 | 1.76E-04 | 1.88E-04 | 1.85E-04 | 7.60E-05 | 2.13E-04 | 2.25E-04 |
| 15.30 | 2.94E-04 | 1.21E-04 | 1.65E-04 | 1.16E-04 | 1.69E-04 | 1.79E-04 | 1.66E-04 | 8.10E-05 | 2.11E-04 | 2.41E-04 |
| 15.32 | 2.96E-04 | 1.07E-04 | 1.71E-04 | 1.12E-04 | 1.74E-04 | 1.79E-04 | 1.72E-04 | 8.20E-05 | 2.20E-04 | 2.47E-04 |
| 15.33 | 2.92E-04 | 1.24E-04 | 1.62E-04 | 1.17E-04 | 1.59E-04 | 1.70E-04 | 1.82E-04 | 6.10E-05 | 2.03E-04 | 2.23E-04 |
| 15.35 | 2.99E-04 | 1.16E-04 | 1.66E-04 | 1.16E-04 | 1.68E-04 | 1.62E-04 | 1.73E-04 | 7.40E-05 | 2.24E-04 | 2.47E-04 |
| 15.37 | 3.07E-04 | 1.19E-04 | 1.76E-04 | 1.06E-04 | 1.72E-04 | 1.69E-04 | 1.76E-04 | 7.00E-05 | 2.14E-04 | 2.39E-04 |
| 15.38 | 2.99E-04 | 1.14E-04 | 1.56E-04 | 1.04E-04 | 1.64E-04 | 1.68E-04 | 1.69E-04 | 8.30E-05 | 2.11E-04 | 2.44E-04 |
| 15.40 | 3.02E-04 | 1.11E-04 | 1.75E-04 | 1.01E-04 | 1.64E-04 | 1.70E-04 | 1.62E-04 | 5.60E-05 | 2.17E-04 | 2.39E-04 |
| 15.42 | 2.84E-04 | 1.13E-04 | 1.75E-04 | 1.07E-04 | 1.49E-04 | 1.52E-04 | 1.74E-04 | 7.10E-05 | 1.93E-04 | 2.42E-04 |
| 15.43 | 2.92E-04 | 1.15E-04 | 1.61E-04 | 1.09E-04 | 1.74E-04 | 1.53E-04 | 1.68E-04 | 6.00E-05 | 2.03E-04 | 2.28E-04 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 15.45 | 2.86E-04 | 9.50E-05 | 1.65E-04 | 1.10E-04 | 1.70E-04 | 1.65E-04 | 1.70E-04 | 6.40E-05 | 2.29E-04 | 2.33E-04 |
| 15.47 | 2.77E-04 | 1.13E-04 | 1.69E-04 | 1.11E-04 | 1.81E-04 | 1.63E-04 | 1.66E-04 | 6.20E-05 | 1.95E-04 | 2.23E-04 |
| 15.48 | 2.88E-04 | 1.01E-04 | 1.55E-04 | 1.11E-04 | 1.68E-04 | 1.60E-04 | 1.65E-04 | 7.30E-05 | 2.19E-04 | 2.38E-04 |
| 15.50 | 2.88E-04 | 9.40E-05 | 1.68E-04 | 1.25E-04 | 1.78E-04 | 1.63E-04 | 1.79E-04 | 7.60E-05 | 2.07E-04 | 2.24E-04 |
| 15.52 | 2.82E-04 | 1.11E-04 | 1.51E-04 | 1.01E-04 | 1.69E-04 | 1.53E-04 | 1.61E-04 | 7.10E-05 | 1.91E-04 | 2.34E-04 |
| 15.53 | 2.87E-04 | 9.60E-05 | 1.71E-04 | 1.26E-04 | 1.73E-04 | 1.50E-04 | 1.68E-04 | 5.70E-05 | 2.23E-04 | 2.17E-04 |
| 15.55 | 2.77E-04 | 1.09E-04 | 1.61E-04 | 9.70E-05 | 1.59E-04 | 1.72E-04 | 1.64E-04 | 6.70E-05 | 2.01E-04 | 2.20E-04 |
| 15.57 | 2.74E-04 | 1.05E-04 | 1.65E-04 | 1.06E-04 | 1.56E-04 | 1.45E-04 | 1.63E-04 | 7.00E-05 | 1.97E-04 | 2.33E-04 |
| 15.58 | 2.81E-04 | 1.02E-04 | 1.70E-04 | 1.06E-04 | 1.59E-04 | 1.61E-04 | 1.52E-04 | 6.40E-05 | 1.98E-04 | 2.29E-04 |
| 15.60 | 2.70E-04 | 1.01E-04 | 1.58E-04 | 1.06E-04 | 1.63E-04 | 1.56E-04 | 1.52E-04 | 6.30E-05 | 2.01E-04 | 2.34E-04 |
| 15.62 | 2.81E-04 | 9.40E-05 | 1.61E-04 | 1.05E-04 | 1.52E-04 | 1.56E-04 | 1.75E-04 | 5.80E-05 | 2.15E-04 | 2.14E-04 |
| 15.63 | 2.68E-04 | 9.20E-05 | 1.65E-04 | 1.02E-04 | 1.56E-04 | 1.60E-04 | 1.76E-04 | 6.90E-05 | 2.02E-04 | 2.23E-04 |
| 15.65 | 2.64E-04 | 9.10E-05 | 1.51E-04 | 9.60E-05 | 1.69E-04 | 1.42E-04 | 1.64E-04 | 5.40E-05 | 1.98E-04 | 2.33E-04 |
| 15.67 | 2.64E-04 | 1.03E-04 | 1.74E-04 | 1.07E-04 | 1.58E-04 | 1.52E-04 | 1.69E-04 | 7.00E-05 | 1.84E-04 | 2.31E-04 |
| 15.68 | 2.63E-04 | 8.40E-05 | 1.51E-04 | 9.30E-05 | 1.53E-04 | 1.52E-04 | 1.64E-04 | 5.20E-05 | 1.98E-04 | 2.29E-04 |
| 15.70 | 2.70E-04 | 1.06E-04 | 1.54E-04 | 1.02E-04 | 1.49E-04 | 1.41E-04 | 1.65E-04 | 5.00E-05 | 1.91E-04 | 2.11E-04 |
| 15.72 | 2.52E-04 | 8.10E-05 | 1.60E-04 | 9.30E-05 | 1.66E-04 | 1.48E-04 | 1.65E-04 | 6.20E-05 | 1.84E-04 | 2.33E-04 |
| 15.73 | 2.58E-04 | 9.30E-05 | 1.55E-04 | 1.04E-04 | 1.86E-04 | 1.51E-04 | 1.64E-04 | 5.80E-05 | 1.92E-04 | 2.20E-04 |
| 15.75 | 2.66E-04 | 8.90E-05 | 1.66E-04 | 9.90E-05 | 1.63E-04 | 1.45E-04 | 1.62E-04 | 6.00E-05 | 2.02E-04 | 2.28E-04 |
| 15.77 | 2.62E-04 | 7.50E-05 | 1.55E-04 | 9.20E-05 | 1.74E-04 | 1.39E-04 | 1.66E-04 | 5.50E-05 | 1.94E-04 | 2.33E-04 |
| 15.78 | 2.58E-04 | 9.60E-05 | 1.44E-04 | 9.90E-05 | 1.64E-04 | 1.50E-04 | 1.61E-04 | 6.00E-05 | 1.92E-04 | 2.13E-04 |
| 15.80 | 2.42E-04 | 7.70E-05 | 1.50E-04 | 9.40E-05 | 1.94E-04 | 1.39E-04 | 1.65E-04 | 3.50E-05 | 1.88E-04 | 2.32E-04 |
| 15.82 | 2.57E-04 | 9.50E-05 | 1.60E-04 | 9.20E-05 | 1.78E-04 | 1.45E-04 | 1.63E-04 | 5.00E-05 | 1.85E-04 | 2.21E-04 |
| 15.83 | 2.52E-04 | 8.30E-05 | 1.61E-04 | 1.03E-04 | 1.79E-04 | 1.53E-04 | 1.61E-04 | 4.40E-05 | 1.89E-04 | 2.24E-04 |
| 15.85 | 2.54E-04 | 9.40E-05 | 1.50E-04 | 1.02E-04 | 1.68E-04 | 1.42E-04 | 1.66E-04 | 6.70E-05 | 1.84E-04 | 2.44E-04 |
| 15.87 | 2.57E-04 | 8.50E-05 | 1.53E-04 | 1.09E-04 | 1.72E-04 | 1.50E-04 | 1.78E-04 | 5.10E-05 | 1.94E-04 | 2.34E-04 |
| 15.88 | 2.44E-04 | 8.90E-05 | 1.50E-04 | 1.05E-04 | 1.83E-04 | 1.58E-04 | 1.56E-04 | 5.40E-05 | 2.09E-04 | 2.33E-04 |
| 15.90 | 2.54E-04 | 8.20E-05 | 1.68E-04 | 1.26E-04 | 1.78E-04 | 1.50E-04 | 1.58E-04 | 4.30E-05 | 1.98E-04 | 2.20E-04 |
| 15.92 | 2.42E-04 | 7.90E-05 | 1.68E-04 | 1.13E-04 | 1.65E-04 | 1.42E-04 | 1.53E-04 | 4.80E-05 | 1.82E-04 | 2.29E-04 |
| 15.93 | 2.15E-04 | 7.90E-05 | 1.54E-04 | 1.24E-04 | 1.66E-04 | 1.44E-04 | 1.64E-04 | 6.50E-05 | 1.79E-04 | 2.25E-04 |
| 15.95 | 2.42E-04 | 8.70E-05 | 1.54E-04 | 1.17E-04 | 1.64E-04 | 1.49E-04 | 1.45E-04 | 4.60E-05 | 1.92E-04 | 2.12E-04 |
| 15.97 | 2.37E-04 | 7.40E-05 | 1.69E-04 | 1.06E-04 | 1.65E-04 | 1.34E-04 | 1.43E-04 | 5.00E-05 | 1.88E-04 | 2.19E-04 |
| 15.98 | 2.35E-04 | 7.00E-05 | 1.52E-04 | 1.10E-04 | 1.62E-04 | 1.45E-04 | 1.44E-04 | 4.50E-05 | 1.80E-04 | 2.34E-04 |
| 16.00 | 2.40E-04 | 8.90E-05 | 1.56E-04 | 1.04E-04 | 1.58E-04 | 1.33E-04 | 1.60E-04 | 5.30E-05 | 1.64E-04 | 2.31E-04 |
| 16.02 | 2.43E-04 | 7.90E-05 | 1.39E-04 | 1.12E-04 | 1.54E-04 | 1.30E-04 | 1.43E-04 | 6.20E-05 | 1.74E-04 | 2.15E-04 |
| 16.03 | 2.33E-04 | 6.70E-05 | 1.51E-04 | 8.00E-05 | 1.58E-04 | 1.44E-04 | 1.53E-04 | 4.70E-05 | 1.68E-04 | 2.21E-04 |
| 16.05 | 2.31E-04 | 8.30E-05 | 1.32E-04 | 8.60E-05 | 1.49E-04 | 1.25E-04 | 1.49E-04 | 3.10E-05 | 1.80E-04 | 2.14E-04 |
| 16.07 | 2.31E-04 | 7.10E-05 | 1.50E-04 | 1.06E-04 | 1.40E-04 | 1.44E-04 | 1.55E-04 | 4.40E-05 | 1.72E-04 | 2.18E-04 |
| 16.08 | 2.30E-04 | 7.50E-05 | 1.49E-04 | 7.20E-05 | 1.39E-04 | 1.33E-04 | 1.48E-04 | 3.80E-05 | 1.71E-04 | 2.07E-04 |
| 16.10 | 2.33E-04 | 6.40E-05 | 1.44E-04 | 9.60E-05 | 1.44E-04 | 1.17E-04 | 1.33E-04 | 4.10E-05 | 1.81E-04 | 2.04E-04 |
| 16.12 | 2.19E-04 | 7.50E-05 | 1.48E-04 | 8.50E-05 | 1.26E-04 | 1.25E-04 | 1.45E-04 | 2.10E-05 | 1.69E-04 | 2.07E-04 |
| 16.13 | 2.45E-04 | 6.40E-05 | 1.45E-04 | 7.90E-05 | 1.42E-04 | 1.23E-04 | 1.34E-04 | 3.70E-05 | 1.71E-04 | 2.13E-04 |
| 16.15 | 2.21E-04 | 6.70E-05 | 1.51E-04 | 6.10E-05 | 1.50E-04 | 1.22E-04 | 1.39E-04 | 2.60E-05 | 1.81E-04 | 2.17E-04 |
| 16.17 | 2.28E-04 | 6.90E-05 | 1.28E-04 | 8.70E-05 | 1.39E-04 | 1.07E-04 | 1.25E-04 | 3.30E-05 | 1.66E-04 | 2.08E-04 |
| 16.18 | 2.17E-04 | 9.50E-05 | 1.44E-04 | 8.40E-05 | 1.41E-04 | 1.20E-04 | 1.42E-04 | 3.60E-05 | 1.69E-04 | 2.03E-04 |
| 16.20 | 2.28E-04 | 7.30E-05 | 1.48E-04 | 9.20E-05 | 1.33E-04 | 1.22E-04 | 1.49E-04 | 2.80E-05 | 1.86E-04 | 2.12E-04 |
| 16.22 | 2.19E-04 | 6.50E-05 | 1.30E-04 | 7.40E-05 | 1.21E-04 | 1.11E-04 | 1.40E-04 | 3.30E-05 | 1.70E-04 | 2.33E-04 |
| 16.23 | 2.09E-04 | 6.60E-05 | 1.41E-04 | 7.60E-05 | 1.50E-04 | 1.23E-04 | 1.30E-04 | 2.30E-05 | 1.64E-04 | 2.14E-04 |
| 16.25 | 1.99E-04 | 7.90E-05 | 1.42E-04 | 7.70E-05 | 1.16E-04 | 1.17E-04 | 1.48E-04 | 3.50E-05 | 1.66E-04 | 2.07E-04 |
| 16.27 | 2.18E-04 | 5.80E-05 | 1.43E-04 | 7.60E-05 | 1.29E-04 | 1.25E-04 | 1.34E-04 | 3.30E-05 | 1.64E-04 | 2.12E-04 |
| 16.28 | 2.07E-04 | 6.40E-05 | 1.28E-04 | 7.40E-05 | 1.33E-04 | 1.13E-04 | 1.46E-04 | 3.10E-05 | 1.65E-04 | 2.13E-04 |
| 16.30 | 2.14E-04 | 6.60E-05 | 1.43E-04 | 8.60E-05 | 1.54E-04 | 1.09E-04 | 1.30E-04 | 3.00E-05 | 1.78E-04 | 2.04E-04 |
| 16.32 | 2.03E-04 | 5.60E-05 | 1.39E-04 | 7.30E-05 | 1.41E-04 | 1.17E-04 | 1.43E-04 | 2.30E-05 | 1.55E-04 | 2.10E-04 |
| 16.33 | 2.14E-04 | 6.60E-05 | 1.41E-04 | 8.00E-05 | 1.13E-04 | 1.03E-04 | 1.35E-04 | 2.40E-05 | 1.53E-04 | 2.08E-04 |
| 16.35 | 2.22E-04 | 6.50E-05 | 1.38E-04 | 7.90E-05 | 1.17E-04 | 1.20E-04 | 1.24E-04 | 3.10E-05 | 1.54E-04 | 2.02E-04 |
| 16.37 | 2.05E-04 | 5.00E-05 | 1.50E-04 | 7.20E-05 | 1.24E-04 | 1.17E-04 | 1.22E-04 | 4.10E-05 | 1.54E-04 | 2.09E-04 |
| 16.38 | 1.92E-04 | 6.40E-05 | 1.55E-04 | 8.20E-05 | 1.24E-04 | 1.03E-04 | 1.33E-04 | 2.70E-05 | 1.58E-04 | 2.09E-04 |
| 16.40 | 1.99E-04 | 6.00E-05 | 1.45E-04 | 6.60E-05 | 1.24E-04 | 1.28E-04 | 1.25E-04 | 1.50E-05 | 1.46E-04 | 2.13E-04 |
| 16.42 | 2.00E-04 | 6.00E-05 | 1.53E-04 | 5.30E-05 | 1.14E-04 | 1.06E-04 | 1.22E-04 | 1.50E-05 | 1.53E-04 | 2.11E-04 |
| 16.43 | 2.05E-04 | 5.50E-05 | 1.40E-04 | 5.50E-05 | 1.29E-04 | 9.10E-05 | 1.33E-04 | 2.00E-05 | 1.43E-04 | 2.10E-04 |
| 16.45 | 2.03E-04 | 4.40E-05 | 1.31E-04 | 6.50E-05 | 1.31E-04 | 1.04E-04 | 1.20E-04 | 2.50E-05 | 1.50E-04 | 2.15E-04 |
| 16.47 | 1.99E-04 | 5.00E-05 | 1.39E-04 | 6.10E-05 | 1.20E-04 | 1.00E-04 | 1.25E-04 | 3.00E-05 | 1.48E-04 | 2.27E-04 |
| 16.48 | 2.05E-04 | 4.80E-05 | 1.50E-04 | 7.10E-05 | 1.46E-04 | 9.90E-05 | 1.28E-04 | 3.00E-05 | 1.41E-04 | 2.08E-04 |
| 16.50 | 2.12E-04 | 5.10E-05 | 1.40E-04 | 5.50E-05 | 1.21E-04 | 1.07E-04 | 1.20E-04 | 1.80E-05 | 1.49E-04 | 2.15E-04 |
| 16.52 | 1.88E-04 | 5.00E-05 | 1.38E-04 | 5.50E-05 | 1.15E-04 | 1.13E-04 | 1.36E-04 | 1.60E-05 | 1.41E-04 | 2.12E-04 |
| 16.53 | 1.92E-04 | 5.40E-05 | 1.49E-04 | 5.10E-05 | 1.15E-04 | 1.11E-04 | 1.31E-04 | 2.60E-05 | 1.50E-04 | 2.01E-04 |
| 16.55 | 1.99E-04 | 5.60E-05 | 1.35E-04 | 5.60E-05 | 1.31E-04 | 1.13E-04 | 1.23E-04 | 2.40E-05 | 1.44E-04 | 2.20E-04 |
| 16.57 | 1.88E-04 | 6.90E-05 | 1.24E-04 | 5.40E-05 | 1.19E-04 | 1.22E-04 | 1.15E-04 | 3.00E-05 | 2.57E-04 | 2.17E-04 |
| 16.58 | 1.95E-04 | 5.30E-05 | 1.48E-04 | 4.80E-05 | 1.25E-04 | 1.17E-04 | 1.38E-04 | 2.00E-05 | 1.54E-04 | 2.04E-04 |
| 16.60 | 2.19E-04 | 5.80E-05 | 1.38E-04 | 5.00E-05 | 1.11E-04 | 1.04E-04 | 1.17E-04 | 1.10E-05 | 1.52E-04 | 2.05E-04 |
| 16.62 | 1.93E-04 | 6.50E-05 | 1.44E-04 | 5.50E-05 | 1.22E-04 | 1.05E-04 | 1.29E-04 | 1.60E-05 | 1.42E-04 | 2.15E-04 |
| 16.63 | 1.81E-04 | 3.60E-05 | 1.38E-04 | 5.40E-05 | 1.34E-04 | 1.10E-04 | 1.60E-04 | 1.20E-05 | 1.48E-04 | 2.04E-04 |
| 16.65 | 1.78E-04 | 4.60E-05 | 1.42E-04 | 5.80E-05 | 1.31E-04 | 1.12E-04 | 1.14E-04 | 3.40E-05 | 1.43E-04 | 2.07E-04 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 16.67 | 1.99E−04 | 4.40E−05 | 1.51E−04 | 7.30E−05 | 1.14E−04 | 1.06E−04 | 1.24E−04 | 2.10E−05 | 1.53E−04 | 2.00E−04 |
| 16.68 | 1.92E−04 | 5.00E−05 | 1.32E−04 | 6.50E−05 | 1.10E−04 | 8.40E−05 | 1.31E−04 | 1.30E−05 | 1.41E−04 | 2.03E−04 |
| 16.70 | 1.93E−04 | 4.10E−05 | 1.38E−04 | 6.10E−05 | 1.12E−04 | 9.60E−05 | 1.10E−04 | 2.00E−06 | 1.42E−04 | 1.99E−04 |
| 16.72 | 2.02E−04 | 5.80E−05 | 1.44E−04 | 6.40E−05 | 1.16E−04 | 1.07E−04 | 1.21E−04 | 1.20E−05 | 1.55E−04 | 1.97E−04 |
| 16.73 | 1.85E−04 | 5.50E−05 | 1.44E−04 | 5.50E−05 | 1.11E−04 | 1.01E−04 | 1.03E−04 | 1.70E−05 | 1.46E−04 | 2.13E−04 |
| 16.75 | 2.01E−04 | 2.50E−05 | 1.38E−04 | 5.60E−05 | 1.24E−04 | 1.11E−04 | 1.20E−04 | 1.40E−05 | 1.32E−04 | 2.08E−04 |
| 16.77 | 1.81E−04 | 5.20E−05 | 1.50E−04 | 4.40E−05 | 1.07E−04 | 1.16E−04 | 1.06E−04 | 0.00E+00 | 1.28E−04 | 1.99E−04 |
| 16.78 | 1.95E−04 | 6.40E−05 | 1.46E−04 | 5.30E−05 | 1.13E−04 | 1.07E−04 | 1.10E−04 | 1.70E−05 | 1.36E−04 | 2.03E−04 |
| 16.80 | 1.94E−04 | 4.30E−05 | 1.41E−04 | 4.40E−05 | 1.14E−04 | 9.40E−05 | 1.11E−04 | 1.00E−05 | 1.51E−04 | 2.04E−04 |
| 16.82 | 1.94E−04 | 5.50E−05 | 1.38E−04 | 4.30E−05 | 1.17E−04 | 1.00E−04 | 1.05E−04 | 1.30E−05 | 1.35E−04 | 2.04E−04 |
| 16.83 | 1.75E−04 | 6.00E−05 | 1.28E−04 | 4.00E−05 | 1.09E−04 | 9.90E−05 | 1.06E−04 | 1.30E−05 | 1.56E−04 | 2.12E−04 |
| 16.85 | 2.01E−04 | 4.60E−05 | 1.55E−04 | 3.10E−05 | 1.09E−04 | 9.70E−05 | 1.09E−04 | 3.00E−06 | 1.41E−04 | 1.94E−04 |
| 16.87 | 1.82E−04 | 6.30E−05 | 1.43E−04 | 5.10E−05 | 1.26E−04 | 9.10E−05 | 1.14E−04 | 1.60E−05 | 1.30E−04 | 1.94E−04 |
| 16.88 | 2.04E−04 | 4.60E−05 | 1.33E−04 | 3.70E−05 | 1.06E−04 | 1.00E−04 | 1.11E−04 | 1.10E−05 | 1.44E−04 | 1.83E−04 |
| 16.90 | 1.85E−04 | 4.10E−05 | 1.46E−04 | 3.70E−05 | 1.12E−04 | 9.20E−05 | 9.90E−05 | 6.00E−06 | 1.42E−04 | 1.98E−04 |
| 16.92 | 1.78E−04 | 3.80E−05 | 1.44E−04 | 4.20E−05 | 1.11E−04 | 1.09E−04 | 9.10E−05 | 3.00E−05 | 1.31E−04 | 1.90E−04 |
| 16.93 | 1.93E−04 | 4.60E−05 | 1.39E−04 | 4.00E−05 | 8.90E−05 | 1.03E−04 | 1.20E−04 | 2.80E−05 | 1.36E−04 | 1.91E−04 |
| 16.95 | 1.94E−04 | 3.80E−05 | 1.50E−04 | 4.60E−05 | 1.02E−04 | 8.70E−05 | 1.07E−04 | 1.50E−05 | 1.30E−04 | 1.98E−04 |
| 16.97 | 1.85E−04 | 4.60E−05 | 1.38E−04 | 4.10E−05 | 1.06E−04 | 9.70E−05 | 1.03E−04 | 2.50E−05 | 1.32E−04 | 1.84E−04 |
| 16.98 | 1.85E−04 | 3.10E−05 | 1.29E−04 | 2.80E−05 | 1.23E−04 | 9.10E−05 | 1.06E−04 | 8.00E−06 | 1.25E−04 | 1.99E−04 |
| 17.00 | 2.01E−04 | 3.40E−05 | 1.46E−04 | 3.50E−05 | 1.00E−04 | 7.70E−05 | 9.70E−05 | 2.00E−05 | 1.29E−04 | 1.88E−04 |
| 17.02 | 1.90E−04 | 4.80E−05 | 1.40E−04 | 3.60E−05 | 1.12E−04 | 9.60E−05 | 1.07E−04 | 1.70E−05 | 1.30E−04 | 1.91E−04 |
| 17.03 | 2.08E−04 | 4.70E−05 | 1.55E−04 | 3.80E−05 | 1.10E−04 | 9.40E−05 | 1.11E−04 | 2.00E−06 | 1.35E−04 | 1.83E−04 |
| 17.05 | 1.83E−04 | 3.50E−05 | 1.33E−04 | 6.10E−05 | 8.50E−05 | 8.70E−05 | 1.10E−04 | 5.00E−06 | 1.29E−04 | 1.85E−04 |
| 17.07 | 1.76E−04 | 3.60E−05 | 1.33E−04 | 3.20E−05 | 1.03E−04 | 9.20E−05 | 9.70E−05 | 2.10E−05 | 1.25E−04 | 1.93E−04 |
| 17.08 | 1.86E−04 | 5.30E−05 | 1.39E−04 | 3.30E−05 | 1.20E−04 | 9.40E−05 | 1.04E−04 | 2.20E−05 | 1.25E−04 | 1.92E−04 |
| 17.10 | 1.85E−04 | 4.80E−05 | 1.48E−04 | 4.30E−05 | 1.02E−04 | 8.50E−05 | 8.30E−05 | 1.50E−05 | 1.49E−04 | 1.91E−04 |
| 17.12 | 1.84E−04 | 4.80E−05 | 1.43E−04 | 5.30E−05 | 1.15E−04 | 8.00E−05 | 8.90E−05 | 7.00E−06 | 1.32E−04 | 1.85E−04 |
| 17.13 | 1.80E−04 | 4.40E−05 | 1.44E−04 | 3.60E−05 | 1.01E−04 | 8.30E−05 | 7.40E−05 | 7.00E−06 | 1.21E−04 | 1.90E−04 |
| 17.15 | 1.95E−04 | 4.80E−05 | 1.38E−04 | 4.30E−05 | 1.02E−04 | 9.30E−05 | 9.90E−05 | −7.00E−06 | 1.45E−04 | 1.89E−04 |
| 17.17 | 1.83E−04 | 4.40E−05 | 1.40E−04 | 3.60E−05 | 1.03E−04 | 9.20E−05 | 9.00E−05 | 1.00E−06 | 1.20E−04 | 1.93E−04 |
| 17.18 | 1.95E−04 | 4.20E−05 | 1.23E−04 | 3.30E−05 | 9.20E−05 | 9.70E−05 | 1.19E−04 | −2.00E−06 | 1.26E−04 | 1.82E−04 |
| 17.20 | 1.91E−04 | 4.20E−05 | 1.40E−04 | 3.80E−05 | 1.19E−04 | 8.10E−05 | 1.01E−04 | −1.00E−05 | 1.25E−04 | 1.92E−04 |
| 17.22 | 1.91E−04 | 5.60E−05 | 1.44E−04 | 4.40E−05 | 1.10E−04 | 1.01E−04 | 1.05E−04 | 5.00E−06 | 1.25E−04 | 1.76E−04 |
| 17.23 | 1.93E−04 | 3.20E−05 | 1.26E−04 | 4.00E−05 | 1.16E−04 | 8.90E−05 | 9.60E−05 | 4.00E−06 | 1.13E−04 | 1.97E−04 |
| 17.25 | 1.91E−04 | 4.50E−05 | 1.44E−04 | 5.50E−05 | 1.12E−04 | 9.40E−05 | 1.07E−04 | 5.00E−06 | 1.28E−04 | 1.83E−04 |
| 17.27 | 1.80E−04 | 4.80E−05 | 1.40E−04 | 4.20E−05 | 1.09E−04 | 8.90E−05 | 9.00E−05 | −7.00E−06 | 1.45E−04 | 1.75E−04 |
| 17.28 | 1.84E−04 | 3.50E−05 | 1.41E−04 | 6.60E−05 | 1.23E−04 | 9.10E−05 | 1.05E−04 | 3.00E−06 | 1.28E−04 | 1.88E−04 |
| 17.30 | 2.03E−04 | 3.20E−05 | 1.48E−04 | 7.00E−05 | 1.12E−04 | 9.70E−05 | 7.70E−05 | 8.00E−06 | 1.24E−04 | 1.89E−04 |
| 17.32 | 2.00E−04 | 3.20E−05 | 1.44E−04 | 6.40E−05 | 1.32E−04 | 9.50E−05 | 1.00E−04 | 1.00E−06 | 1.42E−04 | 1.80E−04 |
| 17.33 | 2.00E−04 | 4.30E−05 | 1.43E−04 | 9.00E−05 | 1.36E−04 | 9.20E−05 | 9.30E−05 | 2.00E−06 | 1.21E−04 | 1.98E−04 |
| 17.35 | 1.94E−04 | 3.30E−05 | 1.52E−04 | 1.04E−04 | 1.22E−04 | 1.07E−04 | 9.60E−05 | 6.00E−06 | 1.25E−04 | 1.80E−04 |
| 17.37 | 1.91E−04 | 3.10E−05 | 1.42E−04 | 9.10E−05 | 1.46E−04 | 1.17E−04 | 9.30E−05 | 8.00E−06 | 1.24E−04 | 1.90E−04 |
| 17.38 | 1.86E−04 | 3.00E−05 | 1.33E−04 | 1.36E−04 | 1.46E−04 | 1.11E−04 | 1.07E−04 | 1.30E−05 | 1.23E−04 | 1.82E−04 |
| 17.40 | 1.88E−04 | 3.70E−05 | 1.38E−04 | 1.30E−04 | 1.66E−04 | 1.11E−04 | 9.10E−05 | 3.00E−06 | 1.31E−04 | 1.86E−04 |
| 17.42 | 2.01E−04 | 3.30E−05 | 1.39E−04 | 1.33E−04 | 1.60E−04 | 1.05E−04 | 9.40E−05 | 1.50E−05 | 1.28E−04 | 1.93E−04 |
| 17.43 | 1.73E−04 | 4.10E−05 | 1.36E−04 | 1.41E−04 | 1.43E−04 | 1.16E−04 | 9.70E−05 | 1.00E−05 | 1.23E−04 | 1.93E−04 |
| 17.45 | 1.88E−04 | 4.00E−05 | 1.26E−04 | 1.49E−04 | 1.45E−04 | 1.17E−04 | 9.90E−05 | 6.00E−06 | 1.15E−04 | 1.92E−04 |
| 17.47 | 1.81E−04 | 4.00E−05 | 1.35E−04 | 1.28E−04 | 1.19E−04 | 1.17E−04 | 9.10E−05 | 5.00E−06 | 1.03E−04 | 1.81E−04 |
| 17.48 | 1.74E−04 | 3.40E−05 | 1.39E−04 | 1.20E−04 | 1.28E−04 | 1.10E−04 | 9.30E−05 | 5.00E−06 | 1.15E−04 | 1.74E−04 |
| 17.50 | 1.78E−04 | 4.10E−05 | 1.32E−04 | 1.14E−04 | 1.14E−04 | 1.07E−04 | 1.00E−04 | 1.00E−06 | 1.14E−04 | 1.88E−04 |
| 17.52 | 1.85E−04 | 3.70E−05 | 1.36E−04 | 1.11E−04 | 1.19E−04 | 1.15E−04 | 9.70E−05 | 2.00E−06 | 1.23E−04 | 1.83E−04 |
| 17.53 | 1.83E−04 | 3.30E−05 | 1.40E−04 | 9.10E−05 | 1.15E−04 | 1.07E−04 | 9.60E−05 | 0.00E+00 | 1.13E−04 | 1.83E−04 |
| 17.55 | 1.88E−04 | 3.80E−05 | 1.29E−04 | 8.40E−05 | 1.17E−04 | 9.60E−05 | 8.40E−05 | 3.00E−06 | 1.17E−04 | 1.84E−04 |
| 17.57 | 1.80E−04 | 4.40E−05 | 1.39E−04 | 8.90E−05 | 9.20E−05 | 8.10E−05 | 8.20E−05 | 5.00E−06 | 1.19E−04 | 1.79E−04 |
| 17.58 | 1.82E−04 | 3.50E−05 | 1.33E−04 | 7.40E−05 | 1.02E−04 | 9.20E−05 | 9.20E−05 | −7.00E−06 | 1.24E−04 | 1.90E−04 |
| 17.60 | 1.78E−04 | 3.50E−05 | 1.17E−04 | 7.20E−05 | 9.50E−05 | 7.90E−05 | 9.70E−05 | 1.00E−05 | 1.22E−04 | 1.76E−04 |
| 17.62 | 1.79E−04 | 3.50E−05 | 1.21E−04 | 5.40E−05 | 8.60E−05 | 8.10E−05 | 9.00E−05 | 1.40E−05 | 1.09E−04 | 1.84E−04 |
| 17.63 | 1.72E−04 | 4.70E−05 | 1.11E−04 | 5.60E−05 | 9.40E−05 | 7.60E−05 | 6.20E−05 | 1.00E−05 | 1.04E−04 | 1.92E−04 |
| 17.65 | 1.80E−04 | 3.50E−05 | 1.23E−04 | 7.40E−05 | 9.00E−05 | 8.50E−05 | 9.00E−05 | −7.00E−06 | 1.29E−04 | 1.65E−04 |
| 17.67 | 1.88E−04 | 3.40E−05 | 1.21E−04 | 5.20E−05 | 9.90E−05 | 9.00E−05 | 8.90E−05 | 8.00E−06 | 1.16E−04 | 1.61E−04 |
| 17.68 | 1.75E−04 | 2.60E−05 | 1.32E−04 | 4.60E−05 | 9.10E−05 | 8.40E−05 | 7.50E−05 | 3.00E−06 | 1.01E−04 | 1.72E−04 |
| 17.70 | 1.76E−04 | 4.20E−05 | 1.19E−04 | 5.70E−05 | 8.10E−05 | 8.90E−05 | 8.60E−05 | 1.00E−06 | 1.04E−04 | 1.69E−04 |
| 17.72 | 1.55E−04 | 3.30E−05 | 1.31E−04 | 4.30E−05 | 8.30E−05 | 8.20E−05 | 8.70E−05 | 6.00E−06 | 1.15E−04 | 1.71E−04 |
| 17.73 | 1.76E−04 | 4.00E−05 | 1.24E−04 | 4.00E−05 | 9.20E−05 | 8.50E−05 | 8.60E−05 | 1.20E−05 | 1.11E−04 | 1.75E−04 |
| 17.75 | 1.59E−04 | 4.60E−05 | 1.20E−04 | 4.00E−05 | 9.90E−05 | 8.00E−05 | 7.90E−05 | −8.00E−06 | 1.05E−04 | 1.64E−04 |
| 17.77 | 1.69E−04 | 3.80E−05 | 1.17E−04 | 3.00E−05 | 9.20E−05 | 7.70E−05 | 9.10E−05 | 3.00E−06 | 1.09E−04 | 1.73E−04 |
| 17.78 | 1.71E−04 | 4.00E−05 | 1.15E−04 | 4.20E−05 | 8.50E−05 | 7.90E−05 | 7.40E−05 | −4.00E−06 | 1.14E−04 | 1.71E−04 |
| 17.80 | 1.82E−04 | 4.70E−05 | 1.24E−04 | 4.20E−05 | 1.04E−04 | 9.20E−05 | 6.70E−05 | 1.50E−05 | 1.05E−04 | 1.73E−04 |
| 17.82 | 1.75E−04 | 3.30E−05 | 1.09E−04 | 4.20E−05 | 9.70E−05 | 8.10E−05 | 6.90E−05 | −3.00E−06 | 1.16E−04 | 1.73E−04 |
| 17.83 | 1.53E−04 | 3.60E−05 | 1.21E−04 | 4.40E−05 | 7.20E−05 | 8.50E−05 | 7.70E−05 | −1.00E−06 | 1.07E−04 | 1.78E−04 |
| 17.85 | 1.66E−04 | 3.80E−05 | 1.22E−04 | 3.60E−05 | 7.90E−05 | 9.20E−05 | 8.90E−05 | 5.00E−06 | 1.06E−04 | 1.73E−04 |
| 17.87 | 1.63E−04 | 3.40E−05 | 1.12E−04 | 5.30E−05 | 7.50E−05 | 7.90E−05 | 9.30E−05 | −1.70E−05 | 1.16E−04 | 1.80E−04 |

TABLE 1-continued

UV 225 nm Absorbance [AU] values for different batches

Batch identifier

| Time [min] | unmodified htCBS C15S | 6-70 | 6-89 | 8-14 | 8-15 | 8-16 | 8-22 | 8-23 | 8-24 | 8-25 |
|---|---|---|---|---|---|---|---|---|---|---|
| 17.88 | 1.56E−04 | 4.00E−05 | 1.11E−04 | 8.00E−05 | 7.30E−05 | 8.30E−05 | 7.20E−05 | 0.00E+00 | 1.16E−04 | 1.73E−04 |
| 17.90 | 1.60E−04 | 3.80E−05 | 1.10E−04 | 4.20E−05 | 7.10E−05 | 8.10E−05 | 7.40E−05 | −6.00E−06 | 1.13E−04 | 1.86E−04 |
| 17.92 | 1.53E−04 | 2.30E−05 | 9.30E−05 | 4.30E−05 | 8.00E−05 | 9.10E−05 | 7.40E−05 | 0.00E+00 | 1.10E−04 | 1.66E−04 |
| 17.93 | 1.50E−04 | 3.40E−05 | 1.03E−04 | 3.60E−05 | 8.10E−05 | 8.00E−05 | 7.30E−05 | −5.00E−06 | 1.07E−04 | 1.84E−04 |
| 17.95 | 1.51E−04 | 3.50E−05 | 1.07E−04 | 3.20E−05 | 6.60E−05 | 7.40E−05 | 7.40E−05 | −4.00E−06 | 1.02E−04 | 1.71E−04 |
| 17.97 | 1.68E−04 | 5.50E−05 | 9.30E−05 | 5.30E−05 | 8.70E−05 | 9.90E−05 | 8.50E−05 | −1.60E−05 | 1.17E−04 | 1.83E−04 |
| 17.98 | 1.60E−04 | 2.50E−05 | 1.24E−04 | 3.80E−05 | 7.40E−05 | 7.70E−05 | 7.00E−05 | −7.00E−06 | 1.23E−04 | 1.59E−04 |
| 18.00 | 1.55E−04 | 3.60E−05 | 1.14E−04 | 4.30E−05 | 9.30E−05 | 8.20E−05 | 8.20E−05 | −8.00E−06 | 1.05E−04 | 1.66E−04 |
| 18.02 | 1.51E−04 | 4.20E−05 | 1.09E−04 | 2.60E−05 | 7.20E−05 | 8.00E−05 | 6.60E−05 | −3.00E−06 | 1.10E−04 | 1.76E−04 |
| 18.03 | 1.60E−04 | 1.80E−05 | 1.07E−04 | 2.70E−05 | 8.30E−05 | 7.90E−05 | 6.70E−05 | 1.10E−05 | 1.10E−04 | 1.74E−04 |
| 18.05 | 1.48E−04 | 4.40E−05 | 1.14E−04 | 3.60E−05 | 6.20E−05 | 6.90E−05 | 8.00E−05 | −1.60E−05 | 9.70E−05 | 1.69E−04 |
| 18.07 | 1.55E−04 | 4.20E−05 | 1.09E−04 | 3.20E−05 | 7.20E−05 | 8.20E−05 | 6.70E−05 | −4.00E−06 | 1.06E−04 | 1.66E−04 |
| 18.08 | 1.36E−04 | 3.80E−05 | 1.10E−04 | 3.20E−05 | 7.50E−05 | 8.10E−05 | 7.10E−05 | 1.10E−05 | 1.15E−04 | 1.81E−04 |
| 18.10 | 1.42E−04 | 1.70E−05 | 1.06E−04 | 4.00E−05 | 7.20E−05 | 6.30E−05 | 7.40E−05 | −8.00E−06 | 1.17E−04 | 1.78E−04 |
| 18.12 | 1.54E−04 | 3.60E−05 | 8.20E−05 | 4.30E−05 | 8.10E−05 | 9.50E−05 | 7.70E−05 | −1.30E−05 | 8.50E−05 | 1.85E−04 |
| 18.13 | 1.43E−04 | 3.40E−05 | 1.09E−04 | 4.80E−05 | 6.90E−05 | 6.70E−05 | 7.40E−05 | −1.30E−05 | 1.03E−04 | 1.73E−04 |
| 18.15 | 1.55E−04 | 2.60E−05 | 1.03E−04 | 3.80E−05 | 6.40E−05 | 6.70E−05 | 7.40E−05 | −5.00E−06 | 1.16E−04 | 1.56E−04 |
| 18.17 | 1.45E−04 | 4.00E−05 | 1.07E−04 | 4.20E−05 | 6.40E−05 | 7.40E−05 | 7.20E−05 | −3.00E−06 | 1.11E−04 | 1.78E−04 |
| 18.18 | 1.53E−04 | 3.80E−05 | 1.00E−04 | 4.80E−05 | 7.60E−05 | 6.90E−05 | 6.40E−05 | 8.00E−06 | 8.50E−05 | 1.65E−04 |
| 18.20 | 1.62E−04 | 3.10E−05 | 1.10E−04 | 3.70E−05 | 7.00E−05 | 9.00E−05 | 6.30E−05 | 6.00E−06 | 1.07E−04 | 1.71E−04 |
| 18.22 | 1.54E−04 | 2.80E−05 | 9.40E−05 | 4.80E−05 | 8.20E−05 | 7.00E−05 | 6.90E−05 | −3.00E−06 | 1.06E−04 | 1.71E−04 |
| 18.23 | 1.36E−04 | 2.50E−05 | 9.70E−05 | 4.00E−05 | 7.90E−05 | 6.60E−05 | 5.80E−05 | −4.00E−06 | 1.00E−04 | 1.70E−04 |
| 18.25 | 1.42E−04 | 3.00E−05 | 1.09E−04 | 3.30E−05 | 7.90E−05 | 9.40E−05 | 7.40E−05 | −5.00E−06 | 1.07E−04 | 1.83E−04 |
| 18.27 | 1.53E−04 | 3.30E−05 | 1.03E−04 | 2.30E−05 | 6.60E−05 | 7.00E−05 | 5.30E−05 | 1.50E−05 | 1.09E−04 | 1.82E−04 |
| 18.28 | 1.45E−04 | 1.60E−05 | 9.40E−05 | 4.40E−05 | 7.50E−05 | 6.40E−05 | 5.70E−05 | −2.00E−06 | 1.13E−04 | 1.89E−04 |
| 18.30 | 1.52E−04 | 4.10E−05 | 8.30E−05 | 5.50E−05 | 7.40E−05 | 7.50E−05 | 7.20E−05 | −1.00E−05 | 1.12E−04 | 1.73E−04 |
| 18.32 | 1.51E−04 | 2.50E−05 | 9.00E−05 | 4.60E−05 | 6.90E−05 | 9.00E−05 | 5.00E−05 | −6.00E−06 | 1.23E−04 | 1.69E−04 |
| 18.33 | 1.44E−04 | 4.80E−05 | 9.90E−05 | 2.80E−05 | 6.10E−05 | 7.10E−05 | 5.60E−05 | 1.00E−05 | 1.02E−04 | 1.78E−04 |
| 18.35 | 1.42E−04 | 2.80E−05 | 1.03E−04 | 3.70E−05 | 7.20E−05 | 7.20E−05 | 6.60E−05 | −6.00E−06 | 1.11E−04 | 1.64E−04 |
| 18.37 | 1.40E−04 | 2.60E−05 | 9.60E−05 | 3.20E−05 | 7.20E−05 | 7.00E−05 | 6.20E−05 | −1.00E−05 | 1.02E−04 | 1.97E−04 |
| 18.38 | 1.51E−04 | 3.40E−05 | 9.40E−05 | 3.50E−05 | 8.10E−05 | 7.20E−05 | 7.70E−05 | −1.60E−05 | 1.03E−04 | 1.80E−04 |
| 18.40 | 1.43E−04 | 3.20E−05 | 9.50E−05 | 3.50E−05 | 6.50E−05 | 7.00E−05 | 5.70E−05 | −1.60E−05 | 1.16E−04 | 1.84E−04 |
| 18.42 | 1.48E−04 | 2.80E−05 | 9.10E−05 | 3.50E−05 | 6.40E−05 | 8.40E−05 | 6.30E−05 | −3.00E−06 | 9.70E−05 | 1.74E−04 |
| 18.43 | 1.32E−04 | 3.40E−05 | 1.00E−04 | 3.40E−05 | 6.50E−05 | 8.40E−05 | 5.00E−05 | −5.00E−06 | 1.10E−04 | 1.91E−04 |
| 18.45 | 1.53E−04 | 3.50E−05 | 1.03E−04 | 4.30E−05 | 6.40E−05 | 7.20E−05 | 6.20E−05 | −1.50E−05 | 1.07E−04 | 1.76E−04 |
| 18.47 | 1.41E−04 | 3.10E−05 | 9.50E−05 | 4.20E−05 | 7.00E−05 | 8.10E−05 | 7.90E−05 | −2.20E−05 | 1.04E−04 | 1.76E−04 |
| 18.48 | 1.26E−04 | 4.70E−05 | 9.00E−05 | 4.40E−05 | 6.10E−05 | 8.40E−05 | 7.70E−05 | −7.00E−06 | 1.03E−04 | 1.79E−04 |
| 18.50 | 1.36E−04 | 4.20E−05 | 9.90E−05 | 1.01E−04 | 7.60E−05 | 7.50E−05 | 5.30E−05 | 7.00E−06 | 1.05E−04 | 1.83E−04 |
| 18.52 | 1.38E−04 | 3.40E−05 | 1.01E−04 | 4.50E−05 | 6.90E−05 | 7.00E−05 | 5.70E−05 | −5.00E−06 | 9.90E−05 | 1.89E−04 |
| 18.53 | 1.26E−04 | 3.30E−05 | 9.90E−05 | 6.20E−05 | 7.00E−05 | 7.40E−05 | 6.40E−05 | −2.10E−05 | 1.09E−04 | 1.61E−04 |
| 18.55 | 1.24E−04 | 4.60E−05 | 8.90E−05 | 4.10E−05 | 7.10E−05 | 5.60E−05 | 5.10E−05 | −1.40E−05 | 1.04E−04 | 1.80E−04 |
| 18.57 | 1.36E−04 | 4.50E−05 | 9.40E−05 | 4.70E−05 | 6.50E−05 | 7.10E−05 | 5.80E−05 | −3.00E−06 | 1.28E−04 | 1.84E−04 |
| 18.58 | 1.33E−04 | 4.00E−05 | 1.06E−04 | 5.40E−05 | 6.10E−05 | 7.50E−05 | 4.70E−05 | −6.00E−06 | 1.11E−04 | 1.90E−04 |
| 18.60 | 1.29E−04 | 4.10E−05 | 1.01E−04 | 4.60E−05 | 7.50E−05 | 9.00E−05 | 7.60E−05 | −6.00E−06 | 1.02E−04 | 1.80E−04 |
| 18.62 | 1.40E−04 | 4.20E−05 | 1.06E−04 | 3.70E−05 | 6.30E−05 | 7.10E−05 | 5.60E−05 | −4.00E−06 | 1.03E−04 | 1.74E−04 |
| 18.63 | 1.34E−04 | 3.10E−05 | 9.60E−05 | 3.70E−05 | 5.80E−05 | 7.60E−05 | 5.00E−05 | −2.00E−06 | 1.11E−04 | 1.90E−04 |
| 18.65 | 1.26E−04 | 3.50E−05 | 8.90E−05 | 3.30E−05 | 5.70E−05 | 7.00E−05 | 4.30E−05 | −1.00E−05 | 1.03E−04 | 1.90E−04 |
| 18.67 | 1.40E−04 | 3.80E−05 | 9.00E−05 | 3.40E−05 | 5.00E−05 | 6.20E−05 | 5.10E−05 | −4.00E−06 | 1.05E−04 | 1.83E−04 |
| 18.68 | 2.31E−04 | 4.30E−05 | 8.40E−05 | 4.80E−05 | 7.00E−05 | 7.40E−05 | 4.70E−05 | −5.00E−06 | 9.60E−05 | 1.75E−04 |
| 18.70 | 1.24E−04 | 4.00E−05 | 9.40E−05 | 3.50E−05 | 7.10E−05 | 7.60E−05 | 6.30E−05 | −1.30E−05 | 9.90E−05 | 1.83E−04 |
| 18.72 | 1.41E−04 | 4.60E−05 | 1.12E−04 | 4.10E−05 | 7.40E−05 | 6.50E−05 | 5.80E−05 | −5.00E−06 | 1.10E−04 | 2.03E−04 |
| 18.73 | 1.56E−04 | 3.70E−05 | 9.40E−05 | 5.20E−05 | 5.60E−05 | 7.60E−05 | 6.40E−05 | −3.00E−06 | 1.07E−04 | 1.66E−04 |
| 18.75 | 1.21E−04 | 2.60E−05 | 1.32E−04 | 3.80E−05 | 5.70E−05 | 5.50E−05 | 6.40E−05 | −8.00E−06 | 1.00E−04 | 1.80E−04 |
| 18.77 | 1.13E−04 | 4.40E−05 | 8.90E−05 | 5.50E−05 | 7.10E−05 | 8.70E−05 | 5.10E−05 | −1.00E−05 | 1.12E−04 | 1.83E−04 |
| 18.78 | 1.33E−04 | 5.60E−05 | 1.03E−04 | 4.70E−05 | 6.00E−05 | 7.20E−05 | 4.30E−05 | −1.50E−05 | 9.60E−05 | 1.66E−04 |
| 18.80 | 1.38E−04 | 6.30E−05 | 8.30E−05 | 4.60E−05 | 7.50E−05 | 6.90E−05 | 5.20E−05 | −1.50E−05 | 1.01E−04 | 1.86E−04 |
| 18.82 | 1.19E−04 | 6.50E−05 | 7.40E−05 | 6.10E−05 | 7.20E−05 | 5.30E−05 | 5.20E−05 | −1.00E−05 | 1.05E−04 | 1.84E−04 |
| 18.83 | 1.34E−04 | 5.40E−05 | 8.70E−05 | 3.50E−05 | 6.20E−05 | 6.50E−05 | 5.80E−05 | −2.10E−05 | 9.90E−05 | 1.81E−04 |
| 18.85 | 1.24E−04 | 5.00E−05 | 1.14E−04 | 4.10E−05 | 5.40E−05 | 5.30E−05 | 6.40E−05 | −3.00E−06 | 9.60E−05 | 1.83E−04 |
| 18.87 | 1.21E−04 | 5.50E−05 | 9.50E−05 | 2.80E−05 | 6.60E−05 | 5.30E−05 | 5.30E−05 | −1.70E−05 | 9.70E−05 | 1.70E−04 |
| 18.88 | 1.38E−04 | 5.40E−05 | 9.60E−05 | 4.40E−05 | 5.00E−05 | 7.70E−05 | 6.00E−05 | −6.00E−06 | 1.07E−04 | 1.76E−04 |
| 18.90 | 1.33E−04 | 4.50E−05 | 8.60E−05 | 4.50E−05 | 5.80E−05 | 8.00E−05 | 5.30E−05 | 7.00E−06 | 9.20E−05 | 1.85E−04 |
| 18.92 | 1.43E−04 | 6.10E−05 | 8.20E−05 | 3.10E−05 | 5.10E−05 | 6.90E−05 | 4.30E−05 | −8.00E−06 | 1.07E−04 | 1.83E−04 |
| 18.93 | 1.22E−04 | 5.60E−05 | 8.50E−05 | 4.10E−05 | 5.10E−05 | 5.60E−05 | 5.40E−05 | −1.10E−05 | 9.50E−05 | 1.78E−04 |
| 18.95 | 1.16E−04 | 7.40E−05 | 9.70E−05 | 5.80E−05 | 7.00E−05 | 7.30E−05 | 7.90E−05 | −1.70E−05 | 9.70E−05 | 1.76E−04 |
| 18.97 | 1.35E−04 | 4.70E−05 | 7.70E−05 | 4.00E−05 | 5.80E−05 | 8.10E−05 | 5.80E−05 | −1.30E−05 | 1.09E−04 | 1.92E−04 |
| 18.98 | 1.28E−04 | 6.30E−05 | 8.50E−05 | 5.10E−05 | 6.20E−05 | 7.90E−05 | 6.70E−05 | −1.20E−05 | 1.07E−04 | 1.73E−04 |
| 19.00 | 1.14E−04 | 6.50E−05 | 8.60E−05 | 3.20E−05 | 8.00E−05 | 6.90E−05 | 4.80E−05 | −2.10E−05 | 1.17E−04 | 1.72E−04 |
| 19.02 | 1.21E−04 | 6.60E−05 | 8.70E−05 | 4.50E−05 | 5.60E−05 | 6.40E−05 | 5.20E−05 | −2.70E−05 | 1.05E−04 | 1.79E−04 |
| 19.03 | 1.05E−04 | 7.10E−05 | 7.90E−05 | 6.30E−05 | 4.70E−05 | 8.10E−05 | 6.10E−05 | −1.00E−05 | 1.06E−04 | 1.85E−04 |
| 19.05 | 1.14E−04 | 5.80E−05 | 8.00E−05 | 6.10E−05 | 5.10E−05 | 7.00E−05 | 6.70E−05 | −1.30E−05 | 1.14E−04 | 1.72E−04 |
| 19.07 | 1.33E−04 | 7.30E−05 | 7.40E−05 | 4.10E−05 | 6.10E−05 | 6.10E−05 | 5.80E−05 | −1.60E−05 | 1.01E−04 | 1.86E−04 |
| 19.08 | 1.28E−04 | 5.80E−05 | 9.30E−05 | 3.80E−05 | 6.40E−05 | 7.00E−05 | 5.60E−05 | −2.70E−05 | 1.02E−04 | 1.81E−04 |

TABLE 1-continued

UV 225 nm Absorbance [AU] values for different batches

| | | | | | Batch identifier | | | | | |
|---|---|---|---|---|---|---|---|---|---|---|
| Time [min] | unmodified htCBS C15S | 6-70 | 6-89 | 8-14 | 8-15 | 8-16 | 8-22 | 8-23 | 8-24 | 8-25 |
| 19.10 | 1.26E-04 | 7.00E-05 | 8.10E-05 | 4.40E-05 | 6.00E-05 | 6.70E-05 | 5.40E-05 | -7.00E-06 | 1.03E-04 | 1.70E-04 |
| 19.12 | 1.24E-04 | 5.70E-05 | 9.70E-05 | 3.10E-05 | 6.20E-05 | 7.70E-05 | 6.00E-05 | -3.20E-05 | 1.03E-04 | 1.82E-04 |
| 19.13 | 1.15E-04 | 6.60E-05 | 7.00E-05 | 5.10E-05 | 8.40E-05 | 6.10E-05 | 5.70E-05 | -2.20E-05 | 1.17E-04 | 1.98E-04 |
| 19.15 | 1.16E-04 | 6.60E-05 | 8.10E-05 | 4.10E-05 | 5.20E-05 | 5.70E-05 | 5.00E-05 | -2.60E-05 | 1.15E-04 | 1.83E-04 |
| 19.17 | 1.21E-04 | 7.20E-05 | 8.30E-05 | 4.40E-05 | 5.80E-05 | 6.30E-05 | 4.30E-05 | -1.50E-05 | 1.05E-04 | 1.79E-04 |
| 19.18 | 1.15E-04 | 6.70E-05 | 8.60E-05 | 5.10E-05 | 4.20E-05 | 7.90E-05 | 6.10E-05 | -6.00E-06 | 1.07E-04 | 1.66E-04 |
| 19.20 | 1.34E-04 | 6.70E-05 | 8.60E-05 | 4.80E-05 | 6.40E-05 | 5.60E-05 | 5.70E-05 | -1.50E-05 | 9.90E-05 | 1.73E-04 |
| 19.22 | 1.14E-04 | 6.70E-05 | 8.50E-05 | 4.20E-05 | 6.50E-05 | 6.30E-05 | 5.20E-05 | -2.60E-05 | 1.05E-04 | 1.89E-04 |
| 19.23 | 1.29E-04 | 7.50E-05 | 8.50E-05 | 4.20E-05 | 5.20E-05 | 7.20E-05 | 5.30E-05 | -1.60E-05 | 9.30E-05 | 1.78E-04 |
| 19.25 | 1.14E-04 | 7.90E-05 | 8.00E-05 | 3.80E-05 | 4.60E-05 | 7.50E-05 | 6.70E-05 | -2.80E-05 | 9.30E-05 | 1.76E-04 |
| 19.27 | 1.15E-04 | 6.90E-05 | 8.20E-05 | 4.70E-05 | 5.60E-05 | 5.70E-05 | 5.70E-05 | -2.10E-05 | 1.00E-04 | 1.89E-04 |
| 19.28 | 1.13E-04 | 7.60E-05 | 8.10E-05 | 4.60E-05 | 5.00E-05 | 8.10E-05 | 5.60E-05 | -2.30E-05 | 1.02E-04 | 1.61E-04 |
| 19.30 | 1.26E-04 | 8.40E-05 | 8.30E-05 | 3.20E-05 | 5.50E-05 | 5.70E-05 | 5.40E-05 | -1.70E-05 | 1.10E-04 | 1.74E-04 |
| 19.32 | 1.09E-04 | 5.50E-05 | 8.60E-05 | 3.00E-05 | 5.60E-05 | 7.20E-05 | 6.40E-05 | -2.20E-05 | 1.10E-04 | 1.71E-04 |
| 19.33 | 1.15E-04 | 4.80E-05 | 7.60E-05 | 3.50E-05 | 6.10E-05 | 5.30E-05 | 4.80E-05 | -3.20E-05 | 1.15E-04 | 1.58E-04 |
| 19.35 | 1.16E-04 | 6.60E-05 | 8.90E-05 | 4.10E-05 | 5.30E-05 | 6.50E-05 | 5.10E-05 | -2.10E-05 | 1.03E-04 | 1.79E-04 |
| 19.37 | 1.23E-04 | 5.50E-05 | 8.70E-05 | 5.00E-05 | 4.40E-05 | 5.60E-05 | 6.40E-05 | 1.40E-05 | 9.90E-05 | 1.73E-04 |
| 19.38 | 1.44E-04 | 7.50E-05 | 8.00E-05 | 5.40E-05 | 4.80E-05 | 6.00E-05 | 4.30E-05 | -1.20E-05 | 9.30E-05 | 1.71E-04 |
| 19.40 | 1.23E-04 | 5.60E-05 | 9.60E-05 | 3.10E-05 | 5.50E-05 | 6.30E-05 | 6.10E-05 | -1.10E-05 | 1.05E-04 | 1.75E-04 |
| 19.42 | 1.24E-04 | 8.10E-05 | 6.50E-05 | 3.60E-05 | 4.00E-05 | 6.30E-05 | 4.50E-05 | -1.50E-05 | 1.02E-04 | 1.71E-04 |
| 19.43 | 1.09E-04 | 6.30E-05 | 7.20E-05 | 4.30E-05 | 4.80E-05 | 7.20E-05 | 5.20E-05 | -1.40E-05 | 9.30E-05 | 1.84E-04 |
| 19.45 | 1.19E-04 | 7.90E-05 | 8.00E-05 | 5.40E-05 | 5.80E-05 | 5.80E-05 | 5.50E-05 | -1.30E-05 | 1.05E-04 | 1.79E-04 |
| 19.47 | 1.09E-04 | 7.10E-05 | 7.40E-05 | 3.80E-05 | 7.10E-05 | 7.20E-05 | 5.60E-05 | -7.00E-06 | 1.01E-04 | 1.84E-04 |
| 19.48 | 1.23E-04 | 5.80E-05 | 7.00E-05 | 3.20E-05 | 5.10E-05 | 5.50E-05 | 5.70E-05 | -1.50E-05 | 1.00E-04 | 1.60E-04 |
| 19.50 | 1.15E-04 | 7.30E-05 | 7.40E-05 | 5.70E-05 | 6.60E-05 | 6.30E-05 | 4.50E-05 | -2.20E-05 | 1.01E-04 | 1.68E-04 |
| 19.52 | 1.21E-04 | 6.10E-05 | 8.00E-05 | 3.50E-05 | 6.30E-05 | 6.20E-05 | 6.50E-05 | -2.70E-05 | 9.70E-05 | 1.84E-04 |
| 19.53 | 1.25E-04 | 7.30E-05 | 7.40E-05 | 4.50E-05 | 7.60E-05 | 7.60E-05 | 7.60E-05 | -1.50E-05 | 9.90E-05 | 1.78E-04 |
| 19.55 | 1.07E-04 | 7.90E-05 | 9.10E-05 | 4.10E-05 | 7.10E-05 | 5.50E-05 | 4.40E-05 | -1.40E-05 | 9.30E-05 | 1.71E-04 |
| 19.57 | 1.19E-04 | 7.50E-05 | 8.70E-05 | 5.50E-05 | 5.80E-05 | 7.00E-05 | 6.40E-05 | -1.70E-05 | 9.50E-05 | 1.62E-04 |
| 19.58 | 1.06E-04 | 7.60E-05 | 7.50E-05 | 3.70E-05 | 6.40E-05 | 6.70E-05 | 6.70E-05 | -1.70E-05 | 1.04E-04 | 1.71E-04 |
| 19.60 | 1.23E-04 | 6.90E-05 | 7.90E-05 | 4.30E-05 | 6.60E-05 | 7.70E-05 | 6.50E-05 | -1.20E-05 | 9.50E-05 | 1.69E-04 |
| 19.62 | 1.12E-04 | 8.10E-05 | 8.30E-05 | 3.20E-05 | 6.60E-05 | 6.70E-05 | 6.40E-05 | -1.70E-05 | 1.04E-04 | 1.82E-04 |
| 19.63 | 9.30E-05 | 9.70E-05 | 7.90E-05 | 3.80E-05 | 5.60E-05 | 8.30E-05 | 5.80E-05 | -1.80E-05 | 1.00E-04 | 2.29E-04 |
| 19.65 | 1.09E-04 | 7.10E-05 | 6.10E-05 | 3.40E-05 | 5.40E-05 | 6.60E-05 | 6.30E-05 | -1.30E-05 | 9.30E-05 | 1.73E-04 |
| 19.67 | 1.15E-04 | 7.30E-05 | 8.10E-05 | 4.50E-05 | 7.20E-05 | 7.90E-05 | 5.30E-05 | -1.00E-05 | 1.01E-04 | 1.78E-04 |
| 19.68 | 1.14E-04 | 7.60E-05 | 7.20E-05 | 3.80E-05 | 5.40E-05 | 8.50E-05 | 6.20E-05 | -1.80E-05 | 9.10E-05 | 1.78E-04 |
| 19.70 | 9.90E-05 | 7.90E-05 | 9.10E-05 | 4.40E-05 | 6.70E-05 | 6.30E-05 | 6.50E-05 | -7.00E-06 | 9.20E-05 | 1.75E-04 |
| 19.72 | 1.14E-04 | 7.60E-05 | 6.40E-05 | 4.20E-05 | 6.50E-05 | 7.20E-05 | 5.70E-05 | -1.80E-05 | 9.40E-05 | 1.65E-04 |
| 19.73 | 1.00E-04 | 7.20E-05 | 8.50E-05 | 5.20E-05 | 8.00E-05 | 6.70E-05 | 5.30E-05 | -1.30E-05 | 9.00E-05 | 1.75E-04 |
| 19.75 | 1.02E-04 | 7.90E-05 | 7.70E-05 | 2.70E-05 | 7.00E-05 | 8.00E-05 | 6.20E-05 | -2.50E-05 | 1.05E-04 | 1.76E-04 |
| 19.77 | 9.70E-05 | 8.60E-05 | 5.60E-05 | 4.10E-05 | 7.10E-05 | 9.10E-05 | 5.20E-05 | -1.30E-05 | 1.06E-04 | 1.71E-04 |
| 19.78 | 1.15E-04 | 8.50E-05 | 7.50E-05 | 3.20E-05 | 8.10E-05 | 7.20E-05 | 5.30E-05 | -8.00E-06 | 9.90E-05 | 1.63E-04 |
| 19.80 | 1.13E-04 | 7.60E-05 | 8.20E-05 | 3.20E-05 | 9.20E-05 | 9.00E-05 | 5.60E-05 | -1.70E-05 | 8.70E-05 | 1.69E-04 |
| 19.82 | 1.16E-04 | 7.20E-05 | 7.00E-05 | 3.50E-05 | 7.70E-05 | 8.20E-05 | 5.00E-05 | -2.30E-05 | 1.01E-04 | 1.73E-04 |
| 19.83 | 1.23E-04 | 6.50E-05 | 6.10E-05 | 3.00E-05 | 7.60E-05 | 8.30E-05 | 4.70E-05 | -1.60E-05 | 9.30E-05 | 1.59E-04 |
| 19.85 | 1.26E-04 | 7.70E-05 | 7.10E-05 | 3.00E-05 | 8.00E-05 | 7.70E-05 | 4.70E-05 | -1.80E-05 | 1.02E-04 | 1.73E-04 |
| 19.87 | 1.23E-04 | 6.60E-05 | 8.00E-05 | 4.60E-05 | 7.50E-05 | 7.70E-05 | 5.80E-05 | -8.00E-06 | 1.00E-04 | 1.74E-04 |
| 19.88 | 1.24E-04 | 7.40E-05 | 7.10E-05 | 1.20E-05 | 7.60E-05 | 7.60E-05 | 6.00E-05 | -1.30E-05 | 9.10E-05 | 1.74E-04 |
| 19.90 | 1.15E-04 | 6.10E-05 | 6.60E-05 | 3.20E-05 | 7.70E-05 | 7.40E-05 | 5.40E-05 | -2.30E-05 | 8.70E-05 | 2.01E-04 |
| 19.92 | 1.34E-04 | 6.30E-05 | 6.90E-05 | 3.80E-05 | 8.40E-05 | 7.40E-05 | 5.80E-05 | -2.30E-05 | 1.03E-04 | 1.62E-04 |
| 19.93 | 1.26E-04 | 8.70E-05 | 8.30E-05 | 3.00E-05 | 8.20E-05 | 8.60E-05 | 5.10E-05 | -1.50E-05 | 1.04E-04 | 1.55E-04 |
| 19.95 | 1.01E-04 | 6.50E-05 | 6.20E-05 | 2.10E-05 | 7.30E-05 | 9.20E-05 | 5.70E-05 | -1.10E-05 | 1.04E-04 | 1.78E-04 |
| 19.97 | 1.10E-04 | 8.10E-05 | 8.10E-05 | 3.20E-05 | 7.10E-05 | 8.50E-05 | 5.00E-05 | -1.10E-05 | 9.00E-05 | 1.61E-04 |
| 19.98 | 1.25E-04 | 8.10E-05 | 6.20E-05 | 2.70E-05 | 7.70E-05 | 6.90E-05 | 4.40E-05 | -1.80E-05 | 1.02E-04 | 1.56E-04 |
| 20.00 | 1.06E-04 | 6.20E-05 | 7.10E-05 | 2.80E-05 | 9.10E-05 | 6.70E-05 | 5.60E-05 | -1.50E-05 | 1.05E-04 | 1.71E-04 |

The advantage of SEC-HPLC analysis was that the insufficiently PEGylated batches, e.g. containing less than 5 PEGylated sites per htCBS C15S protein and/or containing any unmodified htCBS C15S, were characterized by longer retention time than the desired ones and were swiftly identified for rescue by adding more PEG molecules to the reaction mixture (in-process monitoring of PEGylation). The unmodified htCBS C15S sample was observed to have a retention time of 11.97 minutes. The sample from the 6-70 and 8-23 batches were observed to have a retention time of 9.67 minutes. The sample from the 6-89 batch was observed to have a retention time of 9.88 minutes. The sample from the 8-22 batch was observed to have a retention time of 9.95 minutes. Therefore, a retention time of greater than 9.67 minutes was determined to indicate insufficient PEGylation.

The sample from the 8-14 batch was observed to have a retention time of 9.57 minutes. The sample from the 8-15 batch was observed to have a retention time of 9.53 minutes. The sample from the 8-16 batch was observed to have a retention time of 9.55 minutes. The sample from the 8-24 batch was observed to have a retention time of 9.55 minutes. The sample from the 8-25 batch was observed to have a retention time of 9.58 minutes. Therefore, a retention time of less than 9.53 minutes was determined to indicate acceptable PEGylation.

Another method was based on non-reduced capillary electrophoresis allowing resolution and quantification of multiple 20NHS PEG-htCBS C15S species (FIG. 1). Insufficient PEGylation of the batch was characterized by the presence of unmodified enzyme and an increased occurrence of low molecular weight 20NHS PEG-htCBS C15S species. Therefore, this method was found suitable to define strict acceptance criteria for the 20NHS PEG-htCBS C15S final product.

The protein sequence of htCBS C15S contains 30 lysine residues, which all represent potential sites for NHS ester PEGylation. To identify the lysine residues involved in PEGylation, LC-UV-MS was performed three 20NHS PEG-htCBS C15S batches. After de-PEGylation, the formerly PEGylated lysines were left with a linker that enabled their differentiation from unmodified lysines and quantification via peptide mapping after cleavage with Asp-N endopeptidase and comparison to similarly processed unmodified htCBS C15S. LC-MS analysis was performed after Asp-N digest of unmodified htCBS C15S as a reference protein (control).

Table 2 shows the relative abundance of peptides and was used to calculate the number of PEGs per peptide for the reference enzyme, an alkylated, unmodified htCBS C15S, identified by LC/MS/MS. (RT=retention time).

TABLE 2

| | NHS ester PEGylation mapping of a reference enzyme | | | | | | |
|---|---|---|---|---|---|---|---|
| Sequence Location | Sequence | SEQ ID NO | Theoretical mass (Da) | Observed Mass (Da) | Δ mass (ppm) | RT (min) | Abundance |
| 2-34 | PSETPQAEVGPTGSPHRSGPHSAKGSLEKGSPE | 2 | 3294.59 | 3294.59 | 0.64 | 33.8 | 462828 |
| 9-34 | EVGPTGSPHRSGPHSAKGSLEKGSPE | 3 | 2584.26 | 2584.26 | 0.07 | 30.8 | 449108 |
| 35-46 | DKEAKEPLWIRP | 4 | 1480.80 | 1480.80 | -0.08 | 50.6 | 323088 |
| 40-46 | EPLWIRP | 5 | 909.51 | 909.51 | 0.71 | 54.5 | 1369777 |
| 47-78 | DAPSRCTWQLGRPASESPHHHTAPAKSPKILP | 6 | 3528.78 | 3528.78 | 0.13 | 49 | 1805933 |
| 79-85 | DILKKIG | 7 | 785.50 | 785.50 | 0.06 | 41.9 | 1034520 |
| 86-106 | DTPMVRINKIGKKFGLKCELL | 8 | 2459.38 | 2459.38 | 0.07 | 59.8 | 752660 |
| 107-119 | AKCEFFNAGGSVK | 9 | 1413.67 | 1413.67 | 0.28 | 41.5 | 865418 |
| 120-128 | DRISLRMIE | 10 | 1131.61 | 1131.61 | 0.74 | 51.3 | 1259968 |
| 120-128 | DRISLRMIE | 10 | 1147.60 | 1147.60 | 0.34 | 43.8 | 42144 |
| 133-139 | DGTLKPG | 11 | 686.36 | 686.36 | 0.72 | 24 | 665344 |
| 140-178 | DTIIEPTSGNTGIGLALAAAVRGYRCIIVMPEKMSSEKV | 12 | 4147.15 | 4147.15 | -0.29 | 92.2 | 422022 |
| 179-197 | DVLRALGAEIVRTPTNARF | 13 | 2098.16 | 2098.17 | 0.21 | 64.2 | 3651887 |
| 179-197 | DVLRALGAEIVRTPTNARF | 13 | 2099.15 | 2099.15 | 1.17 | 63.7 | 1401992 |
| 198-220 | DSPESHVGVAWRLKNEIPNSHIL | 14 | 2597.34 | 2597.33 | -0.2 | 58.1 | 1160943 |
| 198-220 | DSPESHVGVAWRLKNEIPNSHIL | 14 | 2598.32 | 2598.32 | 0.17 | 58.8 | 543933 |
| 221-233 | DQYRNASNPLAHY | 15 | 1547.71 | 1547.71 | 0.22 | 40.9 | 209797 |
| 221-233 | DQYRNASNPLAHY | 15 | 1548.70 | 1548.70 | 1.59 | 40.3 | 156242 |
| 221-233 | DQYRNASNPLAHY | 15 | 1548.70 | 1548.70 | 0.79 | 41.2 | 708853 |
| 238-244 | DEILQQC | 16 | 904.40 | 904.40 | 0.12 | 33.1 | 258834 |
| 245-248 | DGKL | 17 | 431.24 | 431.24 | 0.01 | 19.7 | 98742 |
| 249-269 | DMLVASVGTGGTITGIARKLK | 18 | 2087.18 | 2087.18 | 0.04 | 59.3 | 458054 |
| 249-269 | DMLVASVGTGGTITGIARKLK | 18 | 2103.17 | 2103.17 | 0.42 | 55.3 | 112910 |
| 270-301 | EKCPGCRIIGVDPEGSILAEPEELNQTEQTTY | 19 | 3632.70 | 3632.70 | -0.18 | 57.7 | 99941 |
| 302-308 | EVEGIGY | 20 | 765.35 | 765.36 | 0.99 | 38.3 | 356953 |
| 309-315 | DFIPTVL | 21 | 803.44 | 803.44 | -0.02 | 66.5 | 1980222 |
| 316-320 | DRTVV | 22 | 588.32 | 588.32 | 0.75 | 27.3 | 891244 |

TABLE 2-continued

NHS ester PEGylation mapping of a reference enzyme

| Sequence Location | Sequence | SEQ ID NO | Theoretical mass (Da) | Observed Mass (Da) | Δ mass (ppm) | RT (min) | Abundance |
|---|---|---|---|---|---|---|---|
| 321-327 | DKWFKSN | 23 | 923.45 | 923.45 | 0.03 | 35.3 | 209620 |
| 328-365 | DEEAFTFARMLIAQEGLLCGGSAGSTVAVAVKAAQELQ | 24 | 3937.96 | 3937.95 | -0.26 | 95.1 | 200461 |
| 333-348 | TFARMLIAQEGL | 25 | 1735.88 | 1735.87 | -1.79 | 47.2 | 212890 |
| 363-375 | ELQEGQRCVVILP | 26 | 1539.81 | 1539.81 | 0.31 | 55.7 | 81479 |
| 366-375 | EGQRCVVILP | 27 | 1169.62 | 1169.62 | -0.36 | 53.8 | 375007 |
| 376-387 | DSVRNYMTKFLS | 28 | 1459.71 | 1459.71 | -0.15 | 55.3 | 1194612 |
| 388-400 | DRWMLQKGFLKEE | 29 | 1678.85 | 1678.85 | 0.44 | 52.2 | 836829 |
| 388-400 | DRWMLQKGFLKEE | 29 | 1694.85 | 1694.85 | 0.39 | 49.4 | 129978 |
| 401-413 | DLTEKKPWWWHLR | 30 | 1793.94 | 1793.94 | 0.19 | 56.7 | 2238451 |

Theoretical molecular masses (mono-isotopic) were calculated using MassHunter BioConfirm software (Agilent, Santa Clara, Calif.). The observed masses (mono-isotopic) were within 5 ppm of their theoretical value. Abundances were determined using MassHunter software (Agilent, Santa Clara, Calif.). Peptide 120-128 was observed to have the modification of a 1*oxidation. Peptide 179-197 was observed to have the modification of a 1*deamidation. Peptide 198-220 was observed to have the modification of a 1*deamidation. Peptide 221-233 was observed to have the modification of a 1*deamidation. Peptide 221-233 was observed to have the modification of a 1*deamidation, 249-269 was observed to have the modification of a 1*oxidation. Peptide 388-400 was observed to have the modification of a 1*oxidation.

LC-MS analysis was performed after Asp-N digest of reduced, alkylated, PEGylated 20NHS PEG-htCBS C15S (batch #1). Table 3 shows the relative abundance of peptides and was used to calculate the number of PEGs per peptide for an Asp-N digest of reduced, alkylated, PEGylated 20NHS PEG-htCBS C15S (batch #1), identified by LC/MS/MS.

TABLE 3

NHS ester PEGylation mapping of Asp-N digest of reduced, alkylated, PEGylated 20NHS PEG-htCBS C15S (batch #1)

| Sequence Location | Sequence | SEQ ID NO | Theoretical mass (Da) | Observed Mass (Da) | Δ mass (ppm) | RT (min) | Abundance |
|---|---|---|---|---|---|---|---|
| 2-34 | PSETPQAEVGPTGSPHRSGPHSAKGSLEKGSPE | 2 | 3294.59 | 3294.59 | -0.46 | 33.8 | 74988 |
| 2-34 | PSETPQAEVGPTGSPHRSGPHSAKGSLEKGSPE | 2 | 3408.62 | 3408.62 | 1.2 | 36.7 | 285758 |
| 2-34 | PSETPQAEVGPTGSPHRSGPHSAKGSLEKGSPE | 2 | 3522.65 | 3522.65 | 0.51 | 39.3 | 251006 |
| 9-34 | EVGPTGSPHRSGPHSAKGSLEKGSPE | 3 | 2584.26 | 2584.26 | 0.43 | 30.8 | 50722 |
| 9-34 | EVGPTGSPHRSGPHSAKGSLEKGSPE | 3 | 2698.29 | 2698.3 | 1.34 | 34.6 | 156217 |
| 9-34 | EVGPTGSPHRSGPHSAKGSLEKGSPE | 3 | 2812.33 | 2812.33 | 0.43 | 37.6 | 59784 |
| 35-46 | DKEAKEPLWIRP | 4 | 1480.8 | 1480.8 | 0.14 | 50.5 | 419366 |
| 35-46 | DKEAKEPLWIRP | 4 | 1594.84 | 1594.83 | -0.42 | 53.3 | 115586 |
| 40-46 | EPLWIRP | 5 | 909.51 | 909.51 | 0.36 | 54.4 | 1267685 |
| 47-78 | DAPSRCTWQLGRPASESPHHHTAPAKSPKILP | 6 | 3528.78 | 3528.78 | 0.35 | 49 | 916229 |
| 47-78 | DAPSRCTWQLGRPASESPHHHTAPAKSPKILP | 6 | 3642.81 | 3642.81 | 0.3 | 51.2 | 536395 |
| 79-85 | DILKKIG | 7 | 785.5 | 785.5 | 0.2 | 41.9 | 1447731 |
| 79-85 | DILKKIG | 7 | 899.53 | 899.53 | 0.01 | 47.1 | 49654 |

TABLE 3-continued

NHS ester PEGylation mapping of Asp-N digest of reduced, alkylated, PEGylated 20NHS PEG-htCBS C15S (batch #1)

| Sequence Location | Sequence | SEQ ID NO | Theoretical mass (Da) | Observed Mass (Da) | Δ mass (ppm) | RT (min) | Abundance |
|---|---|---|---|---|---|---|---|
| 86-106 | DTPMVRINKIGKKFGLKCELL | 8 | 2459.38 | 2459.38 | 0 | 59.8 | 278431 |
| 86-106 | DTPMVRINKIGKKFGLKCELL | 8 | 2573.41 | 2573.41 | 0.2 | 63.4 | 207777 |
| 86-106 | DTPMVRINKIGKKFGLKCELL | 8 | 2573.41 | 2573.41 | 0.39 | 66 | 268441 |
| 107-119 | AKCEFFNAGGSVK | 9 | 1413.67 | 1413.67 | 0.21 | 41.5 | 1031048 |
| 120-128 | DRISLRMIE | 10 | 1131.61 | 1131.61 | 0.63 | 51.2 | 1738225 |
| 120-128 | DRISLRMIE | 10 | 1147.6 | 1147.6 | -0.19 | 43.8 | 74835 |
| 133-139 | DGTLKPG | 11 | 686.36 | 686.36 | 0.53 | 24 | 837583 |
| 140-178 | DTIIEPTSGNTGIGLALAAAVRGYRCIIVMPKMSSEKV | 12 | 4147.15 | 4147.15 | -0.03 | 92.2 | 575055 |
| 179-197 | DVLRALGAEIVRTPTNARF | 13 | 2098.16 | 2098.17 | 0.18 | 64.1 | 4896736 |
| 179-197 | DVLRALGAEIVRTPTNARF | 13 | 2099.15 | 2099.15 | 0.59 | 63.6 | 1870150 |
| 198-220 | DSPESHVGVAWRLKNEIPNSHIL | 14 | 2597.34 | 2597.34 | 0.11 | 58 | 1302818 |
| 198-220 | DSPESHVGVAWRLKNEIPNSHIL | 14 | 2598.32 | 2598.32 | 0.17 | 58.7 | 591137 |
| 198-220 | DSPESHVGVAWRLKNEIPNSHIL | 14 | 2711.37 | 2711.37 | 1 | 63.5 | 65301 |
| 221-233 | DQYRNASNPLAHY | 15 | 1547.71 | 1547.71 | -0.06 | 40.9 | 256919 |
| 221-233 | DQYRNASNPLAHY | 15 | 1548.7 | 1548.7 | 1.11 | 40.3 | 198652 |
| 221-233 | DQYRNASNPLAHY | 15 | 1548.7 | 1548.7 | 0.61 | 41.2 | 802841 |
| 238-244 | DEILQQC | 16 | 904.4 | 904.4 | -0.35 | 33.1 | 216368 |
| 245-248 | DGKL | 17 | 431.24 | 431.24 | 0.15 | 19.9 | 75839 |
| 245-248 | DGKL | 17 | 545.27 | 545.27 | -0.29 | 31.7 | 73171 |
| 249-269 | DMLVASVGTGGTITGIARKLK | 18 | 2087.18 | 2087.18 | -0.18 | 59.2 | 458170 |
| 249-269 | DMLVASVGTGGTITGIARKLK | 18 | 2103.17 | 2103.17 | 0.16 | 55.2 | 130431 |
| 270-301 | EKCPGCRIIGVDPEGSILAEPEELNQTEQTTY | 19 | 3632.7 | 3632.7 | 1.24 | 57.6 | 37257 |
| 270-301 | EKCPGCRIIGVDPEGSILAEPEELNQTEQTTY | 19 | 3746.73 | 3746.72 | -1.28 | 59.5 | 23764 |
| 302-308 | EVEGIGY | 20 | 765.35 | 765.35 | 0.03 | 38.3 | 274612 |
| 309-315 | DFIPTVL | 21 | 803.44 | 803.44 | 0.29 | 66.4 | 2313422 |
| 316-320 | DRTVV | 22 | 588.32 | 588.32 | 0.11 | 27.2 | 1216696 |
| 321-327 | DKWFKSN | 23 | 923.45 | 923.45 | 0.03 | 35.3 | 100188 |
| 321-327 | DKWFKSN | 23 | 1037.48 | 1037.48 | -0.64 | 41.9 | 44718 |
| 328-365 | DEEAFTFARMLIAQEGLLCGGSAGSTVAVAVKAAQELQ | 24 | 3937.96 | 3937.95 | -0.4 | 95.1 | 82719 |
| 333-348 | TFARMLIAQEGL | 25 | 1735.88 | 1735.87 | -1.84 | 47.2 | 158013 |
| 363-375 | ELQEGQRCVVILP | 26 | 1539.81 | 1539.81 | 0.05 | 55.6 | 109572 |
| 366-375 | EGQRCVVILP | 27 | 1169.62 | 1169.62 | 0.17 | 53.7 | 425023 |
| 376-387 | DSVRNYMTKFLS | 28 | 1459.71 | 1459.71 | 0.34 | 55.2 | 1488072 |
| 388-400 | DRWMLQKGFLKEE | 29 | 1678.85 | 1678.85 | -0.04 | 52.1 | 1018180 |
| 388-400 | DRWMLQKGFLKEE | 29 | 1694.85 | 1694.85 | -0.05 | 49.2 | 138406 |

TABLE 3-continued

NHS ester PEGylation mapping of Asp-N digest of reduced, alkylated, PEGylated 20NHS PEG-htCBS C15S (batch #1)

| Sequence Location | Sequence | SEQ ID NO | Theoretical mass (Da) | Observed Mass (Da) | Δ mass (ppm) | RT (min) | Abundance |
|---|---|---|---|---|---|---|---|
| 388-400 | DRWMLQKGFLKEE | 29 | 1792.88 | 1792.88 | -0.32 | 57.4 | 61595 |
| 401-413 | DLTEKKPWWWHLR | 30 | 1793.94 | 1793.94 | 0.13 | 56.7 | 971171 |
| 401-413 | DLTEKKPWWWHLR | 30 | 1907.97 | 1907.97 | 0.08 | 60.8 | 1558334 |
| 401-413 | DLTEKKPWWWHLR | 30 | 2022 | 2022 | 0.4 | 66.5 | 242737 |

Further, 5 peptides with 2 lysines and 1 peptide with 4 lysines were identified, of which one lysine residue was found inconsistently PEGylated: K36/39, K72/75, K82/83, K94/97/98/102, K322/325 and K394/398. The estimated number of PEG/peptide was calculated using the following formula: Estimated (PEG/peptide) ratio=(Abundance (1*Linker)+2*Abundance(2*Linker))/((Abundance(No Linker)+Abundance(1*Linker)+Abundance(2*Linker)). Since PEGs are known in the art to not migrate according to their molecular weight in gels or chromatographic applications due to a significant solvation envelope and thus increased hydrodynamic radius, the extent of PEGylation was estimated to be in the range of 5.0±0.5 PEGs per CBS monomer. Specifically, the number PEG molecules per peptide was estimated to be 1.29 for 2-34, 1.30 for 9-34, 0.22 for 35-46, 0.37 for 47-78, 0.03 for 79-85 and 198-220, 0.63 for 86-106, 0.49 for 245-248, 0.39 for 270-301, 0.31 for 321-327, and 0.05 for 388-400.

Peptide 2-34 was observed to have the modification of a 1*linker. Peptide 2-34 was observed to have the modification of a 2*linker. Peptide 9-34 was observed to have the modification of a 1*linker. Peptide 9-34 was observed to have the modification of a 2*linker. Peptide 35-46 was observed to have the modification of a 1*linker. Peptide 47-78 was observed to have the modification of a 1*linker. Peptide 79-85 was observed to have the modification of a 1*linker. Peptide 86-106 was observed to have the modification of a 1*linker. Peptide 86-106 was observed to have the modification of a 1*linker. Peptide 120-128 was observed to have the modification of a 1*oxidation. Peptide 179-197 was observed to have the modification of a 1*deamidation. Peptide 198-220 was observed to have the modification of a 1*deamidation. Peptide 198-220 was observed to have the modification of a 1*linker. Peptide 221-233 was observed to have the modification of a 1*deamidation. Peptide 221-233 was observed to have the modification of a 1*deamidation. Peptide 245-248 was observed to have the modification of a 1*linker. Peptide 249-269 was observed to have the modification of a 1*oxidation. Peptide 270-301 was observed to have the modification of a 1*linker. Peptide 321-327 was observed to have the modification of a 1*linker. Peptide 388-400 was observed to have the modification of a 1*oxidation. Peptide 388-400 was observed to have the modification of a 1*linker. Peptide 401-413 was observed to have the modification of a 1*linker. Peptide 401-413 was observed to have the modification of a 2*linker.

LC-MS analysis was performed after Asp-N digest of reduced, alkylated, PEGylated 20NHS PEG-htCBS C15S (batch #2). Table 4 shows the relative abundance of peptides and estimated number of PEGs per peptide for an Asp-N digest of a reduced, alkylated, PEGylated 20NHS PEG-htCBS C15S (batch #2), identified by LC/MS/MS.

TABLE 4

NHS ester PEGylation mapping of Asp-N digest of reduced, alkylated, PEGylated 20NHS PEG-htCBS C15S (batch #2)

| Sequence Location | Sequence | SEQ ID NO | Theoretical mass (Da) | Observed Mass (Da) | Δ mass (ppm) | RT (min) | Abundance |
|---|---|---|---|---|---|---|---|
| 2-34 | PSETPQAEVGPTGSPHRSGPHSAKGSLEKGSPE | 2 | 3294.5865 | 3294.5858 | -0.21 | 34.1 | 91654 |
| 2-34 | PSETPQAEVGPTGSPHRSGPHSAKGSLEKGSPE | 2 | 3408.6182 | 3408.6173 | -0.26 | 37.1 | 212552 |
| 2-34 | PSETPQAEVGPTGSPHRSGPHSAKGSLEKGSPE | 2 | 3522.6499 | 3522.6505 | 0.17 | 39.6 | 116731 |
| 9-34 | EVGPTGSPHRSGPHSAKGSLEKGSPE | 3 | 2584.263 | 2584.2621 | -0.35 | 31.2 | 110005 |
| 9-34 | EVGPTGSPHRSGPHSAKGSLEKGSPE | 3 | 2698.2947 | 2698.2944 | -0.1 | 35 | 207053 |
| 9-34 | EVGPTGSPHRSGPHSAKGSLEKGSPE | 3 | 2812.3264 | 2812.3283 | 0.68 | 37.6 | 50468 |
| 35-46 | DKEAKEPLWIRP | 4 | 1480.8038 | 1480.804 | 0.15 | 51.1 | 130726 |
| 35-46 | DKEAKEPLWIRP | 4 | 1594.8355 | 1594.836 | 0.31 | 53.8 | 26208 |
| 40-46 | EPLWIRP | 5 | 909.5072 | 909.5075 | 0.31 | 54.9 | 370392 |
| 47-78 | DAPSRCTWQLGRPASESPHHHTAPAK | 6 | 3528.7797 | 3528.7769 | -0.79 | 49.4 | 608763 |

TABLE 4-continued

NHS ester PEGylation mapping of Asp-N digest of reduced, alkylated, PEGylated 20NHS PEG-htCBS C15S (batch #2)

| Sequence Location | Sequence | SEQ ID NO | Theoretical mass (Da) | Observed Mass (Da) | Δ mass (ppm) | RT (min) | Abundance |
|---|---|---|---|---|---|---|---|
| | SPKILP | | | | | | |
| 47-78 | DAPSRCTWQLGRPASESPHHHTAPAKSPKILP | 6 | 3642.8114 | 3642.8084 | -0.82 | 51.6 | 211918 |
| 79-85 | DILKKIG | 7 | 785.5011 | 785.5017 | 0.78 | 42.3 | 454812 |
| 79-85 | DILKKIG | 7 | 899.5328 | 899.5338 | 1.11 | 47.5 | 11289 |
| 86-106 | DTPMVRINKIGKKFGLKCELL | 8 | 2459.3756 | 2459.3774 | 0.73 | 60.8 | 179277 |
| 86-106 | DTPMVRINKIGKKFGLKCELL | 8 | 2573.4073 | 2573.4077 | 0.16 | 64.6 | 92660 |
| 86-106 | DTPMVRINKIGKKFGLKCELL | 8 | 2573.4073 | 2573.4068 | -0.19 | 67.3 | 117060 |
| 107-119 | AKCEFFNAGGSVK | 9 | 1413.6711 | 1413.6716 | 0.35 | 42 | 495351 |
| 120-128 | DRISLRMIE | 10 | 1131.607 | 1131.6075 | 0.46 | 51.7 | 664834 |
| 120-128 | DRISLRMIE | 10 | 1147.6019 | 1147.6023 | 0.35 | 44.3 | 33046 |
| 133-139 | DGTLKPG | 11 | 686.3599 | 686.3603 | 0.61 | 24.3 | 285635 |
| 140-178 | DTIIEPTSGNTGIGLALAAAVRGYRCIIVMPEKMSSEKV | 12 | 4147.148 | 4147.1451 | -0.7 | 93.5 | 181549 |
| 179-197 | DVLRALGAEIVRTPTNARF | 13 | 2098.1647 | 2098.1657 | 0.49 | 65.3 | 2248724 |
| 179-197 | DVLRALGAEIVRTPTNARF | 13 | 2099.1487 | 2099.1508 | 0.99 | 64.8 | 936714 |
| 198-220 | DSPESHVGVAWRLKNEIPNSHIL | 14 | 2597.335 | 2597.3345 | -0.23 | 58.7 | 635630 |
| 198-220 | DSPESHVGVAWRLKNEIPNSHIL | 14 | 2598.3191 | 2598.3202 | 0.45 | 59.5 | 352959 |
| 198-220 | DSPESHVGVAWRLKNEIPNSHIL | 14 | 2711.3667 | 2711.3649 | -0.66 | 64.5 | 23552 |
| 221-233 | DQYRNASNPLAHY | 15 | 1547.7117 | 1547.7118 | 0.06 | 41.4 | 128480 |
| 221-233 | DQYRNASNPLAHY | 15 | 1548.6957 | 1548.6971 | 0.9 | 40.8 | 111326 |
| 221-233 | DQYRNASNPLAHY | 15 | 1548.6957 | 1548.6955 | -0.17 | 41.7 | 405793 |
| 238-244 | DEILQQC | 16 | 904.396 | 904.3962 | 0.23 | 33.5 | 126894 |
| 245-248 | DGKL | 17 | 431.238 | 431.2381 | 0.12 | 20.5 | 40770 |
| 245-248 | DGKL | 17 | 545.2697 | 545.2699 | 0.37 | 32.2 | 26289 |
| 249-269 | DMLVASVGTGGTITGIARKLK | 18 | 2087.1773 | 2087.178 | 0.34 | 59.8 | 301153 |
| 249-269 | DMLVASVGTGGTITGIARKLK | 18 | 2103.1722 | 2103.174 | 0.86 | 55.3 | 81381 |
| 270-301 | EKCPGCRIIGVDPEGSILAEPEELNQTEQTTY | 19 | 3632.6975 | 3632.6996 | 0.58 | 58.1 | 51146 |
| 270-301 | EKCPGCRIIGVDPEGSILAEPEELNQTEQTTY | 19 | 3746.7292 | 3746.7269 | -0.61 | 60 | 18541 |
| 302-308 | EVEGIGY | 20 | 765.3545 | 765.3549 | 0.49 | 38.7 | 244178 |
| 309-315 | DFIPTVL | 21 | 803.4429 | 803.4436 | 0.86 | 66.9 | 1102772 |
| 316-320 | DRTVV | 22 | 588.3231 | 588.3235 | 0.59 | 27.7 | 482942 |
| 321-327 | DKWFKSN | 23 | 923.4501 | 923.4504 | 0.33 | 35.9 | 41312 |
| 321-327 | DKWFKSN | 23 | 1037.4818 | 1037.4826 | 0.77 | 42.5 | 10692 |
| 328-365 | DEEAFTFARMLIAQEGLLCGGSAGSTVAVAVKAAQELQ | 24 | 3937.9554 | 3937.9519 | -0.89 | 95.6 | 35286 |
| 333-348 | TFARMLIAQEGL | 25 | 1735.875 | 1735.8712 | -2.19 | 47.7 | 113391 |
| 363-375 | ELQEGQRCVVILP | 26 | 1539.8079 | 1539.8083 | 0.26 | 55.9 | 44354 |

TABLE 4-continued

NHS ester PEGylation mapping of Asp-N digest of reduced, alkylated, PEGylated 20NHS PEG-htCBS C15S (batch #2)

| Sequence Location | Sequence | SEQ ID NO | Theoretical mass (Da) | Observed Mass (Da) | Δ mass (ppm) | RT (min) | Abundance |
|---|---|---|---|---|---|---|---|
| 366-375 | EGQRCVVILP | 27 | 1169.6227 | 1169.6238 | 0.95 | 54.1 | 143135 |
| 376-387 | DSVRNYMTKFLS | 28 | 1459.713 | 1459.7144 | 0.96 | 56.1 | 679328 |
| 388-400 | DRWMLQKGFLKEE | 29 | 1678.8501 | 1678.8505 | 0.22 | 52.8 | 428907 |
| 388-400 | DRWMLQKGFLKEE | 29 | 1694.845 | 1694.8454 | 0.24 | 69.9 | 80607 |
| 388-400 | DRWMLQKGFLKEE | 29 | 1792.8818 | 1792.881 | -0.45 | 58.2 | 20614 |
| 401-413 | DLTEKKPWWWHLR | 30 | 1793.9366 | 1793.9372 | 0.38 | 57.6 | 638701 |
| 401-413 | DLTEKKPWWWHLR | 30 | 1907.9683 | 1907.9691 | 0.45 | 62.1 | 633624 |
| 401-413 | DLTEKKPWWWHLR | 30 | 2022 | 2022.001 | 0.49 | 67.8 | 84315 |

The number PEG molecules per peptide was estimated to be 1.06 for 2-24, 0.84 for 9-34, 0.17 for 35-46, 0.26 for 47-78, 0.02 for 79-85 and 198-220, 0.54 for 86-106, 0.39 for 245-248, 0.27 for 270-301, 0.21 for 321-327, 0.04 for 388-400, and 0.59 for 401-413. Peptide 2-34 was observed to have the modification of a 1*linker. Peptide 2-34 was observed to have the modification of a 2*linker. Peptide 9-34 was observed to have the modification of a 1*linker. Peptide 9-34 was observed to have the modification of a 2*linker. Peptide 35-46 was observed to have the modification of a 1*linker. Peptide 47-78 was observed to have the modification of a 1*linker. Peptide 79-85 was observed to have the modification of a 1*linker. Peptide 86-106 was observed to have the modification of a 1*linker. Peptide 86-106 was observed to have the modification of a 1*linker. Peptide 120-128 was observed to have the modification of a 1*oxidation. Peptide 179-197 was observed to have the modification of a 1*deamidation. Peptide 198-220 was observed to have the modification of a 1*deamidation. Peptide 198-220 was observed to have the modification of a 1*linker. Peptide 221-233 was observed to have the modification of a 1*deamidation. Peptide 221-233 was observed to have the modification of a 1*deamidation. Peptide 245-248 was observed to have the modification of a 1*linker. Peptide 249-269 was observed to have the modification of a 1*oxidation. Peptide 270-301 was observed to have the modification of a 1*linker. Peptide 321-327 was observed to have the modification of a 1*linker. Peptide 388-400 was observed to have the modification of a 1*oxidation. Peptide 388-400 was observed to have the modification of a 1*linker. Peptide 401-413 was observed to have the modification of a 1*linker. Peptide 401-413 was observed to have the modification of a 2*linker.

LC-MS analysis was performed after Asp-N digest of reduced, alkylated, PEGylated 20NHS PEG-htCBS C15S (batch #3). Table 5 shows the relative abundance of peptides and estimated number of PEGs per peptide identified by LC/MS/MS for batch #3.

TABLE 5

NHS ester PEGylation mapping of Asp-N digest of reduced, alkylated, PEGylated 20NHS PEG-htCBS C15S (batch #3)

| Sequence Location | Sequence | SEQ ID NO | Theoretical mass (Da) | Observed Mass (Da) | Δ mass (ppm) | RT (min) | Abundance |
|---|---|---|---|---|---|---|---|
| 2-34 | PSETPQAEVGPTGSPHRSGPHSAKGSLEKGSPE | 2 | 3294.5865 | 3294.5829 | -1.09 | 34.3 | 60072 |
| 2-34 | PSETPQAEVGPTGSPHRSGPHSAKGSLEKGSPE | 2 | 3408.6182 | 3408.6154 | -0.82 | 37.2 | 199290 |
| 2-34 | PSETPQAEVGPTGSPHRSGPHSAKGSLEKGSPE | 2 | 3522.6499 | 3522.6508 | 0.26 | 39.7 | 159538 |
| 9-34 | EVGPTGSPHRSGPHSAKGSLEKGSPE | 3 | 2584.263 | 2584.2638 | 0.31 | 31.3 | 105797 |
| 9-34 | EVGPTGSPHRSGPHSAKGSLEKGSPE | 3 | 2698.2947 | 2698.294 | -0.25 | 35.2 | 261221 |
| 9-34 | EVGPTGSPHRSGPHSAKGSLEKGSPE | 3 | 2812.3264 | 2812.3259 | -0.18 | 37.6 | 96655 |
| 35-46 | DKEAKEPLWIRP | 4 | 1480.8038 | 1480.8039 | 0.09 | 51.3 | 86032 |
| 35-46 | DKEAKEPLWIRP | 4 | 1594.8355 | 1594.8362 | 0.44 | 54 | 18790 |
| 40-46 | EPLWIRP | 5 | 909.5072 | 909.5078 | 0.62 | 55 | 395424 |
| 47-78 | DAPSRCTWQLGRPASESPHHHTAPAK | 6 | 3528.7797 | 3528.78 | 0.08 | 49.6 | 595498 |

TABLE 5-continued

NHS ester PEGylation mapping of Asp-N digest of reduced, alkylated, PEGylated 20NHS PEG-htCBS C15S (batch #3)

| Sequence Location | Sequence | SEQ ID NO | Theoretical mass (Da) | Observed Mass (Da) | Δ mass (ppm) | RT (min) | Abundance |
|---|---|---|---|---|---|---|---|
| | SPKILP | | | | | | |
| 47-78 | DAPSRCTWQLGRPASESPHHHTAPAKSPKILP | 6 | 3642.8114 | 3642.8084 | -0.81 | 51.7 | 272886 |
| 79-85 | DILKKIG | 7 | 785.5011 | 785.5017 | 0.81 | 42.5 | 446682 |
| 79-85 | DILKKIG | 7 | 899.5328 | 899.5347 | 2.11 | 47.7 | 12609 |
| 86-106 | DTPMVRINKIGKKFGLKCELL | 8 | 2459.3756 | 2459.3745 | -0.45 | 60.7 | 145186 |
| 86-106 | DTPMVRINKIGKKFGLKCELL | 8 | 2573.4073 | 2573.4088 | 0.58 | 64.5 | 101537 |
| 86-106 | DTPMVRINKIGKKFGLKCELL | 8 | 2573.4073 | 2573.4057 | -0.62 | 67.3 | 126416 |
| 107-119 | AKCEFFNAGGSVK | 9 | 1413.6711 | 1413.6721 | 0.71 | 42.2 | 506761 |
| 120-128 | DRISLRMIE | 10 | 1131.607 | 1131.6075 | 0.42 | 51.9 | 725914 |
| 120-128 | DRISLRMIE | 10 | 1147.6019 | 1147.602 | 0.04 | 44.3 | 29014 |
| 133-139 | DGTLKPG | 11 | 686.3599 | 686.3601 | 0.23 | 24.5 | 273520 |
| 140-178 | DTIIEPTSGNTGIGLALAAAVRGYRCIIVMPEKMSSEKV | 12 | 4147.148 | 4147.1398 | -1.97 | 93.4 | 188751 |
| 179-197 | DVLRALGAEIVRTPTNARF | 13 | 2098.1647 | 2098.1663 | 0.73 | 65.2 | 2212569 |
| 179-197 | DVLRALGAEIVRTPTNARF | 13 | 2099.1487 | 2099.1511 | 1.12 | 64.7 | 930809 |
| 198-220 | DSPESHVGVAWRLKNEIPNSHIL | 14 | 2597.335 | 2597.3339 | -0.44 | 58.7 | 645205 |
| 198-220 | DSPESHVGVAWRLKNEIPNSHIL | 14 | 2598.3191 | 2598.3196 | 0.2 | 59.5 | 348068 |
| 198-220 | DSPESHVGVAWRLKNEIPNSHIL | 14 | 2711.3667 | 2711.3668 | 0.04 | 64.4 | 31254 |
| 221-233 | DQYRNASNPLAHY | 15 | 1547.7117 | 1547.7124 | 0.48 | 41.7 | 119215 |
| 221-233 | DQYRNASNPLAHY | 15 | 1548.6957 | 1548.6981 | 1.56 | 41.1 | 113439 |
| 221-233 | DQYRNASNPLAHY | 15 | 1548.6957 | 1548.6959 | 0.14 | 42 | 404271 |
| 238-244 | DEILQQC | 16 | 904.396 | 904.3962 | 0.16 | 33.7 | 137033 |
| 245-248 | DGKL | 17 | 431.238 | 431.2384 | 0.93 | 20.8 | 41279 |
| 245-248 | DGKL | 17 | 545.2697 | 545.2699 | 0.44 | 32.4 | 38708 |
| 249-269 | DMLVASVGTGGTITGIARKLK | 18 | 2087.1773 | 2087.1766 | -0.32 | 59.8 | 378816 |
| 249-269 | DMLVASVGTGGTITGIARKLK | 18 | 2103.1722 | 2103.1743 | 1 | 55.3 | 81123 |
| 270-301 | EKCPGCRIIGVDPEGSILAEPEELNQTEQTTY | 19 | 3632.6975 | 3632.6934 | -1.13 | 58.1 | 69301 |
| 270-301 | EKCPGCRIIGVDPEGSILAEPEELNQTEQTTY | 19 | 3746.7292 | 3746.7248 | -1.17 | 60 | 28571 |
| 302-308 | EVEGIGY | 20 | 765.3545 | 765.3551 | 0.76 | 39 | 267474 |
| 309-315 | DFIPTVL | 21 | 803.4429 | 803.4434 | 0.66 | 66.9 | 1030604 |
| 316-320 | DRTVV | 22 | 588.3231 | 588.3236 | 0.72 | 27.9 | 474399 |
| 321-327 | DKWFKSN | 23 | 923.4501 | 923.4498 | -0.3 | 36.3 | 46084 |
| 321-327 | DKWFKSN | 23 | 1037.4818 | 1037.4838 | 1.93 | 42.8 | 12212 |
| 328-365 | DEEAFTFARMLIAQEGLLCGGSAGSTVAVAVKAAQELQ | 24 | 3937.9554 | 3937.9541 | -0.33 | 95.6 | 45366 |
| 333-348 | TFARMLIAQEGL | 25 | 1735.875 | 1735.87 | -2.88 | 48 | 99444 |
| 363-375 | ELQEGQRCVVILP | 26 | 1539.8079 | 1539.8083 | 0.26 | 56 | 45283 |

TABLE 5-continued

NHS ester PEGylation mapping of Asp-N digest of reduced, alkylated, PEGylated 20NHS PEG-htCBS C15S (batch #3)

| Sequence Location | Sequence | SEQ ID NO | Theoretical mass (Da) | Observed Mass (Da) | Δ mass (ppm) | RT (min) | Abundance |
|---|---|---|---|---|---|---|---|
| 366-375 | EGQRCVVILP | 27 | 1169.6227 | 1169.6233 | 0.52 | 54.1 | 162480 |
| 376-387 | DSVRNYMTKFLS | 28 | 1459.713 | 1459.7127 | -0.16 | 56.2 | 715580 |
| 388-400 | DRWMLQKGFLKEE | 29 | 1678.8501 | 1678.8503 | 0.08 | 53 | 430875 |
| 388-400 | DRWMLQKGFLKEE | 29 | 1694.845 | 1694.8452 | 0.12 | 50.2 | 71467 |
| 388-400 | DRWMLQKGFLKEE | 29 | 1792.8818 | 1792.8825 | 0.39 | 58.2 | 24688 |
| 401-413 | DLTEKKPWWWHLR | 30 | 1793.9366 | 1793.9372 | 0.38 | 57.7 | 524828 |
| 401-413 | DLTEKKPWWWHLR | 30 | 1907.9683 | 1907.969 | 0.38 | 62 | 701248 |
| 401-413 | DLTEKKPWWWHLR | 30 | 2022 | 2022.0014 | 0.69 | 67.6 | 130215 |

The number PEG molecules per peptide was estimated to be 1.24 for 2-34, 0.98 for 9-34, 0.18 for 35-46, 0.31 for 47-78, 0.03 for 79-85 and 198-220, 0.61 for 86-106, 0.48 for 245-248, 0.29 for 270-301, 0.21 for 321-327, 0.05 for 388-400, and 0.71 for 401-413.

Peptide 2-34 was observed to have the modification of a 1*Linker. Peptide 2-34 was observed to have the modification of a 2*Linker. Peptide 9-34 was observed to have the modification of a 1*Linker. Peptide 9-34 was observed to have the modification of a 2*Linker. Peptide 35-46 was observed to have the modification of a 1*Linker. Peptide 47-78 was observed to have the modification of a 1*Linker. Peptide 79-85 was observed to have the modification of a 1*Linker. Peptide 86-106 was observed to have the modification of a 1*linker. Peptide 86-106 was observed to have the modification of a 1*linker. Peptide 120-128 was observed to have the modification of a 1*oxidation. Peptide 179-197 was observed to have the modification of a 1*deamidation. Peptide 198-220 was observed to have the modification of a 1*deamidation. Peptide 198-220 was observed to have the modification of a 1*linker. Peptide 221-233 was observed to have the modification of a 1*deamidation. Peptide 221-233 was observed to have the modification of a 1*deamidation. Peptide 245-248 was observed to have the modification of a 1*linker. Peptide 249-269 was observed to have the modification of a 1*oxidation. Peptide 270-301 was observed to have the modification of a 1*linker. Peptide 321-327 was observed to have the modification of a 1*linker. Peptide 388-400 was observed to have the modification of a 1*oxidation. Peptide 388-400 was observed to have the modification of a 1*linker. Peptide 401-413 was observed to have the modification of a 1*linker. Peptide 401-413 was observed to have the modification of a 2*linker.

Seven lysines (K25, K30, K211, K247, K271, K405 and K406) were unambiguously identified as being PEGylated to a certain extent, out of which K25 and K30 residues seemed the only ones to be always modified to the full extent among the 3 batches.

Compared to all the previous PEG-htCBS C15S conjugates, the 20NHS PEG-htCBS C15S showed increased viscosity (data not shown) and thus there was a concern of sufficient free, unreacted PEG removal during the final (post PEGylation) buffer exchange. Indeed, processing of the initial batches (for example LAB and 10L) yielded a large amount of unreacted PEG carried over to the final product. Corrective measures, which included removal of 20% DMSO from the mixture, higher MWCO membrane cartridge for TFF unit (100 versus 30 kDa), 3-fold larger surface area and 2-fold dilution of the PEGylation mixture prior buffer exchange, all helped to reduce the viscosity and assisted in better clearance of free PEG during the final formulation (TR1 and TR2).

Example 5. Attenuation of 200MA PEG-htCBS C15S Efficacy in HO Mice

Repeated administration in HO mice was defined as subcutaneous injections of 7.5 mg/kg 200MA PEG-htCBS C15S for 5 consecutive days during the first dose-week. Dosing was interrupted for a period of 10 days and restarted again for an additional 5 consecutive injections in the second dose-week. Plasma samples were collected before the very first dose for baseline values, 24 hours after the 2nd, 4th, and 5th injections in both dose-weeks to track the enzyme's efficacy and during washout periods to follow recovery of the baseline values (a week after the last dose in both dose-weeks, prior to the first dose of the dose-week 2 and two weeks after the very last dose). The study showed in an apparent attenuation of 200MA PEG-htCBS C15S efficacy in the dose-week 2 compared to dose-week 1 (see, Table 7).

A bulkier maleimide PEG molecule did not resolve the attenuation of PEG-htCBS C15S efficacy in washout experiments. Since the use of maleimide PEG, which specifically targets available sulfhydryl residues, was known to yield a well-defined species, the initial approach to reduce the loss of 200MA PEG-htCBS C15S efficacy in washout experiments was to increase the coverage of the htCBS C15S protein with a bulkier maleimide PEG. The previously published data showed that PEGylation of htCBS with larger maleimide PEG molecule did not affect catalytic activity in vitro and that 40 kDa linear (ME-400MA) or branched (GL4-400MA) maleimide PEG molecules had similar pharmacokinetics and pharmacodynamics after a single injection in HO mice compared to 200MA PEG-htCBS C15S. See, Bublil et al., *J Clin Invest* 2016, 126, (6), 2372-84 and International application PCT/2016/061050, which are hereby incorporated by reference in their entireties. Table 6 shows that the PEGylation of htCBS C15S does not substantially affect the enzyme's catalytic activity regardless of the PEG moiety size and the target group.

TABLE 6

CBS specific activities of unmodified htCBS C15S and PEG-htCBS C15S conjugates

| PEG moiety | Size & structure | Active moiety (target group) | CBS specific activity (U/mg of protein ± SD) |
|---|---|---|---|
| None | N/A | N/A | 1233 ± 201 |
| ME-020MA | 2 kDa linear | maleimide (—SH) | 1184 ± 95 |
| ME-200MA0B | 20 kDa linear | maleimide (—SH) | 1339 ± 226 |
| ME-400MA | 40 kDa linear | maleimide (—SH) | 1242 ± 158 |
| GL4-400MA | 40 kDa 4-arm branched | maleimide (—SH) | 1288 ± 221 |
| GL2-800MA | 80 kDa 2-arm branched | maleimide (—SH) | 1168 ± 134 |
| ME-050GS | 5 kDa linear | NHS ester (—NH$_2$) | 1250 ± 52 |
| ME-100GS | 10 kDa linear | NHS ester (—NH$_2$) | 1233 ± 173 |
| ME-200GS | 20 kDa linear | NHS ester (—NH$_2$) | 1339 ± 242 |

The dosing regimen was specifically designed to elicit immune response to rank conjugates based on their immunogenic properties. The repeated uninterrupted dosing of 200MA PEG-htCBS C15S to homocystinuric HO mice has previously been shown to result in a retained efficacy and a significant decrease of plasma Hcy levels 24 hours after injection for a period of 2 months, although both the baseline level (72 hours post injection) of plasma Hcy and the peak effect of 200MA PEG-htCBS C15S (24 hours post injection) were decreasing over time. The most reasonable explanation for such attenuation of activity is the host's immune response, which may adversely impact both the efficacy and the safety and is relatively common among approved therapeutic enzymes. See, Baldo et al., *BioDrugs: clinical immunotherapeutics, biopharmaceuticals and gene therapy* 2015, 29, (1), 31-55, which is hereby incorporated by reference in its entirety.

The immunogenicity may stem from the trace amounts of unmodified enzyme or insufficiently masked htCBS C15S with site selective maleimide PEG molecule conjugation. Therefore, a complete absence of unmodified enzyme and more generous masking of potential immunogenic epitopes of PEG-htCBS C15S conjugate from the immune system by increased PEGylation would be expected to prevent the decrease in efficacy.

Example 6. Retaining Efficacy of 20NHS PEG-htCBS in HO Mice

NHS ester PEG-htCBS C15S conjugates modified with ME-050GS (5NHS PEG-htCBS C15S) and ME-200GS (20NHS PEG-htCBS C15S) were analyzed in washout experiments, and results were compared to results from similar analysis of maleimide PEGylated conjugates. Table 7 provides the percent changes in metabolites resulting from administration of different PEG-htCBS C15S conjugates over 3 weeks. (W1=1 week, W2=2 weeks, and W3=3 weeks)

TABLE 7

Maximal changes in the plasma sulfur amino acid levels after treatment in HO mice with PEGylated htCBS C15S conjugates

| | Hcy decrease at trough (%) | | | Cth increase at peak (%) | | | Cys increase at peak (%) | | |
|---|---|---|---|---|---|---|---|---|---|
| PEG molecule | W1 | W2 | W3 | W1 | W2 | W3 | W1 | W2 | W3 |
| PBS (control) | −8.0 | −8.1 | n/a | −1 | −19 | n/a | −18.1 | 4.7 | n/a |
| ME-400MA | 73.2 | 64.9 | 58.6 | 383 | 329 | 365 | 17.2 | 6.3 | 8.0 |
| GL4-400MA | 74.6 | 41.1 | 34.0 | 715 | 723 | 449 | 97.8 | 47.5 | 51.8 |
| ME-400MA | 74.9 | 52.0 | 41.5 | 696 | 649 | 443 | 71.9 | 44.3 | 43.6 |
| ME-050GS | 74.8 | 58.5 | 42.1 | 978 | 795 | 833 | 70.7 | 75.0 | 58.3 |
| ME-200GS | 76.9 | 70.2 | 65.8 | 676 | 492 | 432 | 58.7 | 60.6 | 50.8 |
| ME-200MA | 68.0 | 24.0 | n/a | 796 | 508 | n/a | 35.7 | 16.1 | n/a |
| ME-200MA | 82.0 | 56.6 | 50.4 | 700 | 866 | 335 | 71.5 | 37.9 | 31.5 |
| ME-200MA | 80.4 | 60.6 | 50.1 | 1023 | 764 | 1100 | 76.6 | 77.3 | 58.3 |

Figure 6:
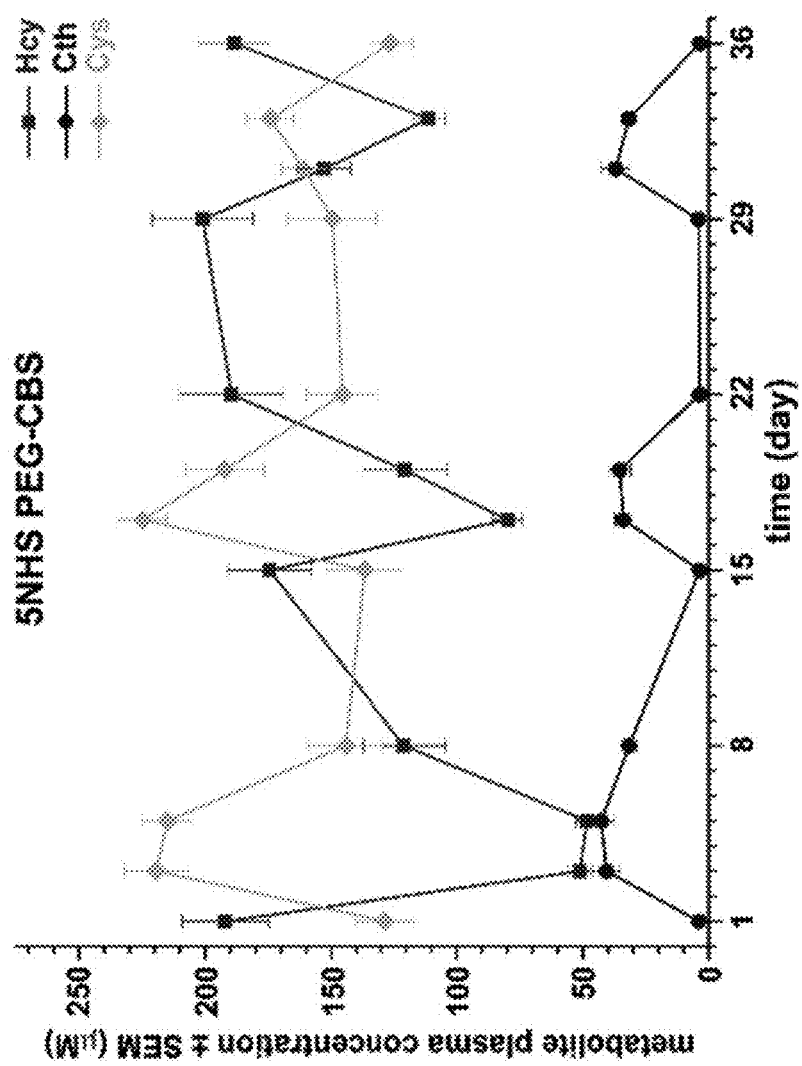
FIG. 6 shows evaluation of 5NHS PEG-htCBS C15S in a washout experiment. Plasma levels of Hcy (squares). Cth (circles) and Cys (diamonds) after repeated administration of 5NHS PEG-htCBS C15S in HO mice (SC, 7.5 mg/kg). Points represent an average value from individual HO mice (n=6) and error bars indicate SEMs.

The 5NHS PEG-htCBS C15S showed an excellent pharmacodynamics response after the first set of injections but a significant loss of efficacy was observed in the subsequent dose-weeks for Hcy. Hcy levels dropped to 48/80/111 µM (baseline levels: 192/175/201 µM) with a simultaneous increase in Cth levels to 43/35/37 µM (baseline levels: 4/4/4 µM) and concurrent increase of Cys levels to 219/225/174 µM (baseline levels: 129/137/146 µM) in dose-weeks 1/2/3 (FIG. 6 and Table 7).

20NHS PEG-CBS showed a balanced response in all three dose-weeks: the plasma Hcy concentration dropped to 38/49/56 µM from baseline levels 164/165/143 µM with a subsequent increase in Cth levels to 40/30/27 µM (baseline levels: 5/4/4 µM) and concurrent increase of Cys levels to 234/237/222 µM (baseline levels: 147/149/148 µM) in dose-weeks 1/2/3. As a control experiment, two additional batches of 200MA PEG-htCBS C15S were analyzed in a washout experiment and attenuated efficacy in subsequent dose-weeks was again observed: plasma Hcy dropped to 44/88/112 µM (baseline levels: 224/215/224 µM) with consequent increase in Cth levels to 40/31/43 µM (baseline levels: 4/3/4 µM) and concurrent increase of Cys levels to 219/219/196 µM (baseline levels: 124/118/144 µM) in dose-weeks 1/2/3. The 20NHS PEG-CBS showed the least attenuation of the pharmacodynamic effect on plasma metabolites after repeated administration of a PEGylated enzyme to HO mice (Table 7).

Example 7. Rescuing the Phenotype of KO Mice by Treatment with 20NHS CBS-PEG To assess the potentially beneficial effects of 20NHS PEG-htCBS C15S treatment on overall health and thriving of KO mice.

Figure 7A:
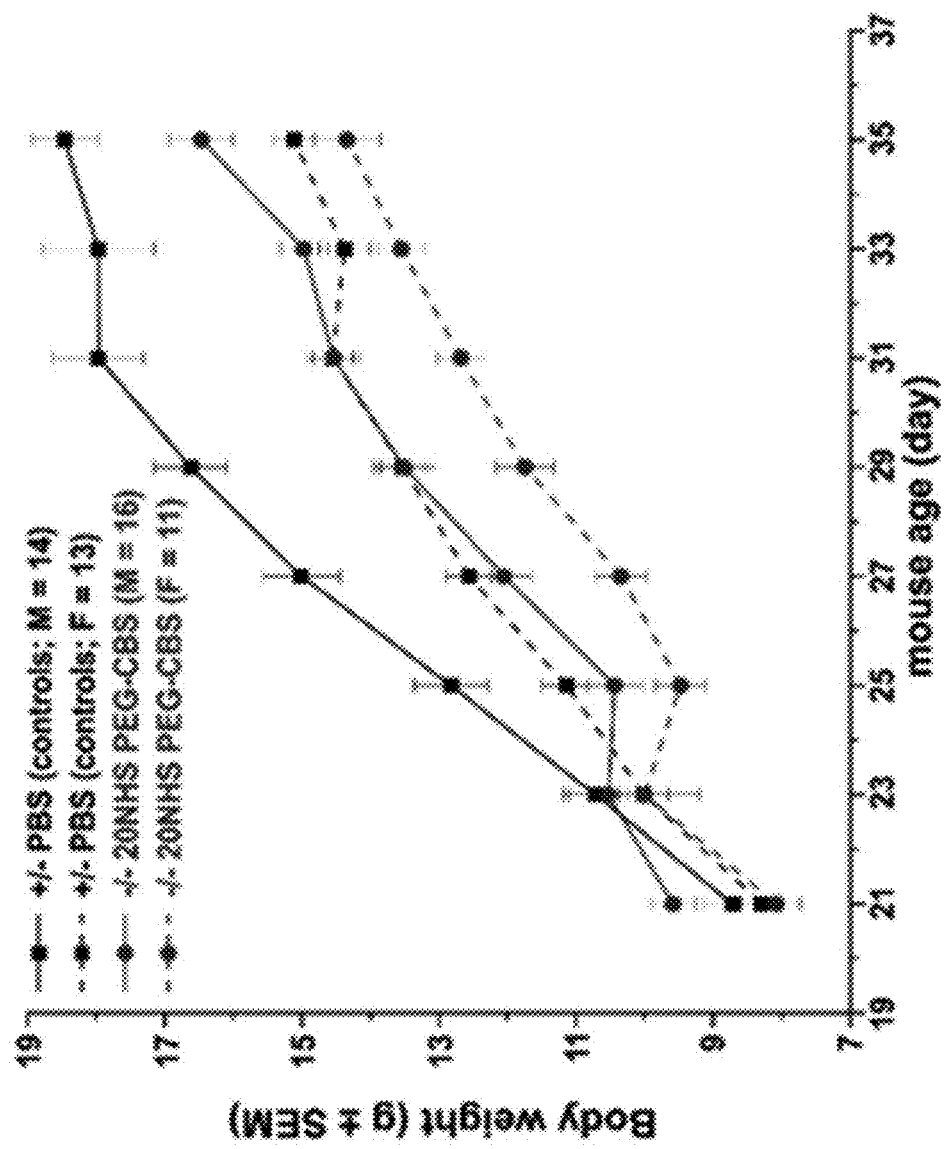
FIG. 7A-7B show body weight (FIG. 7A) and weight gain (FIG. 7B) of 20NHS PEG-htCBS C15S-treated CBS KO male (solid line and circles) and female (dashed line and circles) mice compared to PBS-injected+/−males (solid line and squares) and females (dashed line and squares). The number of subjects in each group is indicated in the plots. Mice received subcutaneous injections of 7.5 mg/kg 3 times per week from day 2 of age.
Figure 7B:
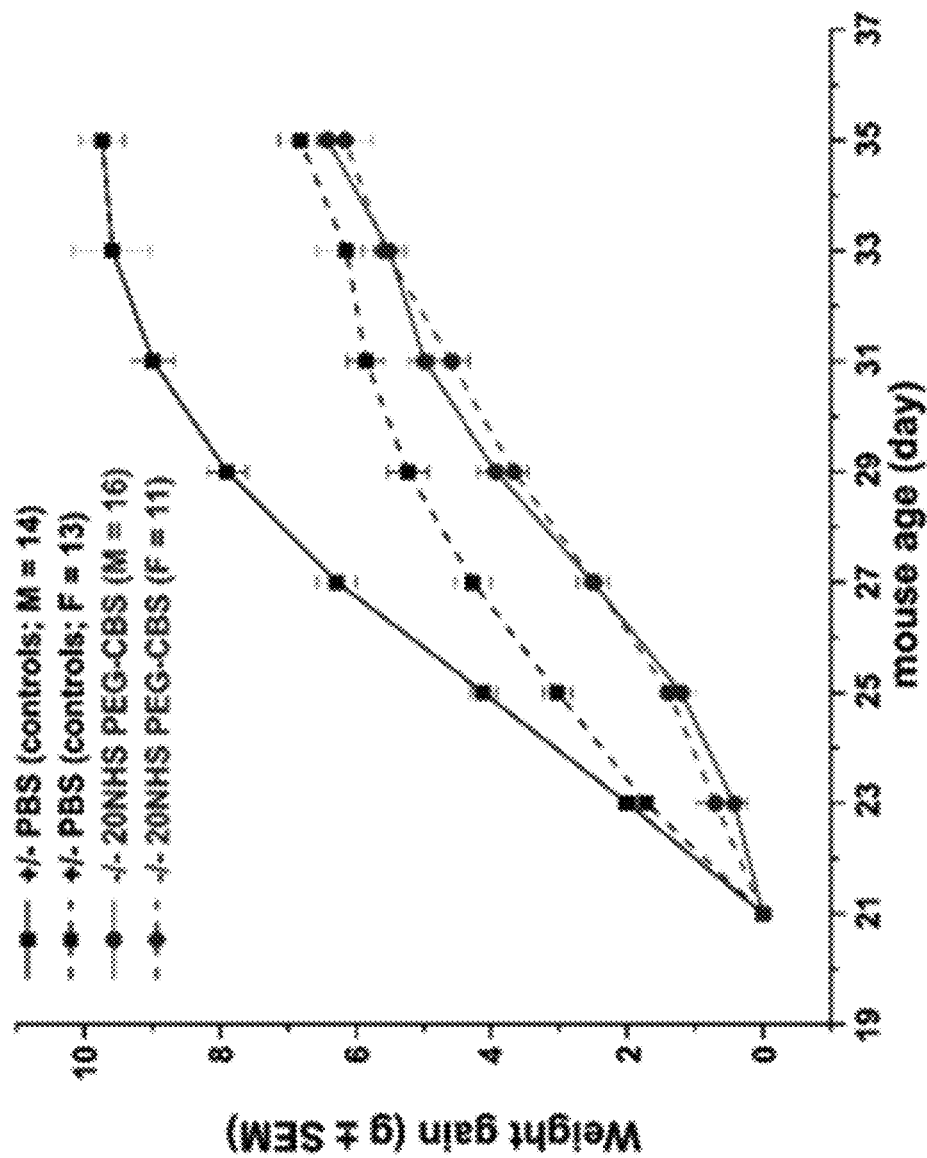

The body weights and weight gains of 20NHS PEG-htCBS C15S-treated mice (n-16M+11F) were determined every other day from weaning (day 21) up to 35 days of age and compared to sex- and age-matched PBS-treated heterozygous+/−mice (n-14M+13F). Mice received subcutaneous injections 3× a week of 7.5 mg/kg from day 2 of age. Body weight (FIG. 7A) and weight gain (FIG. 7B) of 20NHS PEG-htCBS C15S-treated CBS KO male (gray solid line & circles) and female (gray dashed line & circles) mice are compared to PBS-injected+/−males (black solid line & squares) and females (black dashed line & squares).

At the time of weaning (day 21), no significant differences were found in body weights between both heterozygous or KO mice and males or females receiving either PBS or 20NHS PEG-htCBS C15S except for males versus females on 20NHS PEG-htCBS C15S injections ($p<0.01$). Two days later (day 23) no significant difference in body weights among study mice was found. From day 25 on, the +/−males gained weight significantly ($p<0.001$) more and thus increase their body weight more than the +/−females as well as the 20NHS PEG-htCBS C15S-treated KO males or females. In KO mice, weaning led to a brief period of slower growth (days 23 and 25) characterized by a smaller weight gain and practically maintained body weight followed by steady gains in weight. Weight gains of KO males and females treated with 20NHS PEG-htCBS C15S were essentially identical and at days 33 and 35 their weight gains and body weights of treated KO females caught up with those of PBS-injected heterozygous females, while KO males fell behind a bit their heterozygous counterparts. Taken together, 20NHS PEG-htCBS C15S-treated KO mice gained weight steadily with females more than males catching up with the PBS-treated heterozygous mice in terms of body weight at the end of the 5-week treatment period.

Figure 8A:
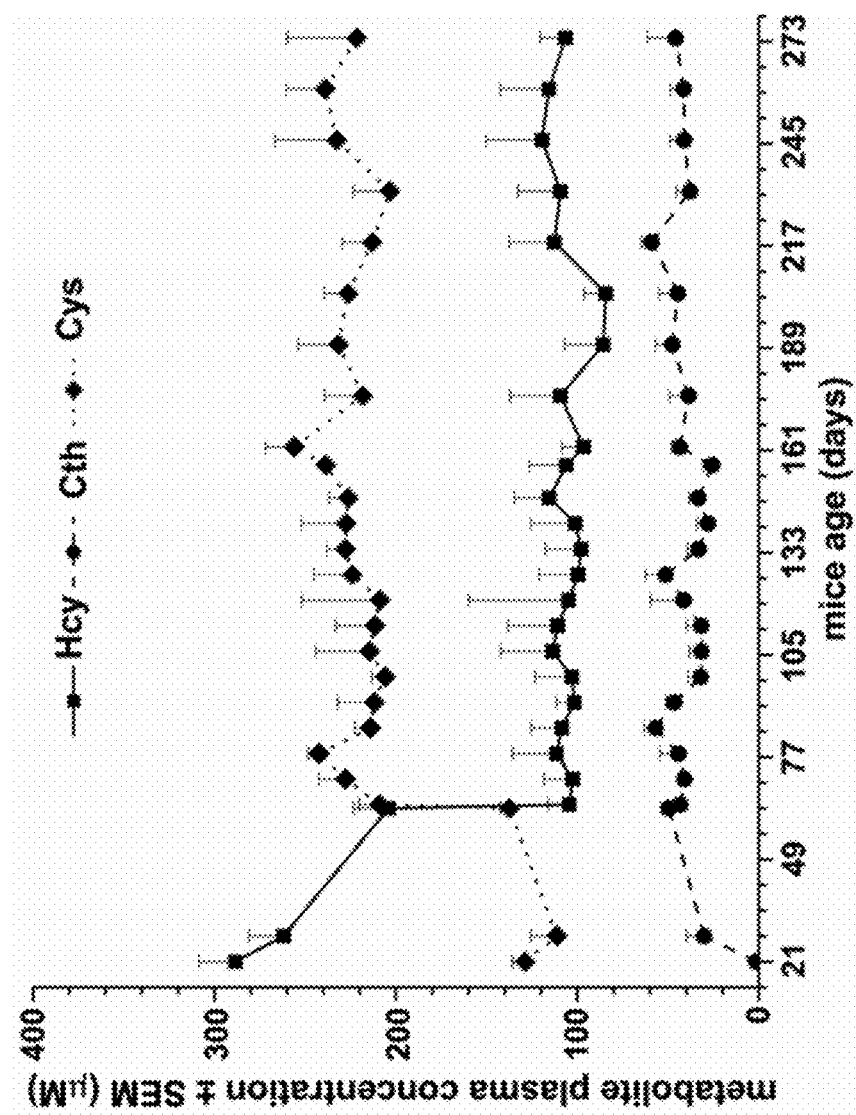
FIG. 8A-8B show effects of a long-term treatment of the 1278T mice with 20NHS PEG-htCBS C15S, which sustains improved plasma sulfur amino acid profiles.
Figure 8B:
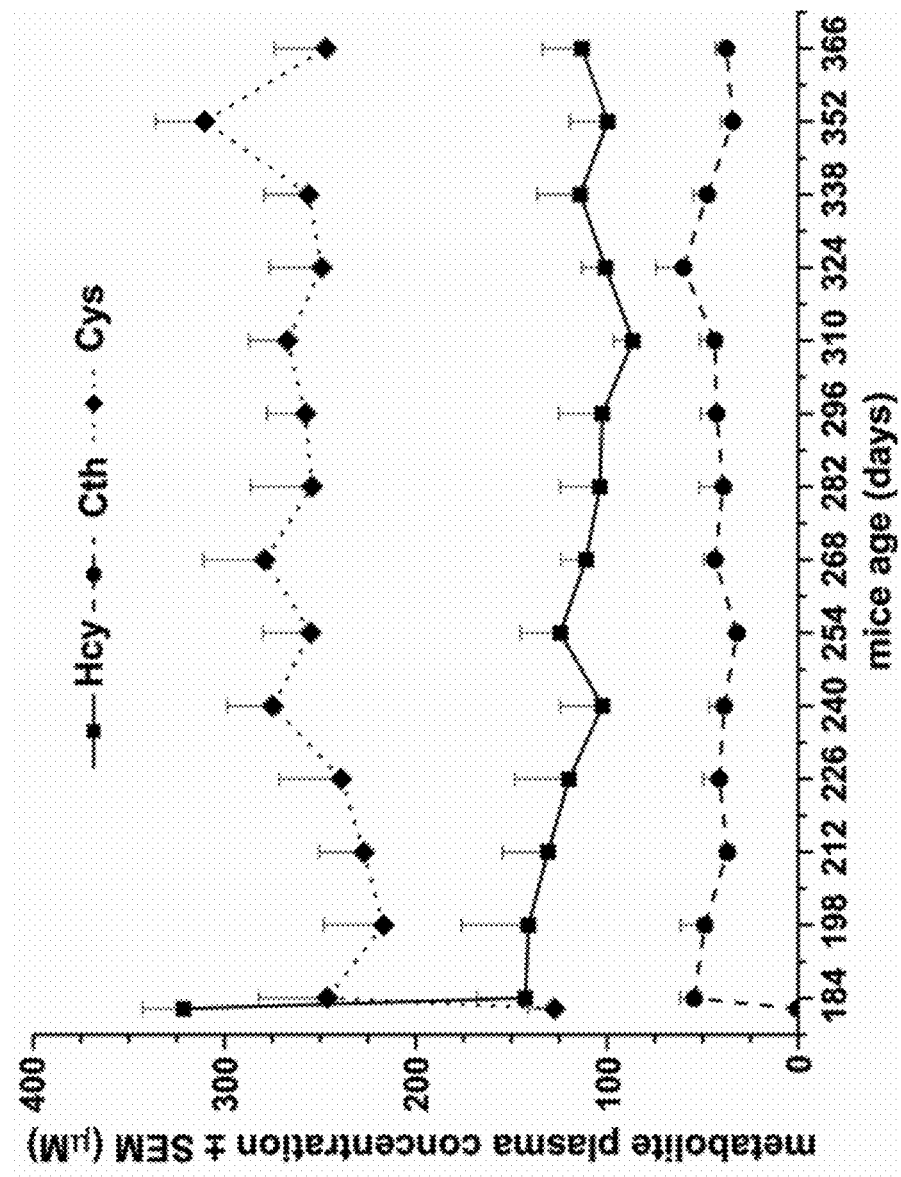

Example 8. Sustaining Improved Plasma Levels by Treatment with 20NHS PEG-htCBS C15S Clinical symptoms of the I278T mice, such as facial alopecia or osteoporosis, take time to develop as well as get corrected with treatment. In this Example, treatment of I278T mice with 20NHS PEG-htCBS C15S was shown to significantly improve or normalize the underlying metabolic imbalance and sustain it over a longer period. FIG. 8A and FIG. 8B show sustained efficacy of 20NHS PEG-htCBS C15S on plasma sulfur amino acids in the I278T mouse model. FIG. 8A showed a sustained improvement in plasma Hcy, Cth, and Cys levels in asymptomatic weaned I278T mice of 3 weeks of age (n=3) treated since then with three weekly SC injections (7.5 mg/kg) for a period of about 9 months. The initial levels recorded prior the first dose at day 21 showed highly elevated Hcy (288 µM), roughly half of the normal Cys levels (129 µM) and low plasma Cth (1.4 µM). Plasma metabolites determined 72 hours after the 3rd (day 28) and the 18th dose (day 63), respectively, illustrated that the lack of dosing during weekends resulted in somewhat a similar profile compared to the initial levels except for Cth, a marker of 20NHS PEG-htCBS C15S activity, for which elevated plasma concentration persisted most likely due to its slow renal clearance.

On the contrary, plasma levels determined 24 hours after 20NHS PEG-htCBS C15S administration (e.g. at day 64 and applies for all the subsequent time points) demonstrate substantially and significantly decreased Hcy levels (105 µM, $p<0.001$), normalized plasma Cys (209 µM, $p<0.001$) and elevated Cth (43 µM, $p<0.001$) compared to the initial values. Similarly, FIG. 8B exemplifies a persistent correction of plasma sulfur amino acids in 26 weeks old 1278T mice (n=10) showing multiple clinical signs of the diseases and treated since then (3× a week, SC, 7.5 mg/kg) for a period of about 6 months. The initial levels recorded prior the first dose at day 182 showed highly elevated Hcy (321 µM), roughly half of the normal Cys levels (127 µM) and low plasma Cth (0.3 µM). The 24 hours after initial administration of 20NHS PEG-htCBS C15S (day 184) resulted in a marked and significant decrease of plasma Hcy (143 µM, $p<0.001$), normalization of plasma Cys (246 µM, $p<0.001$) and elevation of Cth (54 µM, $p<0.001$) compared to the pre-treatment values. The improved plasma metabolite profile was maintained with regular ERT administration for a period of about 6 months. Taken together, regular SC injections of 20NHS PEG-htCBS C15S yielded a sustained improved plasma metabolite profile in the 1278T mouse, thus permitting efficacy studies requiring long-term administration.

Example 9. Normalizing Tissue Metabolite Levels and Improving the Balance of Metabolites Administration of 20NHS PEG-htCBS C15S was observed to result in correction of tissue metabolites, which correlated to improved plasma metabolites balance in adult 1278T mice. Concentrations of sulfur-containing metabolites in liver, kidney and brain homogenates and corresponding plasma levels of about 2-month-old 1278T mice (n=3) treated with 20NHS PEG-htCBS C15S (SC, 7.5 mg/kg) for a period of 3 weeks compared to age-matched healthy heterozygous mice (n=3) as well as untreated 1278T mice (n=3) were measured. The sulfur-containing metabolites included homocysteine (Hcy), cysteine (Cys), cystathionine (Cth), homolanthionine (Hlth), and lanthionine (Lth). Total homocysteine and cysteine was determined in plasma, while nonprotein-bound fractions of these thiols were measured in tissue homogenates. The 1278T adolescent mice (n=3) were treated for a period of 3 weeks with 20NHS PEG-htCBS C15S (3× a week, SC, 7.5 mg/kg) and compared to age-matched untreated 1278T mice (n=3) and untreated healthy heterozygous controls (n=3). Data were compared using ANOVA followed by Tukey's post hoc test to determine significance: * $p<0.05$,  $p<0.01$, * $p<0.001$, ns—non-significant. Results are described by µM in nmol/g of tissue or nM in pmol/g of tissue.

Total Hcy and non-protein bound Hcy was greatly elevated in plasma and liver/kidney/brain homogenates, respectively, in the untreated 1278T mice (310 µM in plasma and 29/21/12 µM in nmols/g of liver/kidney/brain) compared to both heterozygous controls (12 µM in plasma and 8/6/4 µM in nmols/g of liver/kidney/brain) and 20NHS PEG-htCBS C15S-treated 1278T mice (54 µM in plasma and 8/4/1 µM in nmols/g of liver/kidney/brain, $p<0.001$ for plasma and <0.01 for tissues). The 4.5-fold elevated total Hcy in plasma, non-protein bound Hcy in tissues of the treated 1278T mice was not significantly different from the levels in healthy heterozygous mice.

Total Cys was substantially decreased in plasma (91 µM), but the non-protein bound Cys in liver/kidney/brain homogenates of the untreated 1278T mice (21/432/44 µM in nmols/g of liver/kidney/brain) was not observed to be different compared to the 20NHS PEG-htCBS C15S-treated 1278T mice (224 µM in plasma and 36/265/51 µM in nmols/g of liver/kidney/brain, $p<0.01$ for plasma and non-significant for tissues). The Cys levels in the treated 1278T mice were similar to those of healthy heterozygous controls (255 µM in plasma and 81/322/44 µM in nmols/g of liver/kidney/brain, p=non-significant).

As anticipated, Cth levels in both plasma and tissues of untreated 1278T mice were diminished: 0.3 µM in plasma and 0.4/1.2/0.8 µM in nmols/g of liver/kidney/brain. Treatment with 20NHS PEG-htCBS C15S resulted in significant elevation of Cth in plasma (39 M) and kidney homogenate (36 µM in nmols/g of tissue) and lesser increase in liver and brain homogenates (5 and 3 µM in nmols/g of tissue) compared to the untreated 1278T mice (p<0.05 for both plasma and tissue homogenates). Although plasma and kidney levels of Cth were substantially higher in the treated 1278T mice in comparison to healthy heterozygous controls (1 µM in plasma, p<0.01 and 1.2 µM in nmols/g in kidney, p<0.01) likely due to activity of 20NHS PEG-htCBS C15S in circulation, they were not quite normalized to healthy levels in liver (20 µM in nmols/g of tissue, non-significant) and brain homogenates (8 µM in nmols/g of tissue, p<0.05).

No significant differences were observed in plasma and tissue levels of Met or GSH among the untreated 1278T mice, the 20NHS PEG-htCBS C15S-treated 1278T mice and healthy heterozygous controls.

Levels of thioethers homolathionine (Hlth) and lanthionine (Lth) in plasma and tissue homogenates have also been identified as emerging surrogate markers of $H_2S$ biogenesis. The levels of Hlth were markedly elevated in plasma (143 nM) and liver/kidney/brain homogenates of the untreated 1278T mice (6351/3324/1065 nM in pmol/g of tissue) and the 20NHS PEG-htCBS C15S treatment resulted in substantial correction of these levels to 45 nM in plasma (non-significant) and 170/1317/520 nM in pmols/g of liver/kidney/brain tissue (p<0.05/0.05/0.01). Interestingly, while liver Hlth in healthy heterozygous mice was significantly higher (996 nM in pmol/g of tissue, p<0.01) compared to the treated 1278T mice, the treatment resulted just in partial reduction of Hlth levels in the remaining compartments compared to those found in heterozygous mice: 8 nM in plasma (p<0.05) and 247/22 nM in pmol/g of kidney/brain tissues (p<0.01/0.001).

Regarding the second thioether Lth, only the plasma levels were significantly elevated in treated 1278T compared to the untreated ones (75 versus 17 nM, p<0.01), while levels of Lth in tissue homogenates remained similar (21/113/110 versus 14/92/104 nM in pmols/g of liver/kidney/brain tissue) due to low tissue permeability or a lack of a specific transporter for Lth. Plasma Lth in healthy heterozygous mice was significantly lower (32 nM, p<0.01), while its tissue levels were either elevated in liver (122 nM in pmols/g of tissue, p<0.05) and brain (304 nM in pmols/g of tissue, p<0.001) or remained similar in kidney (145 nM in pmols/g of tissue) when compared to the levels observed in the treated 1278T mice. Therefore, administration of 20NHS PEG-htCBS C15S improved or restored metabolic balance in plasma and tissues of the treated 1278T mice.

Example 10. Comparing methylation capacity among KO, HO, and 1278T mice treated with 20NHS PEG-htCBS CBS Plasma and Tissue Levels of the SAM/SAH Ratio in 1278T and KO Mice were compared to the ratio in healthy heterozygous control mice and untreated mice. The 1278T adolescent mice (n=3) were treated for a period of 3 weeks with PEG-htCBS C15S (3× a week, SC, 7.5 mg/kg) and compared to age-matched untreated 1278T mice (n=3) and untreated healthy heterozygous controls (n=3). Treated KO mice were dosed 3× a week 7.5 mg/kg from day 2 of age. Each group consisted of at least three 18 days old mice. All data were compared using multivariate ANOVA followed by Tukey's post hoc test to determine significance: * p<0.05,  p<0.01, * p<0.001, ns—non-significant.

Methylation capacity of the untreated 1278T mice was substantially decreased based on SAM/SAH ratio in plasma (0.4) and liver/kidney/brain homogenates (0.3/0.4/0.2) and was substantially ameliorated to a ratio of 3 in plasma (p<0.001) and 0.7/2.1/1.5 in liver/kidney/brain homogenates (non-significant for liver; but p<0.01 for both kidney and brain tissue) in the treated group. The improved methylation capacity of the 20NHS PEG-htCBS C15S-treated 1278T mice approached or even normalized the one determined in healthy heterozygous mouse plasmas (5, p<0.01) and liver/kidney/brain homogenates (1.3/3.9/2.0, non-significant for liver and brain, but p<0.05 for kidney).

Administration of 20NHS PEG-htCBS C15S was also observed to significantly improve the SAM/SAH ratio in plasma and tissues of the treated KO mice compared to the untreated ones but did not normalize it to the levels seen in healthy heterozygous controls. The SAM/SAH ratio was quite small in the livers of WT controls compared to plasma and other tissue levels and, more importantly, comparable to the levels found in KO mice (0.78 and 0.94 in control healthy heterozygous and KO, p=ns). In addition, the 20NHS PEG-htCBS C15S treatment further decreased the SAM/SAH ratio in the treated KO mice compared to untreated ones significantly (0.28, p<0.01). Therefore, administration of 20NHS PEG-htCBS C15S improved or restored the metabolic balance in plasma and tissues of the treated KO mice.

Example 11. Pharmacokinetics of 20NHS PEG-htCBS C15S in Rats

Figure 9A:
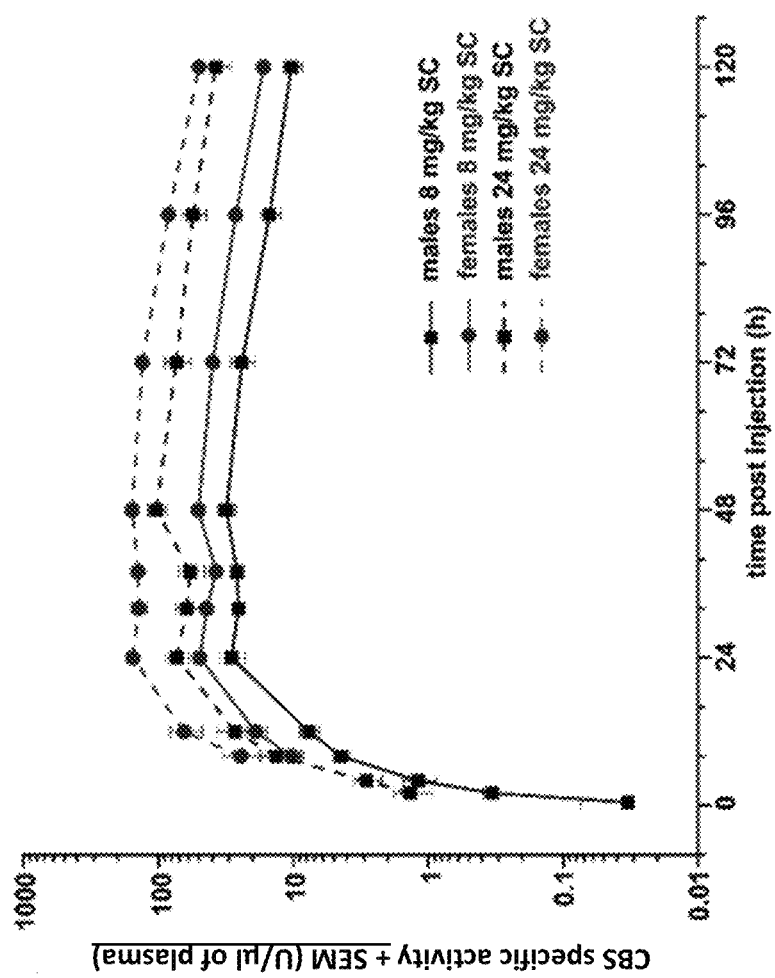
FIG. 9A-9C show pharmacokinetics of 20NHS PEG-htCBS C15S after a single dose administration and after a repeated administration to Sprague Dawley rats.

Pharmacokinetic properties of 20NHS PEG-htCBS C15S were also determined in wild-type Sprague Dawley rats. CBS specific activity in plasma of male (black, n=11 each group) and female rats (gray, n=8 each group) after a single SC administration of 8 mg/kg (solid lines) or 24 mg/kg 20NHS PEG-htCBS C15S (dashed lines) in log scale is shown in FIG. 9A.

The bioavailability of 20NHS PEG-htCBS C15S was observed to be nearly identical at the different doses (8 and 24 mg/kg) suggesting that the observed differences in absorption in rats were likely due to sexual dimorphism. The elimination phase of 20NHS PEG-htCBS C15S was log-linear in all cohorts and conformed to first order kinetics meaning that the time required for half the concentration of 20NHS PEG-htCBS C15S activity to clear from the plasma was constant. The mean value of elimination half-life across groups was 42±2 hours. Despite differences between male and female rats, the PK parameters estimated from plasma levels of 20NHS PEG-htCBS C15S activity after SC dosing were dose proportional to 24 mg/kg.

Figure 9B:
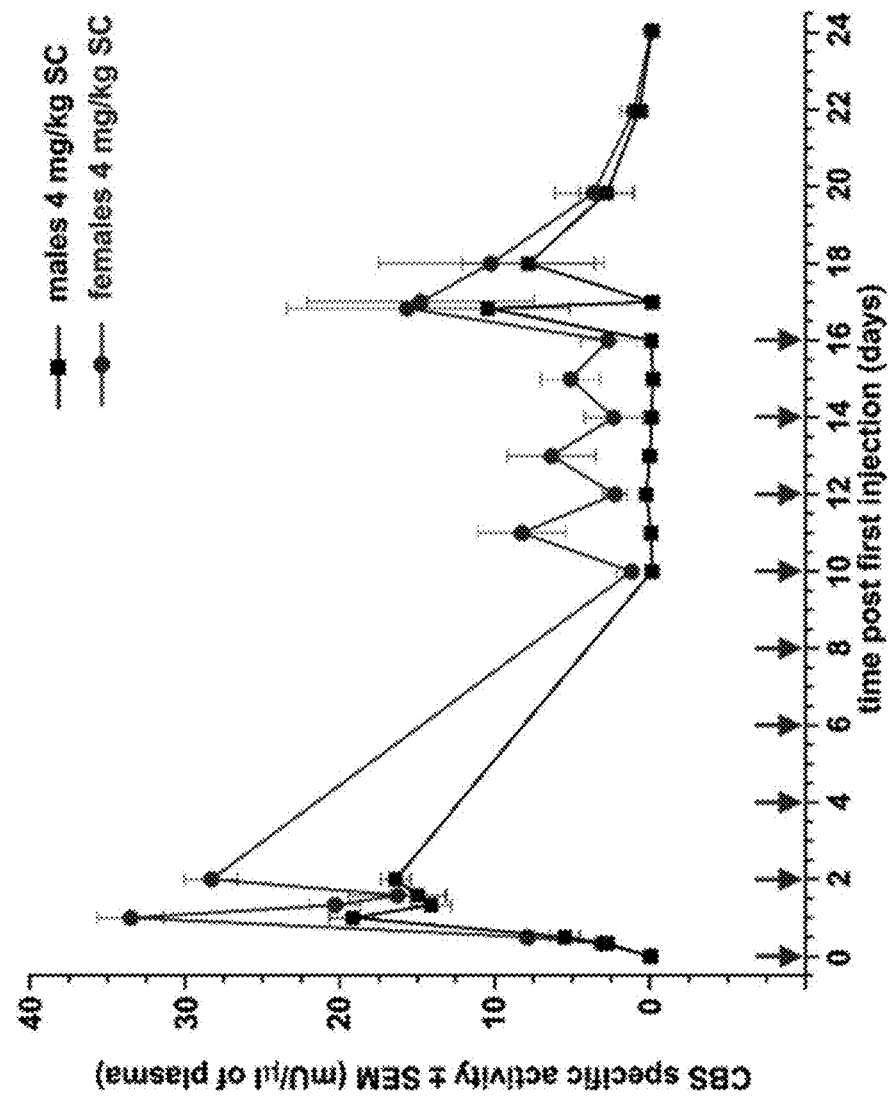
Figure 9C:
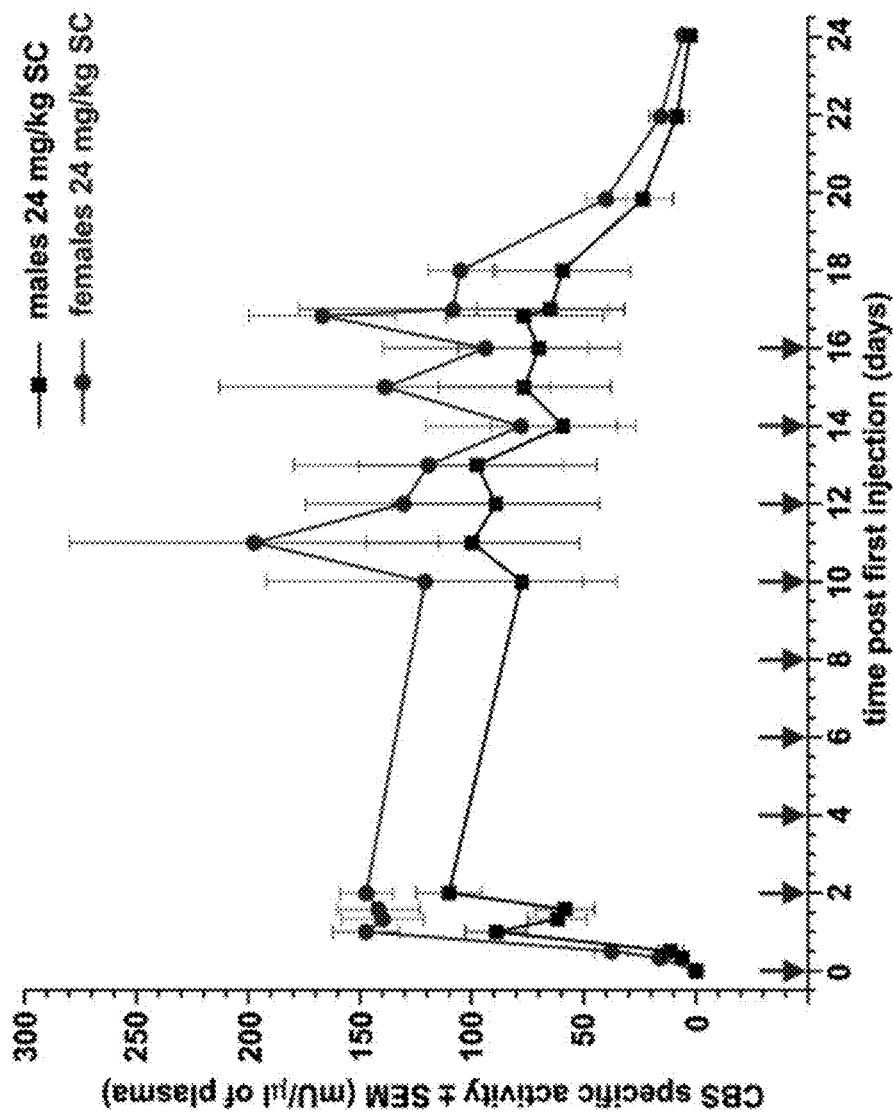

Differences due to sexual dimorphism in rats were also observed in a repeated dosing study, where the rats received a total of 9 injections 48 hours apart of 4, 8, and 24 mg/kg 20NHS PEG-htCBS C15S (FIG. 9B and FIG. 9C). In general, initial as well as steady state levels of 20NHS PEG-htCBS C15S activity in plasma were higher in female than male rats at the same dose level correlating with the observation for the single dose study. Plasma levels of 20 NHS PEG-htCBS C15S after repeated dosing demonstrated little or no accumulation at any dose level, even though the doses were administered when only slightly more than half of the 20NHS PEG-htCBS C15S have cleared from the plasma (48 hours dosing interval versus average t1/2-E=42 hours). To aid in the understanding of these unexpected observations, the approach to steady state and the predicted steady state plasma levels were calculated after hypothetical repeated dosing using the simulation function in the PK software. After multiple doses, the observed plasma levels of 20NHS PEG-htCBS C15S activity were 15-52% and 0-35% of the predicted values for the peaks and troughs at steady state, as shown in Table 8. (N/A=not applicable)

TABLE 8

Predicted and observed $c_{max\text{-}SS}$ and $c_{min\text{-}SS}$

| PK parameter | Male (8 mg/kg) | | Female (8 mg/kg) | | Male (24 mg/kg) | | Female (24 mg/kg) | |
|---|---|---|---|---|---|---|---|---|
| | Observed | Predicted | Observed | Predicted | Observed | Predicted | Observed | Predicted |
| $c_{max}$ (mU/µl) | 26 | N/A | 43 | N/A | 110 | N/A | 167 | N/A |
| $c_{max\text{-}SS}$ (mU/µl) | 10 | 66 | 42 | 127 | 99 | 227 | 196 | 378 |
| $c_{min\text{-}SS}$ (mU/µl) | 0 | 41 | 3 | 61 | 60 | 171 | 78 | 249 |
| Observed versus predicted 20NHS PEG-ht CBS C15S plasma activity at steady state (% or predicted value) | | | | | | | | |
| $c_{max\text{-}SS}$ | 15 | | 33 | | 44 | | 52 | |
| $c_{min\text{-}SS}$ | 0 | | 5 | | 35 | | 31 | |

The observed $c_{max}$ and $c_{min}$ correspond to the highest and lowest concentration of 20NHS PEG-htCBS C15S observed in plasma after the 2nd dose. The predicted values are from simulations using the time-concentration curves from the single dose PK study. The plasma levels after repeated dosing were observed to be closer to their predicted values at 24 mg/kg dose than at 8 mg/kg dose in both sexes.

EQUIVALENTS AND SCOPE

Those skilled in the art will recognize or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a", "an", and "the" may mean one or more than one unless indicated to the contrary or otherwise evident from the context. Claims or descriptions that include "or" between one or more members of a group are considered satisfied if one, more than one, or all the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims to provide the broadest possible interpretation of such claims in view of the prior art and, therefore, to effectively encompass the intended scope of the invention.

The invention claimed is:

1. A method of PEGylating human truncated cystathionine β-synthase (CBS) protein containing a mutation of a cysteine to a serine at amino acid position 15 of SEQ ID NO: 1 (htCB C15S), the method comprising:

(a) conjugating htCBS C15S with one or a plurality of NHS ester PEG molecules in solution at a molar excess of the NHS ester PEG molecules up to about 20-fold to create a batch, wherein the NHS ester PEG molecules are 5 kDa, 10 kDa, or 20 kDa NHS ester PEG molecules;

(b) comparing a retention time from a chromatographic profile from Size Exclusion Chromatography-High Performance Liquid Chromatography (SEC-HPLC) analysis of the batch to a retention time from a chromatographic profile from SEC-HPLC analysis of a sample of NHS PEGylated htCBS C15S with acceptable PEGylation, wherein the sample of NHS PEGylated htCBS C15S with acceptable PEGylation contains htCBS C15S molecules with at least 5 PEGylated sites; and (c) if the batch has a retention time greater than a retention time of the sample of NHS PEGylated htCBS C15S with acceptable PEGylation, adding additional NHS ester PEG molecules to the batch to increase PEGylation of the htCBS C15S in the batch.

2. The method of claim 1, wherein the plurality of NHS ester PEG molecules consists of 5 kDa NHS ester (5NHS) PEG molecules.

3. The method of claim 1, wherein the plurality of NHS ester PEG molecules consists of 10 kDa NHS ester (10NHS) PEG molecules.

4. The method of claim 1, wherein the plurality of NHS ester PEG molecules consists of 20 kDa NHS ester (20NHS) PEG molecules.

5. The method of claim 1, wherein each of the plurality of NHS ester PEG molecules is less than about 20 kDa.

6. The method of claim 1, wherein the retention time of the batch is greater than about 9.50 minutes.

7. The method of claim 1, wherein the retention time of the batch is between about 9.60 minutes and about 9.70 minutes.

8. The method of claim 1, wherein the retention time of the batch is within a range from about 9.50 to about 9.60 minutes.

9. The method of claim 1, wherein the retention time of the sample of NHS PEGylated htCBS C15S with acceptable PEGylation is less than about 9.53 minutes.

10. The method of claim 1, wherein the retention time of the batch is greater than about 9.75 minutes.

11. The method of claim 1, wherein the retention time of the batch is greater than about 10.00 minutes.

12. The method of claim 1, wherein the retention time of the batch is greater than about 10.25 minutes.

* * * * *

UNITED STATES PATENT AND TRADEMARK OFFICE
CERTIFICATE OF CORRECTION

PATENT NO. : 11,324,811 B2  
APPLICATION NO. : 16/605918  
DATED : May 10, 2022  
INVENTOR(S) : Tomas Majtan et al.

Page 1 of 1

It is certified that error appears in the above-identified patent and that said Letters Patent is hereby corrected as shown below:

In the Claims

Column 91, Claim 1, Line 60:
"SEQ ID NO: 1 (htCB C15S)," should read: --SEQ ID NO: 1 (htCBS C15S),--.

Column 91, Claim 1, Line 61:
"with one or a plurality" should read: --with a plurality--.

Signed and Sealed this
Twenty-third Day of April, 2024

Katherine Kelly Vidal
*Director of the United States Patent and Trademark Office*

SEQUENCE LISTING

```
<160> NUMBER OF SEQ ID NOS: 32

<210> SEQ ID NO 1
<211> LENGTH: 413
<212> TYPE: PRT
<213> ORGANISM: Homo sapiens

<400> SEQUENCE: 1

Met Pro Ser Glu Thr Pro Gln Ala Glu Val Gly Pro Thr Gly Cys Pro
1               5                   10                  15

His Arg Ser Gly Pro His Ser Ala Lys Gly Ser Leu Glu Lys Gly Ser
            20                  25                  30

Pro Glu Asp Lys Glu Ala Lys Glu Pro Leu Trp Ile Arg Pro Asp Ala
        35                  40                  45
```

```
Pro Ser Arg Cys Thr Trp Gln Leu Gly Arg Pro Ala Ser Glu Ser Pro
     50                  55                  60

His His His Thr Ala Pro Ala Lys Ser Pro Lys Ile Leu Pro Asp Ile
 65                  70                  75                  80

Leu Lys Lys Ile Gly Asp Thr Pro Met Val Arg Ile Asn Lys Ile Gly
                 85                  90                  95

Lys Lys Phe Gly Leu Lys Cys Glu Leu Leu Ala Lys Cys Glu Phe Phe
             100                 105                 110

Asn Ala Gly Gly Ser Val Lys Asp Arg Ile Ser Leu Arg Met Ile Glu
             115                 120                 125

Asp Ala Glu Arg Asp Gly Thr Leu Lys Pro Gly Asp Thr Ile Ile Glu
130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
            180                 185                 190

Thr Asn Ala Arg Phe Asp Ser Pro Glu Ser His Val Gly Val Ala Trp
        195                 200                 205

Arg Leu Lys Asn Glu Ile Pro Asn Ser His Ile Leu Asp Gln Tyr Arg
210                 215                 220

Asn Ala Ser Asn Pro Leu Ala His Tyr Asp Thr Thr Ala Asp Glu Ile
225                 230                 235                 240

Leu Gln Gln Cys Asp Gly Lys Leu Asp Met Leu Val Ala Ser Val Gly
                245                 250                 255

Thr Gly Gly Thr Ile Thr Gly Ile Ala Arg Lys Leu Lys Glu Lys Cys
            260                 265                 270

Pro Gly Cys Arg Ile Ile Gly Val Asp Pro Glu Gly Ser Ile Leu Ala
        275                 280                 285

Glu Pro Glu Glu Leu Asn Gln Thr Glu Gln Thr Thr Tyr Glu Val Glu
290                 295                 300

Gly Ile Gly Tyr Asp Phe Ile Pro Thr Val Leu Asp Arg Thr Val Val
305                 310                 315                 320

Asp Lys Trp Phe Lys Ser Asn Asp Glu Glu Ala Phe Thr Phe Ala Arg
                325                 330                 335

Met Leu Ile Ala Gln Glu Gly Leu Leu Cys Gly Gly Ser Ala Gly Ser
            340                 345                 350

Thr Val Ala Val Ala Val Lys Ala Ala Gln Glu Leu Gln Glu Gly Gln
        355                 360                 365

Arg Cys Val Val Ile Leu Pro Asp Ser Val Arg Asn Tyr Met Thr Lys
370                 375                 380

Phe Leu Ser Asp Arg Trp Met Leu Gln Lys Gly Phe Leu Lys Glu Glu
385                 390                 395                 400

Asp Leu Thr Glu Lys Lys Pro Trp Trp Trp His Leu Arg
                405                 410

<210> SEQ ID NO 2
<211> LENGTH: 33
<212> TYPE: PRT
<213> ORGANISM: Homo sapiens

<400> SEQUENCE: 2

Pro Ser Glu Thr Pro Gln Ala Glu Val Gly Pro Thr Gly Ser Pro His
  1               5                  10                  15
```

Arg Ser Gly Pro His Ser Ala Lys Gly Ser Leu Glu Lys Gly Ser Pro
            20                  25                  30

Glu

<210> SEQ ID NO 3
<211> LENGTH: 26
<212> TYPE: PRT
<213> ORGANISM: Homo sapiens

<400> SEQUENCE: 3

Glu Val Gly Pro Thr Gly Ser Pro His Arg Ser Gly Pro His Ser Ala
1               5                   10                  15

Lys Gly Ser Leu Glu Lys Gly Ser Pro Glu
            20                  25

<210> SEQ ID NO 4
<211> LENGTH: 12
<212> TYPE: PRT
<213> ORGANISM: Homo sapiens

<400> SEQUENCE: 4

Asp Lys Glu Ala Lys Glu Pro Leu Trp Ile Arg Pro
1               5                   10

<210> SEQ ID NO 5
<211> LENGTH: 7
<212> TYPE: PRT
<213> ORGANISM: Homo sapiens

<400> SEQUENCE: 5

Glu Pro Leu Trp Ile Arg Pro
1               5

<210> SEQ ID NO 6
<211> LENGTH: 32
<212> TYPE: PRT
<213> ORGANISM: Homo sapiens

<400> SEQUENCE: 6

Asp Ala Pro Ser Arg Cys Thr Trp Gln Leu Gly Arg Pro Ala Ser Glu
1               5                   10                  15

Ser Pro His His His Thr Ala Pro Ala Lys Ser Pro Lys Ile Leu Pro
            20                  25                  30

<210> SEQ ID NO 7
<211> LENGTH: 7
<212> TYPE: PRT
<213> ORGANISM: Homo sapiens

<400> SEQUENCE: 7

Asp Ile Leu Lys Lys Ile Gly
1               5

<210> SEQ ID NO 8
<211> LENGTH: 21
<212> TYPE: PRT
<213> ORGANISM: Homo sapiens

<400> SEQUENCE: 8

Asp Thr Pro Met Val Arg Ile Asn Lys Ile Gly Lys Lys Phe Gly Leu
1               5                   10                  15

Lys Cys Glu Leu Leu

```
            20

<210> SEQ ID NO 9
<211> LENGTH: 13
<212> TYPE: PRT
<213> ORGANISM: Homo sapiens

<400> SEQUENCE: 9

Ala Lys Cys Glu Phe Phe Asn Ala Gly Gly Ser Val Lys
1               5                   10

<210> SEQ ID NO 10
<211> LENGTH: 9
<212> TYPE: PRT
<213> ORGANISM: Homo sapiens

<400> SEQUENCE: 10

Asp Arg Ile Ser Leu Arg Met Ile Glu
1               5

<210> SEQ ID NO 11
<211> LENGTH: 7
<212> TYPE: PRT
<213> ORGANISM: Homo sapiens

<400> SEQUENCE: 11

Asp Gly Thr Leu Lys Pro Gly
1               5

<210> SEQ ID NO 12
<211> LENGTH: 39
<212> TYPE: PRT
<213> ORGANISM: Homo sapiens

<400> SEQUENCE: 12

Asp Thr Ile Ile Glu Pro Thr Ser Gly Asn Thr Gly Ile Gly Leu Ala
1               5                   10                  15

Leu Ala Ala Ala Val Arg Gly Tyr Arg Cys Ile Ile Val Met Pro Glu
                20                  25                  30

Lys Met Ser Ser Glu Lys Val
            35

<210> SEQ ID NO 13
<211> LENGTH: 19
<212> TYPE: PRT
<213> ORGANISM: Homo sapiens

<400> SEQUENCE: 13

Asp Val Leu Arg Ala Leu Gly Ala Glu Ile Val Arg Thr Pro Thr Asn
1               5                   10                  15

Ala Arg Phe

<210> SEQ ID NO 14
<211> LENGTH: 23
<212> TYPE: PRT
<213> ORGANISM: Homo sapiens

<400> SEQUENCE: 14

Asp Ser Pro Glu Ser His Val Gly Val Ala Trp Arg Leu Lys Asn Glu
1               5                   10                  15

Ile Pro Asn Ser His Ile Leu
            20
```

<210> SEQ ID NO 15
<211> LENGTH: 13
<212> TYPE: PRT
<213> ORGANISM: Homo sapiens

<400> SEQUENCE: 15

Asp Gln Tyr Arg Asn Ala Ser Asn Pro Leu Ala His Tyr
1               5                   10

<210> SEQ ID NO 16
<211> LENGTH: 7
<212> TYPE: PRT
<213> ORGANISM: Homo sapiens

<400> SEQUENCE: 16

Asp Glu Ile Leu Gln Gln Cys
1               5

<210> SEQ ID NO 17
<211> LENGTH: 4
<212> TYPE: PRT
<213> ORGANISM: Homo sapiens

<400> SEQUENCE: 17

Asp Gly Lys Leu
1

<210> SEQ ID NO 18
<211> LENGTH: 21
<212> TYPE: PRT
<213> ORGANISM: Homo sapiens

<400> SEQUENCE: 18

Asp Met Leu Val Ala Ser Val Gly Thr Gly Thr Ile Thr Gly Ile
1               5                   10                  15

Ala Arg Lys Leu Lys
            20

<210> SEQ ID NO 19
<211> LENGTH: 32
<212> TYPE: PRT
<213> ORGANISM: Homo sapiens

<400> SEQUENCE: 19

Glu Lys Cys Pro Gly Cys Arg Ile Ile Gly Val Asp Pro Glu Gly Ser
1               5                   10                  15

Ile Leu Ala Glu Pro Glu Glu Leu Asn Gln Thr Glu Gln Thr Thr Tyr
            20                  25                  30

<210> SEQ ID NO 20
<211> LENGTH: 7
<212> TYPE: PRT
<213> ORGANISM: Homo sapiens

<400> SEQUENCE: 20

Glu Val Glu Gly Ile Gly Tyr
1               5

<210> SEQ ID NO 21
<211> LENGTH: 7
<212> TYPE: PRT
<213> ORGANISM: Homo sapiens

<400> SEQUENCE: 21

```
Asp Phe Ile Pro Thr Val Leu
1               5

<210> SEQ ID NO 22
<211> LENGTH: 5
<212> TYPE: PRT
<213> ORGANISM: Homo sapiens

<400> SEQUENCE: 22

Asp Arg Thr Val Val
1               5

<210> SEQ ID NO 23
<211> LENGTH: 7
<212> TYPE: PRT
<213> ORGANISM: Homo sapiens

<400> SEQUENCE: 23

Asp Lys Trp Phe Lys Ser Asn
1               5

<210> SEQ ID NO 24
<211> LENGTH: 38
<212> TYPE: PRT
<213> ORGANISM: Homo sapiens

<400> SEQUENCE: 24

Asp Glu Glu Ala Phe Thr Phe Ala Arg Met Leu Ile Ala Gln Glu Gly
1               5                   10                  15

Leu Leu Cys Gly Gly Ser Ala Gly Ser Thr Val Ala Val Ala Val Lys
            20                  25                  30

Ala Ala Gln Glu Leu Gln
        35

<210> SEQ ID NO 25
<211> LENGTH: 12
<212> TYPE: PRT
<213> ORGANISM: Homo sapiens

<400> SEQUENCE: 25

Thr Phe Ala Arg Met Leu Ile Ala Gln Glu Gly Leu
1               5                   10

<210> SEQ ID NO 26
<211> LENGTH: 13
<212> TYPE: PRT
<213> ORGANISM: Homo sapiens

<400> SEQUENCE: 26

Glu Leu Gln Glu Gly Gln Arg Cys Val Val Ile Leu Pro
1               5                   10

<210> SEQ ID NO 27
<211> LENGTH: 10
<212> TYPE: PRT
<213> ORGANISM: Homo sapiens

<400> SEQUENCE: 27

Glu Gly Gln Arg Cys Val Val Ile Leu Pro
1               5                   10

<210> SEQ ID NO 28
<211> LENGTH: 12
```

```
<212> TYPE: PRT
<213> ORGANISM: Homo sapiens

<400> SEQUENCE: 28

Asp Ser Val Arg Asn Tyr Met Thr Lys Phe Leu Ser
1               5                   10

<210> SEQ ID NO 29
<211> LENGTH: 13
<212> TYPE: PRT
<213> ORGANISM: Homo sapiens

<400> SEQUENCE: 29

Asp Arg Trp Met Leu Gln Lys Gly Phe Leu Lys Glu Glu
1               5                   10

<210> SEQ ID NO 30
<211> LENGTH: 13
<212> TYPE: PRT
<213> ORGANISM: Homo sapiens

<400> SEQUENCE: 30

Asp Leu Thr Glu Lys Lys Pro Trp Trp Trp His Leu Arg
1               5                   10

<210> SEQ ID NO 31
<211> LENGTH: 51
<212> TYPE: PRT
<213> ORGANISM: Homo sapiens

<400> SEQUENCE: 31

Cys Pro Gly Cys Arg Ile Ile Gly Val Asp Pro Glu Gly Ser Ile Leu
1               5                   10                  15

Ala Glu Pro Glu Glu Leu Asn Gln Thr Glu Gln Thr Thr Tyr Glu Val
            20                  25                  30

Glu Gly Ile Gly Tyr Asp Phe Ile Pro Thr Val Leu Asp Arg Thr Val
        35                  40                  45

Val Asp Lys
    50

<210> SEQ ID NO 32
<211> LENGTH: 27
<212> TYPE: PRT
<213> ORGANISM: Homo sapiens

<400> SEQUENCE: 32

Cys Asp Gly Lys Leu Asp Met Leu Val Ala Ser Val Gly Thr Gly Gly
1               5                   10                  15

Thr Ile Thr Gly Ile Ala Arg Lys Leu Lys Glu
            20                  25
```